US012588353B2

(12) United States Patent
Cho et al.

(10) Patent No.: US 12,588,353 B2
(45) Date of Patent: Mar. 24, 2026

(54) PLURALITY OF HOST MATERIALS, ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Sang-Hee Cho, Gyeonggi-do (KR); Bitnari Kim, Gyeonggi-do (KR); Young-Jae Kim, Gyeonggi-do (KR); So-Young Jung, Gyeonggi-do (KR); Mi-Ja Lee, Gyeonggi-do (KR); Su-Hyun Lee, Gyeonggi-do (KR); Tae-Jun Han, Gyeonggi-do (KR); HaeYeon Kim, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 942 days.

(21) Appl. No.: 17/825,399

(22) Filed: May 26, 2022

(65) Prior Publication Data

US 2023/0006147 A1 Jan. 5, 2023

(30) Foreign Application Priority Data

Jun. 3, 2021 (KR) ........................ 10-2021-0072144
Apr. 7, 2022 (KR) ........................ 10-2022-0043598

(51) Int. Cl.

| | |
|---|---|
| ***H10K 50/11*** | (2023.01) |
| ***C07D 209/94*** | (2006.01) |
| ***C07D 403/10*** | (2006.01) |
| ***C07D 405/10*** | (2006.01) |
| ***C07D 409/10*** | (2006.01) |
| ***C07D 487/04*** | (2006.01) |
| ***H10K 85/00*** | (2023.01) |
| ***H10K 85/60*** | (2023.01) |
| ***H10K 101/00*** | (2023.01) |

(52) U.S. Cl.

CPC ........... *H10K 50/11* (2023.02); *C07D 209/94* (2013.01); *C07D 403/10* (2013.01); *C07D 405/10* (2013.01); *C07D 409/10* (2013.01); *C07D 487/04* (2013.01); *H10K 85/00* (2023.02); *H10K 85/636* (2023.02); *H10K 85/6572* (2023.02); *H10K 85/6574* (2023.02); *H10K 85/6576* (2023.02); *H10K 2101/90* (2023.02)

(58) Field of Classification Search

CPC .................................................. H10K 2101/90
See application file for complete search history.

(56) References Cited

U.S. PATENT DOCUMENTS

| | | | | |
|---|---|---|---|---|
| 2018/0351113 | A1* | 12/2018 | Ahn | H10K 85/6572 |
| 2019/0312212 | A1 | 10/2019 | Moon et al. | |
| 2020/0013965 | A1 | 1/2020 | Yang et al. | |
| 2021/0336153 | A1 | 10/2021 | Kim et al. | |

FOREIGN PATENT DOCUMENTS

| | | | | |
|---|---|---|---|---|
| WO | WO-2020091446 | A1 * | 5/2020 | C09K 11/06 |
| WO | 2020175797 | A1 | 9/2020 | |

* cited by examiner

*Primary Examiner* — Vu A Nguyen
(74) *Attorney, Agent, or Firm* — G. Creston Campbell

(57) ABSTRACT

The present disclosure relates to a plurality of host materials and an organic electroluminescent device comprising the same. By comprising the specific combination of compounds according to the present disclosure as a plurality of host materials according to the present disclosure, it is possible to provide an organic electroluminescent device having improved driving voltage, luminous efficiency, and/or lifetime property compared to the conventional organic electroluminescent devices.

9 Claims, No Drawings

PLURALITY OF HOST MATERIALS, ORGANIC ELECTROLUMINESCENT COMPOUND AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

A small molecular green organic electroluminescent device (OLED) was first developed by Tang, et al., of Eastman Kodak in 1987 by using TPD/Alq3 bi-layer consisting of a light-emitting layer and a charge transport layer. Thereafter, the development of organic electroluminescent devices was rapidly effected and organic electroluminescent devices have been commercialized. At present, organic electroluminescent devices primarily use phosphorescent materials having excellent luminous efficiency in panel implementation. In many applications such as TVs and lightings, an OLED is facing the problem of insufficient lifetime, and an OLED having high efficiency is still required. In general, the higher the luminance of an OLED corresponds to a shorter lifetime of the OLED. Therefore, an OLED having high luminous efficiency and/or long lifetime is required for long-term use and high resolution of the display.

In order to enhance luminous efficiency, driving voltage and/or lifetime, various materials or concepts for an organic layer of an OLED have been proposed. However, they were not satisfied in practical use.

Korean Patent Application Laid-Open No. 2020-0000329 discloses a plurality of host materials comprising a compound in which heteroaryl is linked to a phenanthrene-based moiety and a compound in which heteroaryl is linked to a carbazole-based moiety. Korean Patent Application Laid-Open No. 2017-0043439 discloses a compound of a carbazole derivative. However, they do not specifically disclose the specific combinations of the host materials claimed herein. In addition, there is a continuous need to develop a light-emitting material having improved performance, such as improved driving voltage, luminous efficiency, power efficiency, and/or lifetime properties, compared to the combinations of the specific compounds disclosed in the aforementioned references.

DISCLOSURE OF INVENTION

Technical Problem

The objective of the present disclosure is to provide an improved plurality of host materials capable of providing an organic electroluminescent device having improved driving voltage, luminous efficiency, and/or lifetime property. Another objective of the present disclosure is to provide an organic electroluminescent device having improved driving voltage, luminous efficiency and/or lifetime property by comprising the specific combinations of the compounds of the present disclosure.

Solution to Problem

As a result of intensive research to solve the above technical problems, the present inventors found that the above objective can be achieved by a plurality of host materials comprising a first host material comprising the compound represented by formula 1 and a second host material comprising the compound represented by formula 2.

(1)

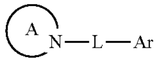

In formula 1,

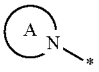

is a structure in which 5 to 8 rings selected from the group consisting of a substituted or unsubstituted (C6-C30) arene ring and a substituted or unsubstituted (3- to 30-membered) heteroarene ring are fused around a heptagonal or octagonal ring, and at least one pentagonal ring(s) containing nitrogen is comprised;

L represents a single bond, a substituted or unsubstituted (C1-C30)alkylene, a substituted or unsubstituted (C3-C30)cycloalkylene, a substituted or unsubstituted (C6-C30)arylene, or a substituted or unsubstituted (3- to 30-membered)heteroarylene;

Ar represents deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-NR_{11}R_{12}$, or $-SiR_{13}R_{14}R_{15}$; and $R_{11}$ to $R_{15}$, each independently, represent a substituted or unsubstituted (C1-C30)alkyl, a substituted or unsubstituted (C6-C30)aryl, or a substituted or unsubstituted (3- to 30-membered)heteroaryl.

(2)

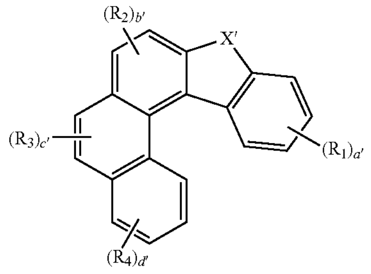

In formula 2,

X' represents O, S, or $CR_5R_6$;

$R_1$ to $R_4$, each independently, represent hydrogen, deuterium, a cyano, a substituted or unsubstituted (C1-C30) alkyl, a substituted or unsubstituted (C3-C30)cycloalkyl, a substituted or unsubstituted (C3-C30) cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-L_3-NR_{16}R_{17}$, or $-SiR_{18}R_{19}R_{20}$; or may be linked to adjacent substituent(s) to form a ring(s);

wherein, at least one of $R_1$ to $R_4$ represents a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, a substituted or unsubstituted (3- to 30-membered)heteroaryl, $-L_3-NR_{16}R_{17}$, or $—SiR_{18}R_{19}R_{20}$;

$L_3$ represents a single bond, a substituted or unsubstituted (C6-C30)arylene, or a substituted or unsubstituted (3- to 30-membered)heteroarylene;

$R_5$ and $R_6$, each independently, represent a substituted or unsubstituted (C1-C30)alkyl, a substituted or unsubstituted (C6-C30)aryl, or a substituted or unsubstituted (3- to 30-membered)heteroaryl, or $R_5$ and $R_6$ may be linked to each other to form a ring(s);

$R_{10}$ to $R_{20}$, each independently, represent a substituted or unsubstituted (C1-C30)alkyl, a substituted or unsubstituted (C6-C30)aryl, or a substituted or unsubstituted (3- to 30-membered)heteroaryl; and a' and d', each independently, represent an integer of 1 to 4, b' and c', each independently, represent an integer of 1 or 2, and where if each of a' to d' is an integer of 2 or more, each of $R_1$ to each of $R_4$ may be the same or different from each other.

Advantageous Effects of Invention

The organic electroluminescent device having low driving voltage, high luminous efficiency, and/or excellent lifetime properties compared to conventional organic electroluminescent devices is provided by comprising the specific combination of compounds according to the present disclosure as a plurality of host materials, and it is possible to produce a display system or a lighting system using the same.

MODE FOR THE INVENTION

Hereinafter, the present disclosure will be described in detail. However, the following description is intended to explain the present disclosure and is not meant in any way to restrict the scope of the present disclosure.

The term "organic electroluminescent compound" in the present disclosure refers to a compound that may be used in an organic electroluminescent device, and may be comprised in any layer constituting an organic electroluminescent device, as necessary.

The term "an organic electroluminescent material" in the present disclosure refers to a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of host materials" in the present disclosure refers to a host material comprising a combination of at least two compounds, which may be comprised in any light-emitting layer constituting an organic electroluminescent device. It may mean both materials before being comprised in an organic electroluminescent device (for example, before vapor deposition) and a material after being comprised in an organic electroluminescent device (for example, after vapor deposition). As one embodiment, the plurality of host materials of the present disclosure may be a combination of at least two host materials, and may optionally further include a conventional material(s) included in an organic electroluminescent device. At least two compounds comprised in the plurality of host materials of the present disclosure may be comprised together in one light-emitting layer or may respectively be comprised in different light-emitting layers. For example, at least two host materials may be mixture-evaporated or co-evaporated, or may be individually evaporated.

Herein, the term "(C1-C30)alkyl" or "(C1-C30)alkylene" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, sec-butyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7 ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl," "(C6-C30)arylene" or "(C6-C30)arene" is meant to be a monocyclic or fused ring radical derived from an aromatic hydrocarbon having 6 to 30 ring backbone carbon atoms. The above aryl may be partially saturated, and may comprise a spiro structure. The above aryl may include phenyl, biphenyl, terphenyl, naphthyl, binaphthyl, phenylnaphthyl, naphthylphenyl, fluorenyl, phenylfluorenyl, diphenylfluorenyl, benzofluorenyl, dibenzofluorenyl, phenanthrenyl, phenylphenanthrenyl, benzophenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluorene]yl, spiro[cyclopentene-fluorene]yl, spiro[dihydroindene-fluorene]yl, azulenyl, tetramethyldihydrophenanthrenyl, etc. Specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl," (3- to 30-membered)heteroarylene" or (3- to 30-membered)heteroarene" is meant to be an aryl or an arylene having 3 to 30 ring backbone atoms, and including at least one, preferably 1 to 4 heteroatoms selected from the group consisting of B, N, O, S, Si, and P. The above heteroaryl or heteroarylene may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, naphthyridinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, benzoquinazolinyl, quinoxalinyl, benzoquinoxalinyl, carbazolyl, benzocarbazolyl, dibenzocarbazolyl, phenoxazinyl, phenanthridinyl, benzodioxolyl, dihydroacridinyl, benzotriazolphenazinyl, imidazopyridyl, chromenoquinazolinyl, thiochromenoquinazolinyl, dimethylbenzopermidinyl, indolocarbazolyl, indenocarbazolyl, etc. More specifically, the above heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]- benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Furthermore, "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl, the substituted alkylene, the substituted aryl, the substituted arylene, the substituted arene, the substituted heteroaryl, the substituted heteroarylene, the substituted heteroarene, the substituted cycloalkyl, the substituted cycloalkylene, the substituted cycloalkenyl, the substituted heterocycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-alkenylamino, the substituted mono- or di-arylamino, the substituted mono- or di-heteroarylamino, the substituted alkylalkenylamino, the substituted alkylarylamino, the substituted alkylheteroarylamino, the substituted alkenylarylamino, the substituted alkenylheteroarylamino, and the substituted arylheteroarylamino, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 50-membered)heteroaryl unsubstituted or substituted with at least one of a (C1-C30)alkyl(s), a (C6-C30)aryl(s), a (3- to 50-membered)heteroaryl(s), and a di(C6-C30)arylamino(s); a (C6-C30)aryl unsubstituted or substituted with at least one of deuterium(s), a cyano(s), a (C1-C30)alkyl(s), a (3- to 50-membered)heteroaryl(s), a mono- or di-(C6-C30)arylamino(s), and a tri(C6-C30)arylsilyl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituent(s), each independently, are at least one selected from the group consisting of deuterium; a cyano; a (C1-C20)alkyl; a (C6-C25)aryl unsubstituted or substituted with at least one of deuterium(s), a cyano(s), a (C1-C20)alkyl(s), and a (5- to 30-membered)heteroaryl(s); and a (5- to 30-membered)heteroaryl unsubstituted or substituted with at least one of a (C6-C25)aryl(s) and a (5- to 30-membered)heteroaryl(s). According to another embodiment of the present disclosure, the substituent(s), each independently, are at least one selected from the group consisting of deuterium; a cyano; a (C1-C10)alkyl; a (C6-C18)aryl unsubstituted or substituted with at least one of deuterium(s), a cyano(s), a (C1-C10)alkyl(s), and a (5- to 26-membered)heteroaryl(s); and a (5- to 26-membered)heteroaryl unsubstituted or substituted with at least one of a (C6-C18)aryl(s) and a (5- to 26-membered)heteroaryl(s). For example, the substituent(s) may be at least one selected from the group consisting of deuterium; a cyano; a methyl; a phenyl unsubstituted or substituted with at least one of deuterium(s), a cyano(s), and a (26-membered)heteroaryl(s); a naphthyl, a biphenyl; a naphthylphenyl; a phenylnaphthyl; a phenanthrenyl; a dimethylfluorenyl; a dimethylbenzofluorenyl; a spirobifluorenyl; a terphenyl; a triphenylenyl; a pyridyl unsubstituted or substituted with a phenyl(s); a pyrimidinyl; a triazinyl substituted with at least one of a phenyl(s), a naphthyl(s), a biphenyl(s) and a pyrimidinyl(s); a dibenzofuranyl; a dibenzothiophenyl; a benzonaphthothiophenyl; a carbazolyl unsubstituted or substituted with a phenyl(s); a benzocarbazolyl unsubstituted or substituted with a phenyl(s); a dibenzocarbazolyl; a (26-membered)heteroaryl; and a diphenylamino.

Herein, a ring formed by a linkage of adjacent substituents means that at least two adjacent substituents are linked to or fused with each other to form a substituted or unsubstituted, mono- or polycyclic, (3- to 30-membered) alicyclic or aromatic ring, or the combination thereof. Preferably, the ring may be a substituted or unsubstituted, mono- or polycyclic, (3- to 26-membered) alicyclic or aromatic ring, or the combination thereof. More preferably, the ring may be a mono- or polycyclic, (5- to 25-membered) aromatic ring unsubstituted or substituted with at least one of a (C1-C6) alkyl(s), a (C6-C18)aryl(s) and a (3- to 20-membered) heteroaryl(s). In addition, the formed ring may contain at least one heteroatom selected from B, N, O, S, Si, and P, preferably at least one heteroatom selected from N, O, and S. For example, the ring may be a benzene ring, a cyclopentane ring, an indene ring, an indane ring, a fluorene ring, a phenanthrene ring, an indole ring, a benzofuran ring, a xanthene ring, etc., wherein the ring may be substituted with at least one methyl(s).

In the present disclosure, heteroaryl, heteroarylene, and heterocycloalkyl may, each independently, contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered) heteroarylamino, a substituted or unsubstituted (C2-C30) alkenyl(C6-C30)arylamino, a substituted or unsubstituted (C2-C30)alkenyl(3- to 30-membered)heteroarylamino, and a substituted or unsubstituted (C6-C30)aryl(3- to 30-membered)heteroarylamino.

The plurality of host materials of the present disclosure comprises a first host material(s) and a second host material(s), wherein the first host material(s) comprises at least one compound(s) represented by formula 1, and the second host material(s) comprises at least one compound(s) represented by formula 2. According to one embodiment of the present disclosure, the compound represented by formula 1 is different from the compound represented by formula 2.

In formula 1, L represents a single bond, a substituted or unsubstituted (C1-C30)alkylene, a substituted or unsubstituted (C3-C30)cycloalkylene, a substituted or unsubstituted (C6-C30)arylene, or a substituted or unsubstituted (3- to 30-membered)heteroarylene. According to one embodiment of the present disclosure, L represents a single bond, a substituted or unsubstituted (C6-C25)arylene, or a substituted or unsubstituted (5- to 20-membered)heteroarylene. According to another embodiment of the present disclosure, L represents a single bond, an unsubstituted (C6-C18) arylene, or a (5- to 20-membered)heteroarylene unsubstituted or substituted with a (C6-C18)arylene(s). For example, L may be a single bond, a phenylene, a naphthylene, a biphenylene, a pyridylene, a pyrimidinylene, a triazinylene, a quinolinylene, a quinazolinylene, a quinoxalinylene, a naphthyridinylene, a carbazolylene, a dibenzofuranylene, a benzofuropyrimidinylene, a benzothienopyrimidinylene, a pyrimidoindolylene, a benzoquinazolinylene, a benzoquinoxalinylene, a phenylquinazolinylene, a phenylquinoxalinylene, etc.

In formula 1, Ar represents deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $—NR_{11}R_{12}$, or $—SiR_{13}R_{14}R_{15}$. According to one embodiment of the present disclosure, Ar represents a substituted or unsubstituted (C6-C25)aryl, a substituted or unsubstituted (5- to 20-membered)heteroaryl, or $—NR_{11}R_{12}$. According to another embodiment of the present disclosure, Ar represents a (C6-C25)aryl unsubstituted or substituted with a (C1-C6) alkyl(s); a (5- to 20-membered)heteroaryl unsubstituted or substituted with at least one of deuterium(s), a (C1-C6) alkyl(s), a (C6-C18)aryl(s) and a (5- to 26-membered) heteroaryl; or $—NR_{11}R_{12}$. For example, Ar may be at least one of an unsubstituted phenyl, a phenyl substituted with at least one deuterium(s), a phenyl substituted with a (26-membered)heteroaryl(s), a naphthyl, a biphenyl, a fluorenyl substituted with a methyl(s), a benzofluorenyl substituted with a methyl(s), a spirobifluorenyl, a terphenyl, a triphenylenyl, a pyridyl unsubstituted or substituted with a phenyl(s), a pyrimidinyl substituted with a phenyl(s), a substituted triazinyl, a substituted quinoxalinyl, a substituted quinazolinyl, a quinolyl substituted with a phenyl(s), a naphthyridinyl substituted with a phenyl(s), a benzoquinazolinyl substituted with a phenyl(s), a benzoquinoxalinyl substituted with a phenyl(s), a carbazolyl unsubstituted or substituted with a phenyl(s), a dibenzofuranyl unsubstituted or substituted with a phenyl(s), a dibenzothiophenyl unsubstituted or substituted with a phenyl(s), a benzofuropyrimidinyl substituted with a phenyl(s), a benzothienopyrimidinyl substituted with a phenyl(s), a pyrimidoindolyl substituted with a phenyl(s), or $—NR_{11}R_{12}$. The substituent(s) of the substituted triazinyl, substituted quinoxalinyl, and substituted quinazolinyl, each independently, are at least one of a phenyl(s) unsubstituted or substituted with at least one of deuterium(s) and a (26-membered) heteroaryl(s), a naphthyl(s), a biphenyl(s), a terphenyl(s), a dimethylfluorenyl(s), a pyridyl substituted with a phenyl(s), a dibenzofuranyl(s) and a dibenzothiophenyl(s).

$R_{11}$ to $R_{15}$, each independently, represent a substituted or unsubstituted (C1-C30)alkyl, a substituted or unsubstituted (C6-C30)aryl, or a substituted or unsubstituted (3- to 30-membered)heteroaryl. According to one embodiment of the present disclosure, $R_{11}$ to $R_{15}$, each independently, represent a substituted or unsubstituted (C6-C15)aryl, or a substituted or unsubstituted (5- to 25-membered)heteroaryl. According to another embodiment of the present disclosure, $R_1$ to $R_{15}$, each independently, represent a (C6-C18)aryl unsubstituted or substituted with a (C1-C6)alkyl(s), or a (5- to 20-membered)heteroaryl unsubstituted or substituted with a (C6-C18)aryl(s). For example, $R_{11}$ to $R_{15}$, each independently, may be a phenyl, a naphthyl, a biphenyl, or a dimethylfluorenyl, etc.

In formula 1,

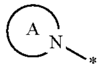

is a structure in which 5 to 8 rings selected from the group consisting of a substituted or unsubstituted (C6-C30) arene ring and a substituted or unsubstituted (3- to 30-membered) heteroarene ring are fused around a heptagonal or octagonal ring, and at least one pentagonal ring(s) containing nitrogen is comprised. * represents a bonding position with L. According to one embodiment of the present disclosure,

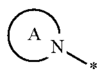

may be represented by any one of the following formulas 1-1 to 1-3:

(1-1)

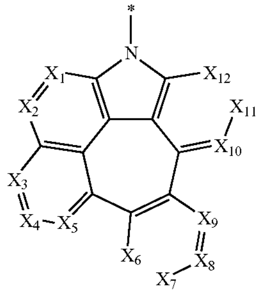

(1-2)

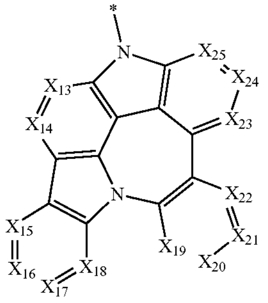

(1-3)

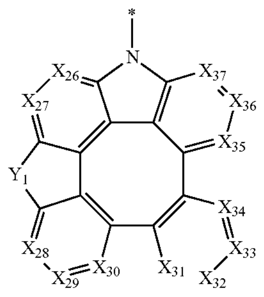

In formulas 1-1 to 1-3, $X_1$ to $X_{37}$, each independently, represent —N= or —C($R_a$)=. According to one embodiment of the present disclosure, $X_1$ to $X_{37}$, each independently, represent —C($R_a$)=.

$R_a$, each independently, represent hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered) heteroarylamino, a substituted or unsubstituted (C2-C30) alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino, or the adjacent $R_a$'s may be linked to each other to form a ring(s), and where if there is a plurality of $R_a$, each $R_a$ may be the same or different from each other. According to one embodiment of the present disclosure, $R_a$, each independently, represent hydrogen, a substituted or unsubstituted (C6-C25)aryl, or a substituted or unsubstituted (5- to 25-membered)heteroaryl, or the adjacent $R_a$'s may be linked to each other to form a substituted or unsubstituted, mono- or polycyclic, (3- to 30-membered) alicyclic or aromatic ring(s), or the combination thereof. According to another embodiment of the present disclosure, $R_a$, each independently, represent hydrogen, an unsubstituted (C6-C18)aryl, or a (5- to 20-membered)heteroaryl unsubstituted or substituted with a (C6-C18)aryl(s), or the adjacent $R_a$'s may be linked to each other to form a substituted or unsubstituted, mono- or polycyclic, (5- to 20-membered) alicyclic or aromatic ring(s), or the combination thereof. For example, $R_a$, each independently, may be hydrogen, a phenyl, a naphthyl, or a triazinyl substituted with a phenyl(s), or adjacent $R_a$'s may be linked to each other to form a benzene ring(s), a benzofuran ring(s), or an indene ring(s) substituted with a methyl(s).

In formula 1-3, $Y_1$ represents —N($L'_1$-($Ar'_1$)$_n$)—, —O—, —S—, or —C($R_b$)($R_c$)—.

$L'_1$ represents a single bond, a substituted or unsubstituted (C1-C30)alkylene, a substituted or unsubstituted (C6-C30) arylene, a substituted or unsubstituted (3- to 30-membered) heteroarylene, or a substituted or unsubstituted (C3-C30) cycloalkylene. For example, $L'_1$ may be a single bond.

$Ar'_1$ represents a substituted or unsubstituted (C6-C30) aryl, a substituted or unsubstituted (3- to 30-membered) heteroaryl, or —N($R_d$)($R_e$). According to one embodiment of the present disclosure, $Ar'_1$ represents a substituted or unsubstituted (C6-C25)aryl, or a substituted or unsubstituted (5- to 25-membered)heteroaryl. According to another embodiment of the present disclosure, $Ar'_1$ represents a (C6-C18)aryl unsubstituted or substituted with deuterium(s), or an unsubstituted (5- to 20-membered)heteroaryl. For example, $Ar'_1$ may be a phenyl unsubstituted or substituted with deuterium(s), a biphenyl, or a pyridyl.

$R_b$ to $R_e$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to adjacent substituent(s) to form a ring(s). According to one embodiment of the present disclosure, $R_b$ to $R_e$, each independently, represent a substituted or unsubstituted (C1-C10)alkyl. For example, $R_b$ to $R_e$, each independently, may be a methyl.

n represents an integer of 1 or 2, and where if n is an integer of 2, each of $Ar'_1$ may be the same or different from each other.

Formula 1-1 may be represented by the following formula 1-1-1:

(1-1-1)

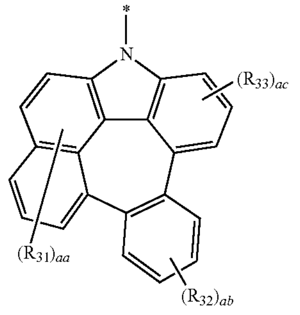

in formula 1-1-1, $R_{31}$ to $R_{33}$, each independently, are the same as the definition of $R_a$; and aa represents an integer of 1 to 5, ab represents an integer of 1 to 4, ac represents an integer of 1 to 3, and where if each of aa, ab, and ac is an integer of 2 or more, each of $R_{31}$, each of $R_{32}$, and each of $R_{33}$ may be the same or different from each other.

Formula 1-2 may be represented by the following formula 1-2-1:

(1-2-1)

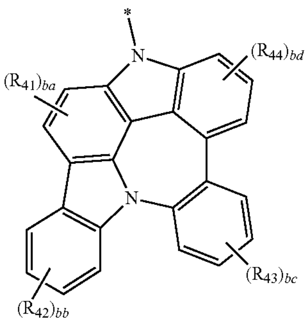

in formula 1-2-1, $R_{41}$ to $R_{44}$, each independently, are the same as the definition of $R_a$; and ba represents an integer of 1 or 2, bb and bc, each independently, represent an integer of 1 to 4, bd represents an integer of 1 to 3, and where if each of ba, bb, bc, and bd is an integer of 2 or more, each of $R_{41}$, each of $R_{42}$, each of $R_{43}$, and each of $R_{44}$ may be the same or different from each other.

Formula 1-3 may be represented by the following formula 1-3-1:

(1-3-1)

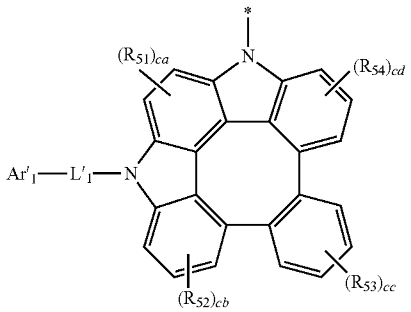

in formula 1-3-1, $R_{51}$ to $R_{54}$, each independently, are the same as the definition of $R_a$;

ca represents an integer of 1 or 2, cb and cd, each independently, represent an integer of 1 to 3, cc represents an integer of 1 to 4, and where if each of ca, cb, cc, and cd is an integer of 2 or more, each of $R_{51}$, each of $R_{52}$, each of $R_{53}$, and each of $R_{54}$ may be the same or different from each other; and $L'_1$ and $Ar'_1$ are each the same as defined in formula 1-3.

In formula 2, X represents O, S, or $CR_5R_6$.

$R_5$ and $R_6$, each independently, represent a substituted or unsubstituted (C1-C30)alkyl, a substituted or unsubstituted (C6-C30)aryl, or a substituted or unsubstituted (3- to 30-membered)heteroaryl, or $R_5$ and $R_6$ may be linked to each other to form a ring(s). According to one embodiment of the present disclosure, $R_5$ and $R_6$, each independently, represent a substituted or unsubstituted (C1-C10)alkyl. According to another embodiment of the present disclosure, $R_5$ and $R_6$, each independently, represent an unsubstituted (C1-C6)alkyl. For example, $R_5$ and $R_6$, each independently, may be a methyl.

In formula 2, $R_1$ to $R_4$, each independently, represent hydrogen, deuterium, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, a substituted or unsubstituted (3- to 30-membered) heteroaryl, -LU-$NR_{16}R_{17}$, or —$SiR_{18}R_{19}R_{20}$; or may be linked to adjacent substituent(s) to form a ring(s). According to one embodiment of the present disclosure, $R_1$ to $R_4$, each independently, represent hydrogen, deuterium, a substituted or unsubstituted (C6-C25)aryl, a substituted or unsubstituted (5- to 25-membered)heteroaryl, or -$L_3$-$NR_{16}R_{17}$; or may be linked to adjacent substituent(s) to form a ring(s). According to another embodiment of the present disclosure, $R_1$ to $R_4$, each independently, represent hydrogen; deuterium; a (C6-C18)aryl unsubstituted or substituted with a (3- to 30-membered)heteroaryl(s); a (5- to 20-membered)heteroaryl unsubstituted or substituted with at least one of a cyano(s), a (C6-C18)aryl(s), and a (5- to 20-membered)heteroaryl(s); or -$L_3$-$NR_{16}R_{17}$; or may be linked to adjacent substituent(s) to form a ring(s).

Here, at least one of $R_1$ to $R_4$ represents a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, -$L_3$-$NR_{16}R_{17}$, or —$SiR_{18}R_{19}R_{20}$. According to one embodiment of the present disclosure, at least one of $R_1$ to $R_4$ may represent a (C6-C30)aryl unsubstituted or substituted with a (3- to 30-membered)heteroaryl(s), a substituted or unsubstituted (3- to 30-membered)heteroaryl, or $-L_3-NR_{16}R_{17}$. According to another embodiment of the present disclosure, at least one of $R_1$ to $R_4$ may represent a (C6-C18)aryl unsubstituted or substituted with a (5- to 25-membered)heteroaryl(s), a (5- to 20-membered)heteroaryl unsubstituted or substituted with at least one of a cyano(s), a (C6-C18)aryl(s), and a (5- to 20-membered)heteroaryl(s); or $-L_3-NR_{16}R_{17}$. According to one embodiment of the present disclosure, at least one of $R_1$ to $R_4$ represents $-L_2$-HAr or $-L_3-NR_{16}R_{17}$.

$L_2$ and $L_3$, each independently, represent a single bond, a substituted or unsubstituted (C6-C30)arylene, or a substituted or unsubstituted (3- to 30-membered)heteroarylene. According to one embodiment of the present disclosure, $L_2$ and $L_3$, each independently, represent a single bond, a substituted or unsubstituted (C6-C25)arylene, or a substituted or unsubstituted (5- to 25-membered)heteroarylene. According to another embodiment of the present disclosure, $L_2$ and $L_3$, each independently, represent a single bond, an unsubstituted (C6-C18)arylene, or an unsubstituted (5- to 20-membered)heteroarylene. For example, $L_2$ and $L_3$, each independently, may be a single bond, a phenylene, a naphthylene, a biphenylene, or a pyridylene.

HAr represents a substituted or unsubstituted (3- to 30-membered)heteroaryl comprising at least one of N, O and S. According to one embodiment of the present disclosure, HAr represents a (5- to 25-membered)heteroaryl comprising at least one of N, O and S, unsubstituted or substituted with a (C6-C30)aryl(s). According to another embodiment of the present disclosure, HAr represents a N-containing (5- to 25-membered)heteroaryl substituted with a (C6-C25)aryl(s). For example, HAr may be a substituted pyrimidinyl, a substituted triazinyl, a quinoxalinyl substituted with a naphthyl(s), a quinazolinyl substituted with a biphenyl(s), or a benzofuropyrimidinyl substituted with a phenyl(s), in which the substituent(s) of the substituted pyrimidinyl and the substituted triazinyl, each independently, may be at least one of a phenyl(s), a phenyl(s) substituted with a cyano(s), a naphthyl, a biphenyl, a phenylnaphthyl, a naphthylphenyl, a phenanthrenyl, a terphenyl, a dimethylfluorenyl, a pyrimidinyl, a dibenzofuranyl, and dibenzothiophenyl.

$R_{16}$ to $R_{20}$, each independently, represent a substituted or unsubstituted (C1-C30)alkyl, a substituted or unsubstituted (C6-C30)aryl, or a substituted or unsubstituted (3- to 30-membered)heteroaryl. According to one embodiment of the present disclosure, $R_{16}$ to $R_{20}$, each independently, represent a substituted or unsubstituted (C6-C25)aryl, or a substituted or unsubstituted (5- to 25-membered)heteroaryl. According to another embodiment of the present disclosure, $R_{16}$ to $R_{20}$, each independently, represent a (C6-C25)aryl unsubstituted or substituted with a (C1-C6)alkyl, or an unsubstituted (5- to 20-membered)heteroaryl. For example, $R_{16}$ to $R_{20}$, each independently, may be a phenyl, a naphthyl, a biphenyl, a dimethylfluorenyl, a diphenylfluorenyl, a spirobifluorenyl, a phenanthrenyl, a naphthylphenyl, a phenylnaphthyl, a terphenyl, a dibenzofuranyl, or a dibenzothiophenyl.

In formula 2, a' and d', each independently, represent an integer of 1 to 4, b' and c', each independently, represent an integer of 1 or 2, and where if each of a' to d' is an integer of 2 or more, each of $R_1$ to each of $R_4$ may be the same or different from each other.

The compound represented by formula 2 may be represented by any one of the following formulas 2-1 to 2-4:

(2-1)

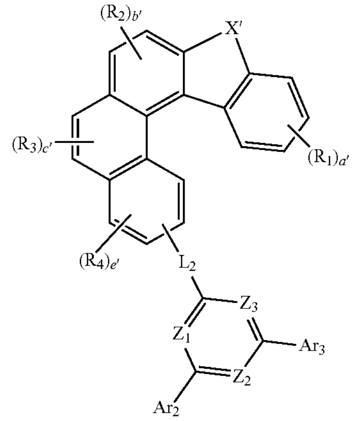

(2-2)

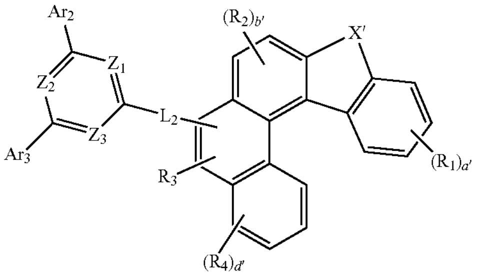

(2-3)

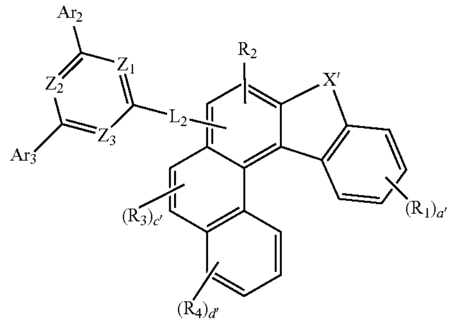

(2-4)

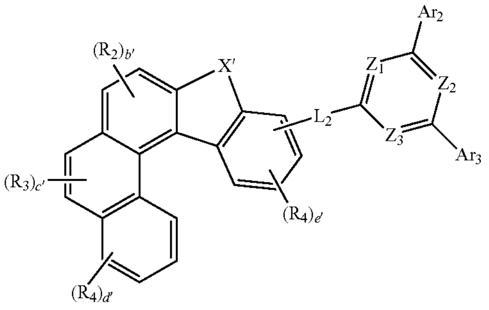

in formulas 2-1 to 2-4,

X', $R_1$ to $R_4$, and a' to d' are as defined in formula 2;

$L_2$, each independently, represents a single bond, a substituted or unsubstituted (C6-C30)arylene, or a substituted or unsubstituted (3- to 30-membered)heteroarylene;

$Z_1$ to $Z_3$, each independently, represent N or CH, provided that at least one of $Z_1$ to $Z_3$ is N;

$Ar_2$ and $Ar_3$, each independently, represent a substituted or unsubstituted (C6-C30)aryl, or a substituted or unsubstituted (3- to 30-membered)heteroaryl;

e', each independently, represents an integer of 1 to 3, and where if e' is an integer of 2 or more, each of $R_1$ and each of $R_4$ may be the same or different from each other.

According to one embodiment of the present disclosure, at least two of $Z_1$ to $Z_3$ are N. According to another embodiment of the present disclosure, all of $Z_1$ to $Z_3$ are N.

According to one embodiment of the present disclosure, $Ar_2$ and $Ar_3$, each independently, represent a substituted or unsubstituted (C6-C25)aryl, or a substituted or unsubstituted (5- to 25-membered)heteroaryl. According to another embodiment of the present disclosure, $Ar_2$ and $Ar_3$, each independently, represent a substituted or unsubstituted (C6-C18)aryl unsubstituted or substituted with at least one of a cyano(s) and a (C1-C6)alkyl(s), or an unsubstituted (5- to 20-membered)heteroaryl. For example, $Ar_2$ and $Ar_3$, each independently, may be a phenyl unsubstituted or substituted with a cyano(s), a naphthyl, a biphenyl, a phenylnaphthyl, a naphthylphenyl, a phenanthrenyl, a terphenyl, a dimethylfluorenyl, a pyrimidinyl, a dibenzofuranyl, or a dibenzothiophenyl.

The compound represented by formula 2 may be represented by any one of the following formulas 2-5 to 2-8:

(2-5)

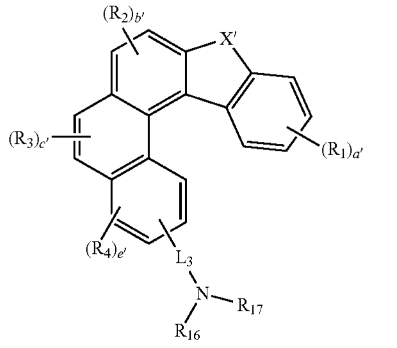

(2-6)

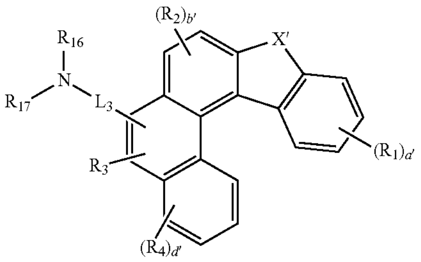

(2-7)

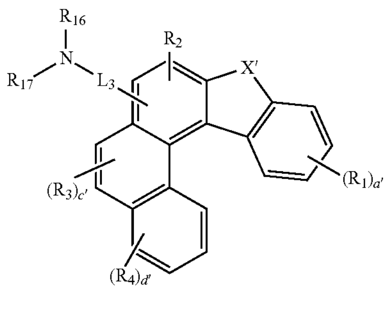

-continued (2-8)

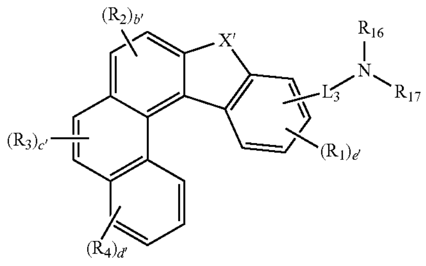

in formulas 2-5 to 2-8,

X', $L_3$, $R_1$ to $R_4$, $R_{16}$, $R_{17}$, and a' to d' are as defined in formula 2;

e', each independently, represents an integer of 1 to 3, and where if e' is an integer of 2 or more, each of $R_1$ and each of $R_4$ may be the same or different from each other.

The compound represented by formula 1 may be at least one selected from the group consisting of the following compounds, but is not limited thereto.

H1-1

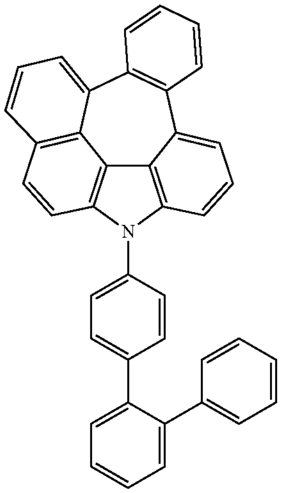

H1-2

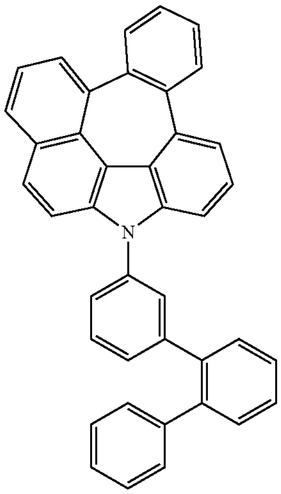

-continued
H1-3
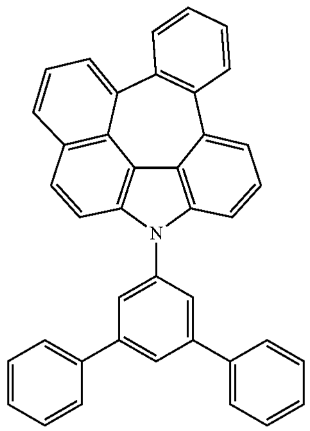
H1-4
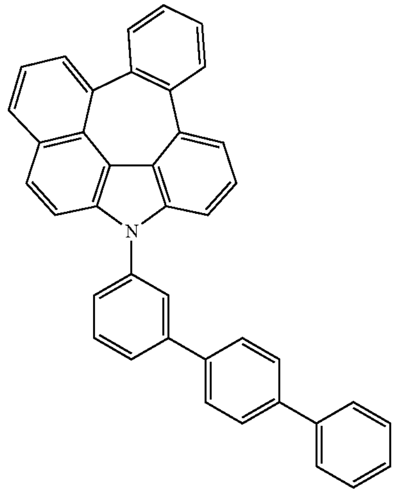
H1-5
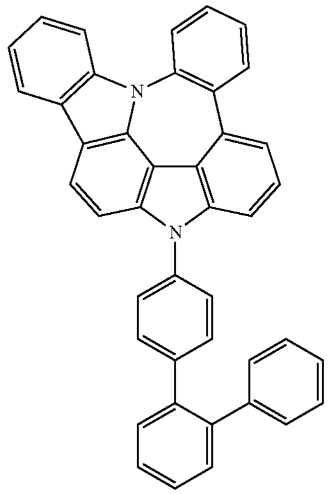
-continued
H1-6
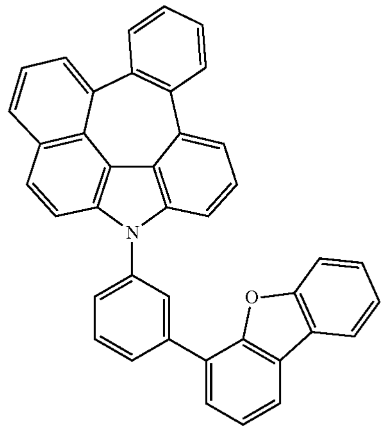
H1-7
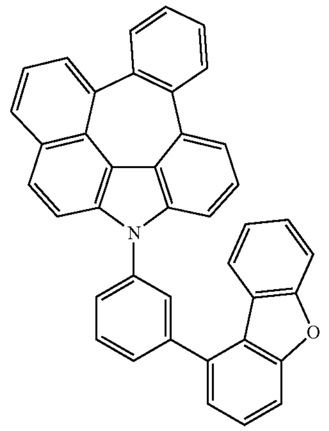
H1-8
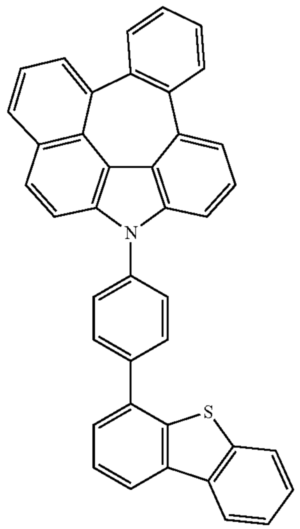

-continued
H1-9
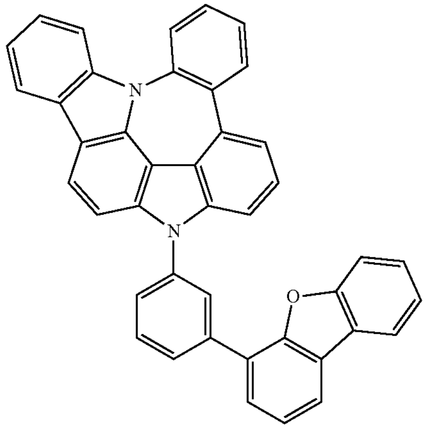
H1-10
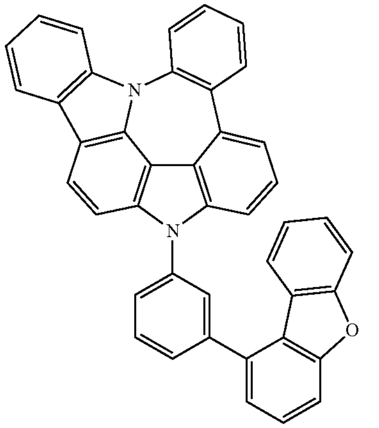
H1-11
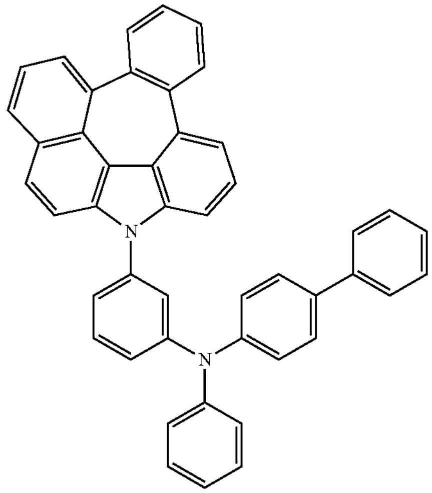
-continued
H1-12
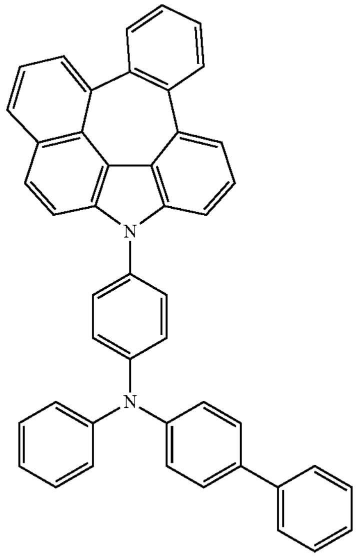
H1-13
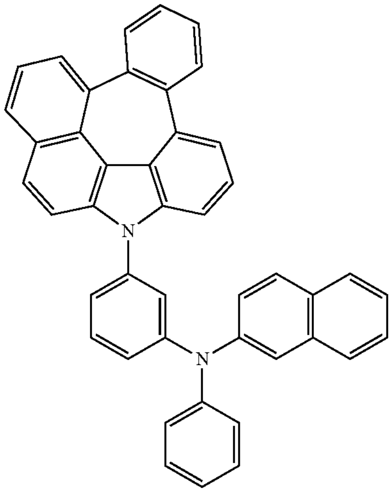
H1-14
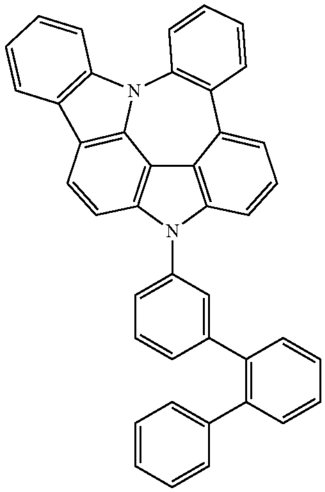

-continued
H1-15
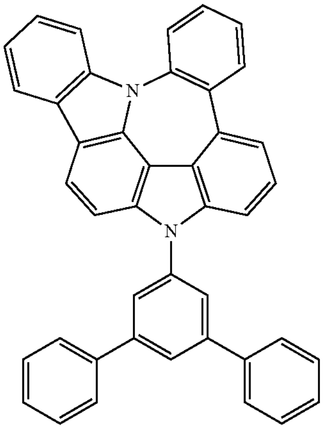
H1-16
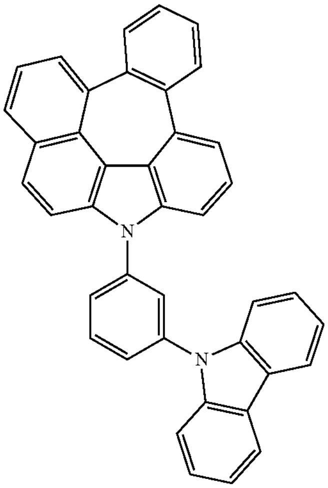
H1-17
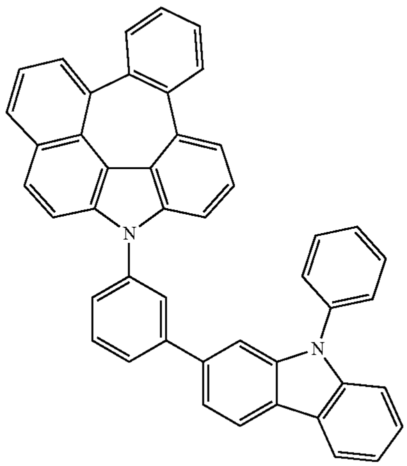
-continued
H1-18
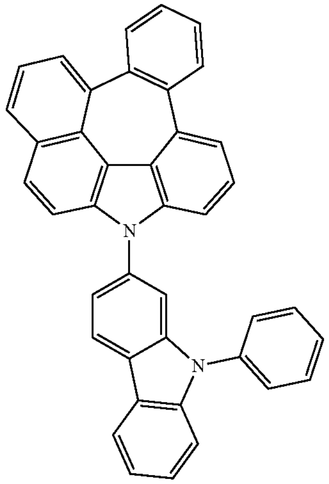
H1-19
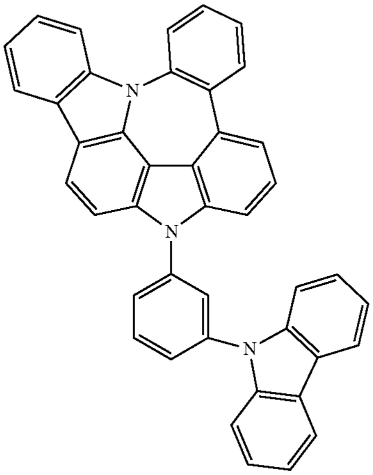
H1-20
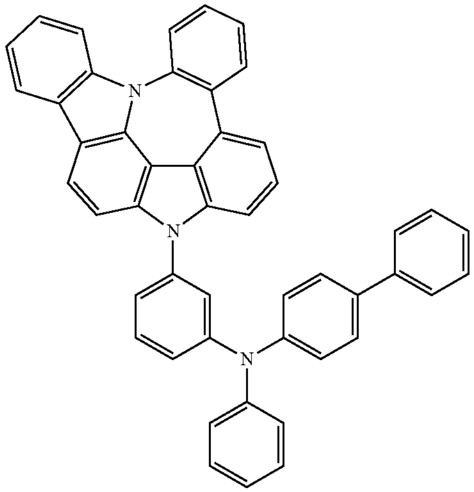

-continued
H1-21
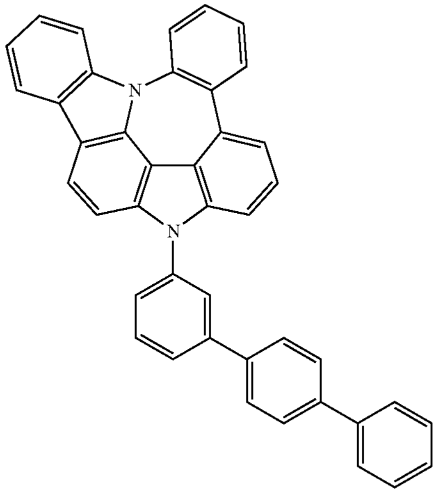
H1-22
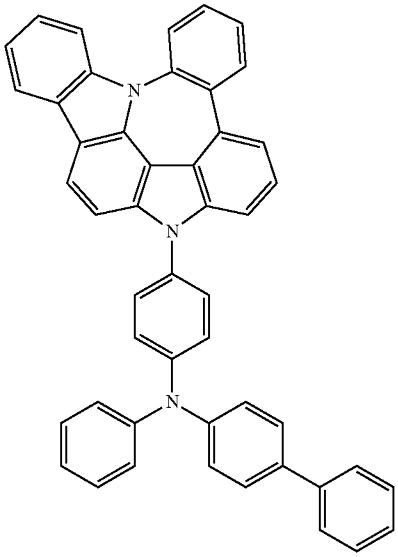
H1-23
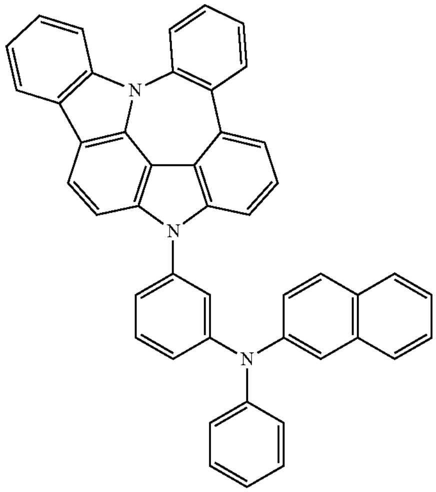
-continued
H1-24
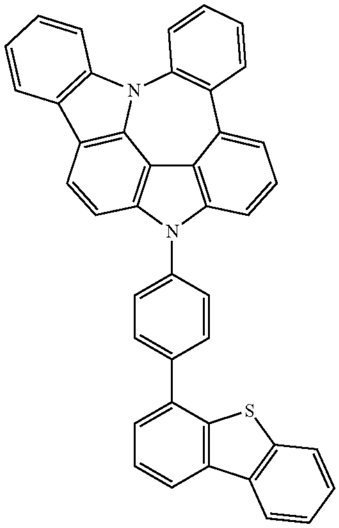
H1-25
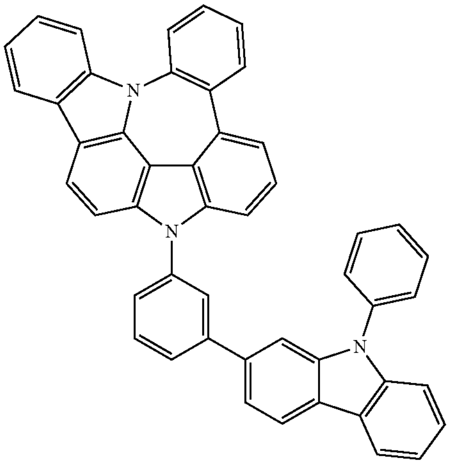
H1-26
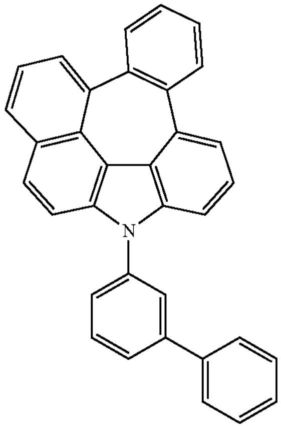

-continued
H1-27
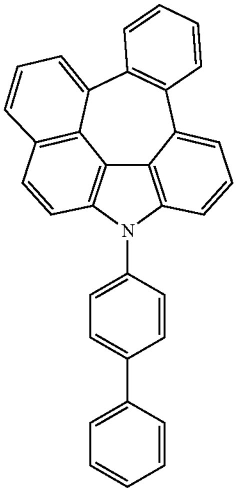
H1-28
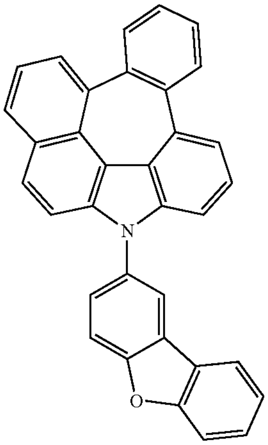
H1-29
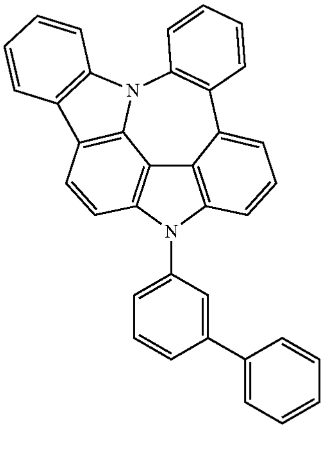
-continued
H1-30
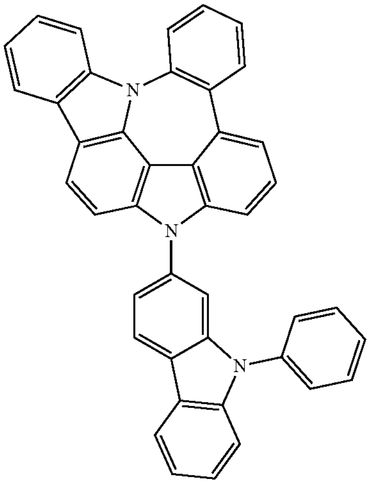
H1-31
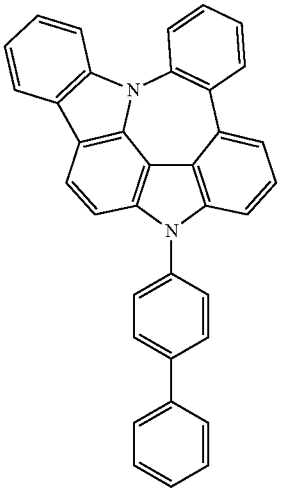
H1-32
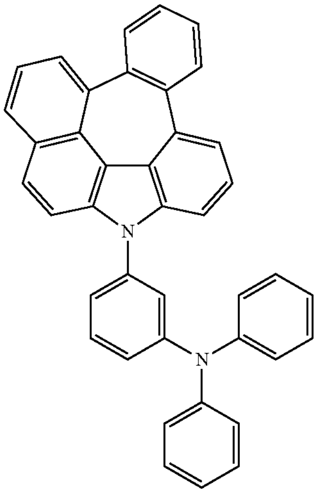

-continued
H1-33
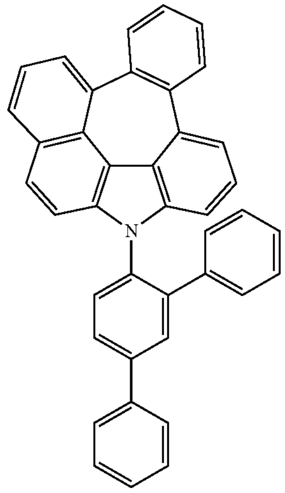
H1-34
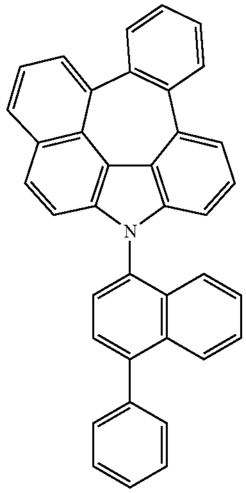
H1-35
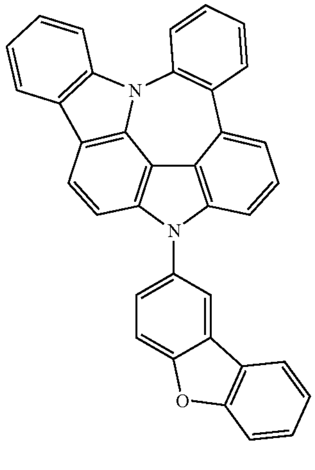
-continued
H1-36
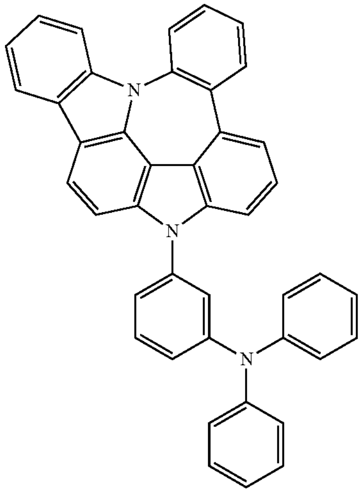
H1-37
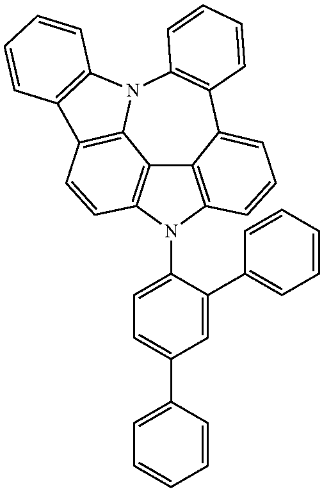
H1-38
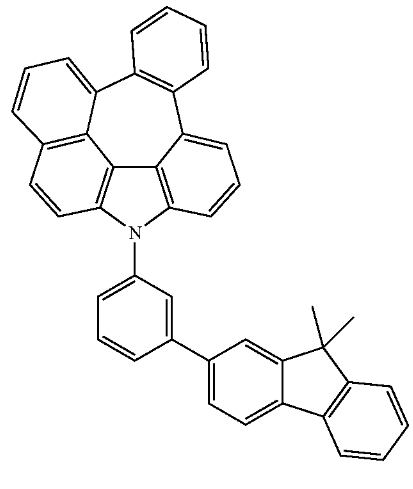

-continued
H1-39
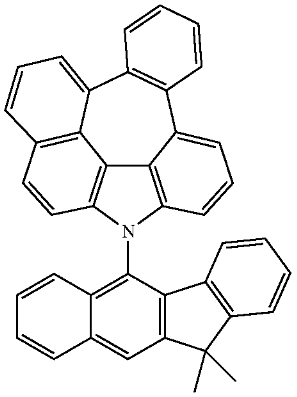
H1-40
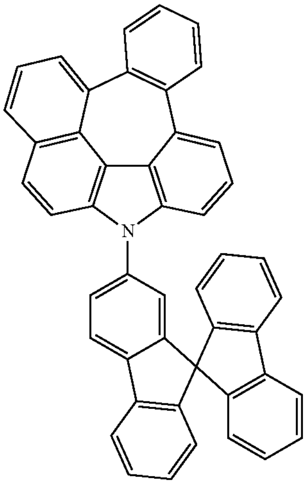
H1-41
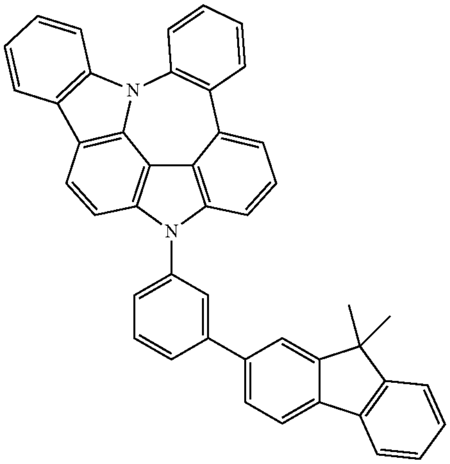
-continued
H1-42
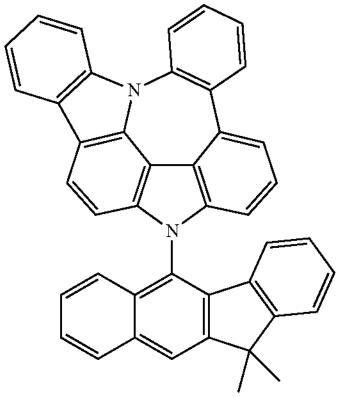
H1-43
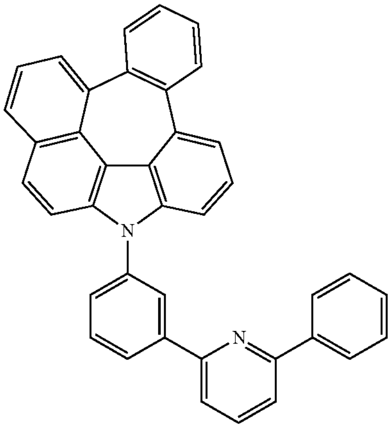
H1-44
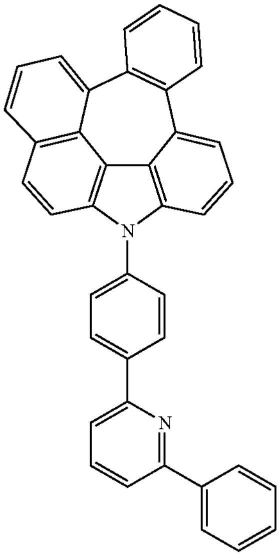

-continued
H1-45
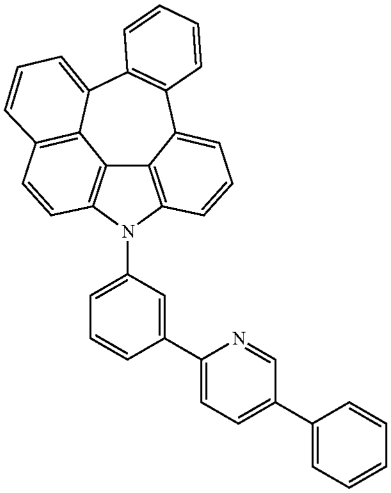
H1-46
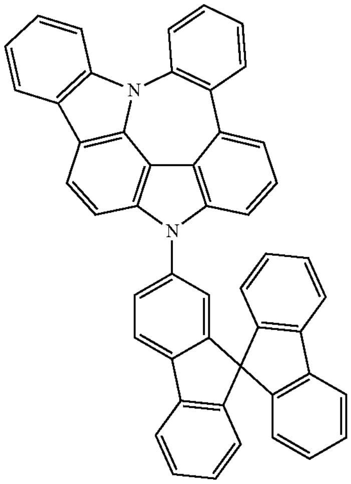
H1-47
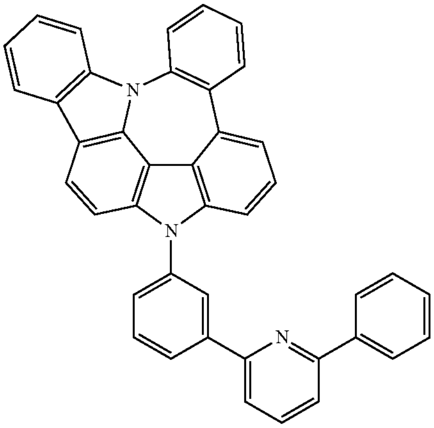
-continued
H1-48
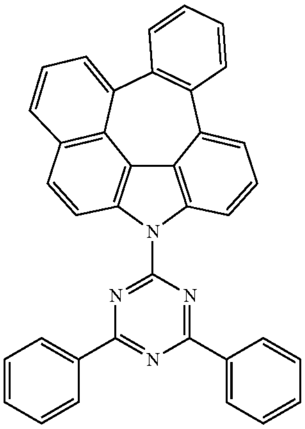
H1-49
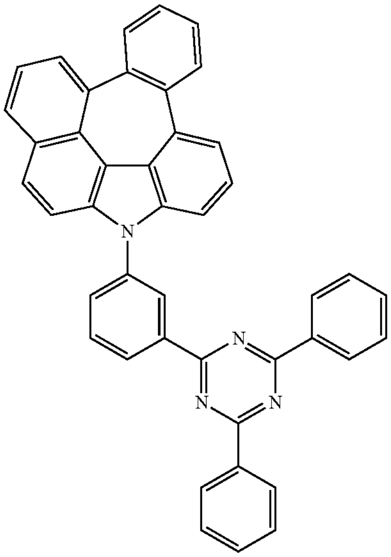
H1-50
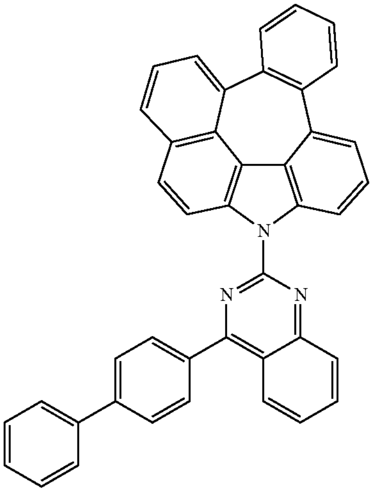

-continued
H1-51
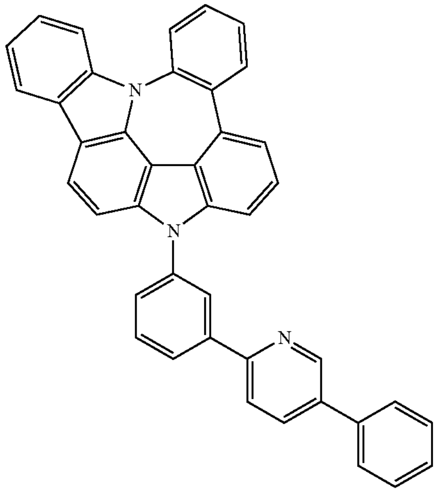
H1-52
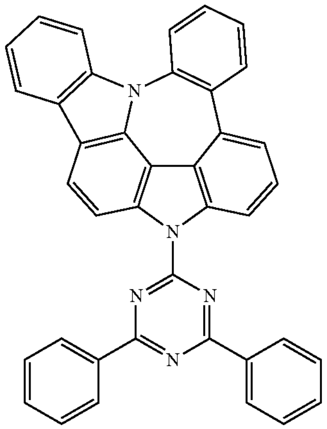
H1-53
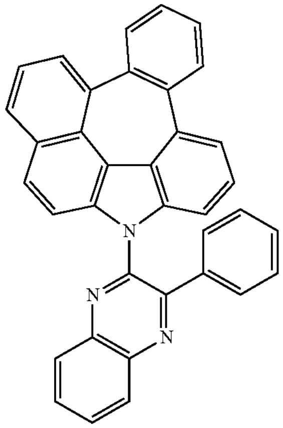
-continued
H1-54
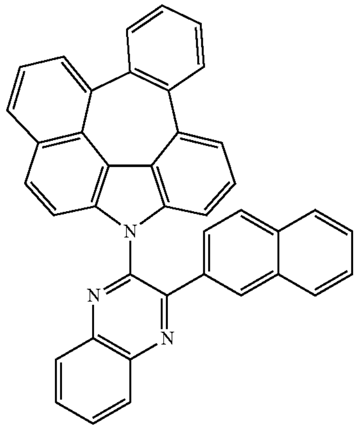
H1-55
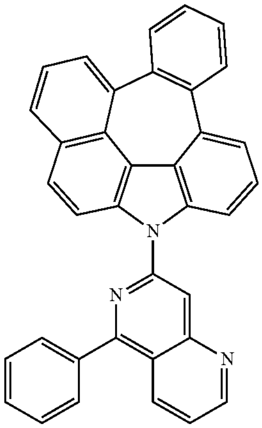
H1-56
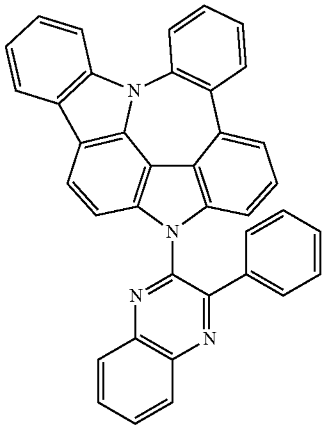

-continued
H1-57
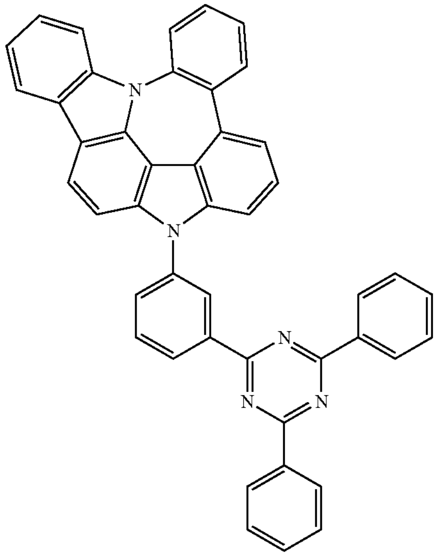
H1-58
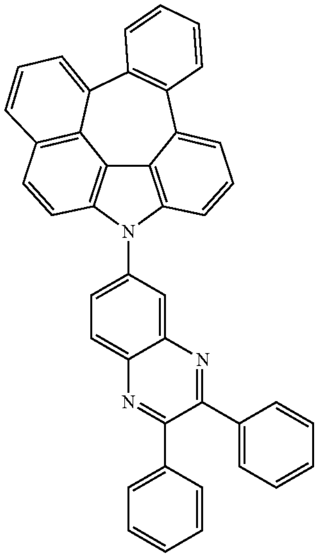
H1-59
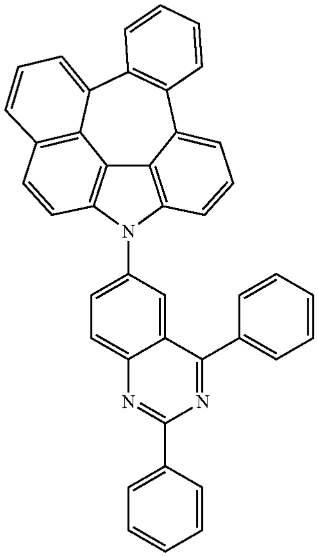
-continued
H1-60
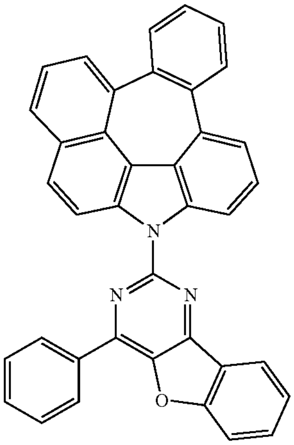
H1-61
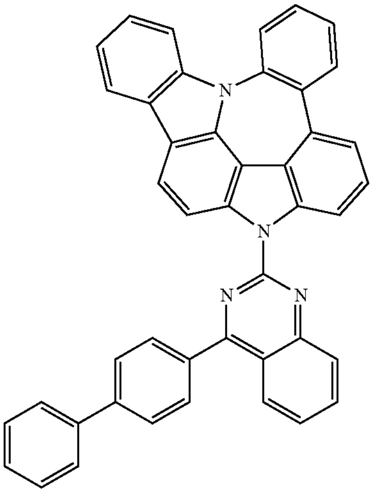
H1-62
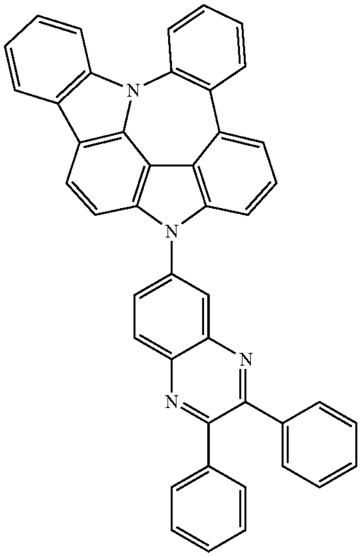

-continued
H1-63
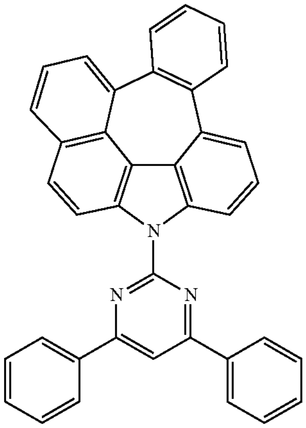
H1-64
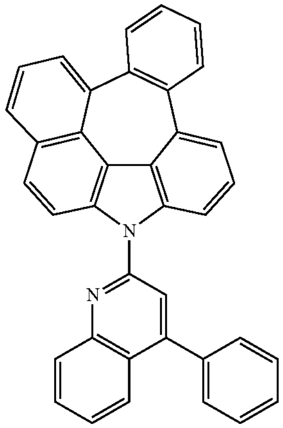
H1-65
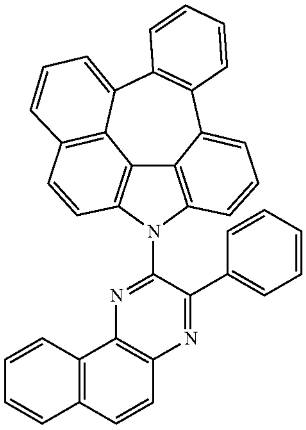
-continued
H1-66
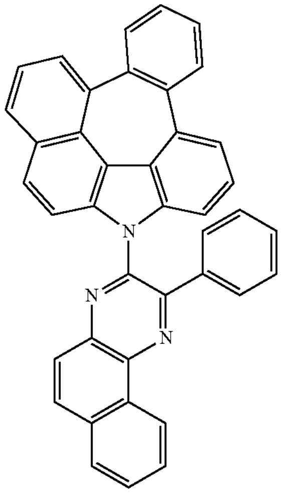
H1-67
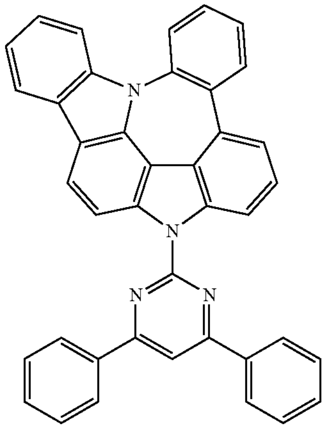
H1-68
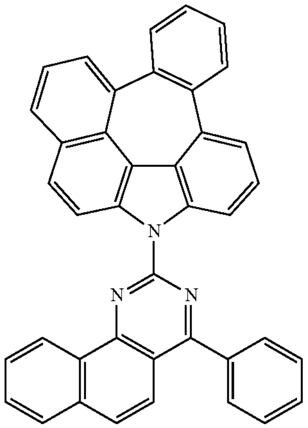

-continued
H1-69
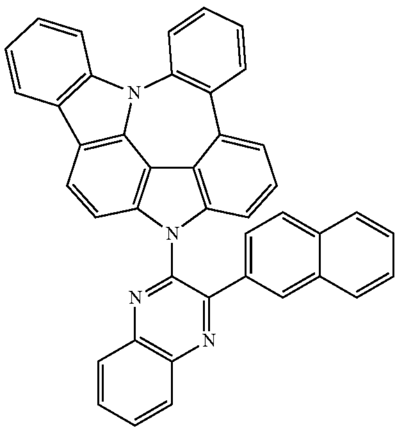
H1-70
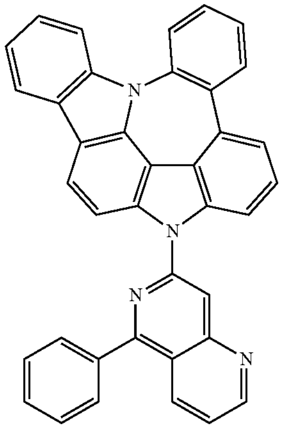
H1-71
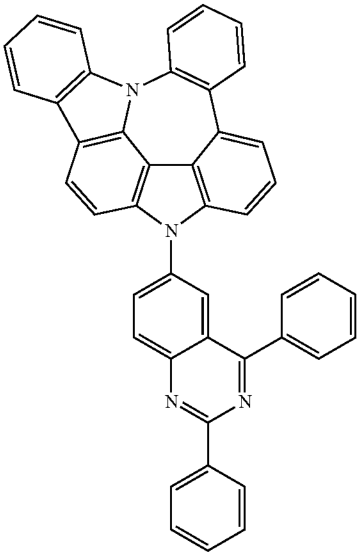
-continued
H1-72
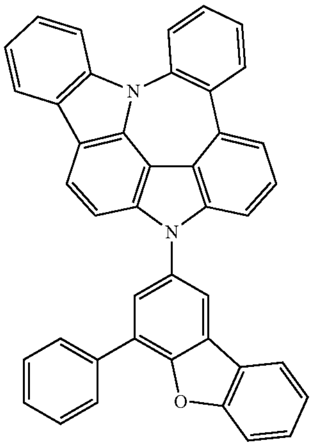
H1-73
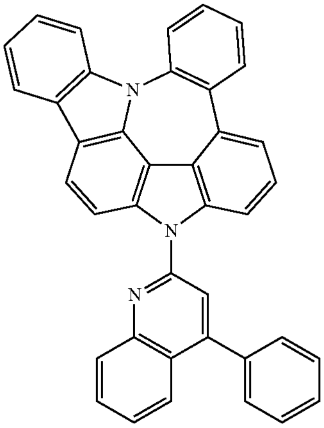
H1-74
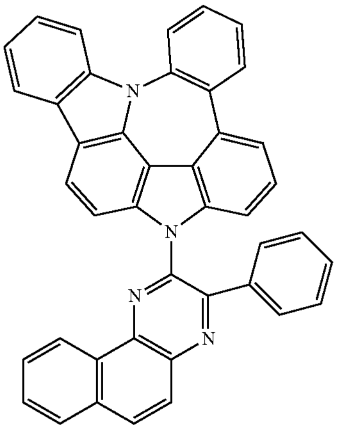

-continued
H1-75
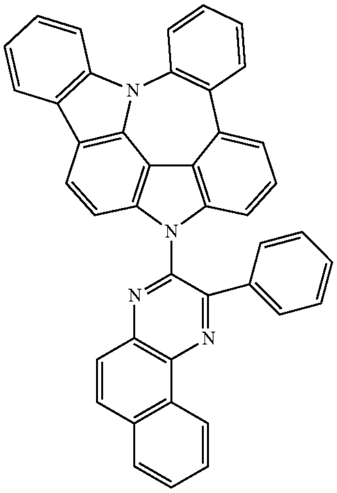
H1-76
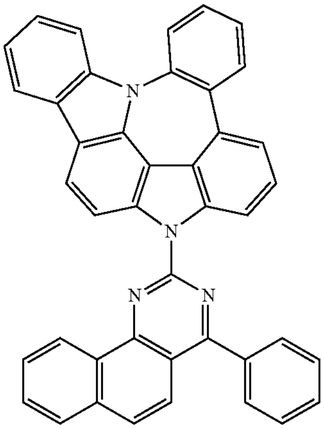
H1-77
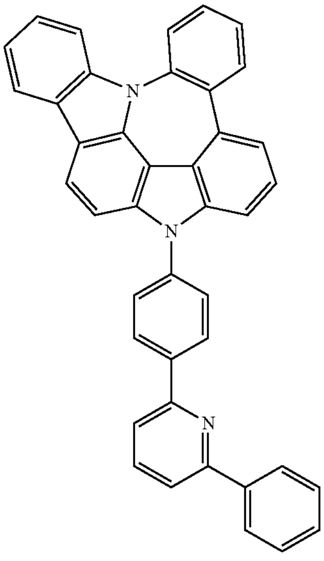
-continued
H1-78
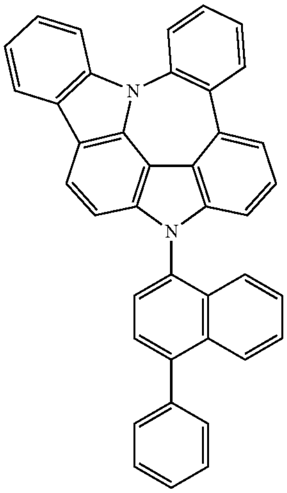
H1-79
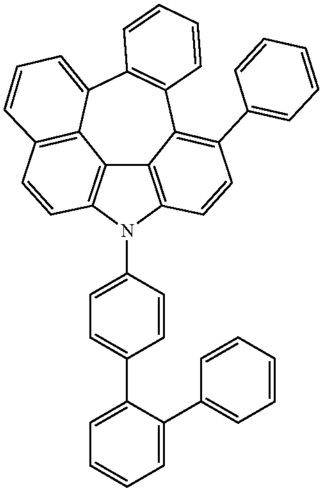
H1-80
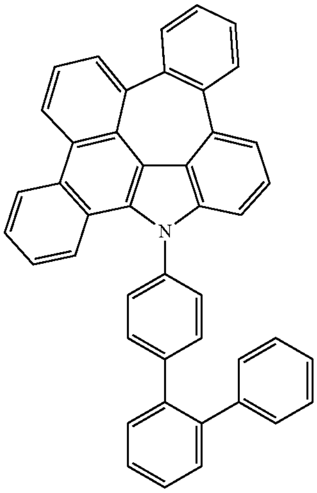

-continued
H1-81
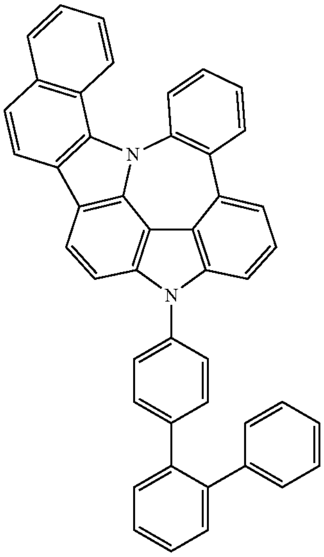
H1-82
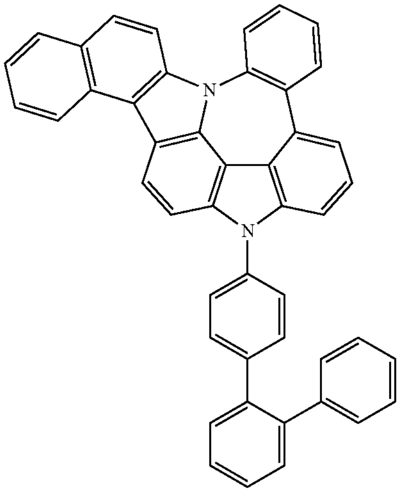
H1-83
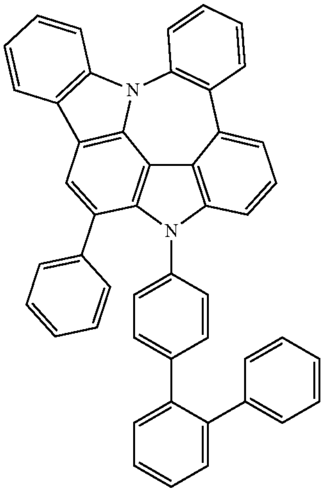
-continued
H1-84
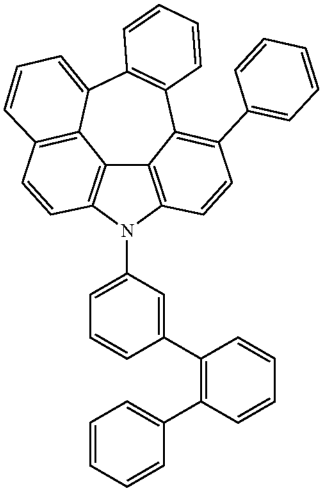
H1-85
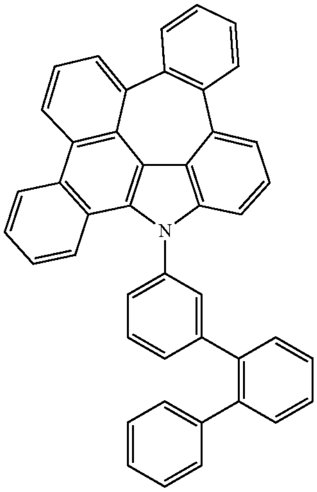
H1-86
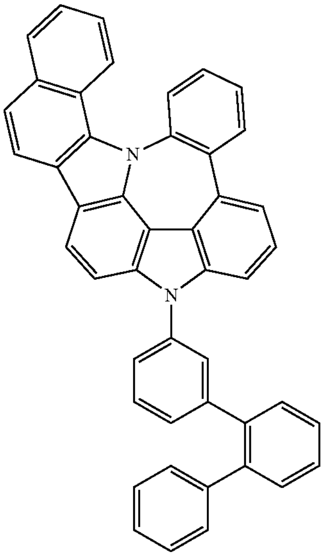

-continued
H1-87
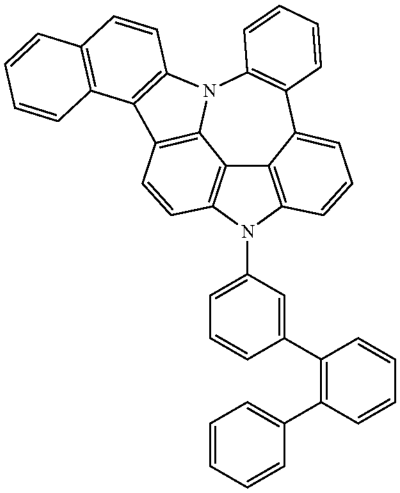
H1-88
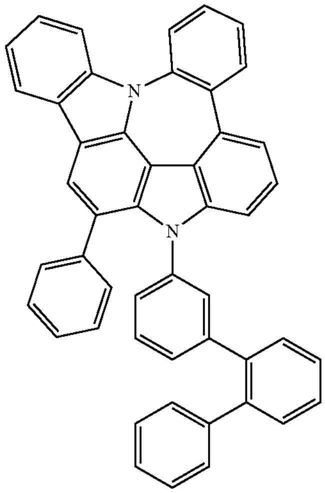
H1-89
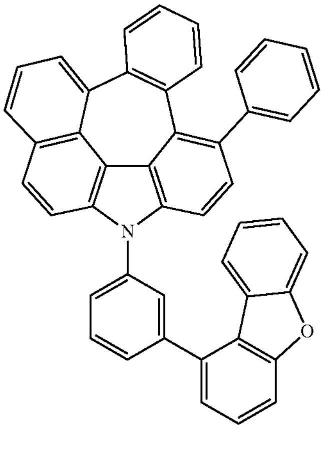
-continued
H1-90
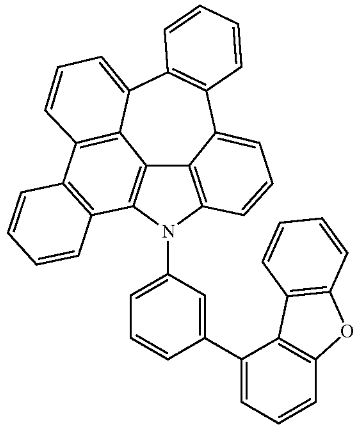
H1-91
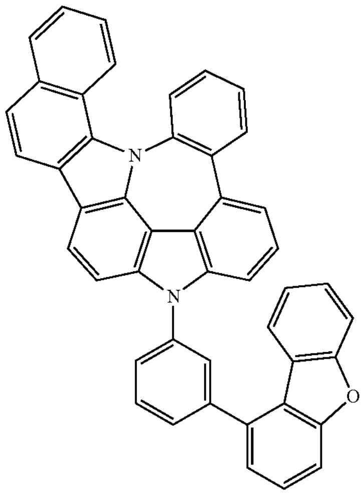
H1-92
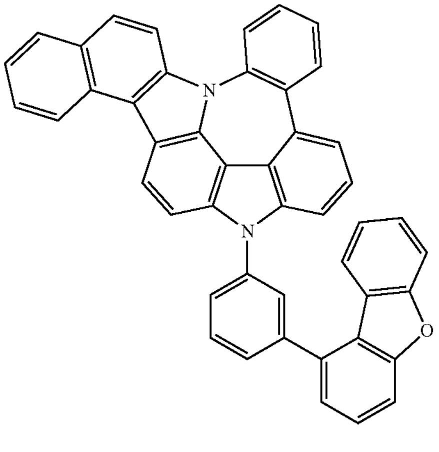

-continued
H1-93
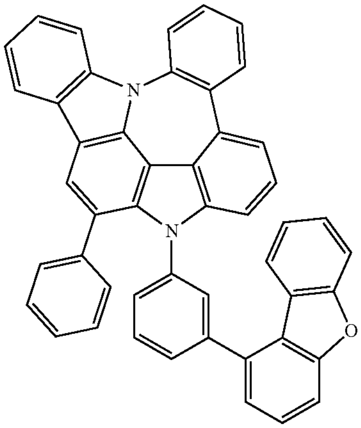
H1-94
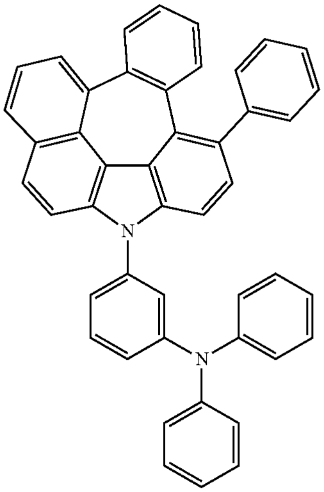
H1-95
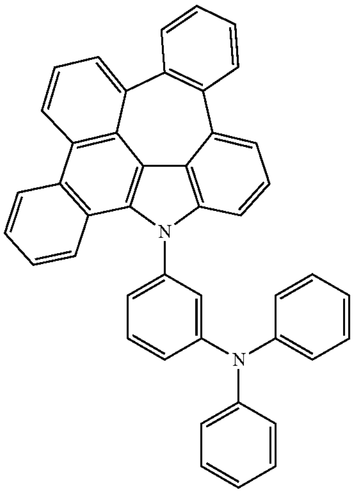
-continued
H1-96
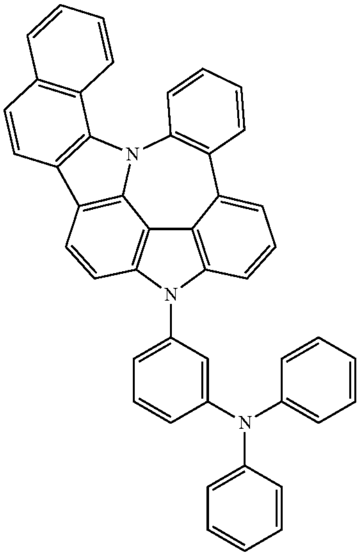
H1-97
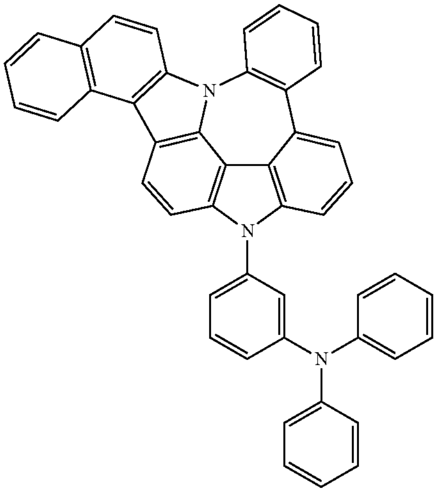
H1-98
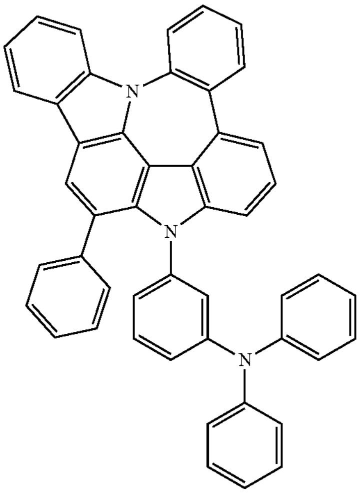

-continued
H1-99
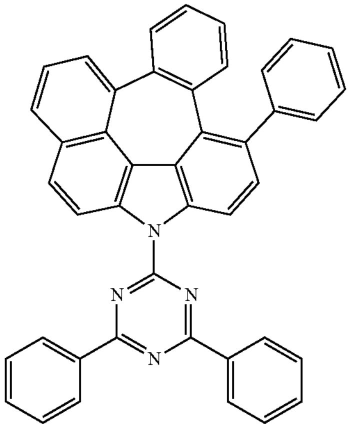
H1-100
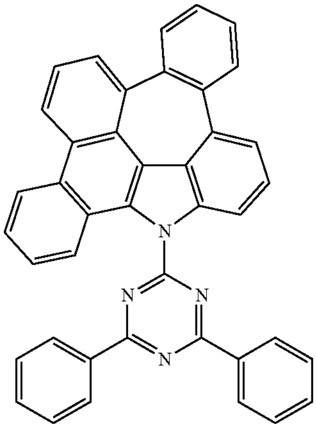
H1-101
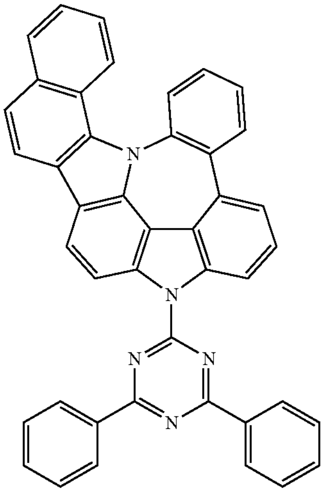
-continued
H1-102
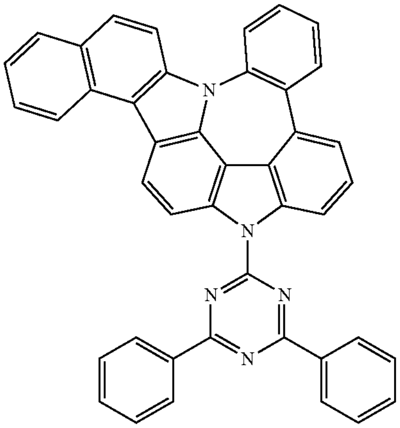
H1-103
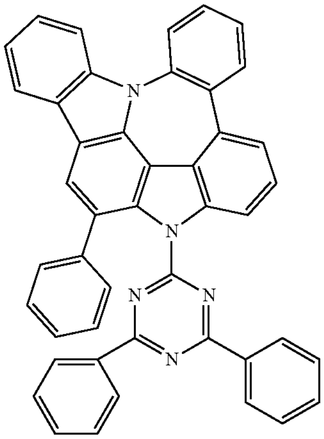
H1-104
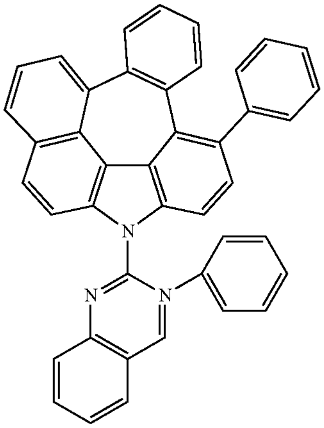

-continued
H1-105
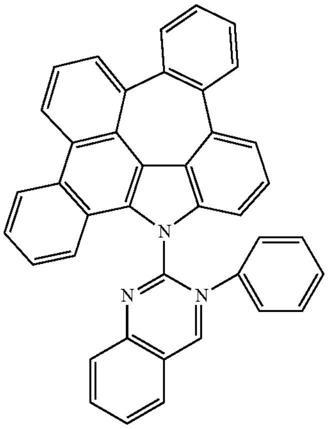
H1-106
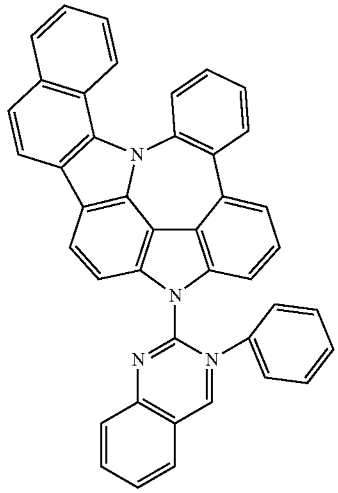
H1-107
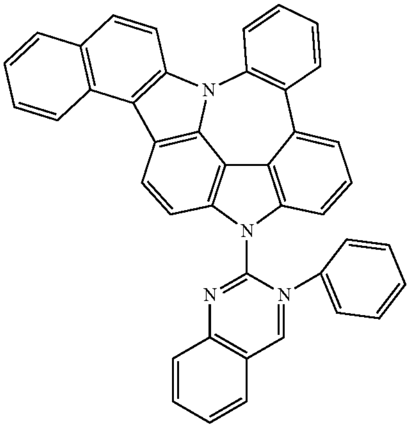
-continued
H1-108
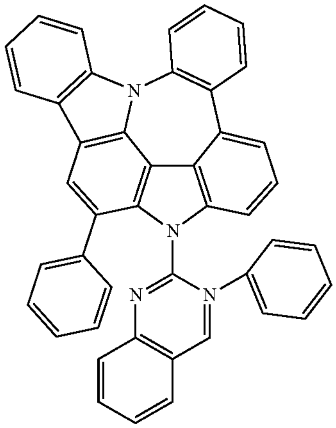
H1-109
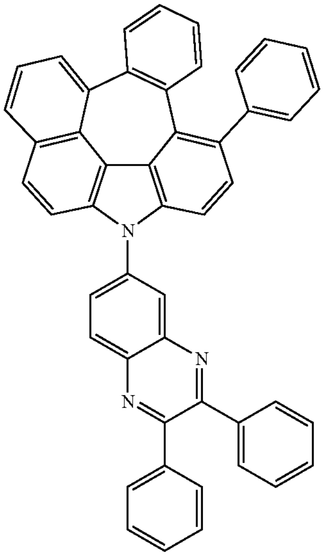
H1-110
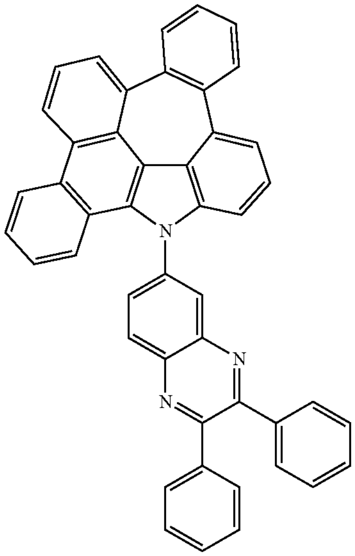

-continued
H1-111
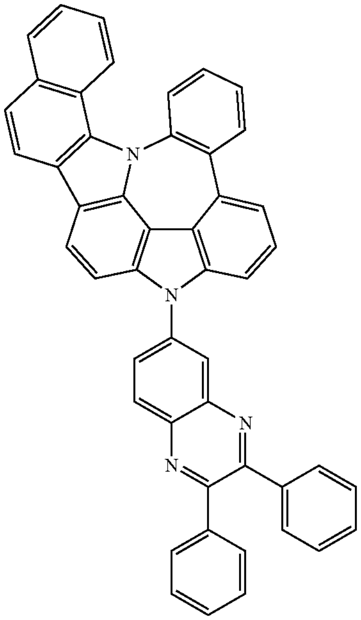
H1-112
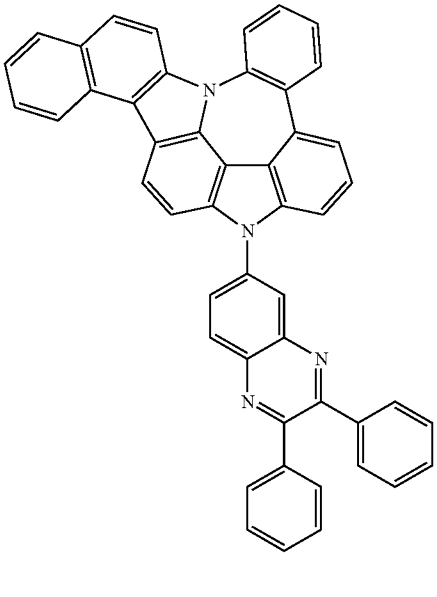
-continued
H1-113
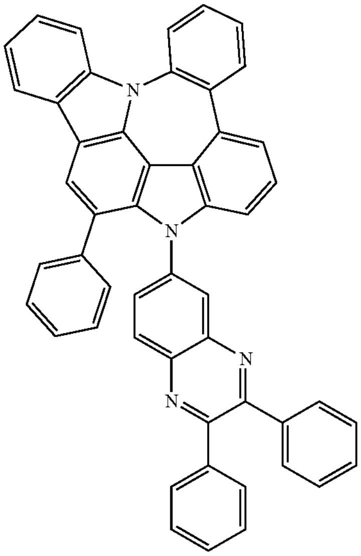
H1-114
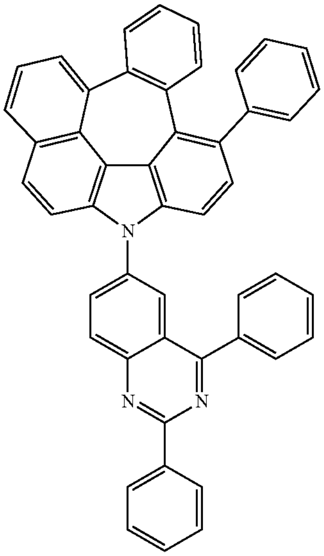
H1-115
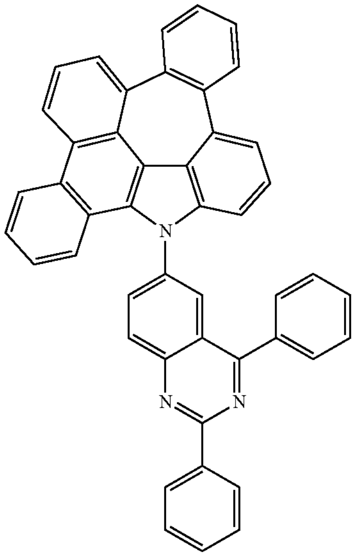

-continued
H1-116
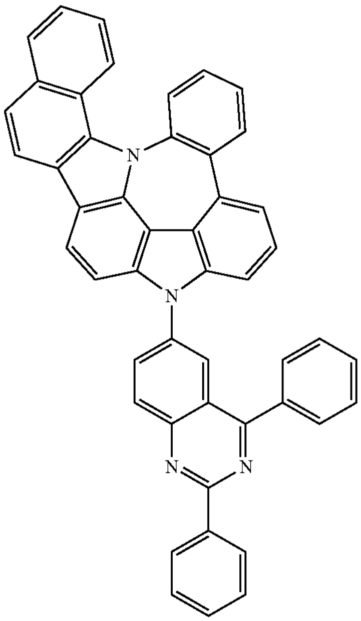
H1-117
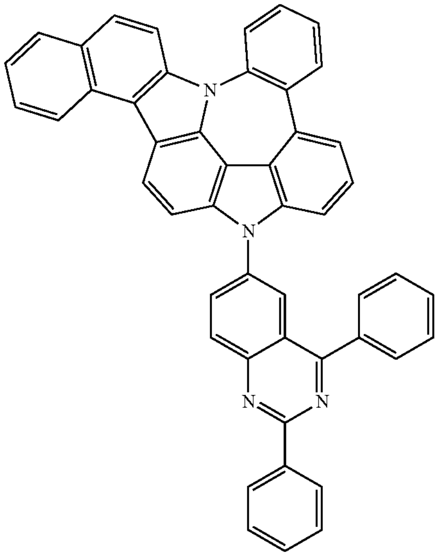
-continued
H1-118
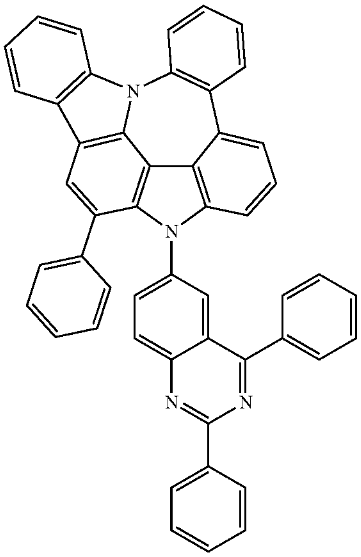
H1-119
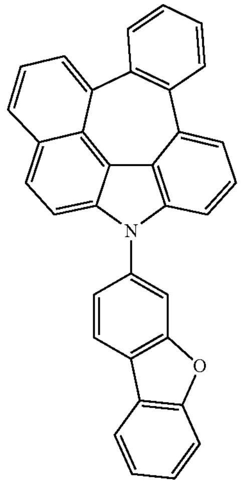
H1-120
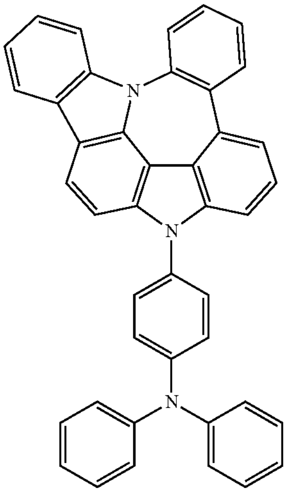

-continued
H1-121
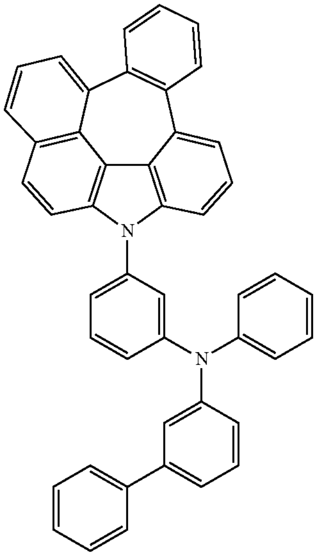
H1-122
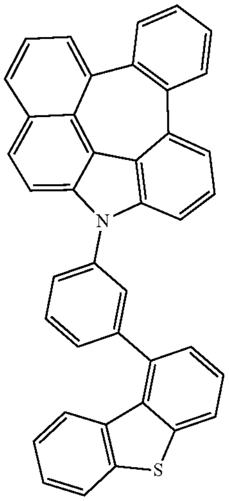
H1-123
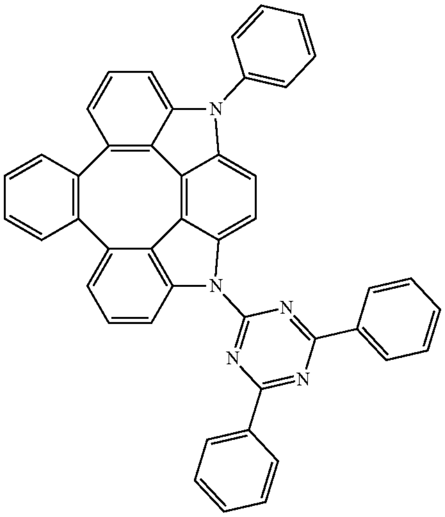
-continued
H1-124
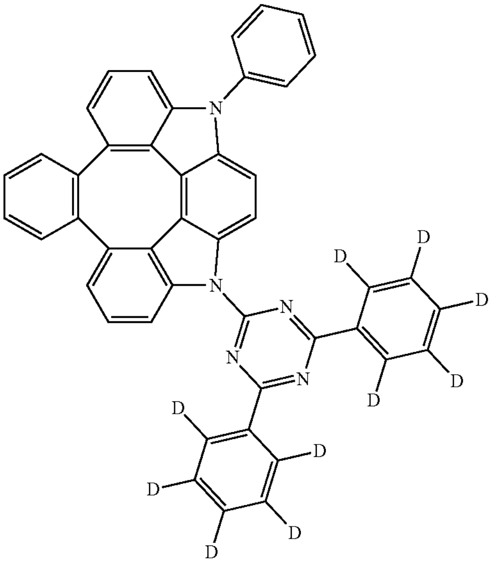
H1-125
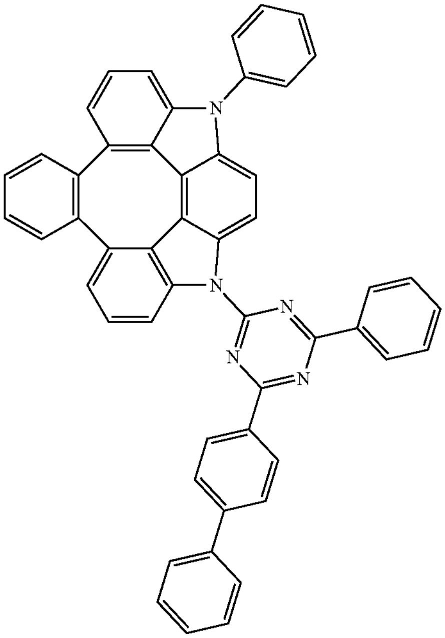

-continued
H1-126
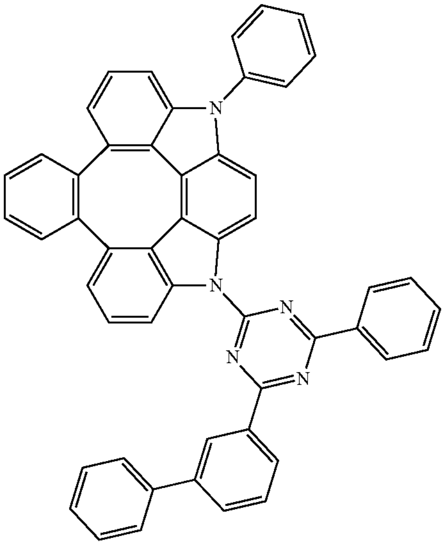
H1-127
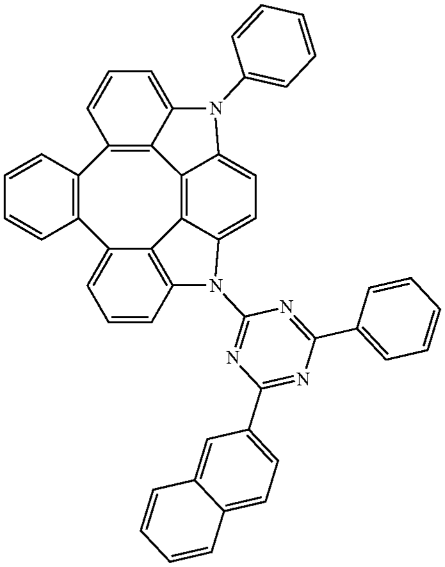
H1-128
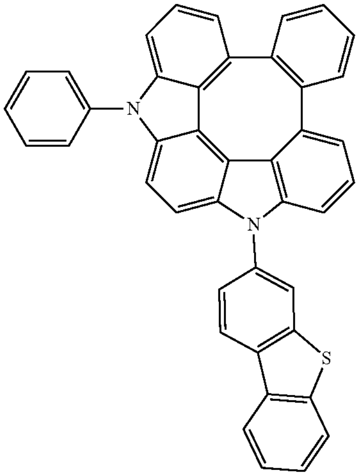
-continued
H1-129
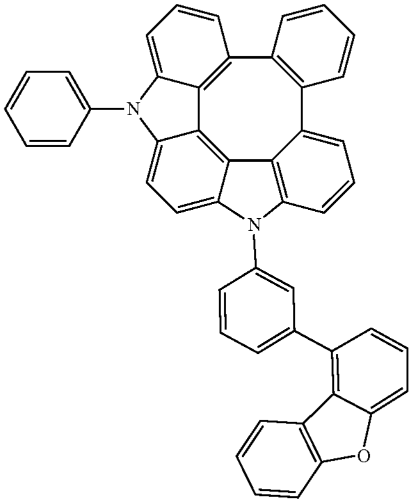
H1-130
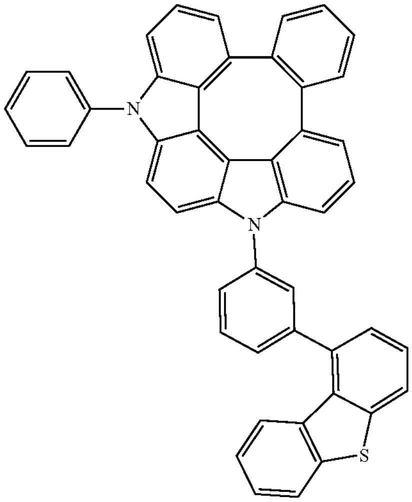
H1-131
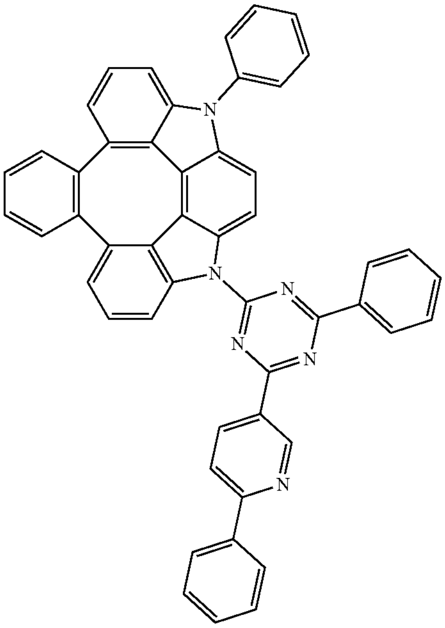

-continued
H1-132
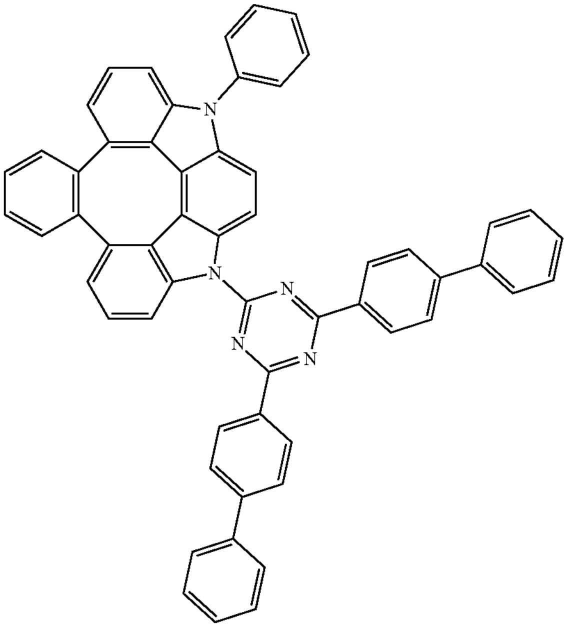
H1-133
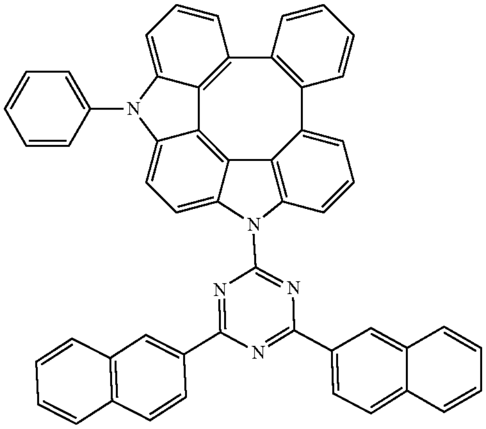
H1-134
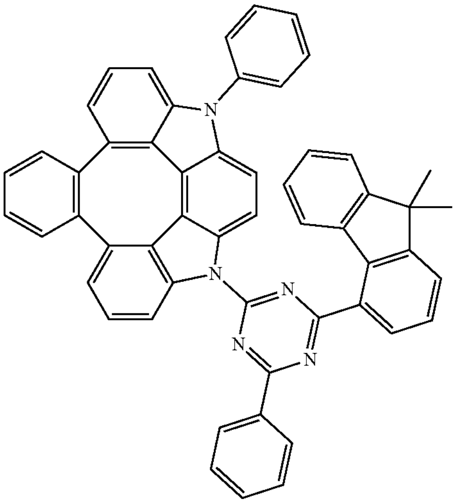
-continued
H1-135
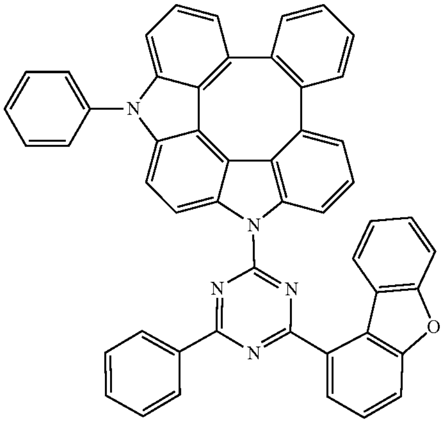
H1-136
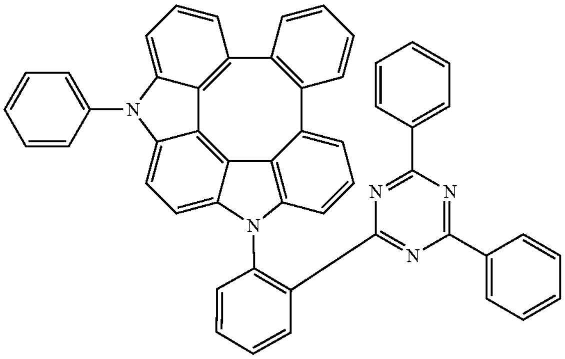
1-137
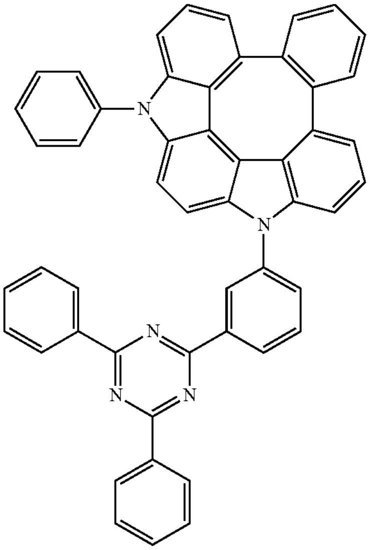

-continued
H1-138
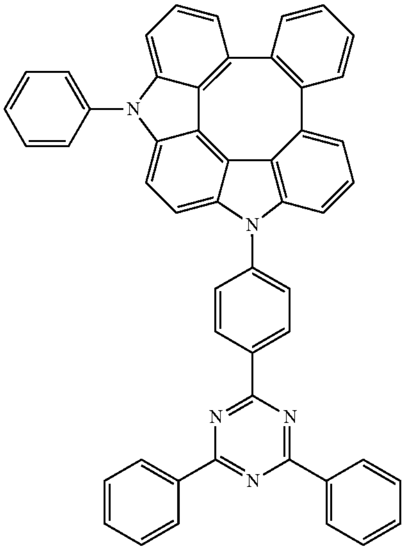
H1-139
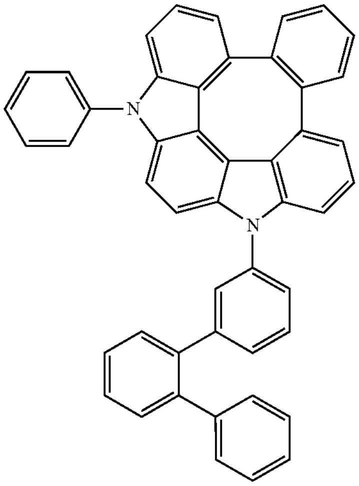
H1-140
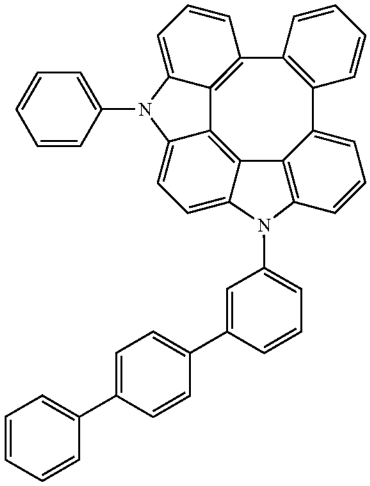
-continued
H1-141
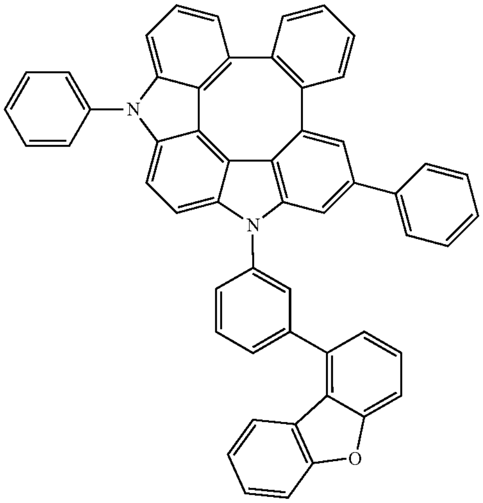
H1-142
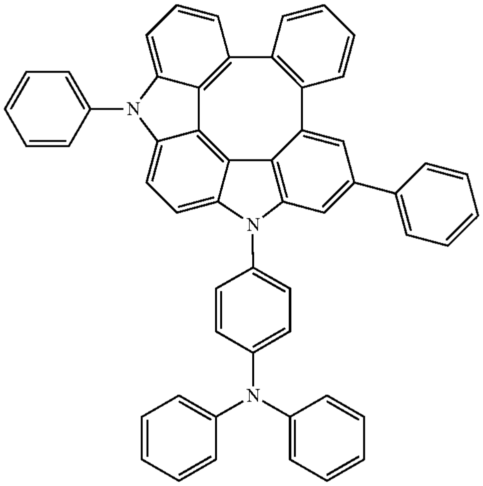
H1-143
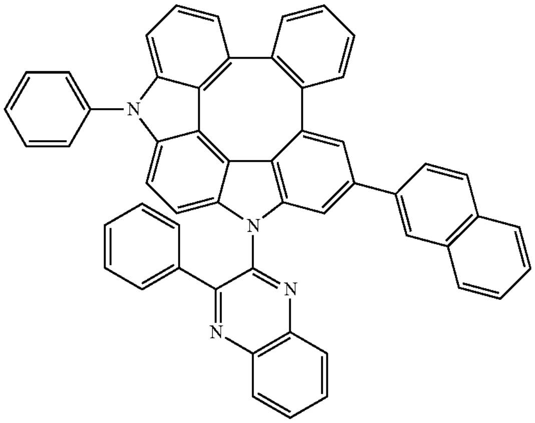

-continued
H1-144
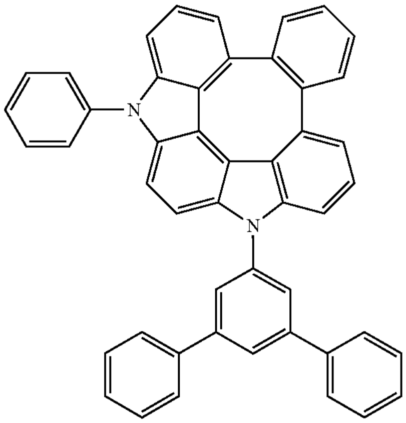
H1-145
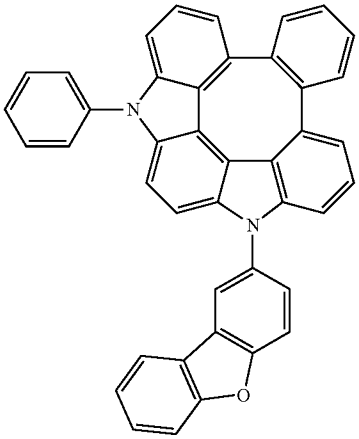
H1-146
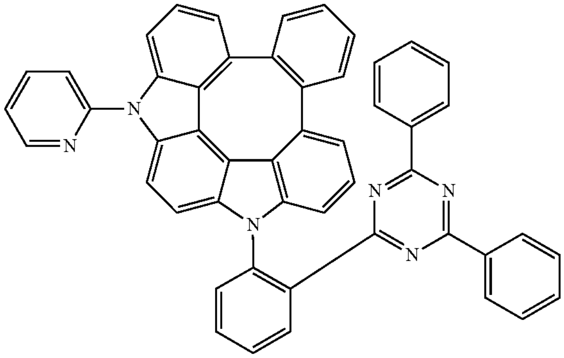
-continued
H1-147
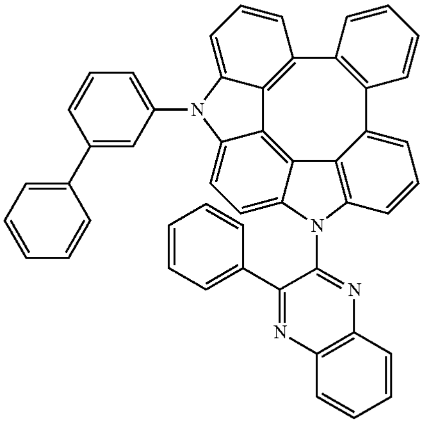
H1-148
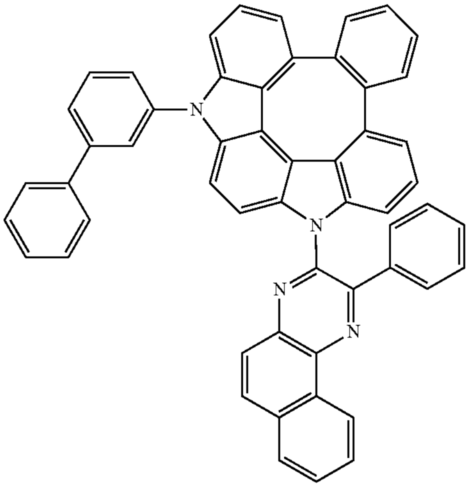
H1-149
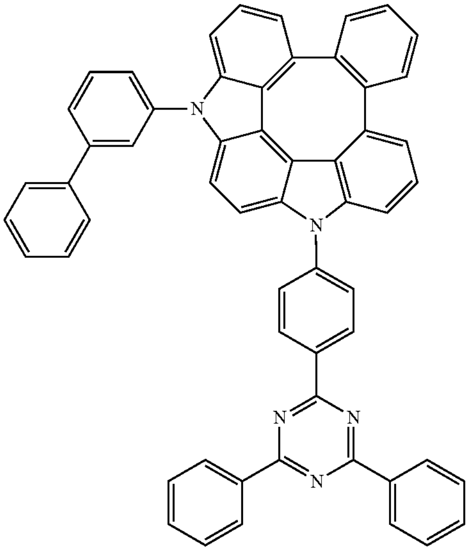

-continued
H1-150
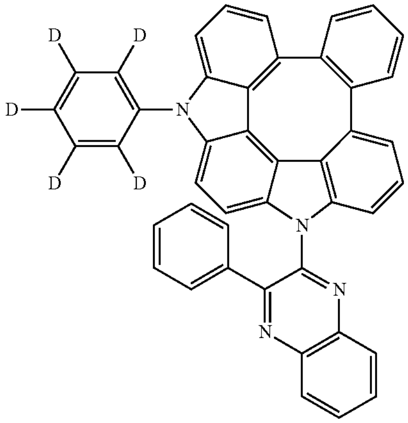
H1-151
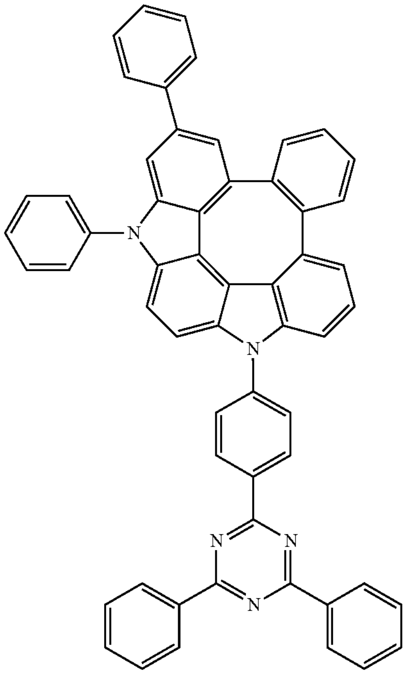
-continued
H1-152
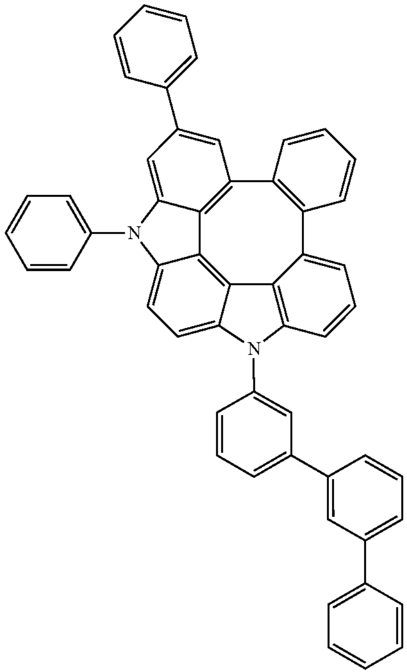
H1-153
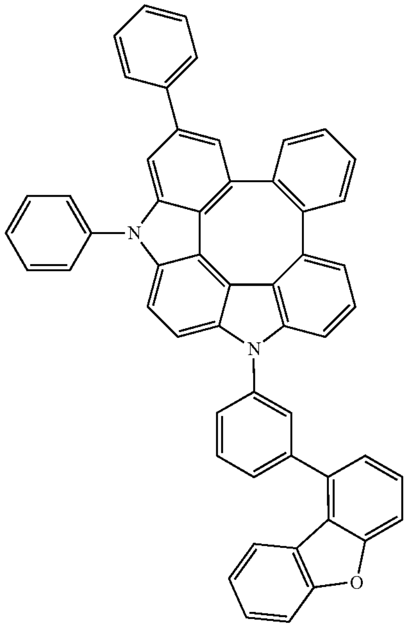

-continued
H1-154
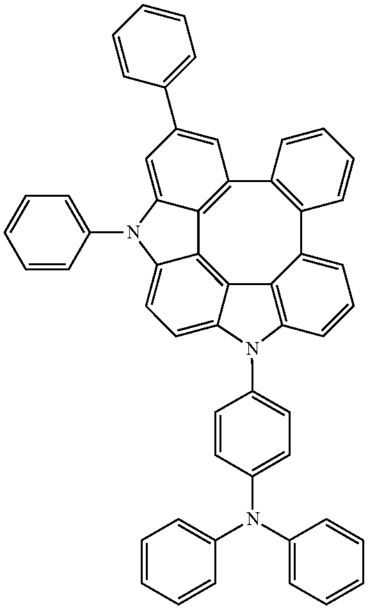
H1-155
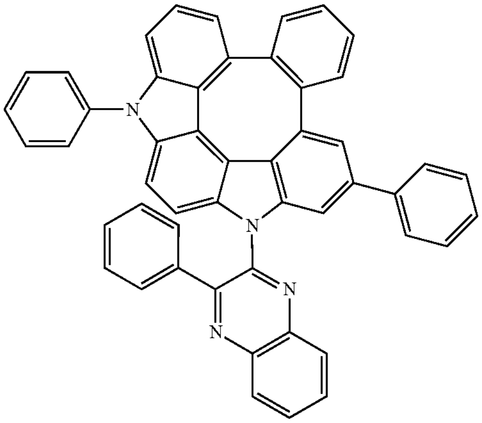
H1-156
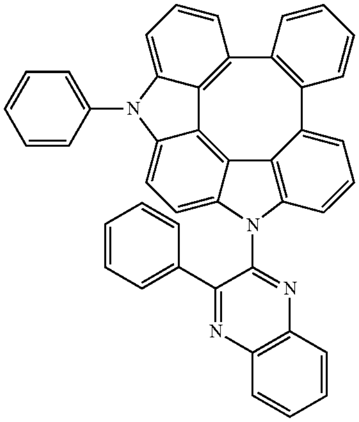
-continued
H1-157
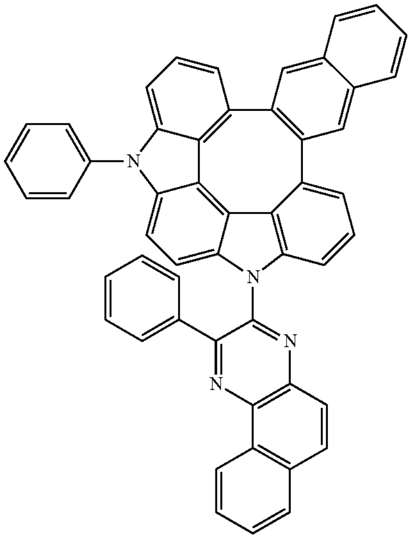
H1-158
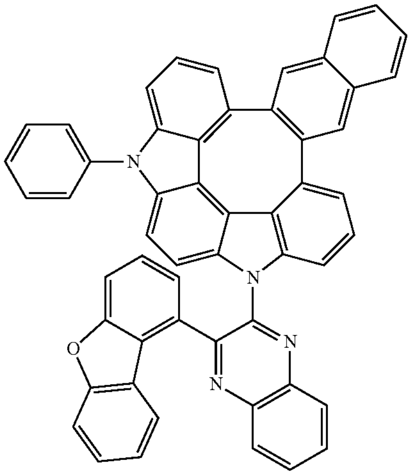
H1-159
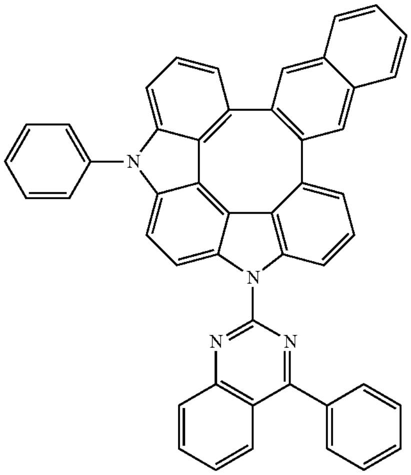

-continued
H1-160
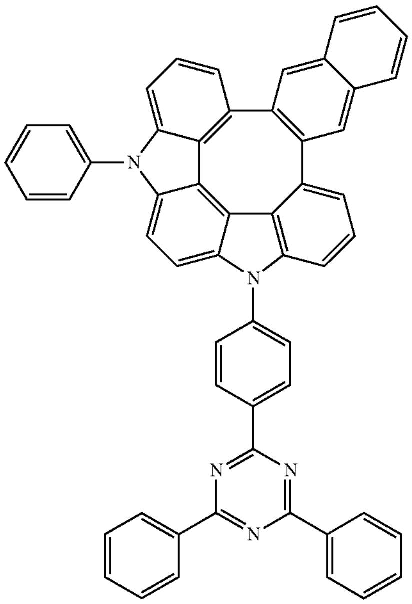
H1-161
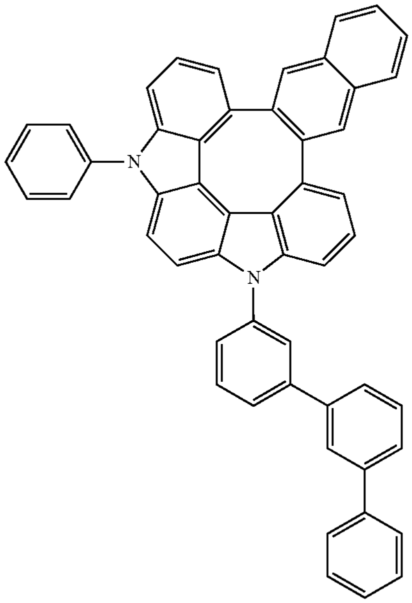
-continued
H1-162
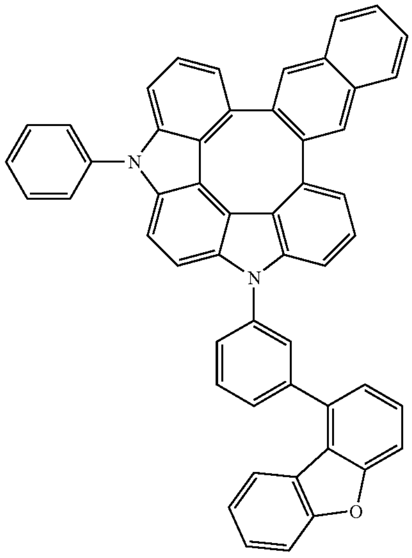
H1-163
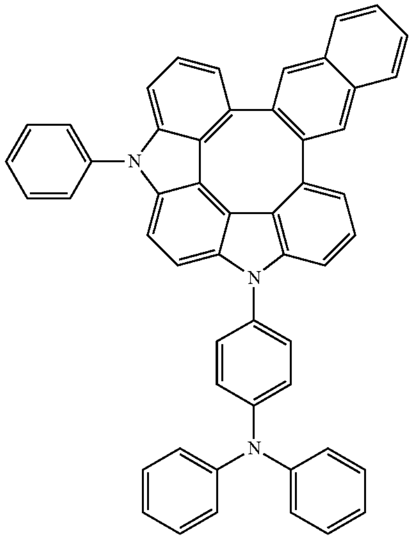
H1-164
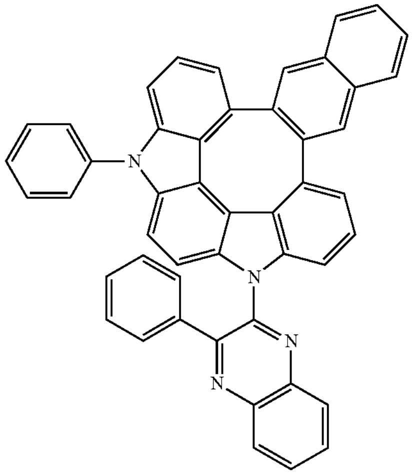

-continued
H1-165
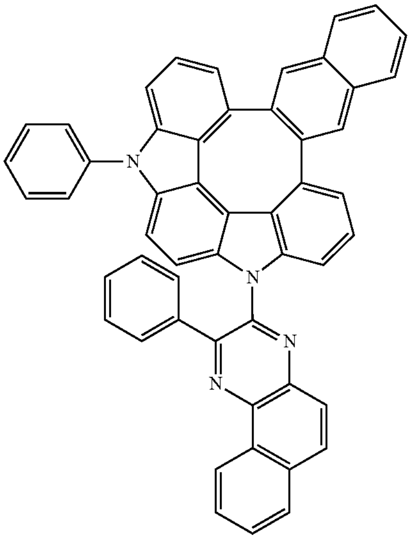
H1-166
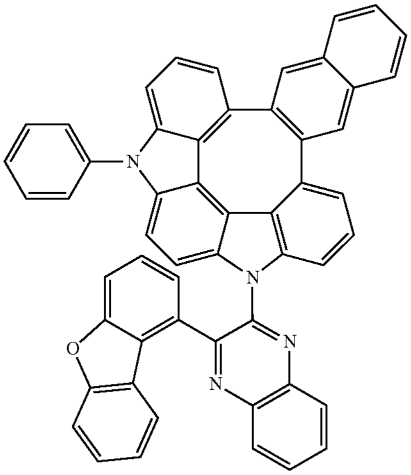
H1-167
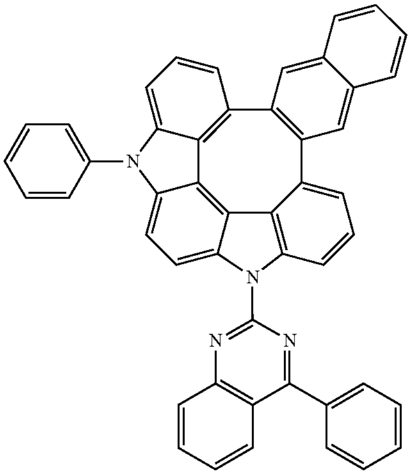
-continued
H1-168
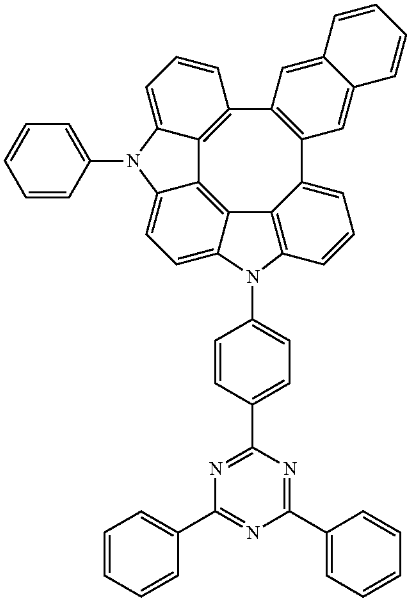
H1-169
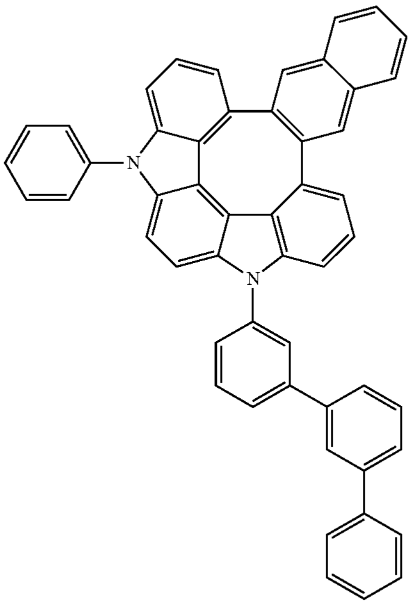

-continued
H1-170
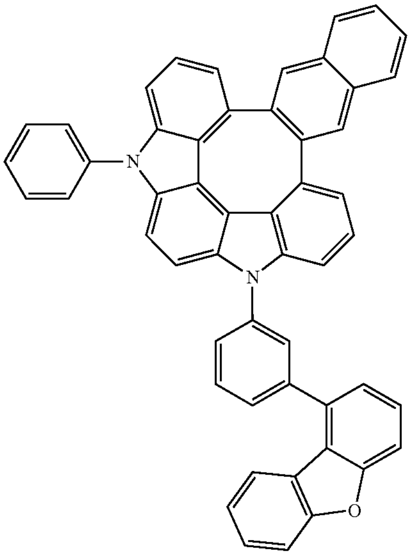
H1-171
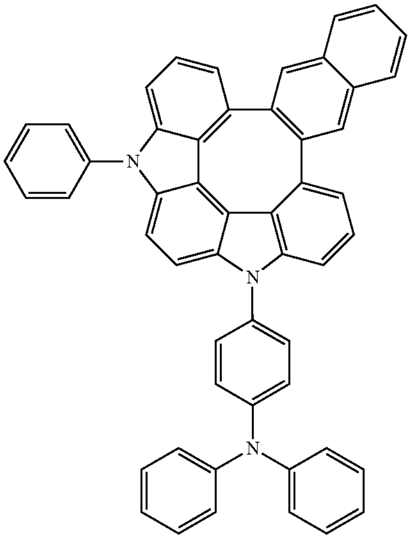
H1-172
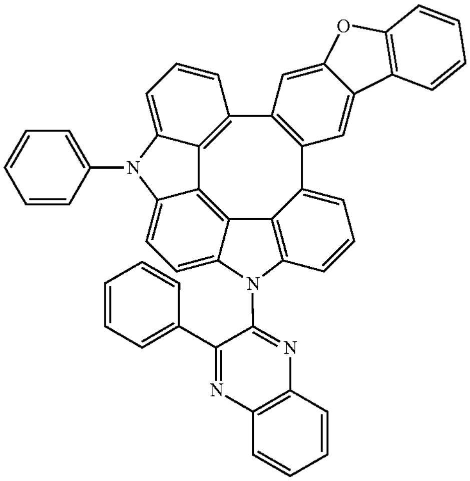
-continued
H1-173
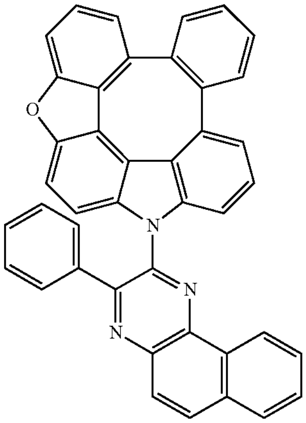
H1-174
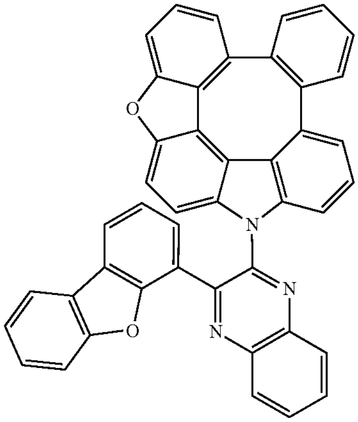
H1-175
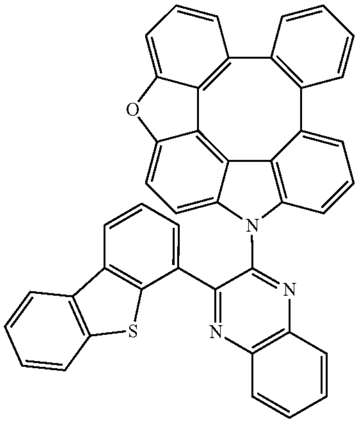

-continued
H1-176
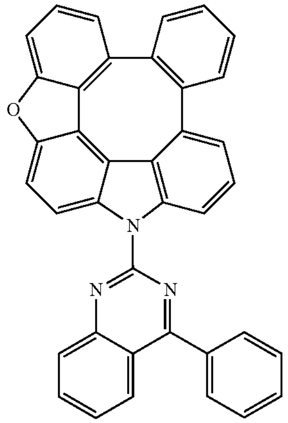
H1-177
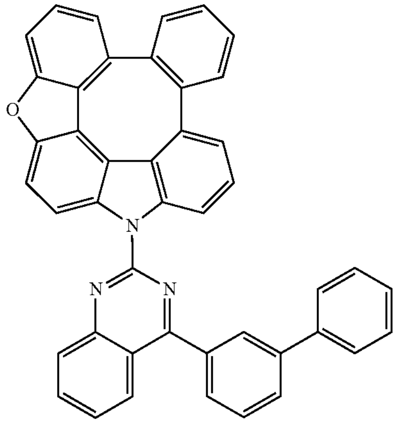
H1-178
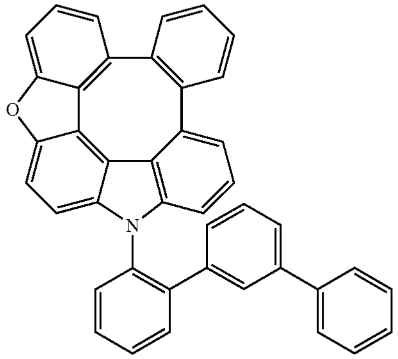
-continued
H1-179
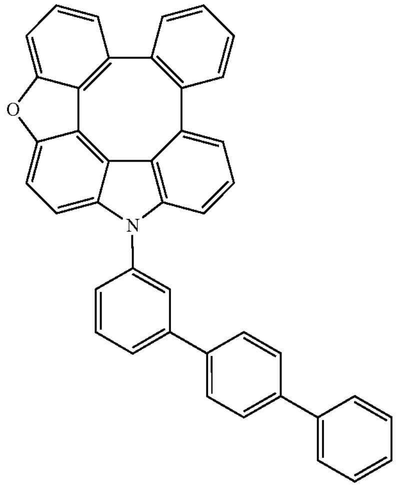
H1-180
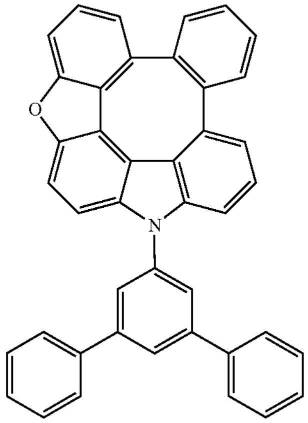
H1-181
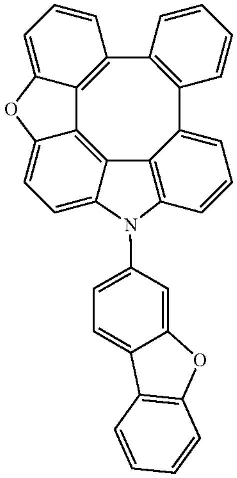

-continued
H1-182
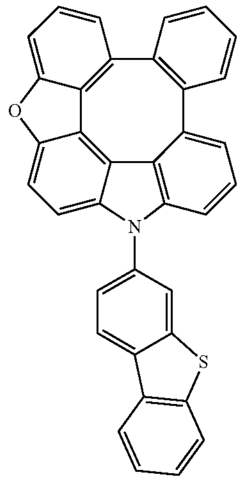
H1-183
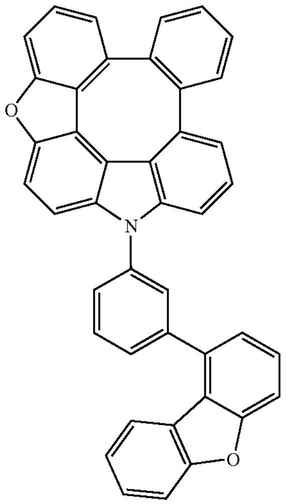
H1-184
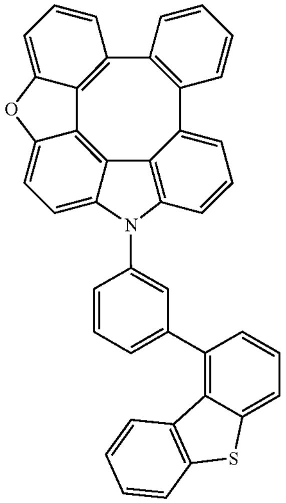
-continued
H1-185
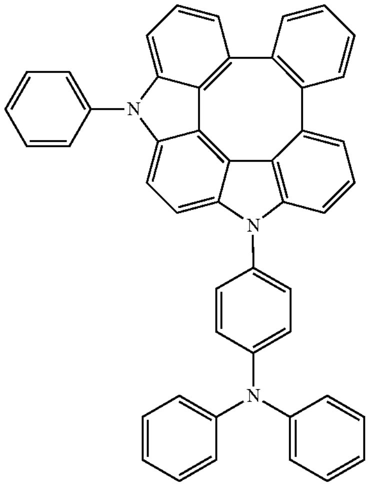
H1-186
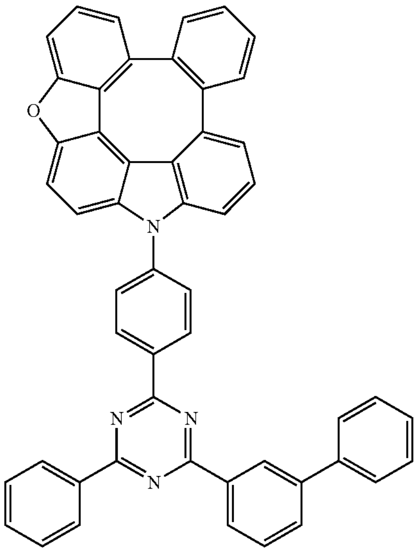
H1-187
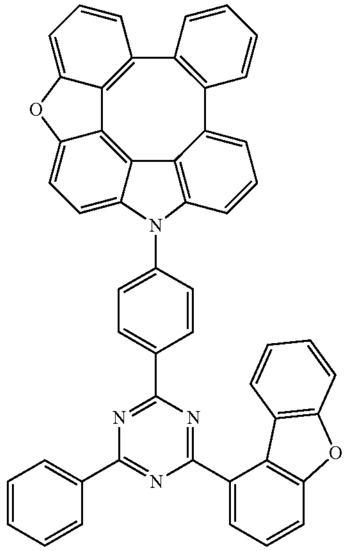

-continued
H1-188
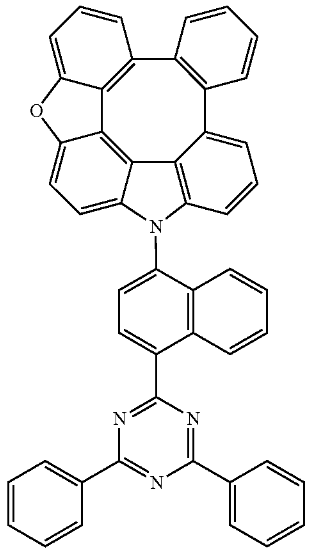
H1-189
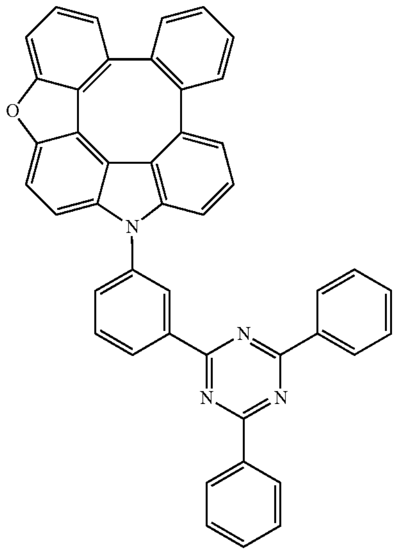
-continued
H1-190
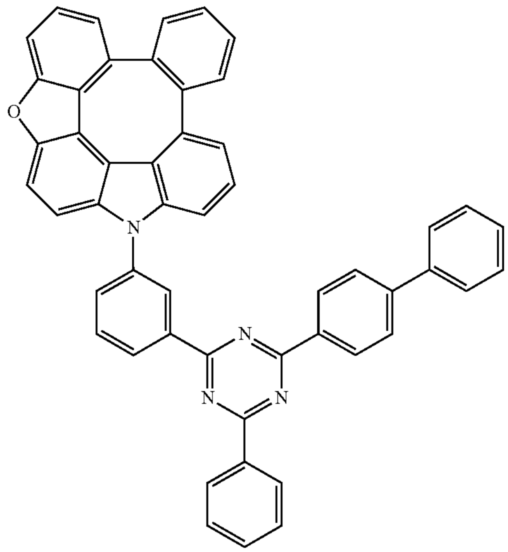
H1-191
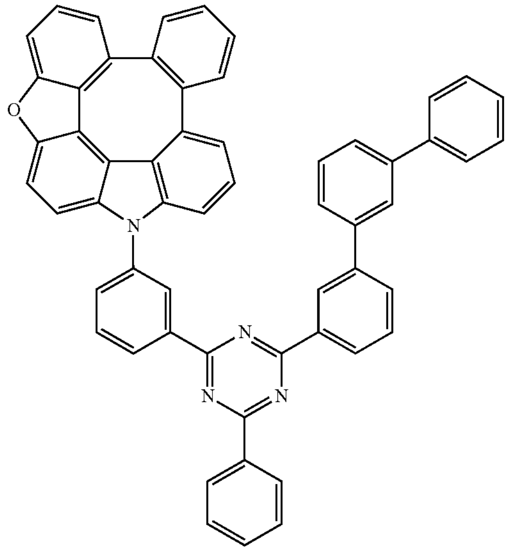

H1-192
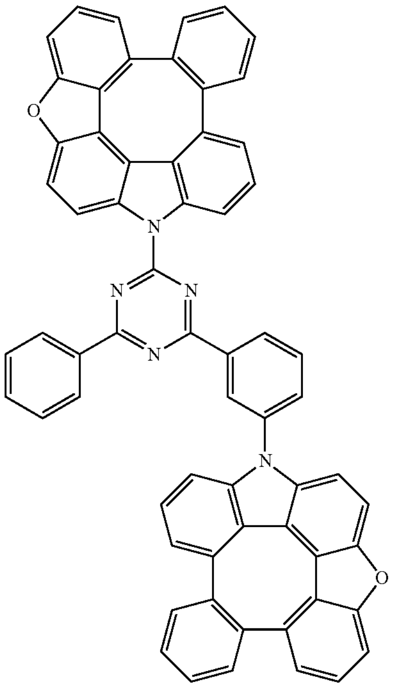
H1-193
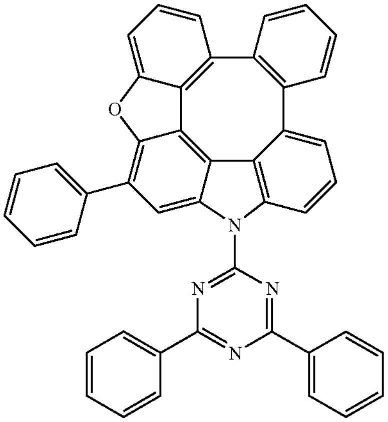
H1-194
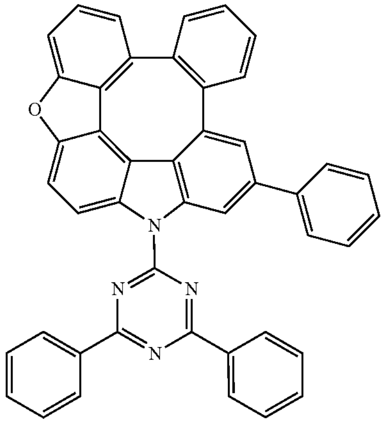
H1-195
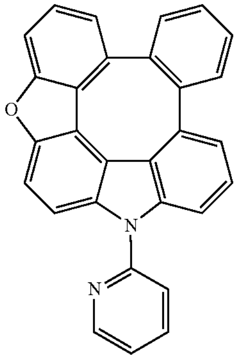
H1-196
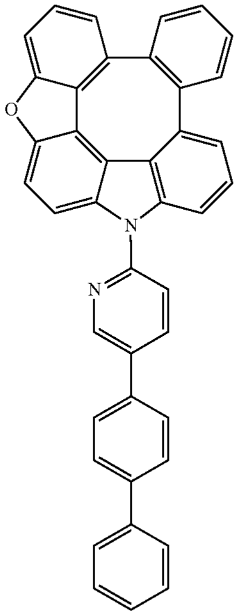
H1-197
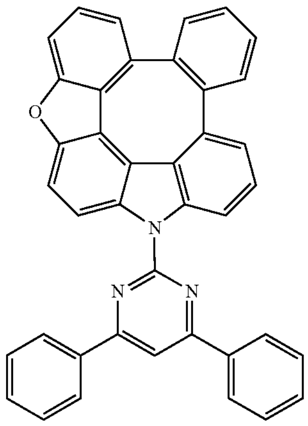

-continued
H1-198
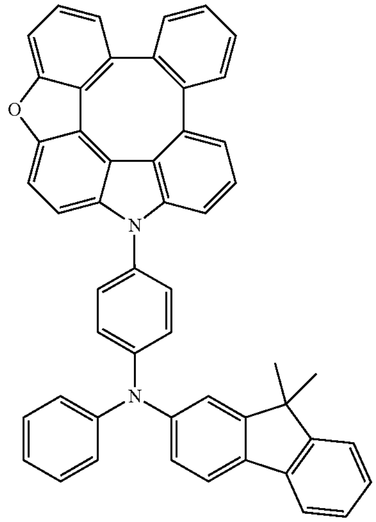
H1-199
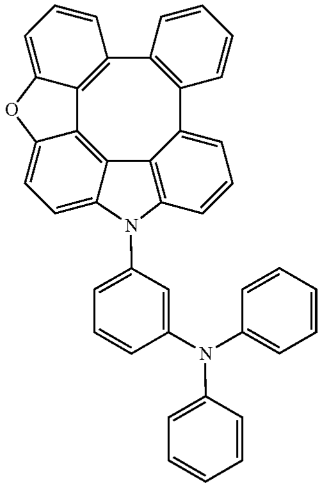
H1-200
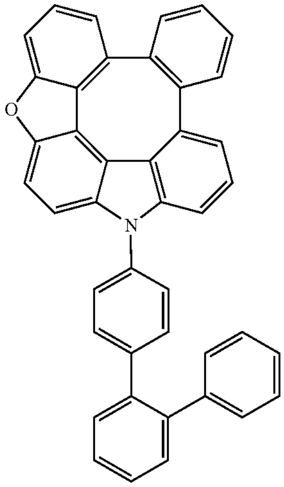
-continued
H1-201
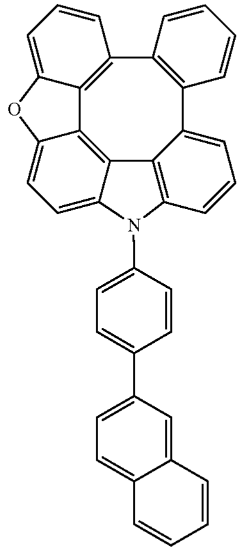
H1-202
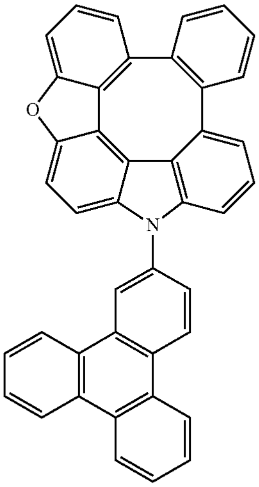
H1-203
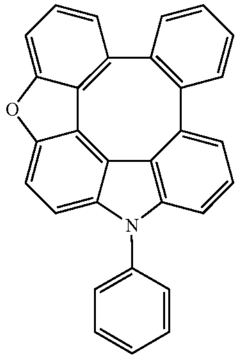

-continued
H1-204
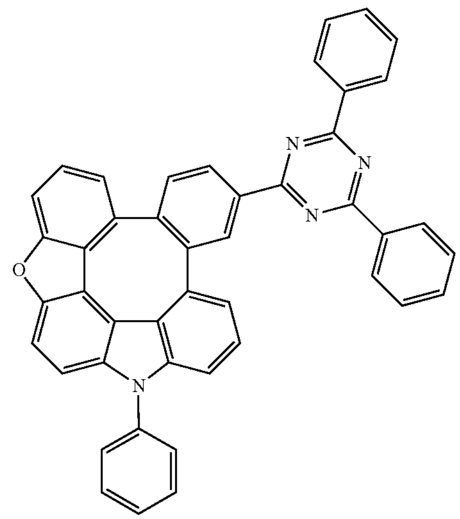
H1-205
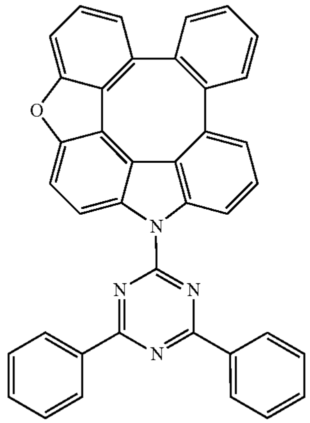
H1-206
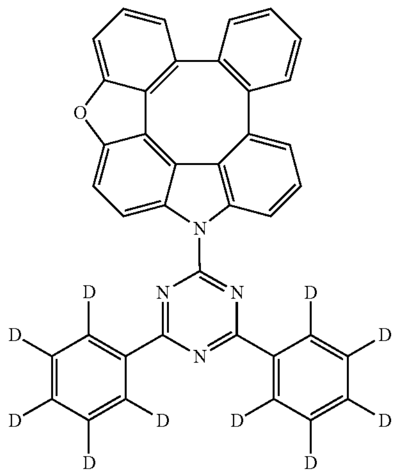
-continued
H1-207
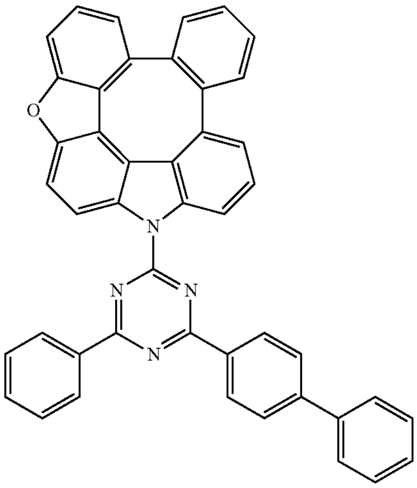
H1-208
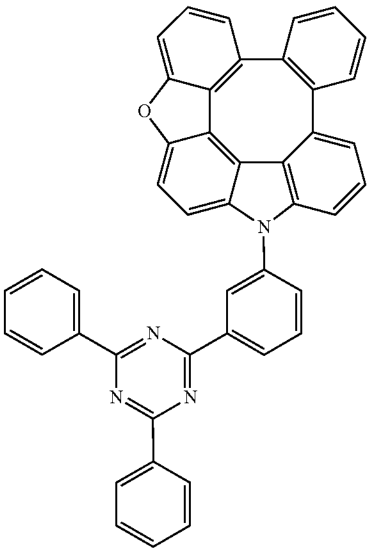
H1-209
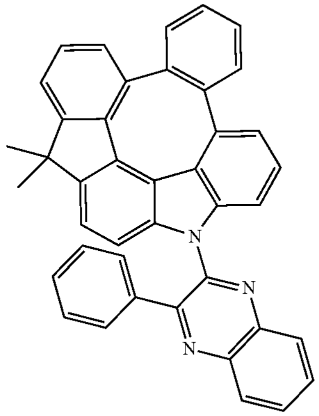

-continued
H1-210
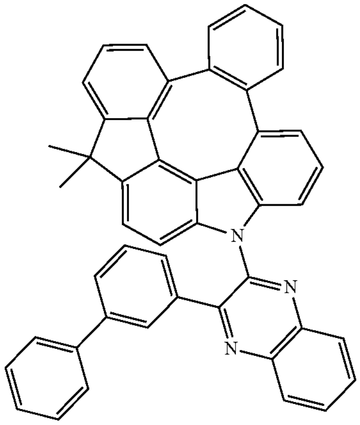
H1-211
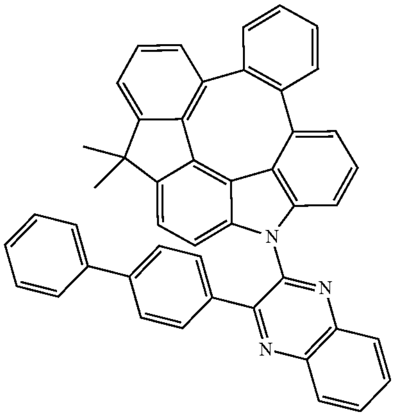
H1-212
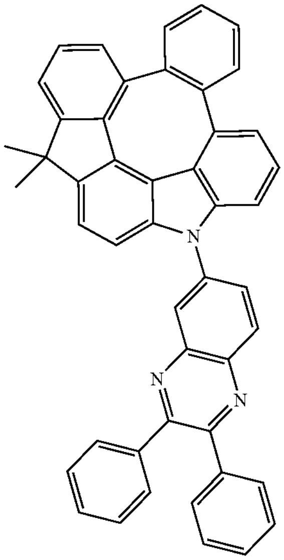
-continued
H1-213
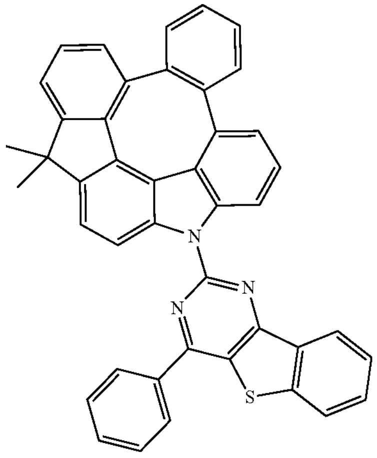
H1-214
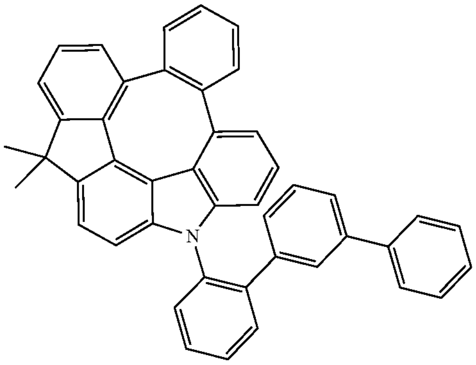
H1-215
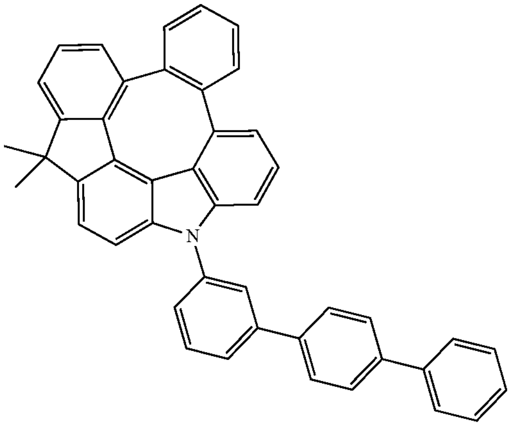

-continued
H1-216
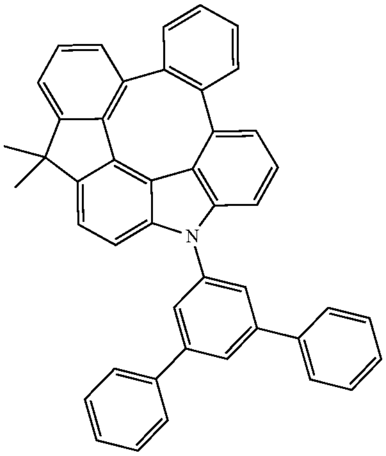
H1-217
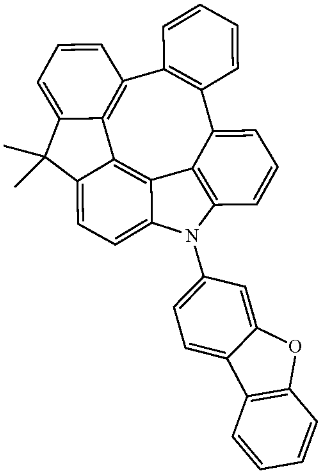
H1-218
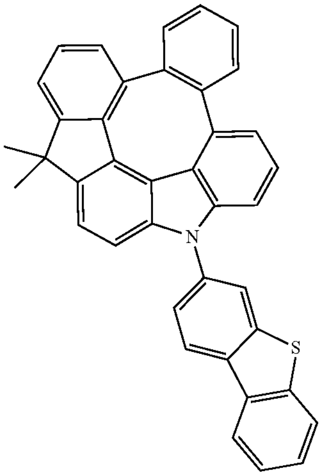
-continued
H1-219
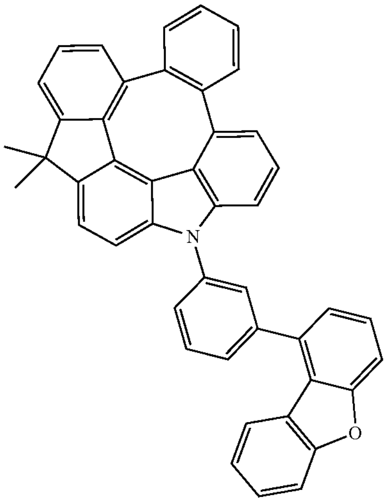
H1-220
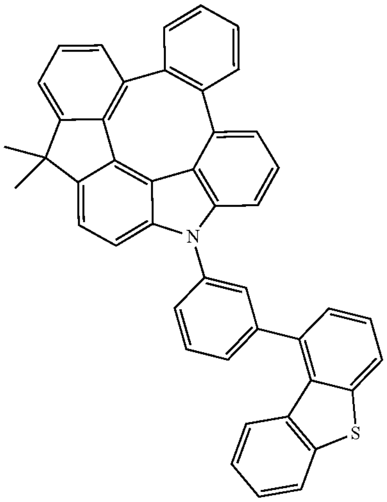
H1-221
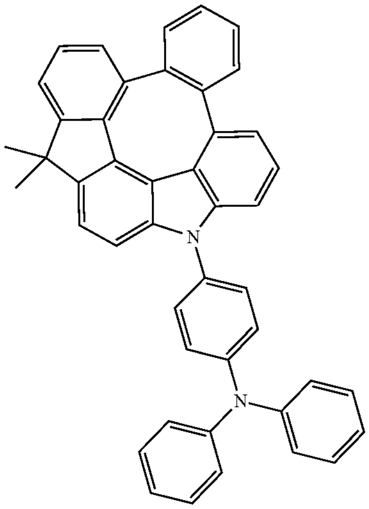

-continued
H1-222
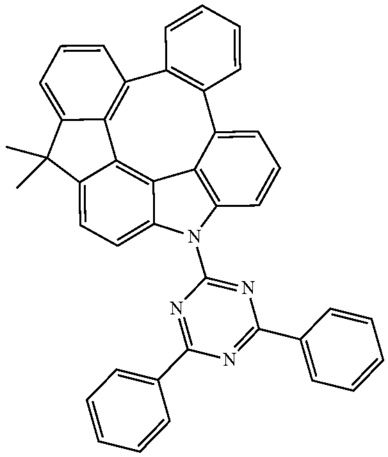
H1-223
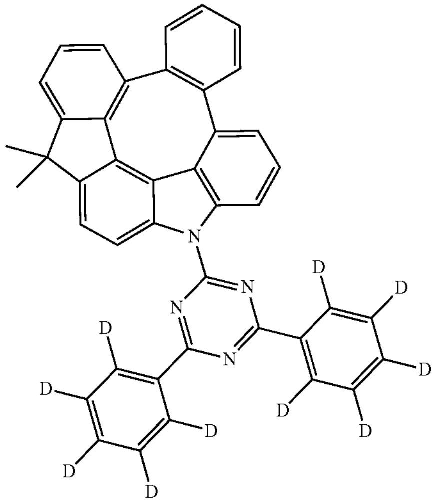
H1-224
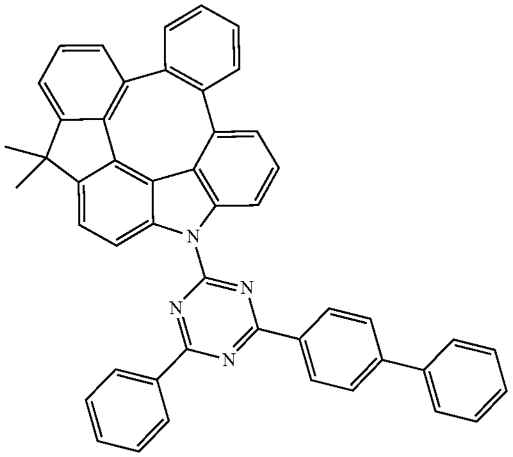
-continued
H1-225
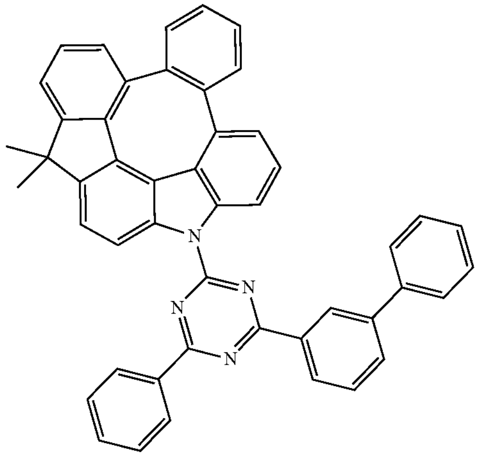
H1-226
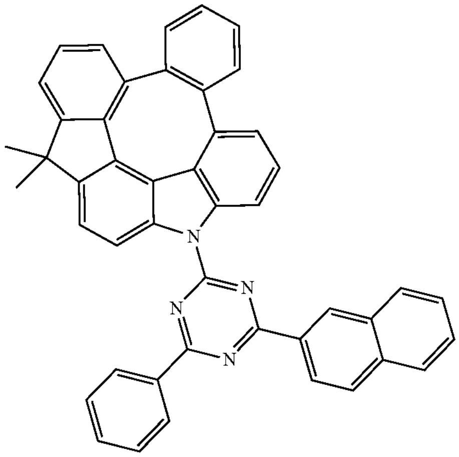
H1-227
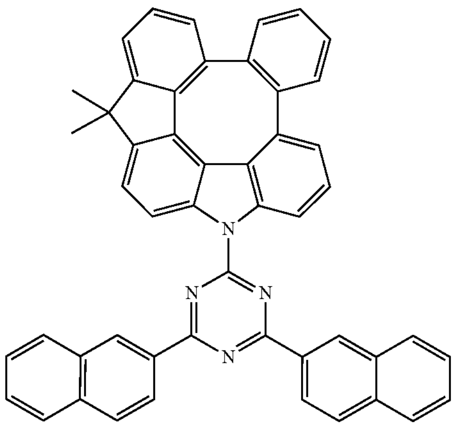

-continued
H1-228
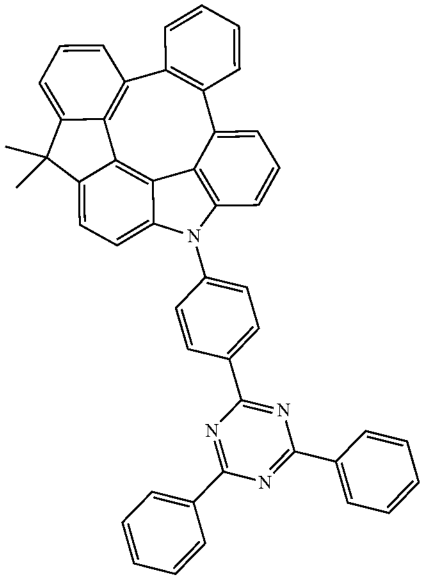
H1-229
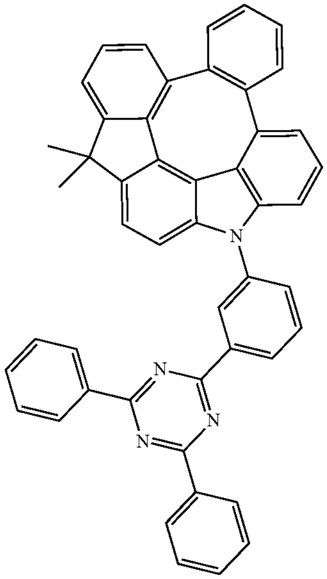
H1-230
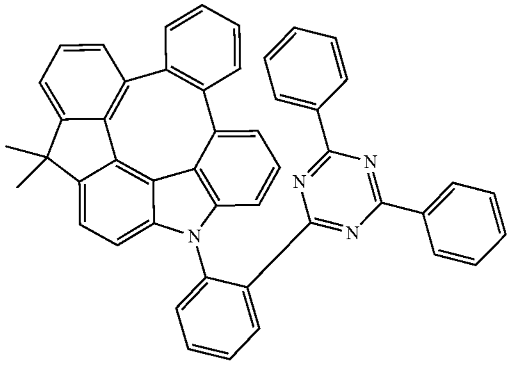
-continued
H1-231
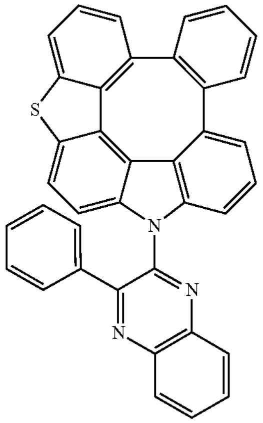
H1-232
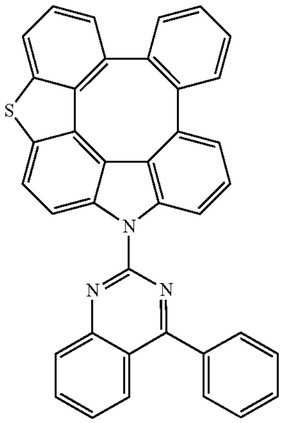
H1-233
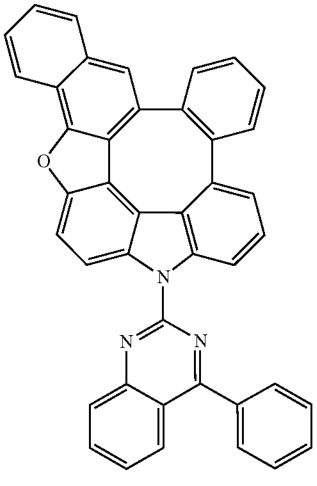

-continued
H1-234
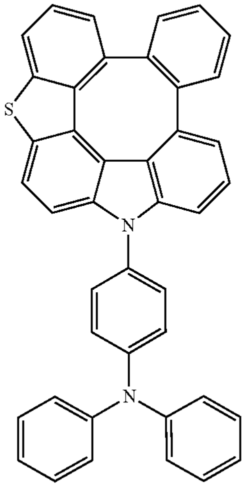
H1-235
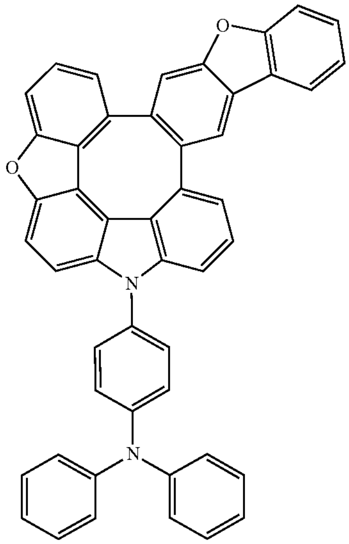
H1-236
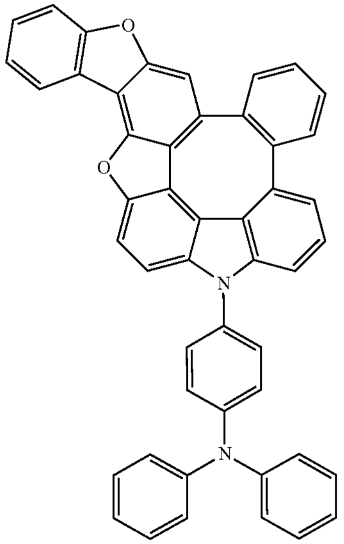
-continued
H1-237
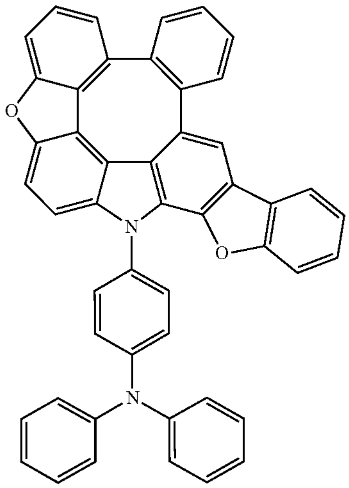
H1-238
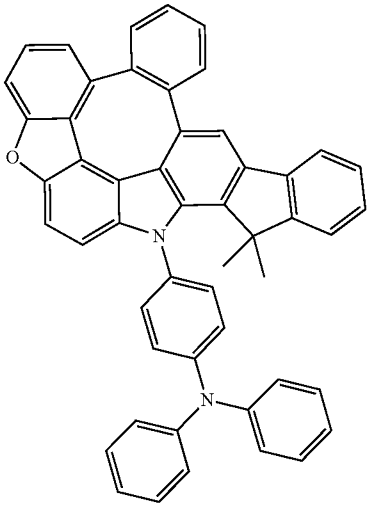
H1-239
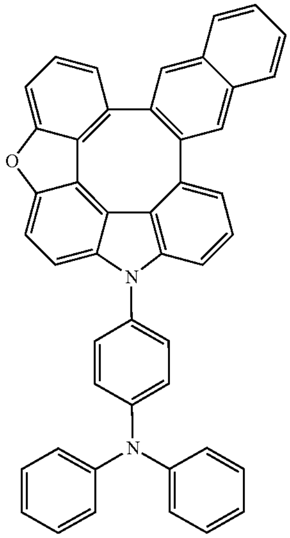

H1-240
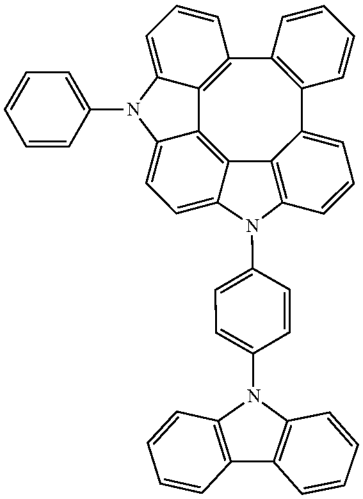
H1-241
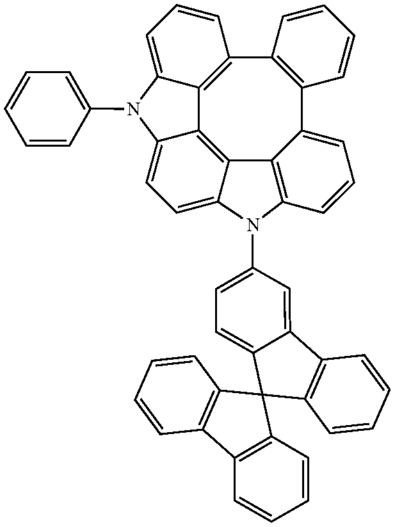
H1-242
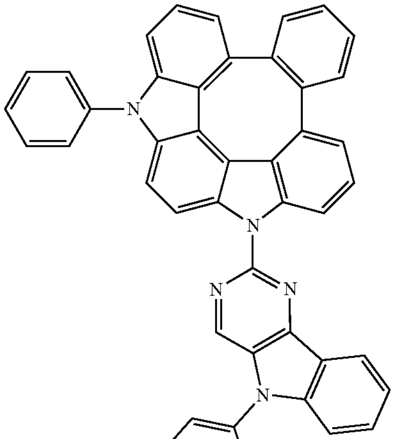
H1-243
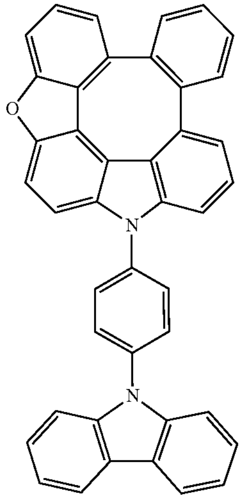
H1-244
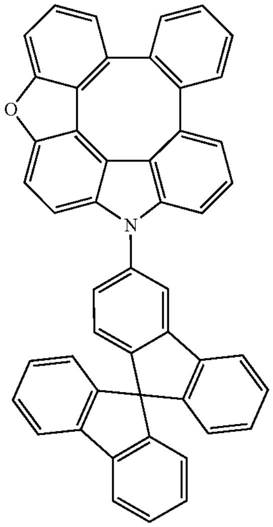
H1-245
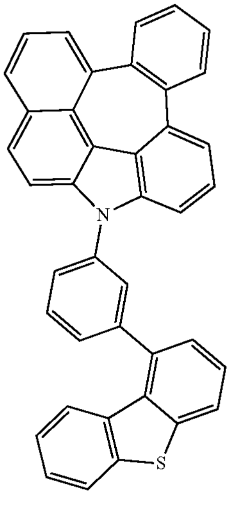
The compound represented by formula 2 may be at least one selected from the group consisting of the following compounds, but is not limited thereto.

H2-1
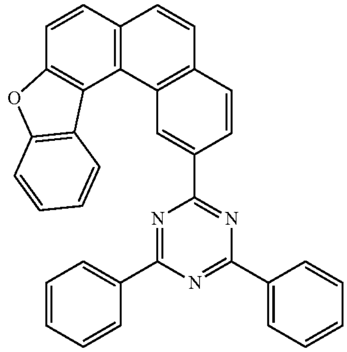
H2-2
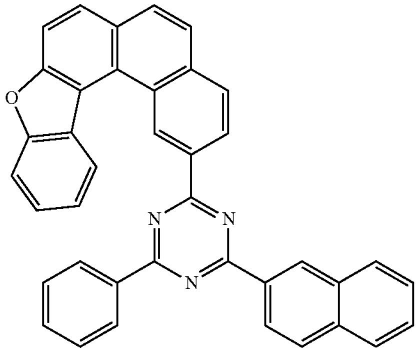
H2-3
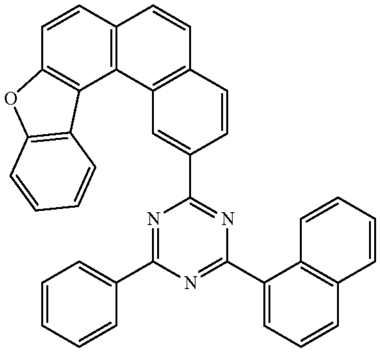
H2-4
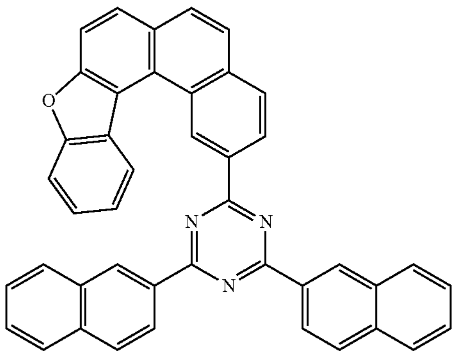
-continued
H2-5
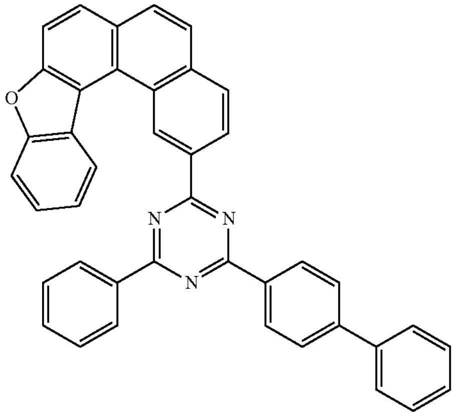
H2-6
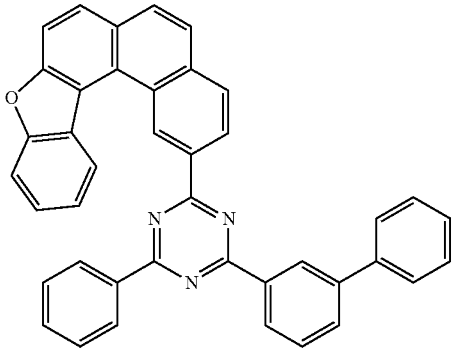
H2-7
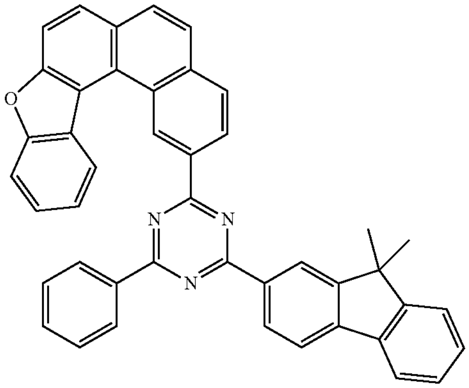
H2-8
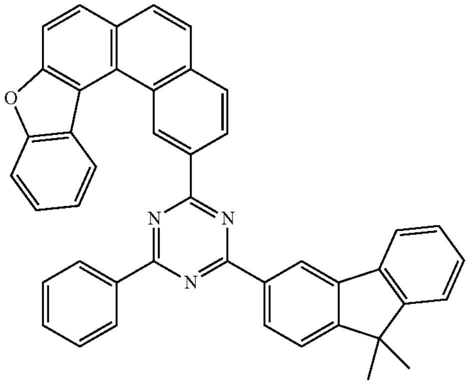

-continued
H2-9
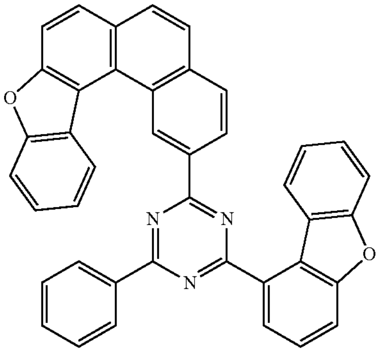
H-10
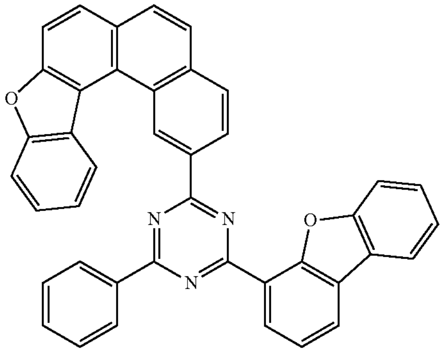
H2-11
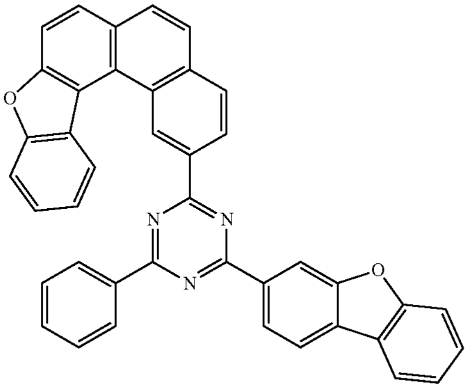
H2-12
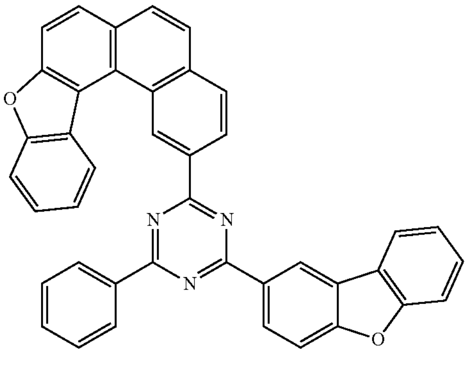
-continued
H2-13
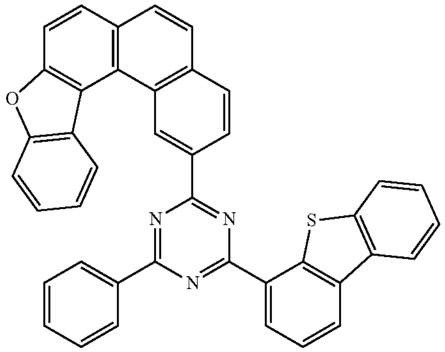
H2-14
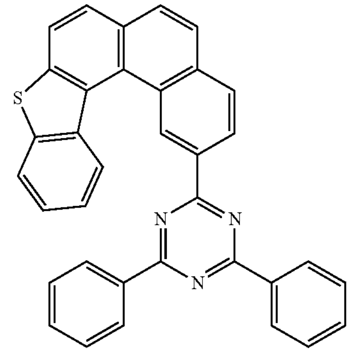
H2-15
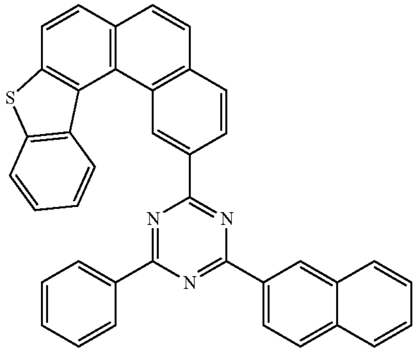
H2-16
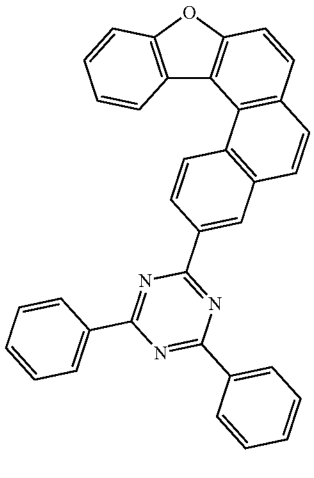

-continued
H2-17
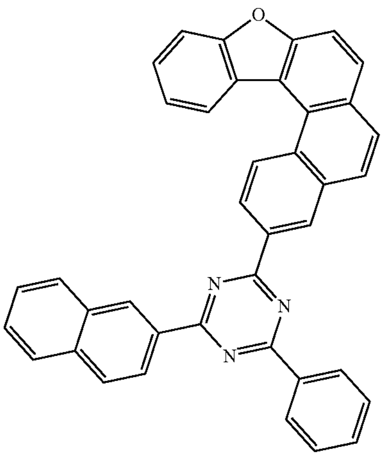
H2-18
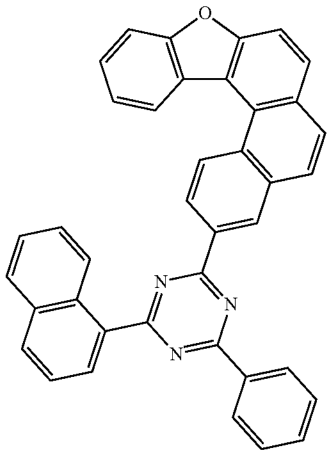
H2-19
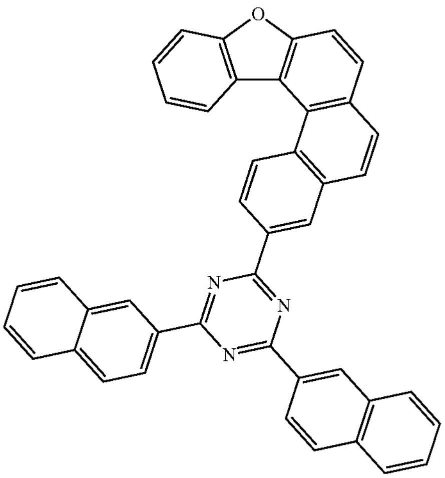
-continued
H2-20
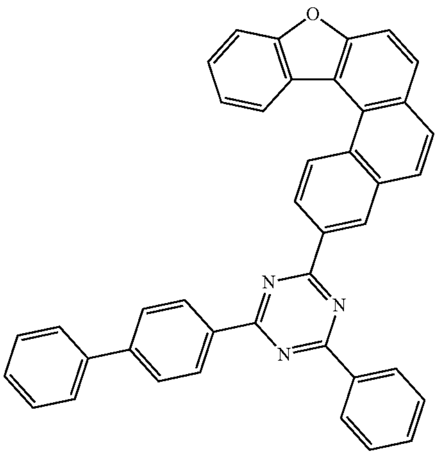
H2-21
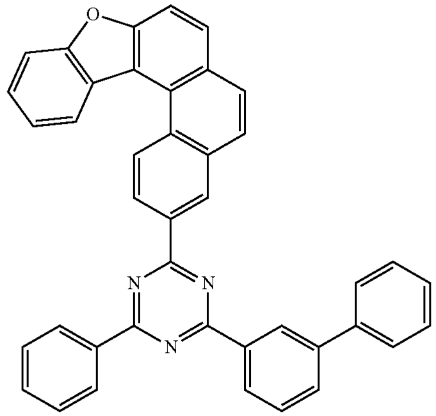
H2-22
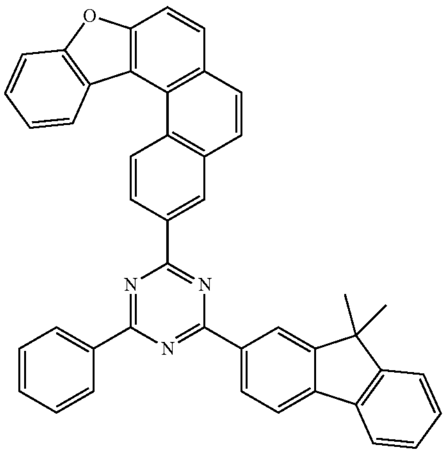

-continued
H2-23
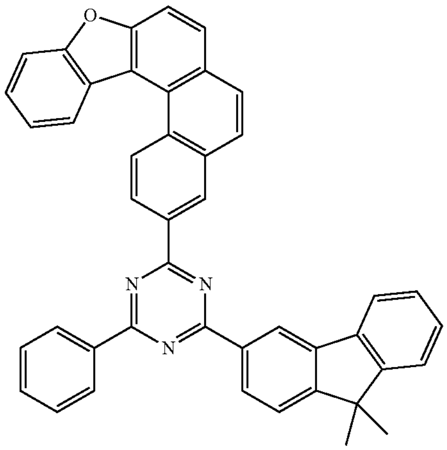
H2-24
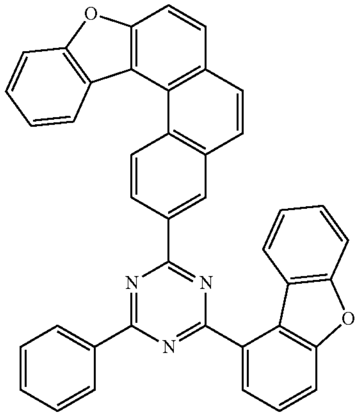
H2-25
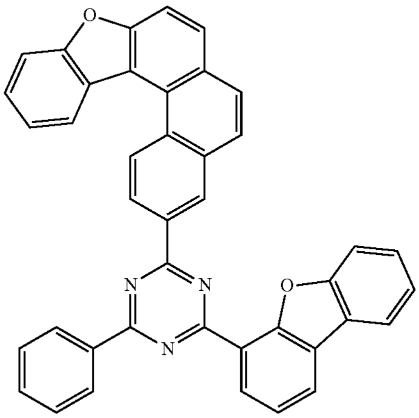
-continued
H2-26
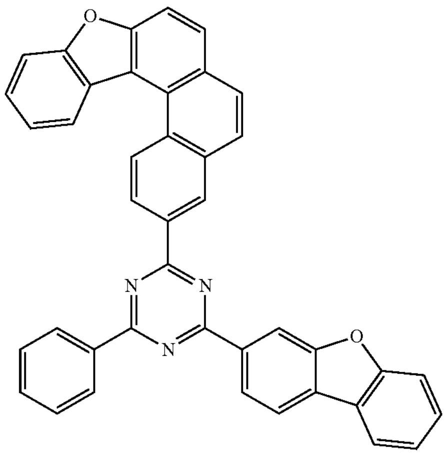
H2-27
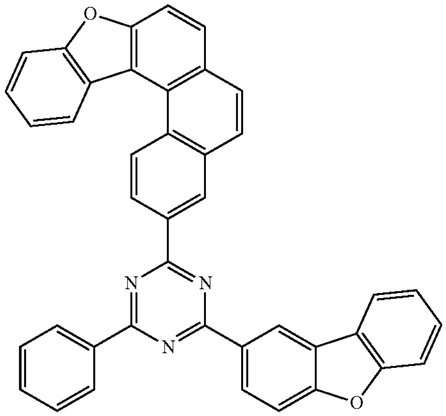
H2-28
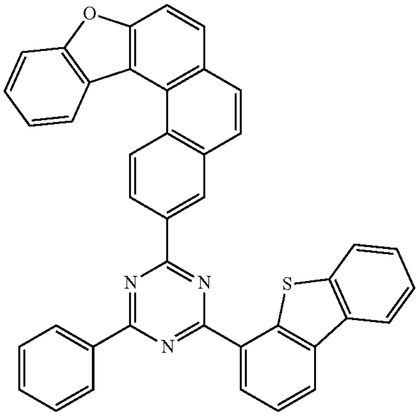

-continued
H2-29
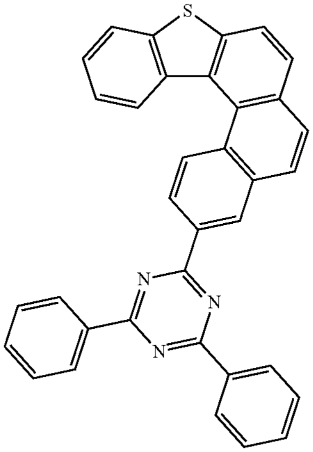
H2-30
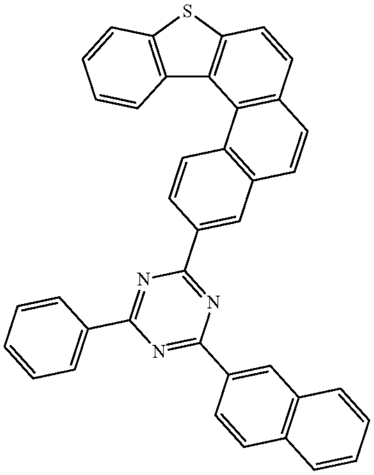
H2-31
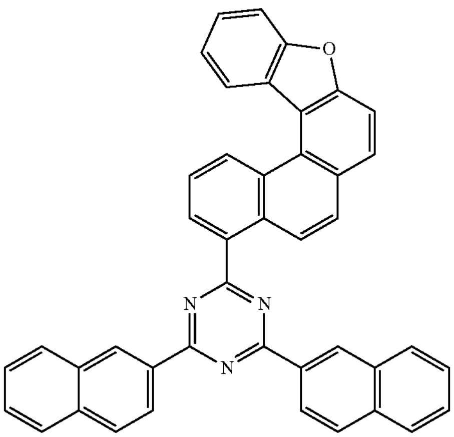
-continued
H2-32
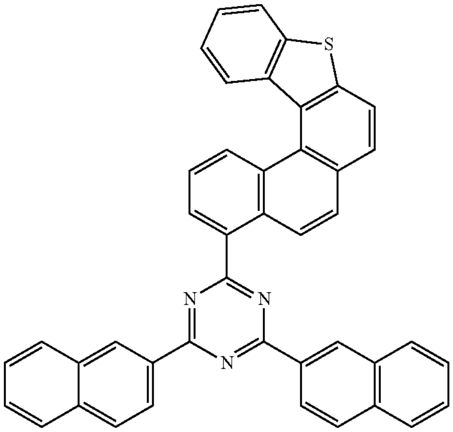
H2-33
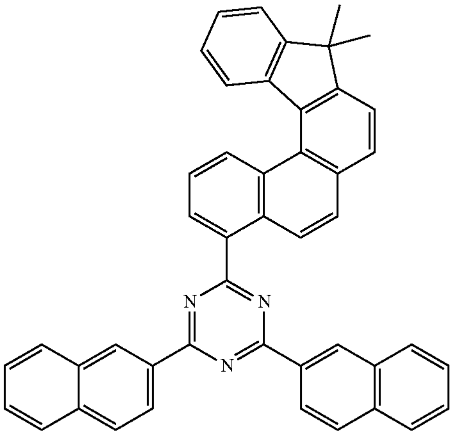
H2-34
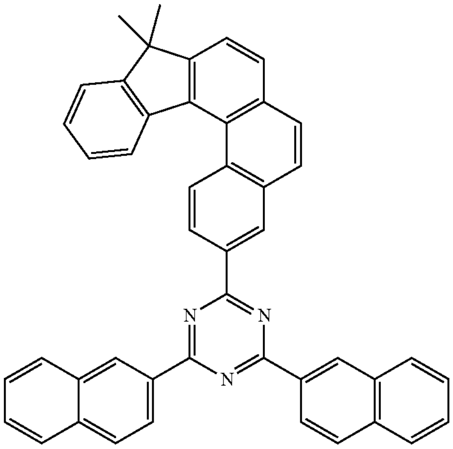

-continued
H2-35
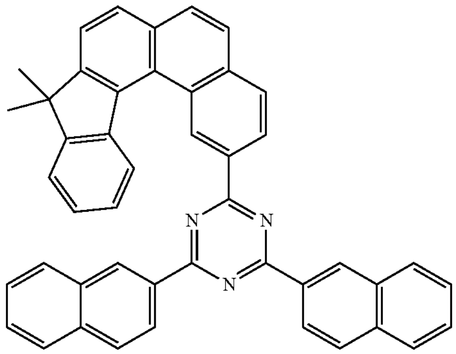
H2-36
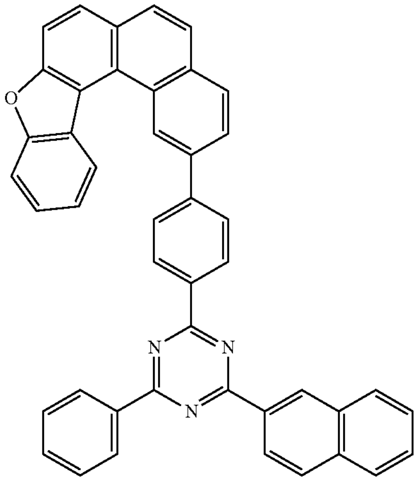
H2-37
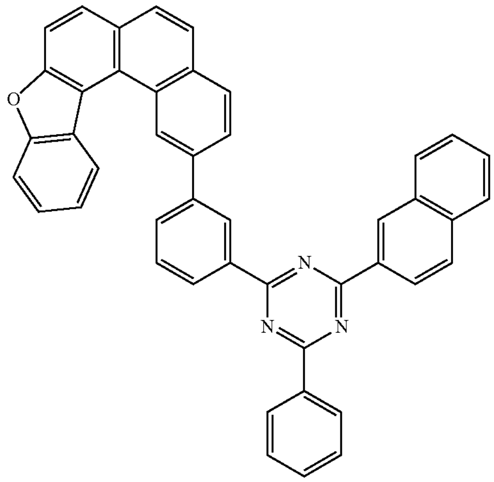
-continued
H2-38
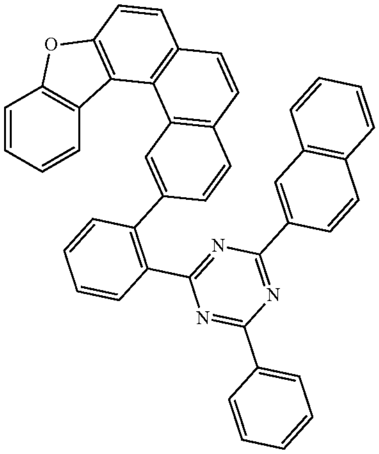
H2-39
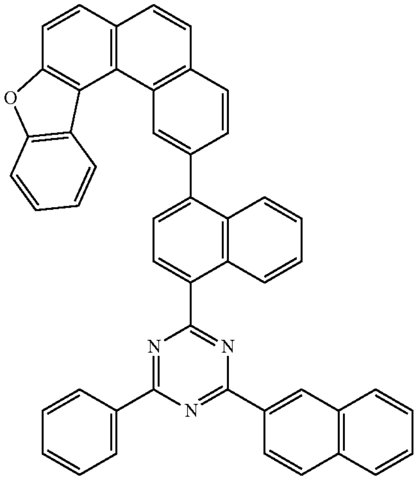
H2-40
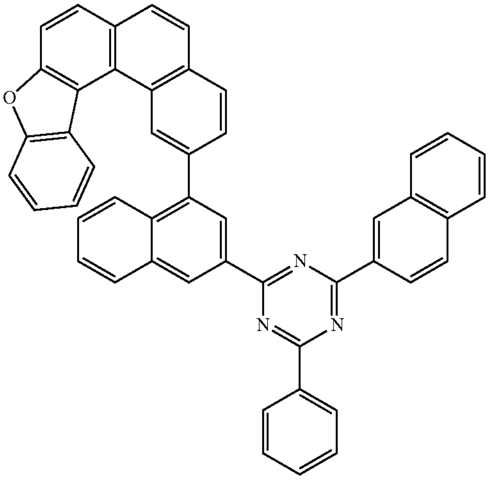

-continued
H2-41
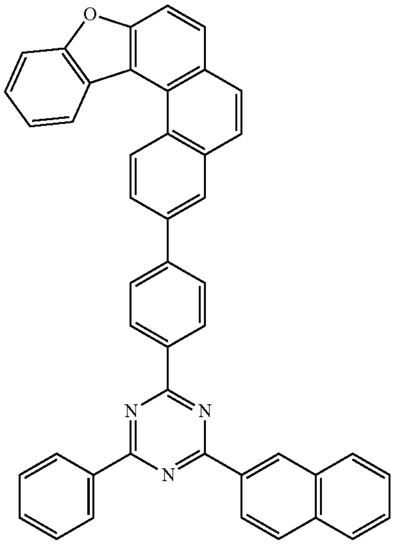
H2-42
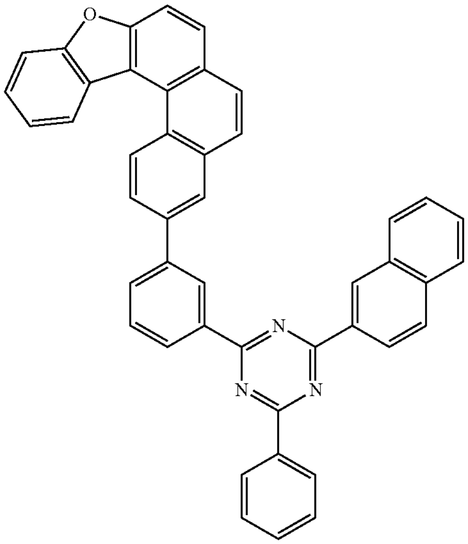
H2-43
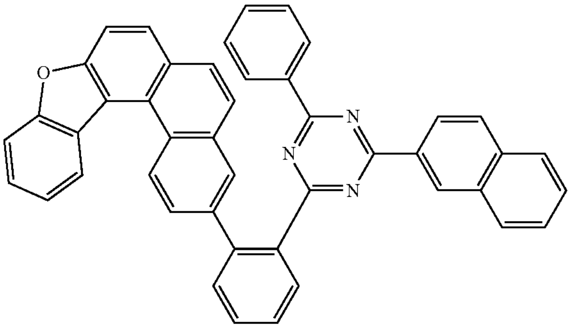
-continued
H2-44
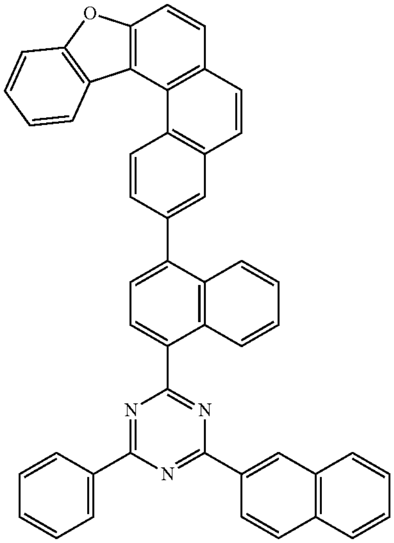
H2-45
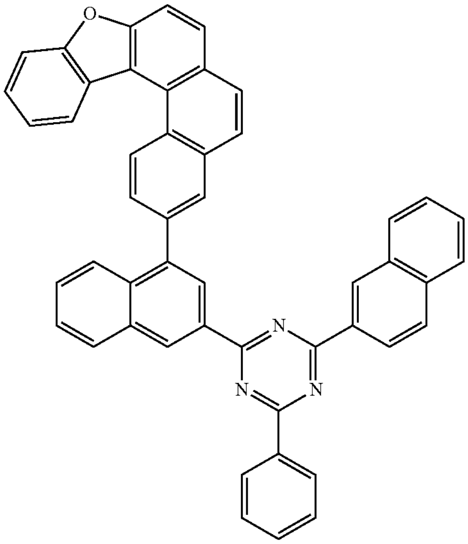
H2-46
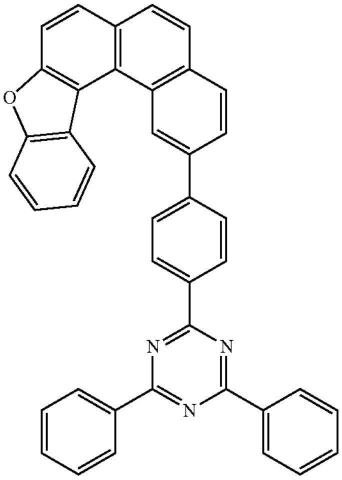

-continued
H2-47
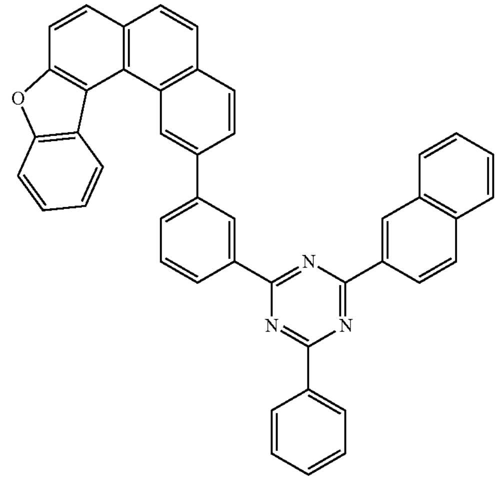
H2-48
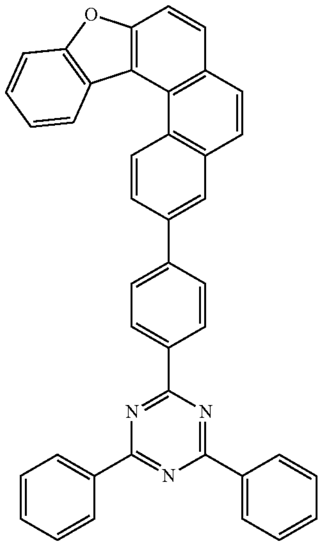
H2-49
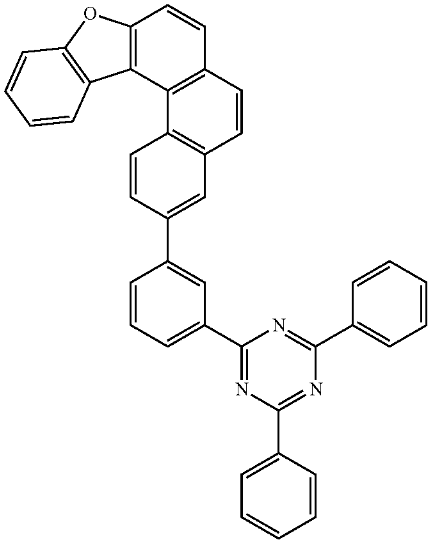
-continued
H2-50
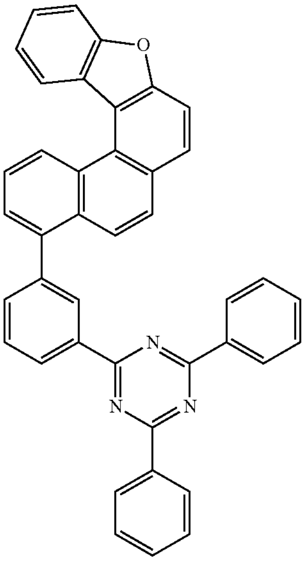
H2-51
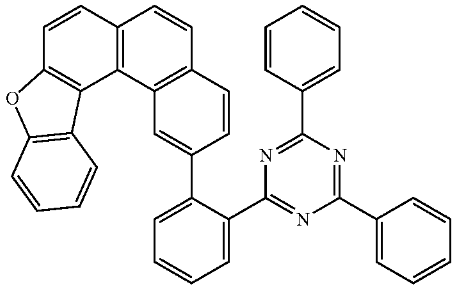
H2-52
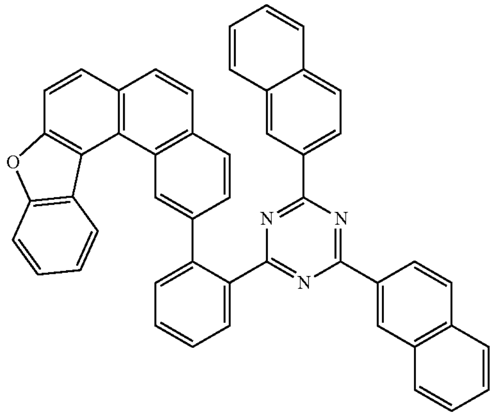

-continued
H2-53
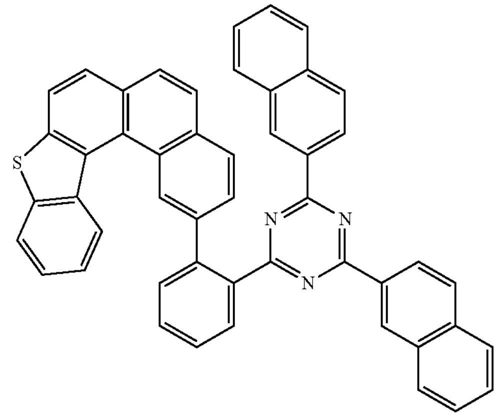
H2-54
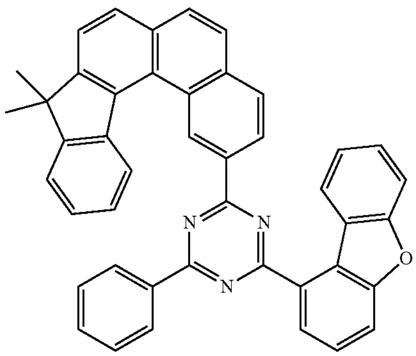
H2-55
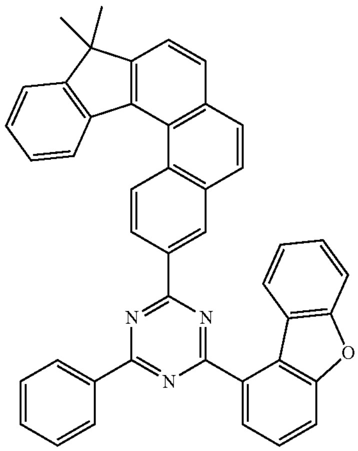
-continued
H2-56
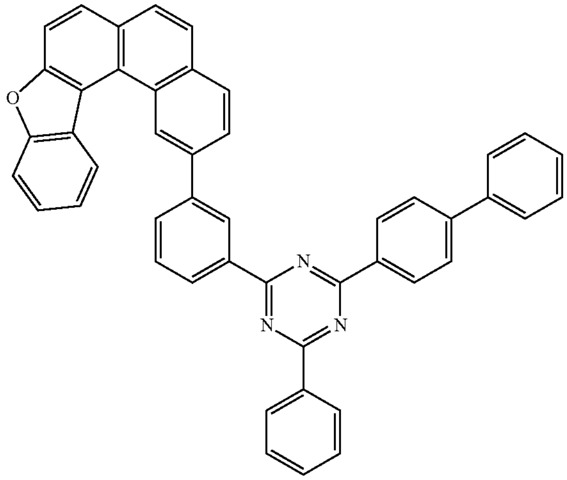
H2-57
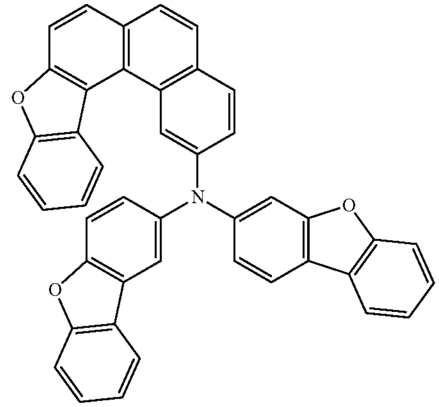
H2-58
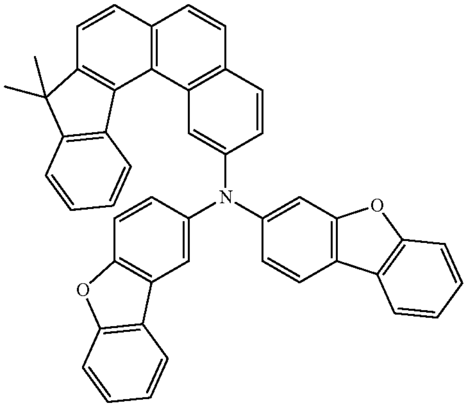

-continued
H2-59
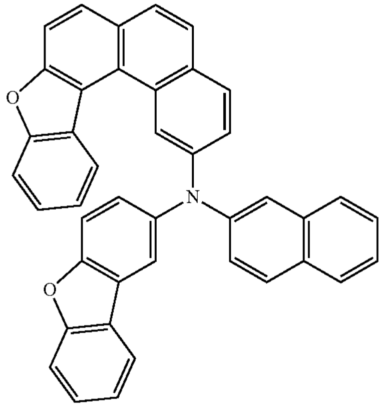
H2-60
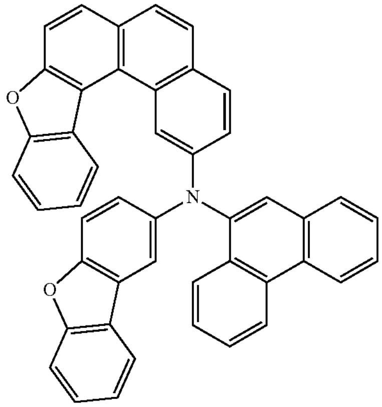
H2-61
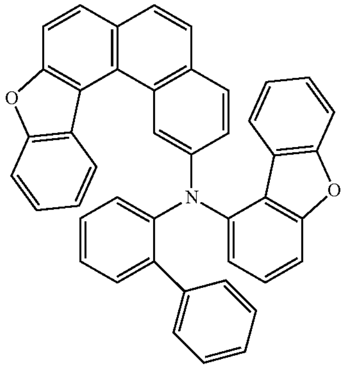
H2-62
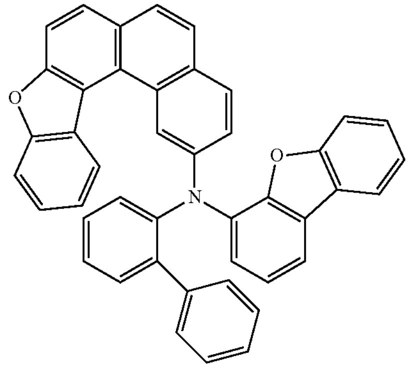
-continued
H2-63
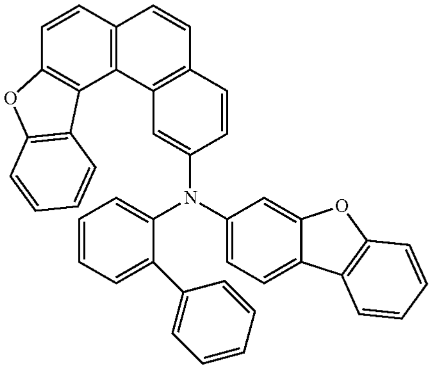
H2-64
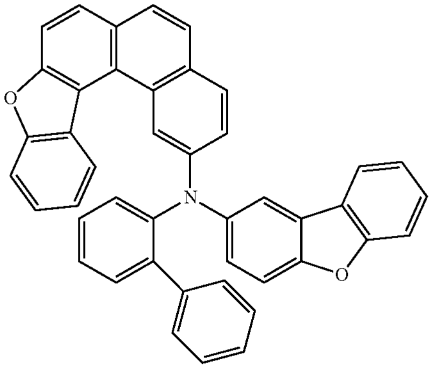
H2-65
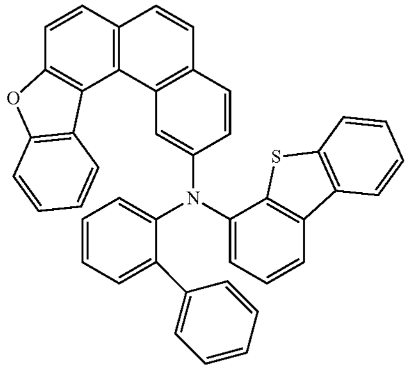
H2-66
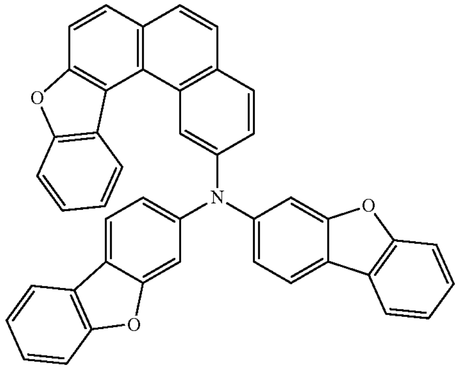

-continued
H2-67
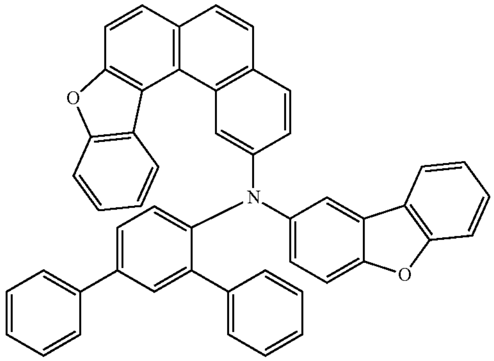
H2-68
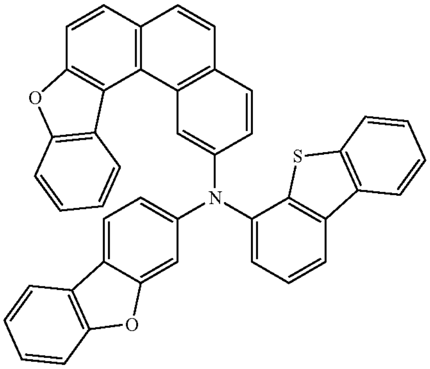
H2-69
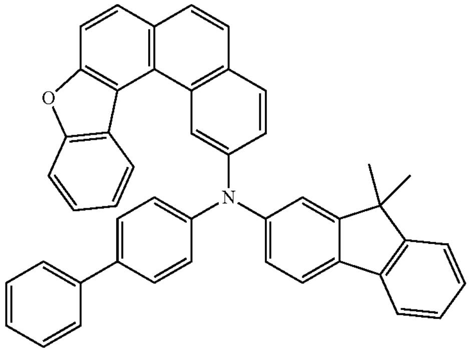
H2-70
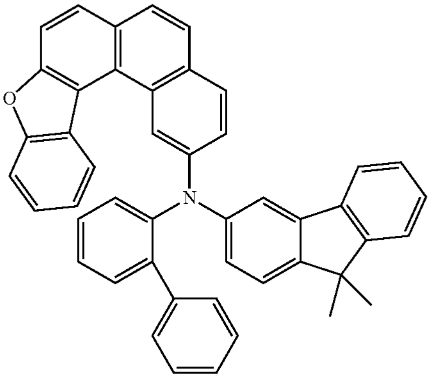
-continued
H2-71
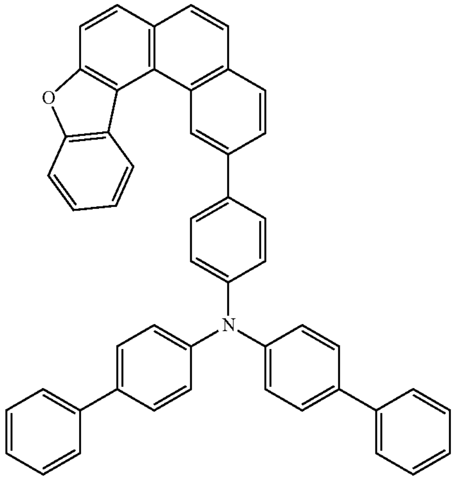
H2-72
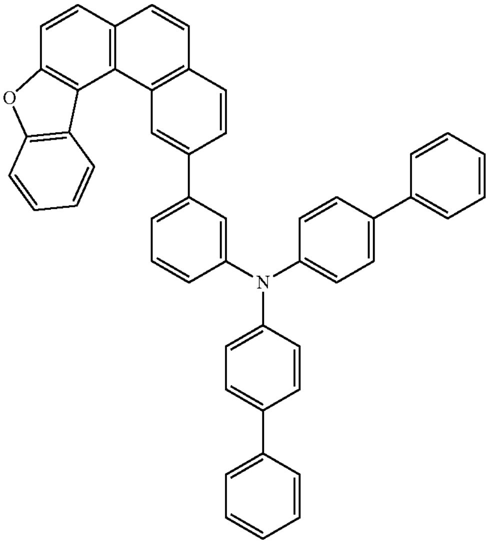
H2-73
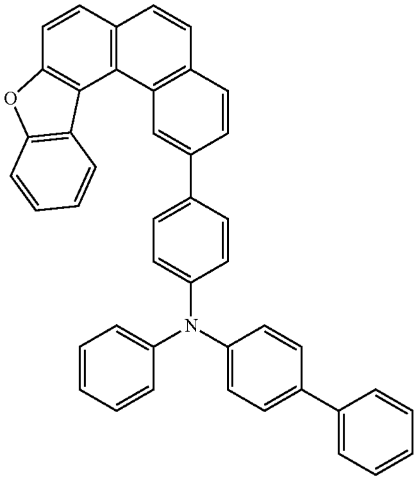

-continued
H2-74
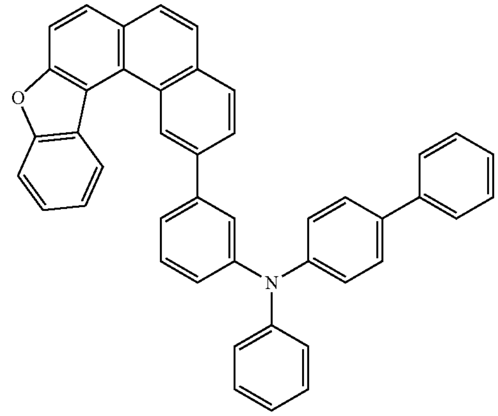
H2-75
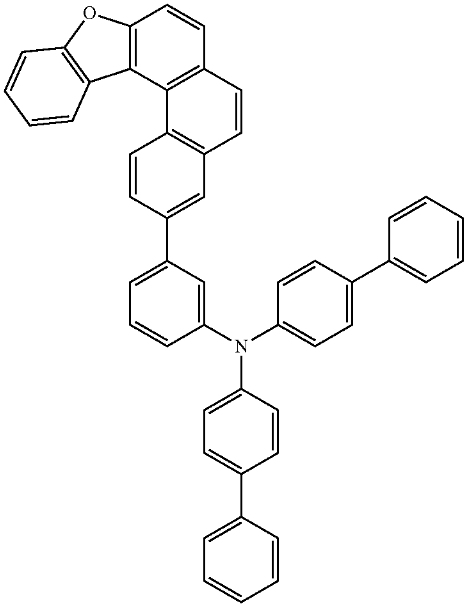
H2-76
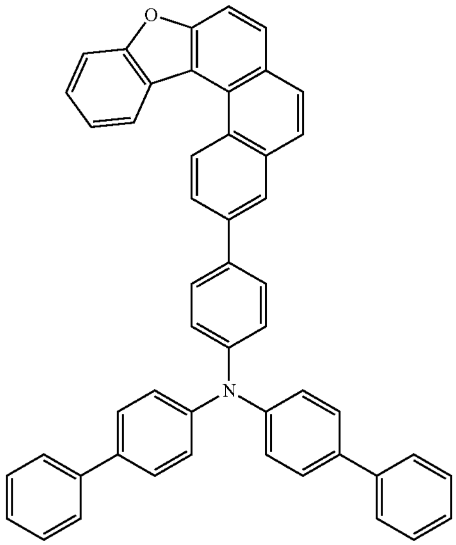
-continued
H2-77
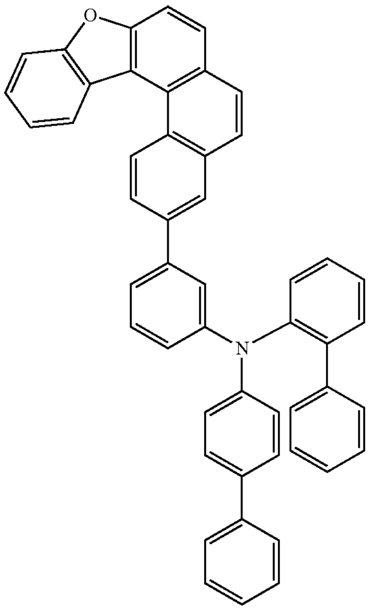
H2-78
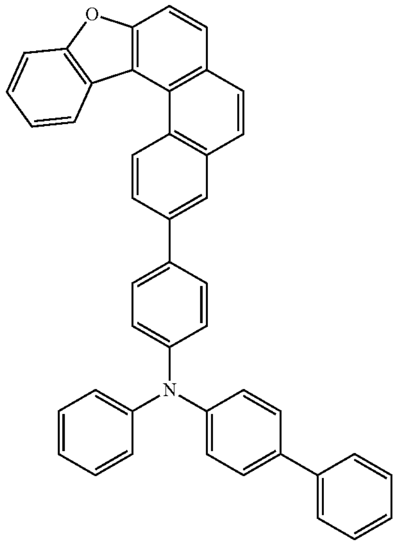
H2-79
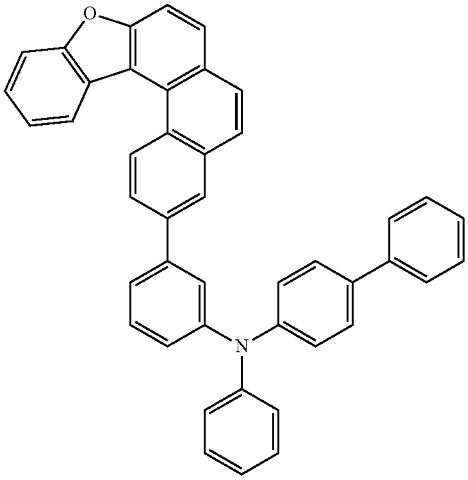

-continued
H2-80
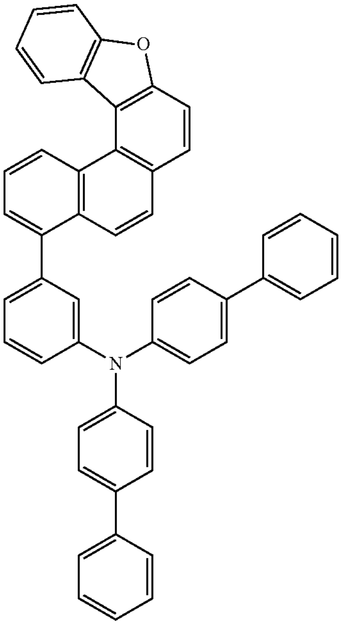
H2-81
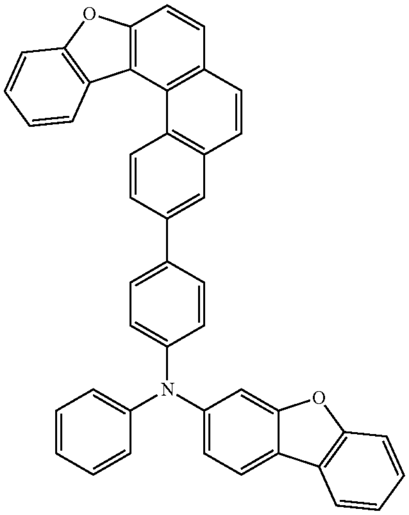
H2-82
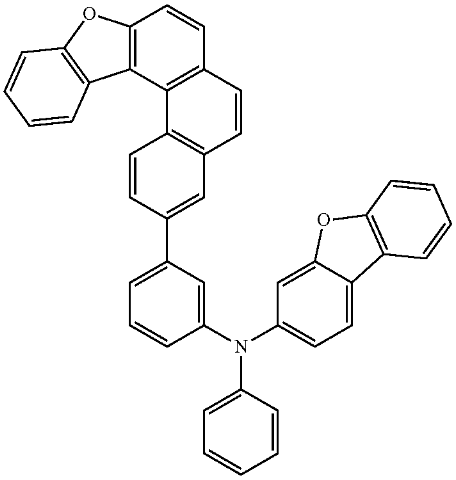
-continued
H2-83
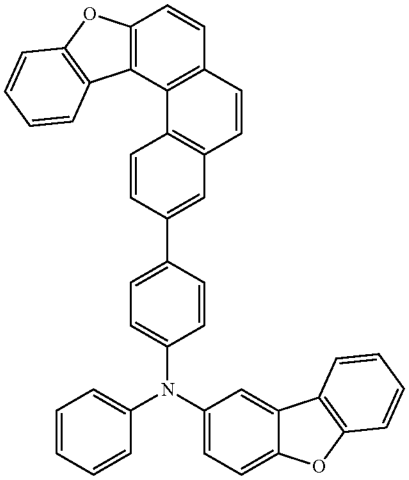
H2-84
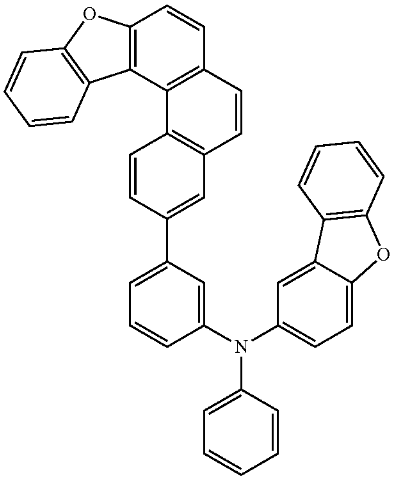
H2-85
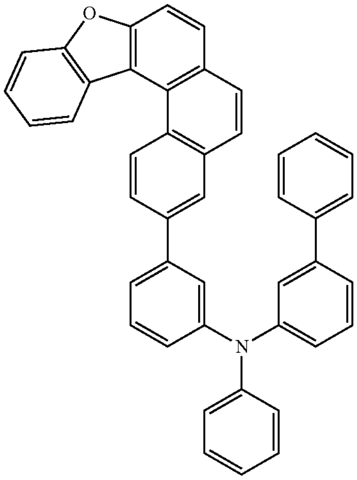

-continued
H2-86
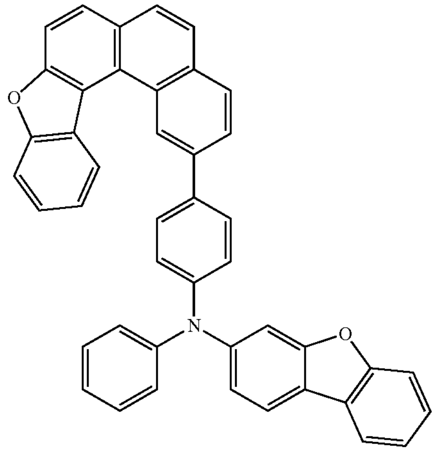
H2-87
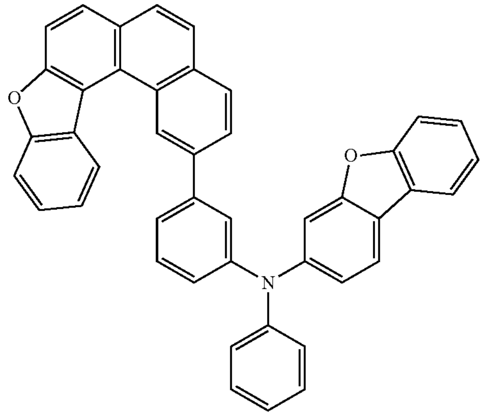
H2-88
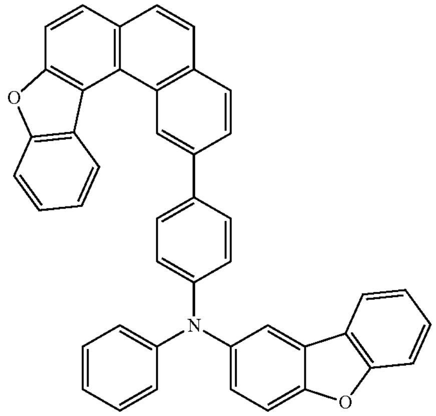
-continued
H2-89
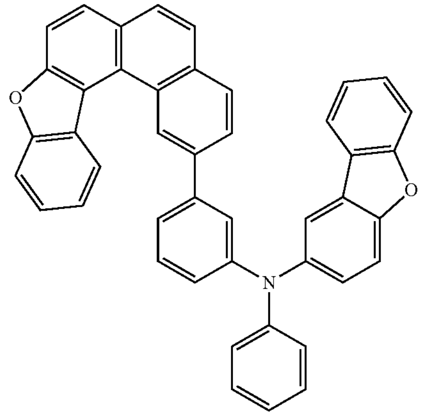
H2-90
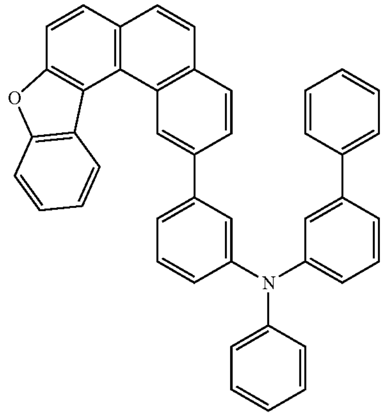
H2-91
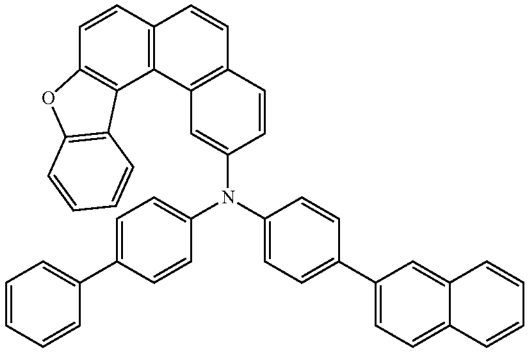
H2-92
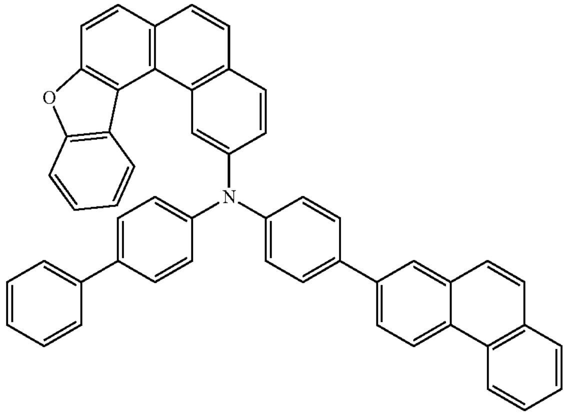

H2-93
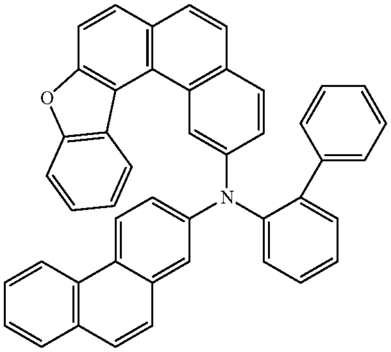
H2-94
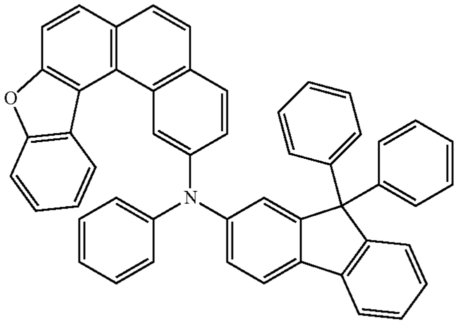
H2-95
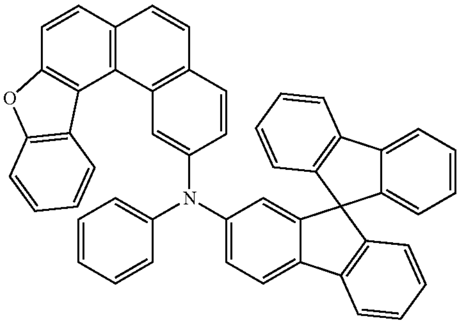
H2-96
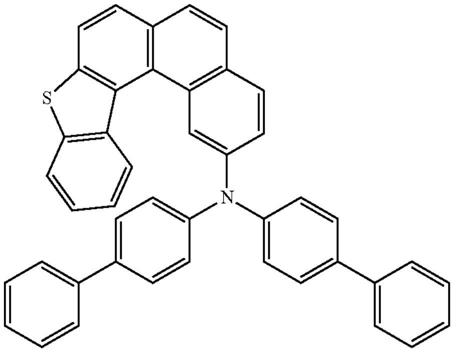
H2-97
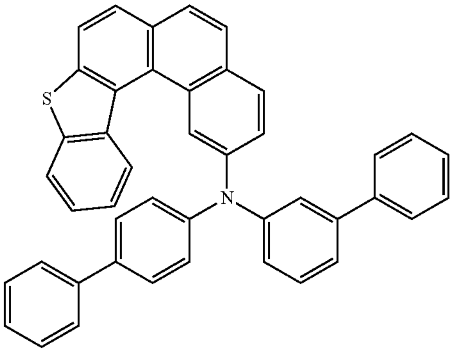
H2-98
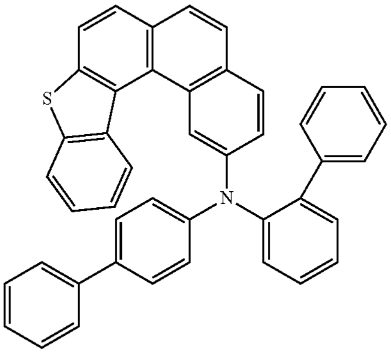
H2-99
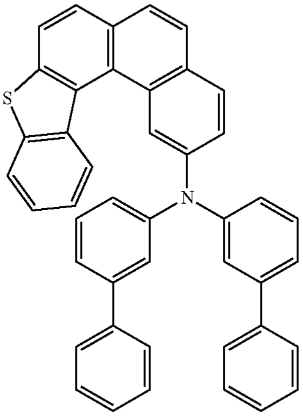
H2-100
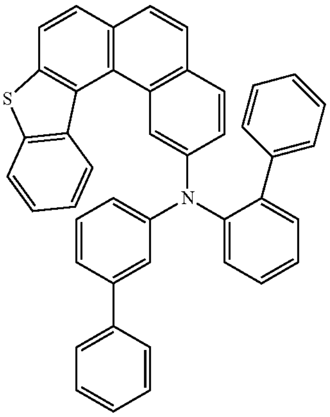

-continued
H2-101
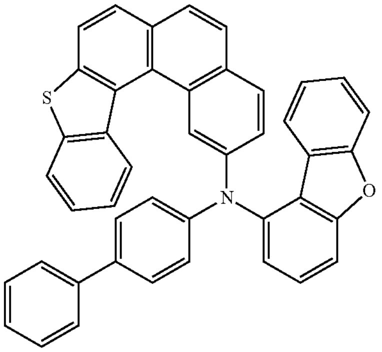
H2-102
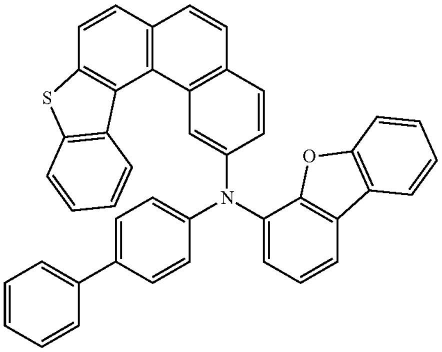
H2-103
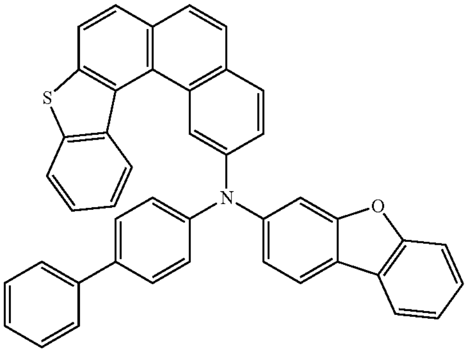
H2-104
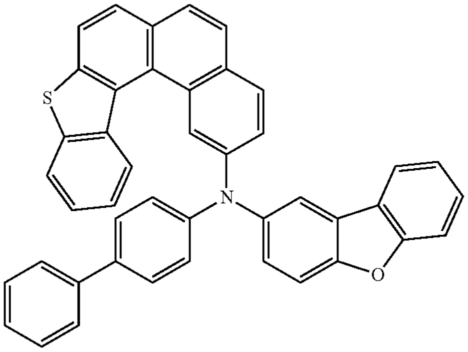
-continued
H2-105
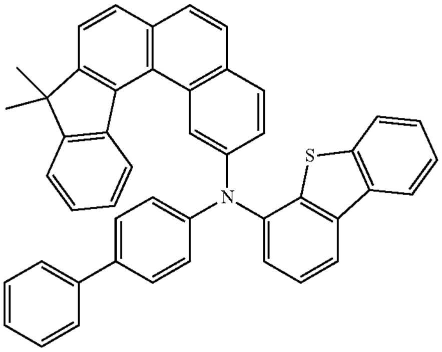
H2-106
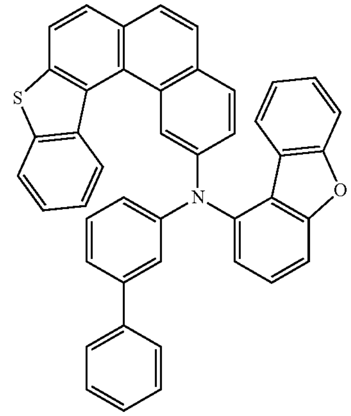
H2-107
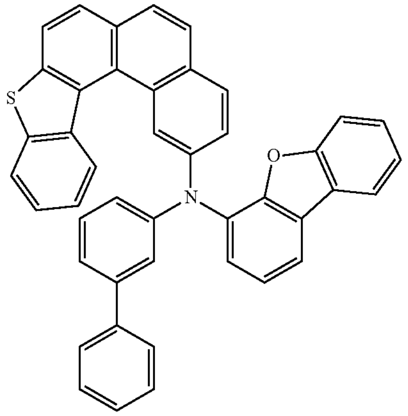
H2-108
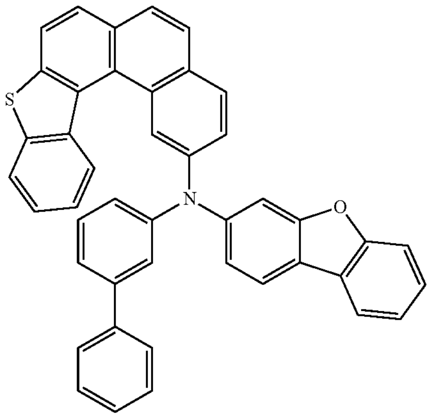

-continued
H2-109
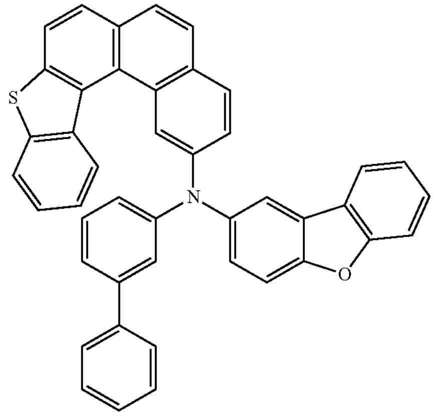
H2-110
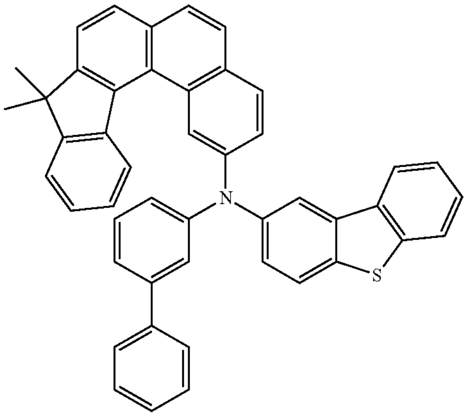
H2-111
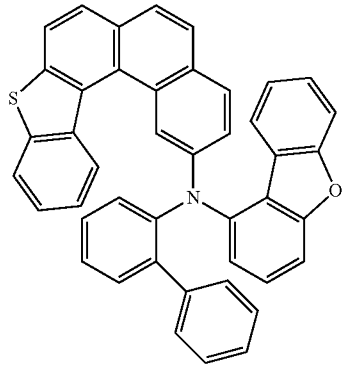
H2-112
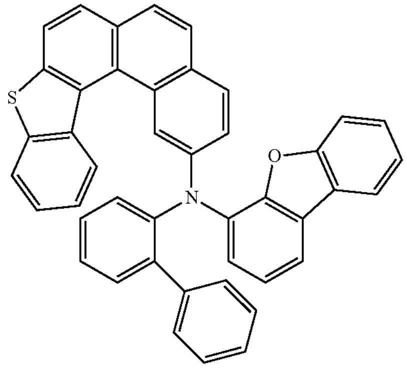
-continued
H2-113
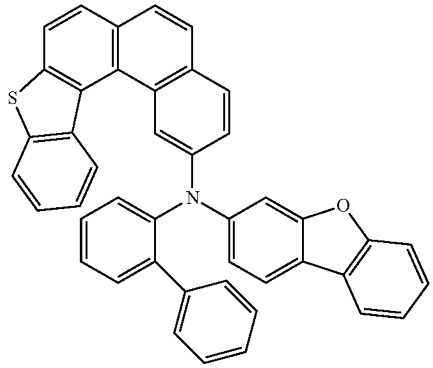
H2-114
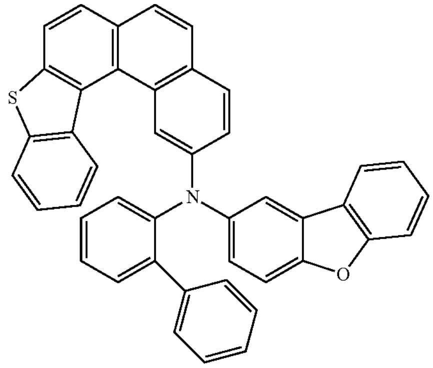
H2-115
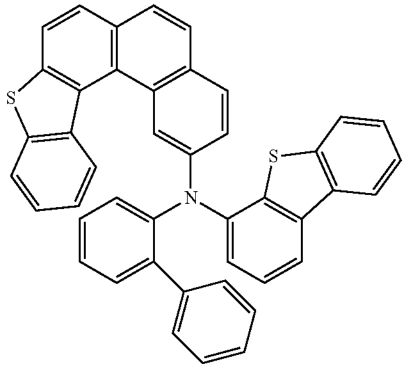
H2-116
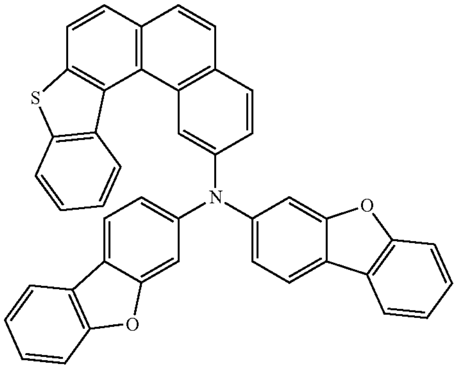

-continued
H2-117
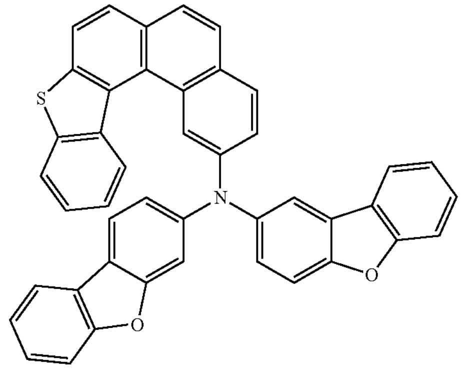
H2-118
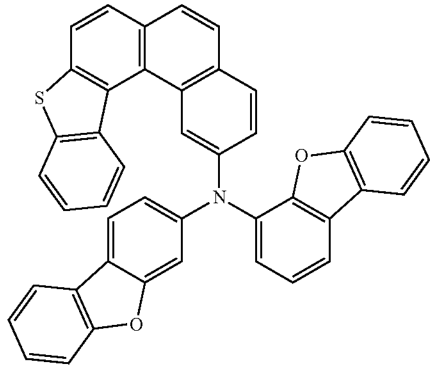
H2-119
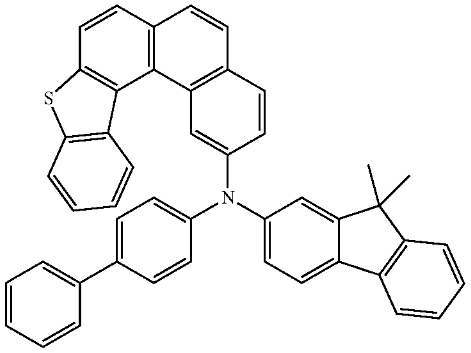
H2-120
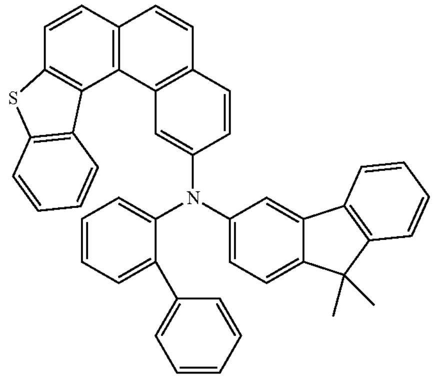
-continued
H2-121
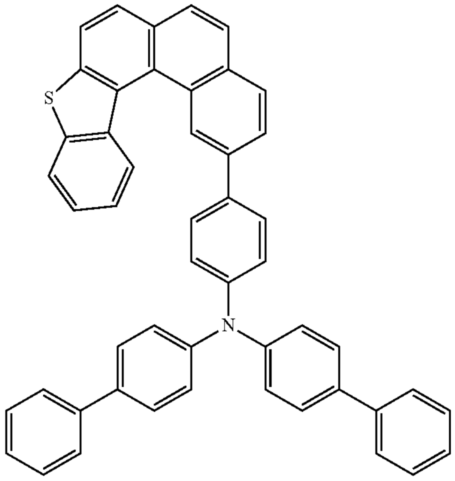
H2-122
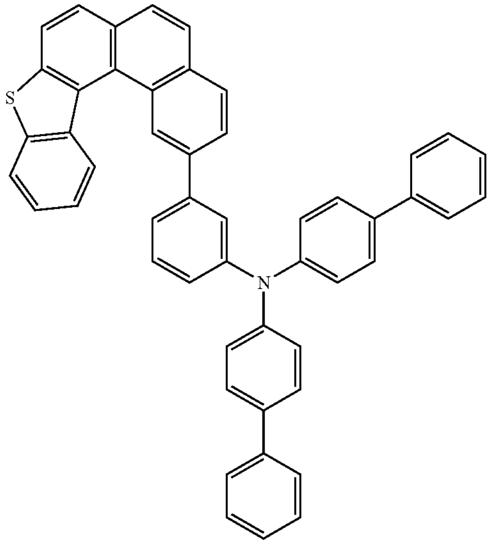
H2-123
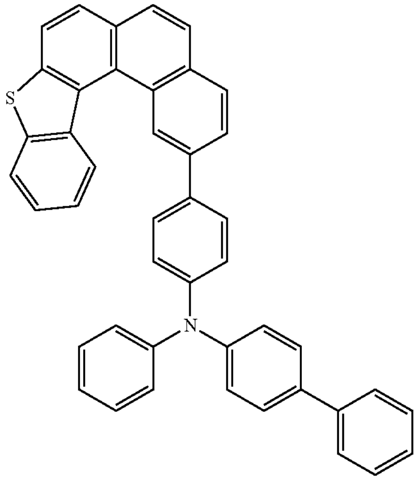

-continued
H2-124
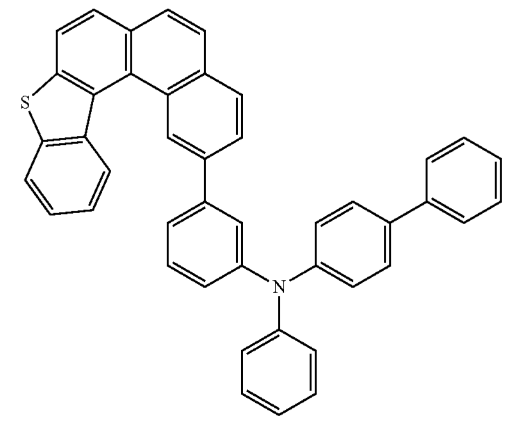
H2-125
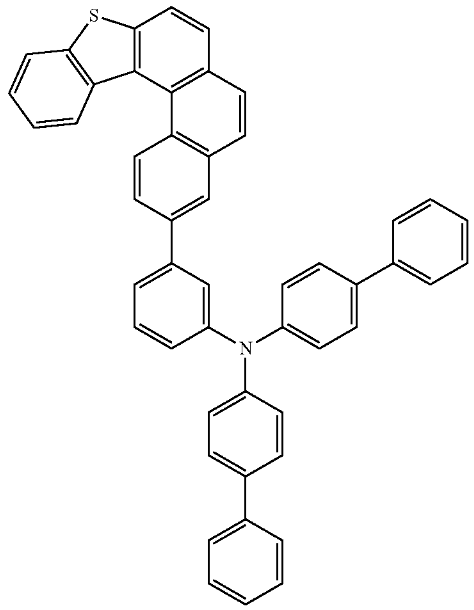
H2-126
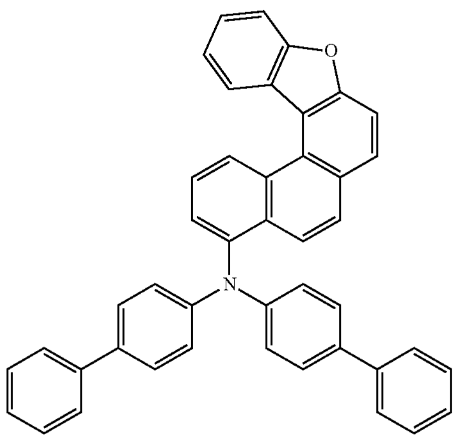
-continued
H2-127
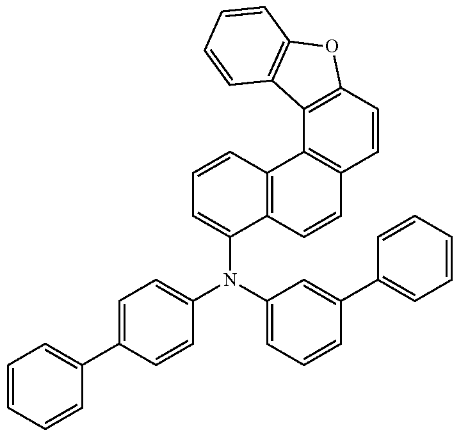
H2-128
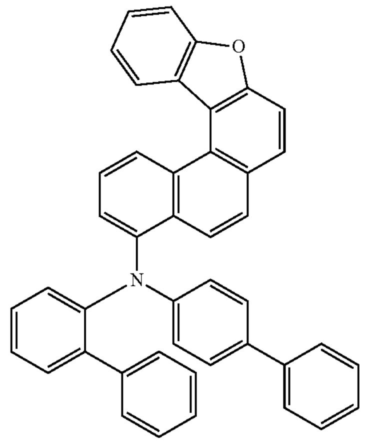
H2-129
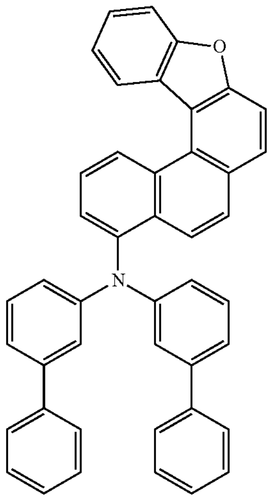

-continued
H2-130
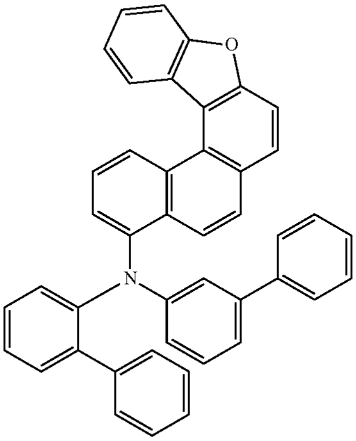
H2-131
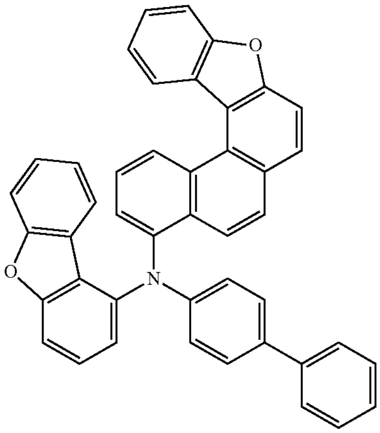
H2-132
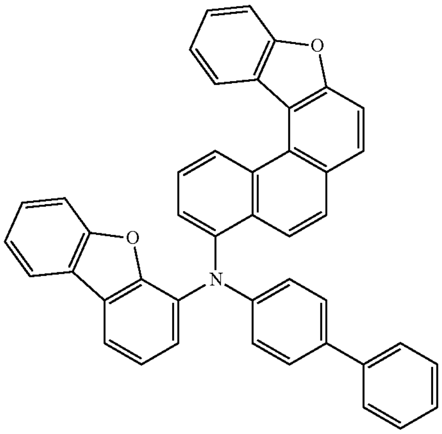
-continued
H2-133
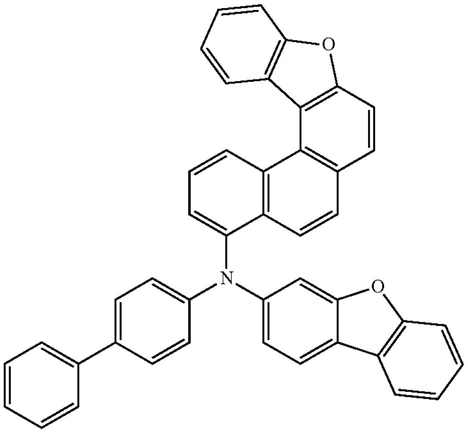
H2-134
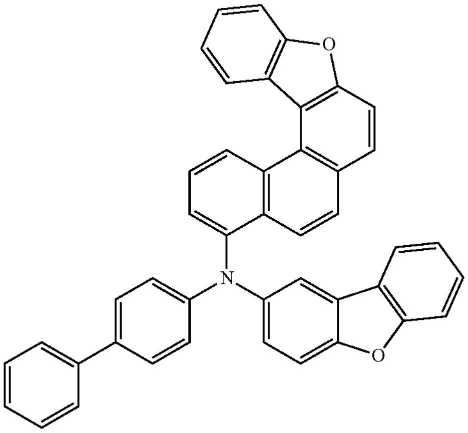
H2-135
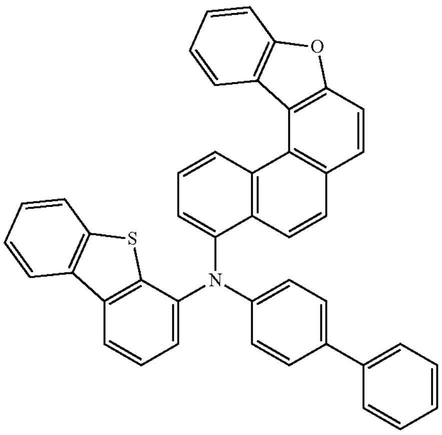

-continued
H2-136
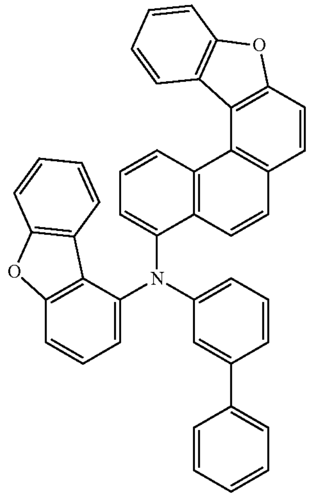
H2-137
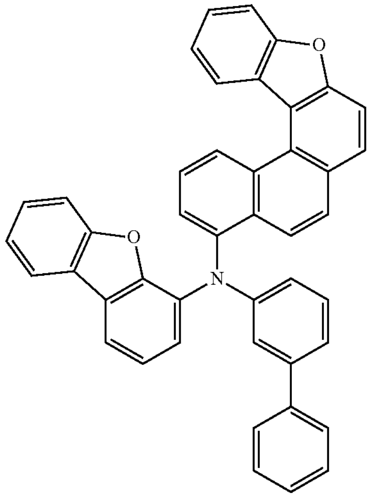
H2-138
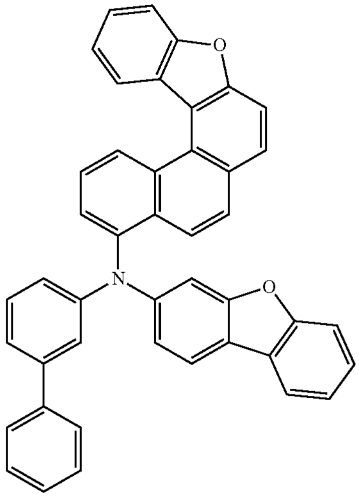
-continued
H2-139
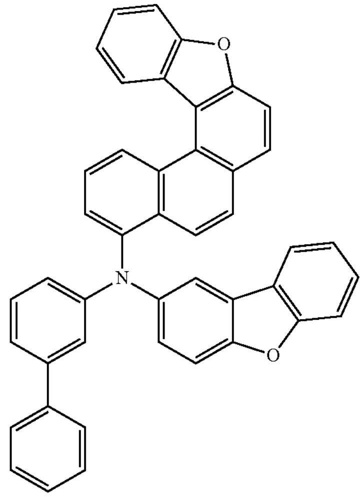
H2-140
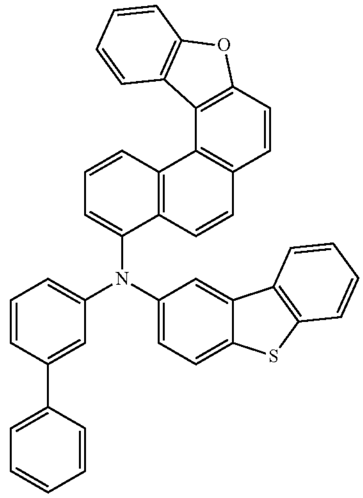
H2-141
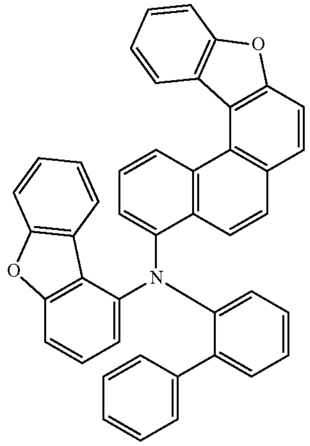

H2-142
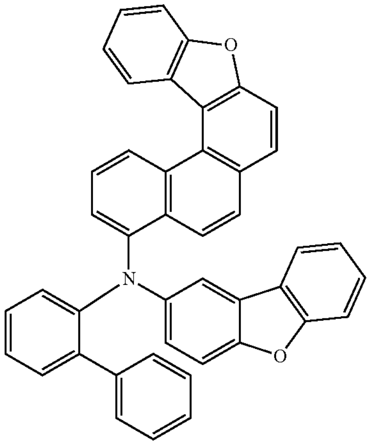
H2-143
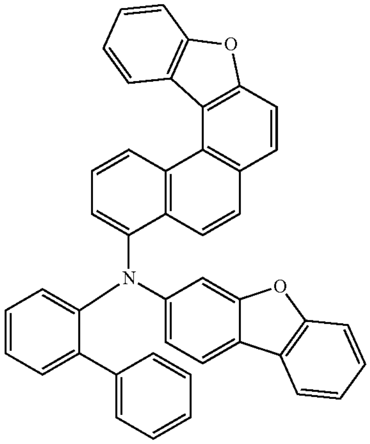
H2-144
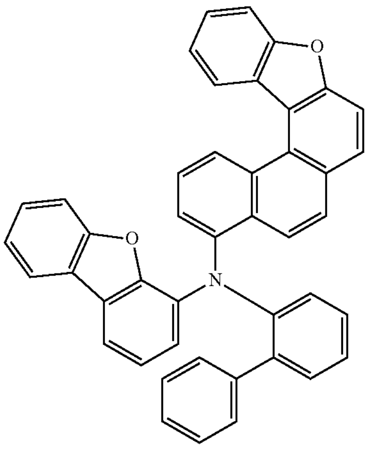
H2-145
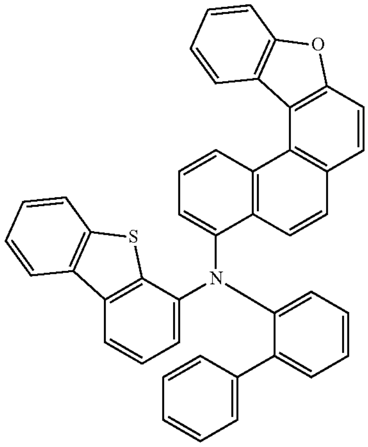
H2-146
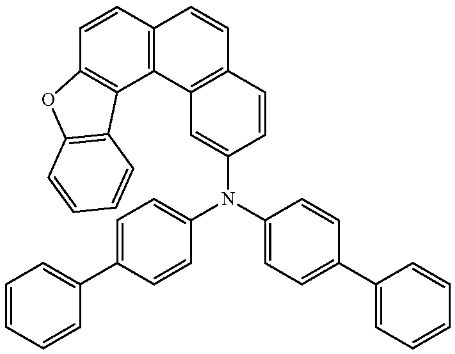
H2-147
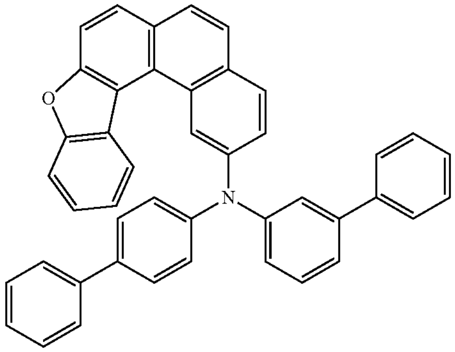
H2-148
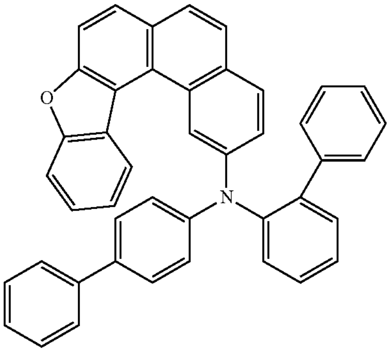

-continued
H2-149
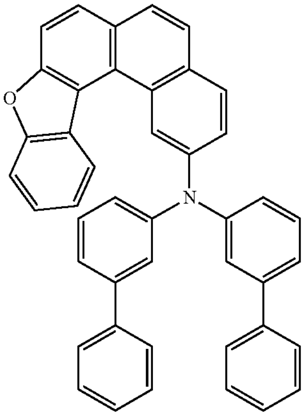
H2-150
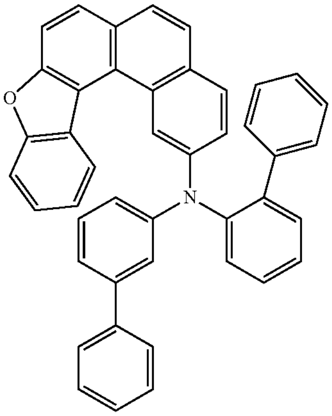
H2-151
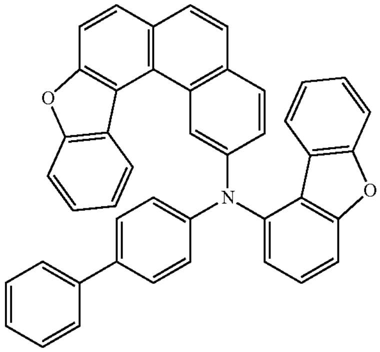
H2-152
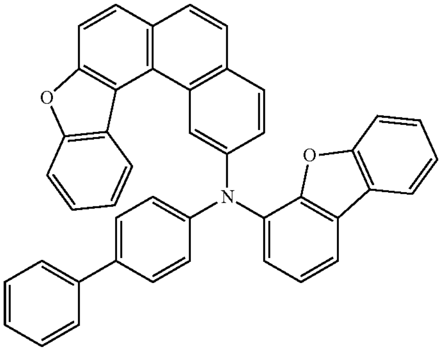
-continued
H12-153
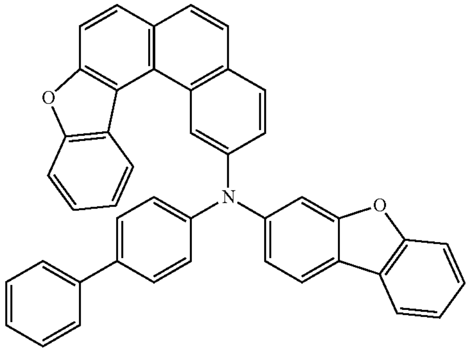
H2-154
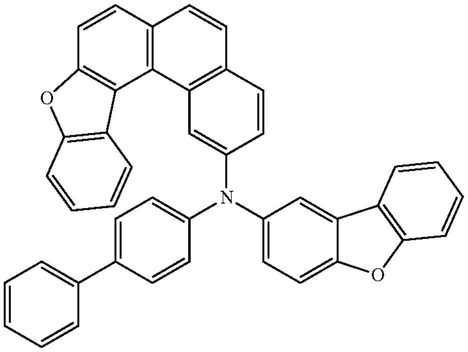
H2-155
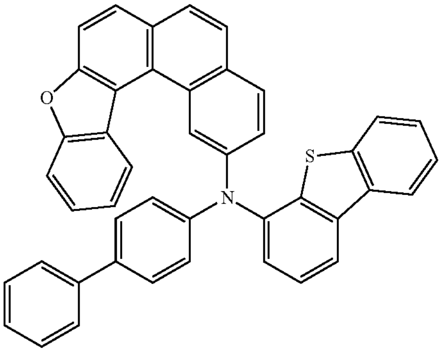
H2-156
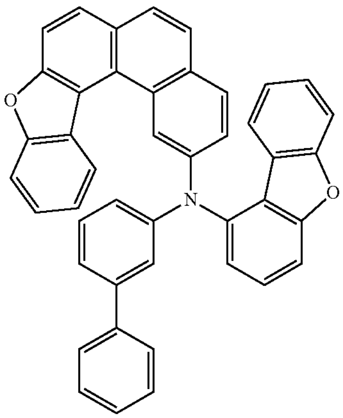

-continued
H2-157
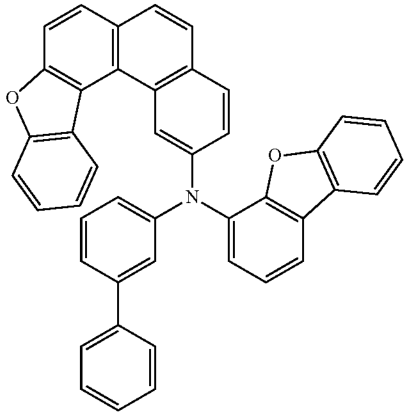
H2-158
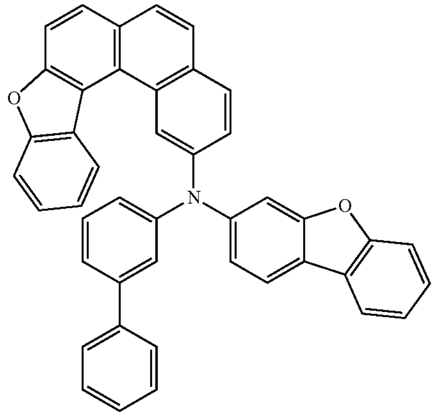
H2-159
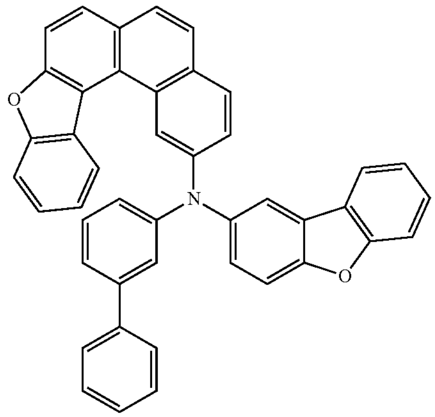
-continued
H2-160
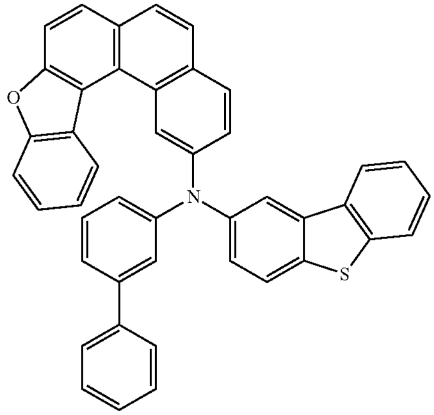
H2-161
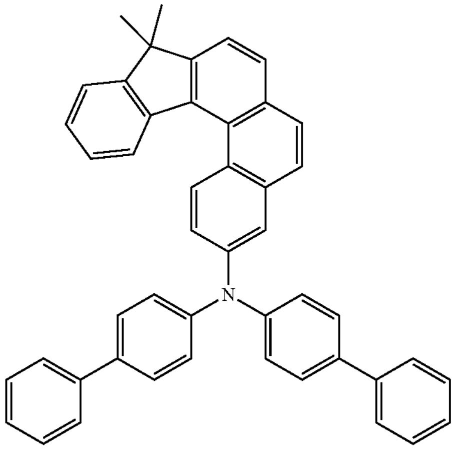
H2-162
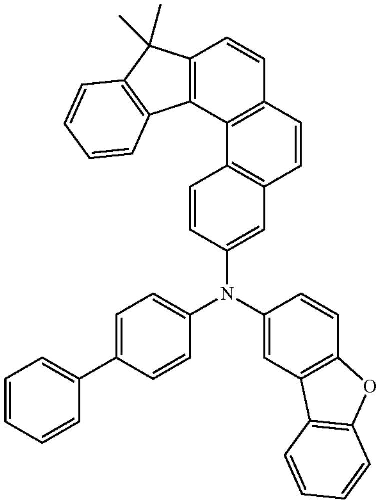

-continued
H2-163
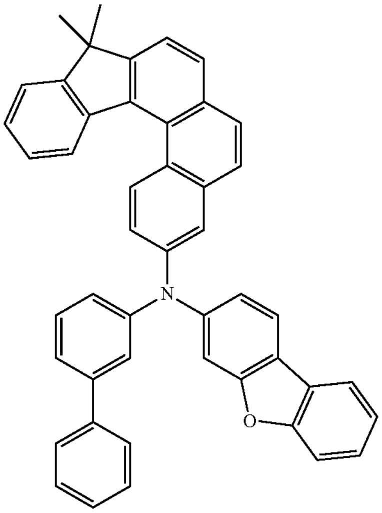
H2-164
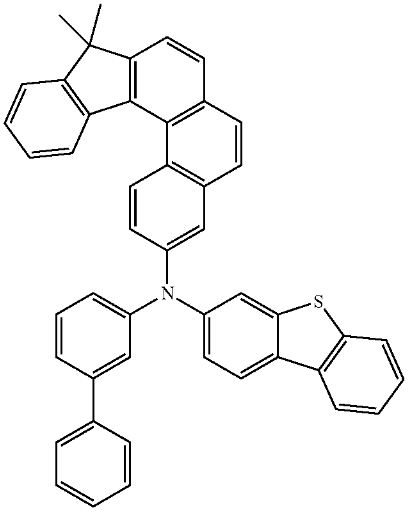
H2-165
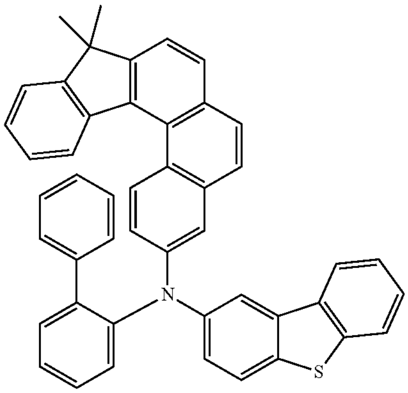
-continued
H2-166
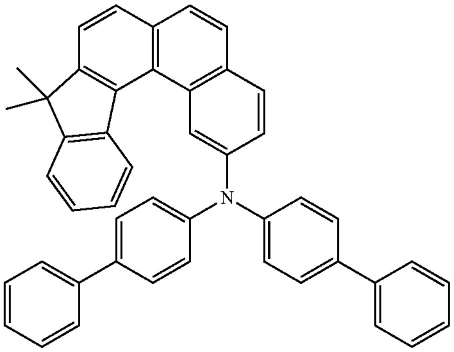
H2-167
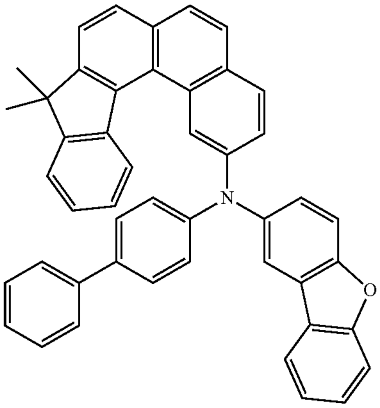
H2-168
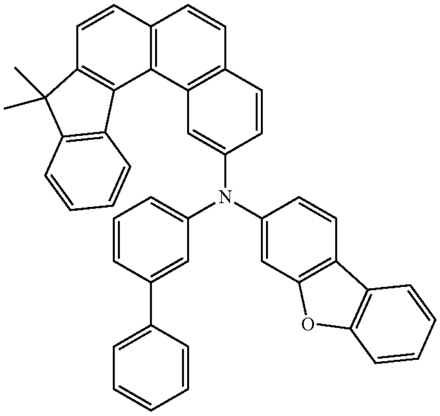
H2-169
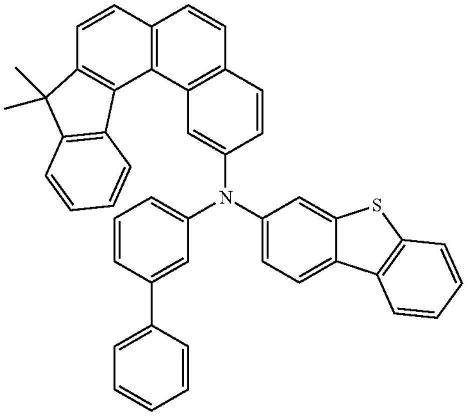

-continued
H2-170
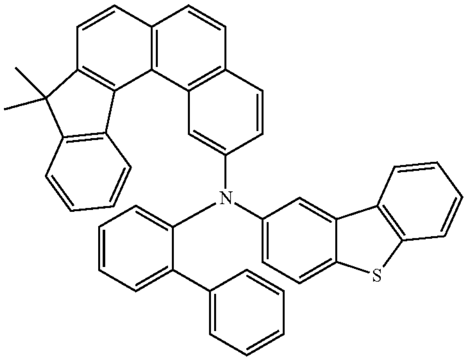
H2-171
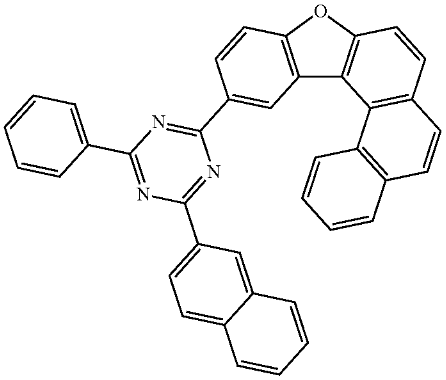
H2-172
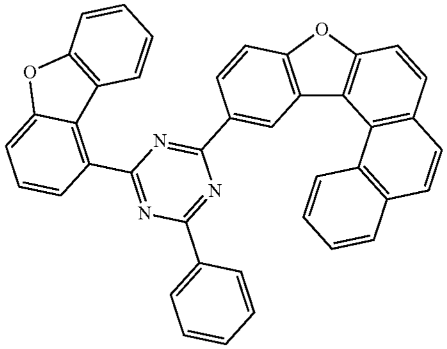
H2-173
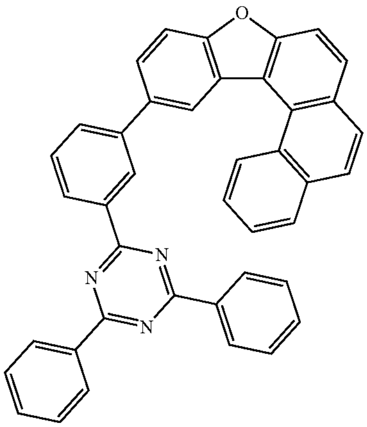
-continued
H2-174
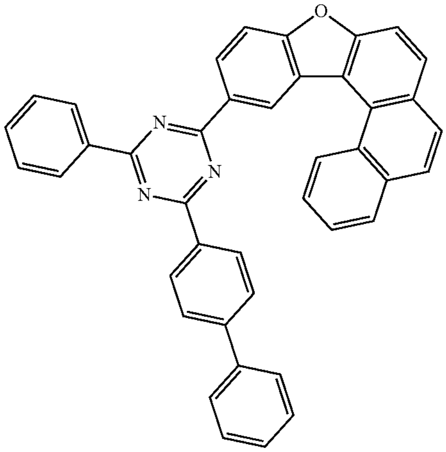
H2-175
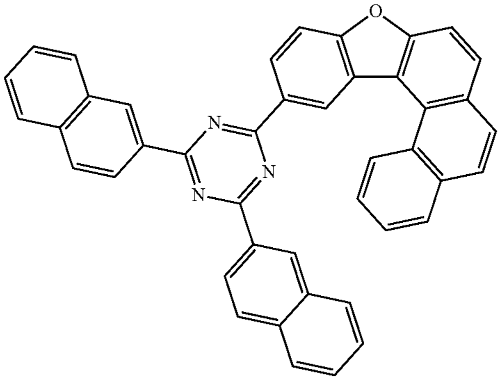
H2-176
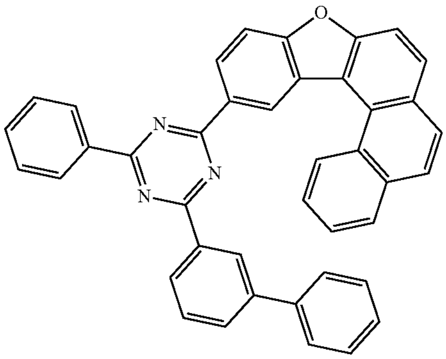

-continued
H2-177
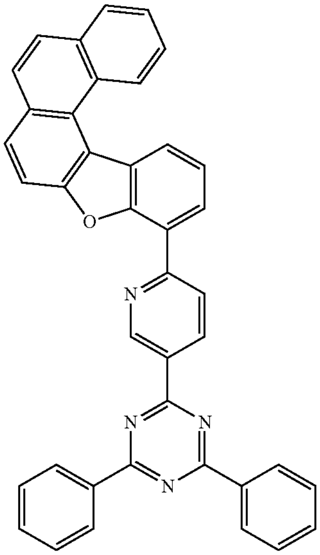
H2-178
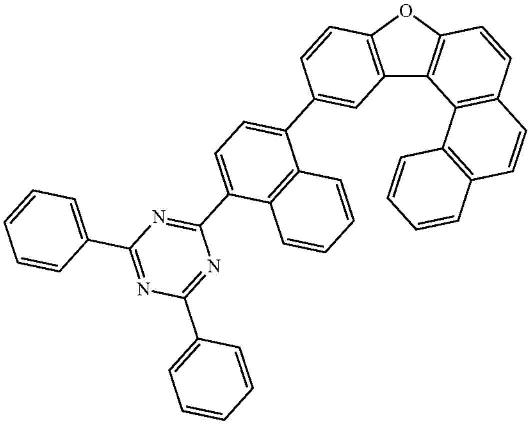
H2-179
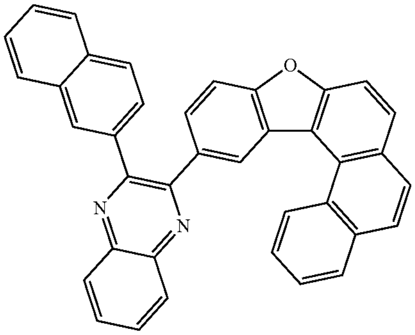
-continued
H2-180
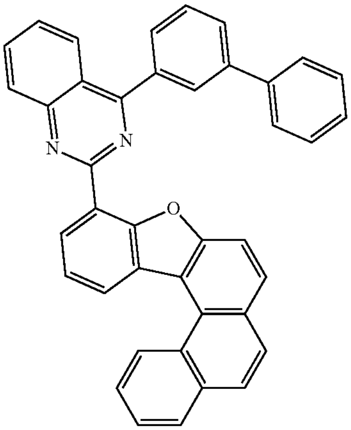
H2-181
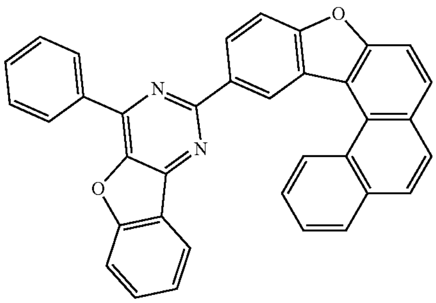
H2-182
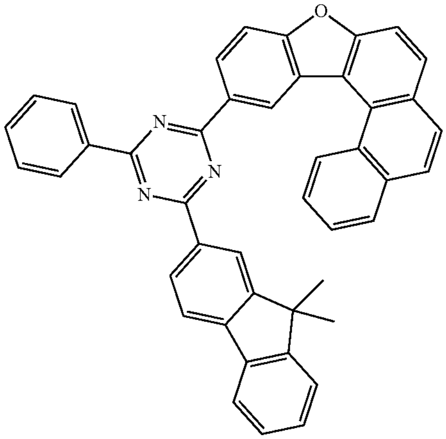
H2-183
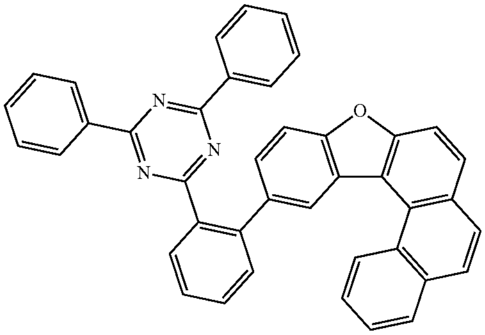

-continued
H2-184
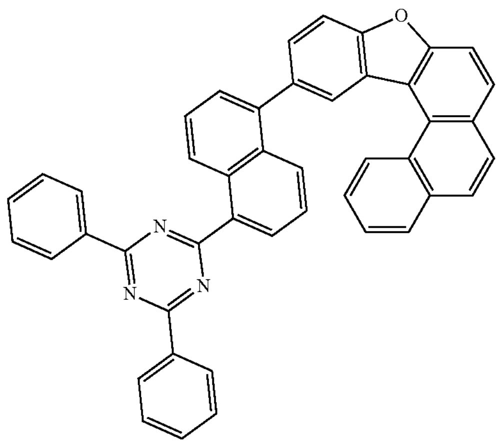
H2-185
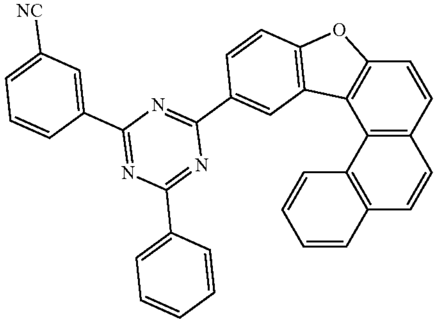
H2-186
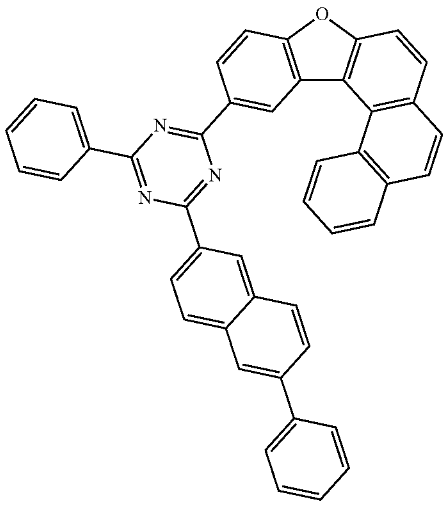
-continued
H2-187
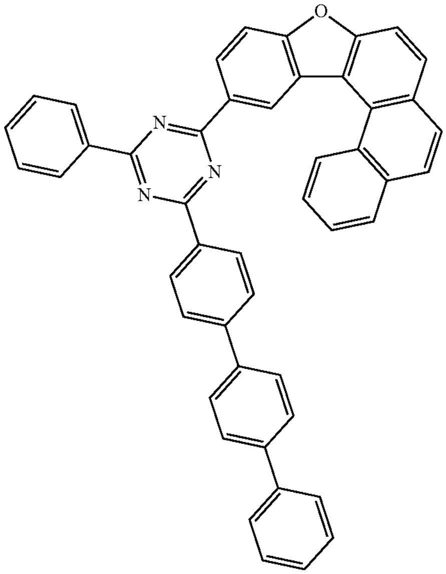
H2-188
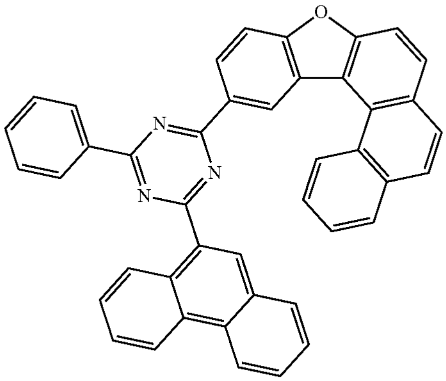
H2-189
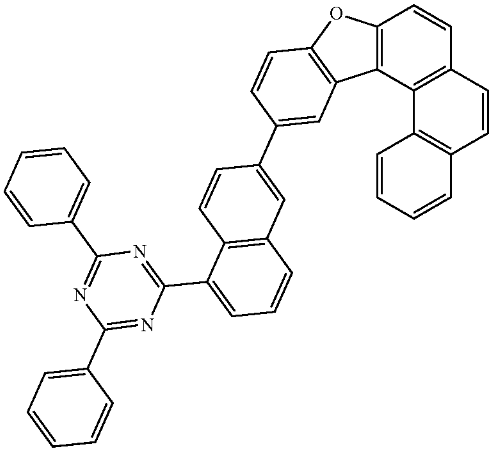

-continued
H2-190
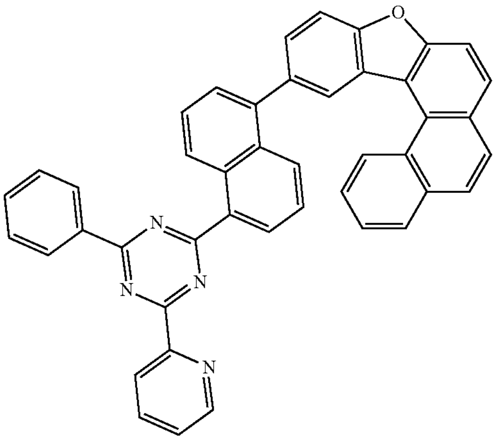
H2-191
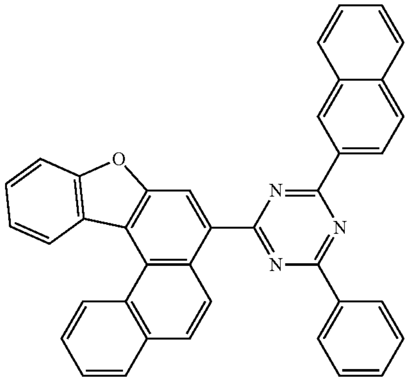
H2-192
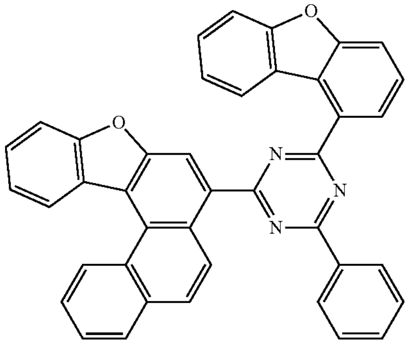
H2-193
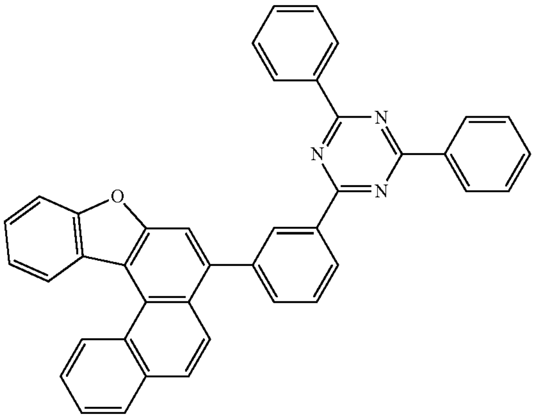
-continued
H2-194
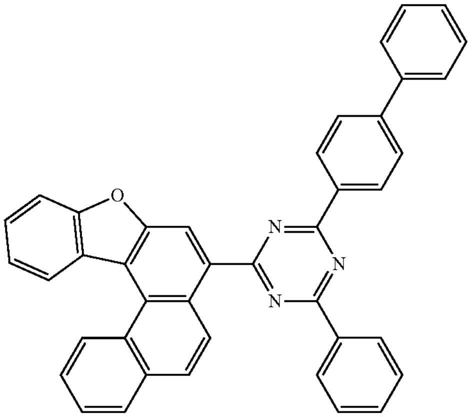
H2-195
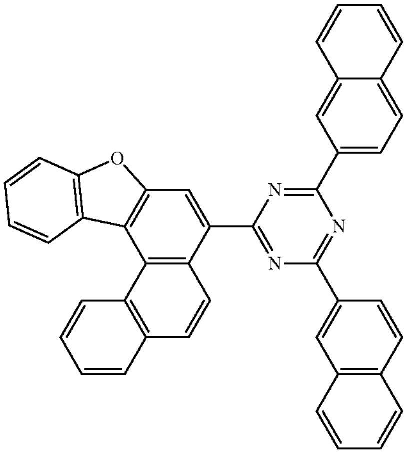
H2-196
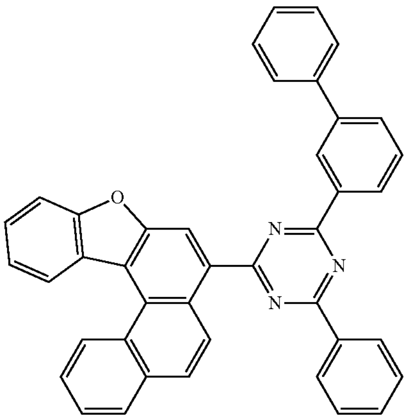

-continued
H2-197
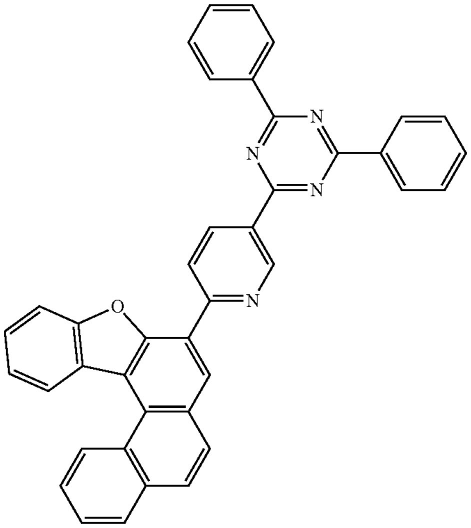
H2-198
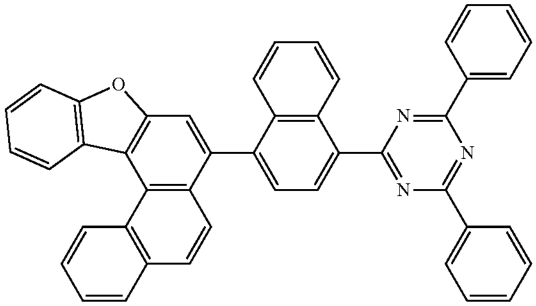
H2-199
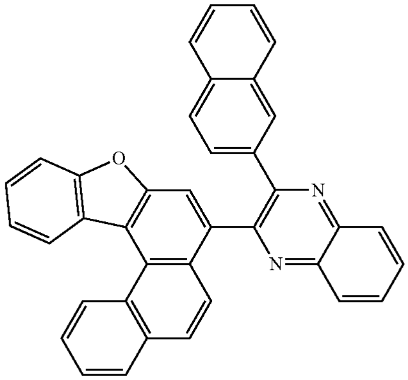
H2-200
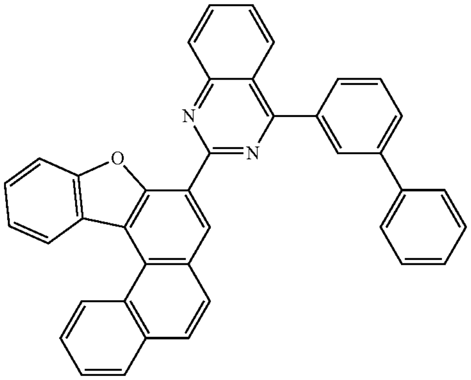
-continued
H2-201
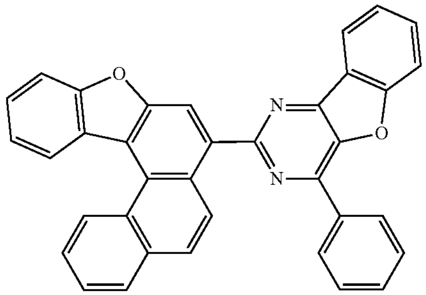
H2-202
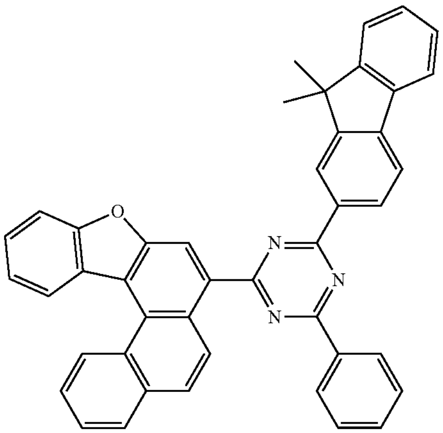
H2-203
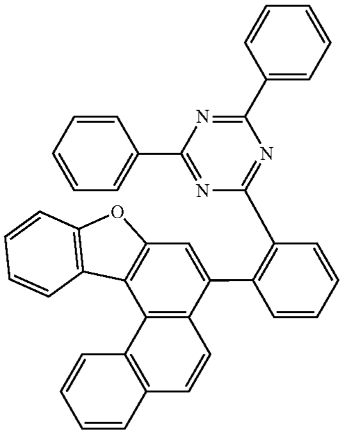

-continued
H2-204
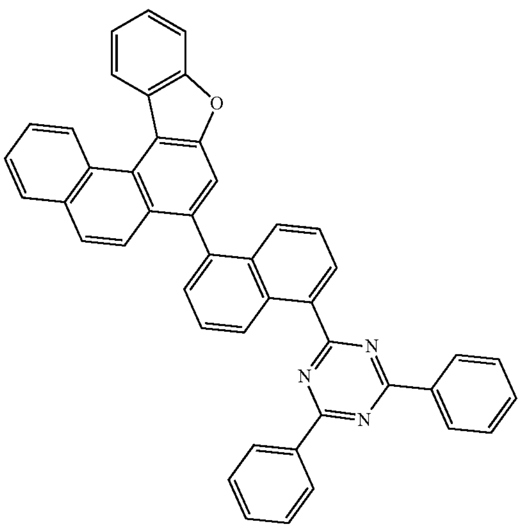
H2-205
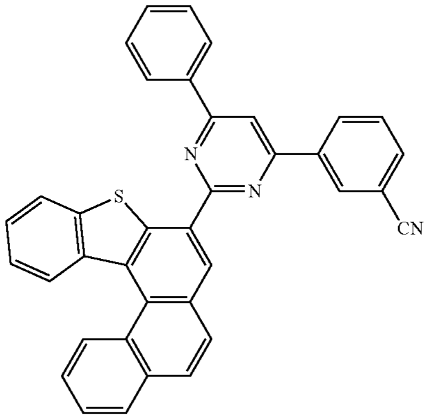
H2-206
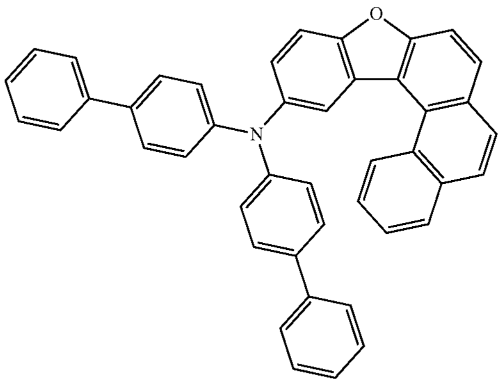
-continued
H2-207
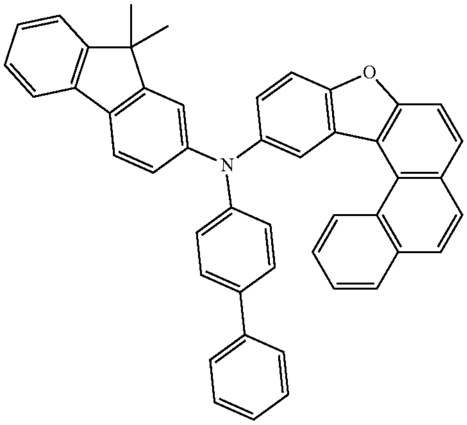
H2-208
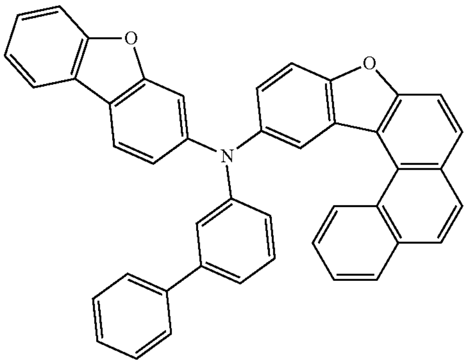
H2-209
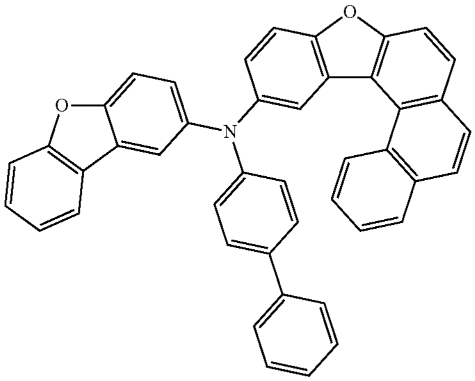
H2-210
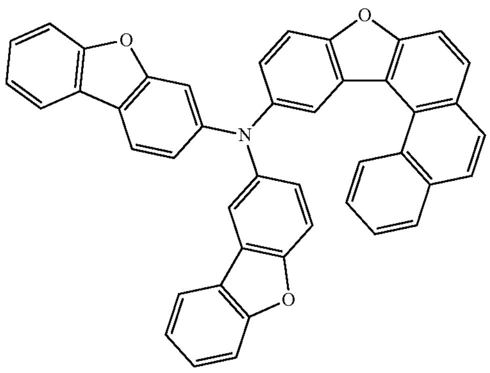

-continued
H2-211
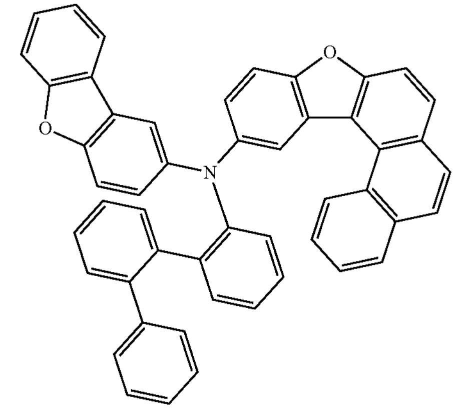
H2-212
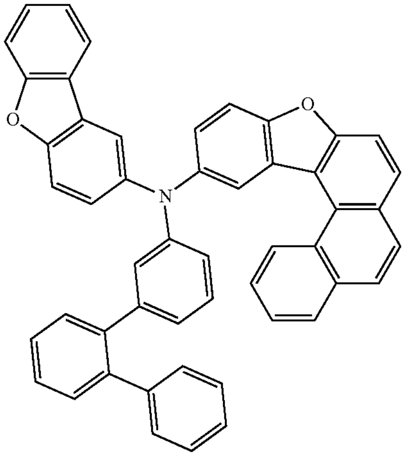
H2-213
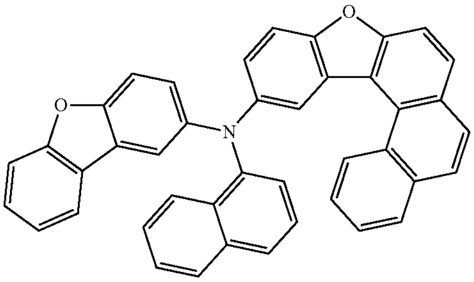
H2-214
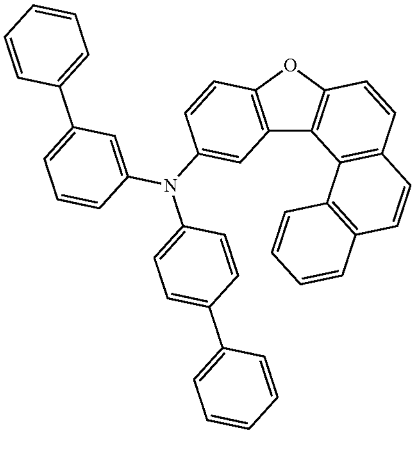
-continued
H2-215
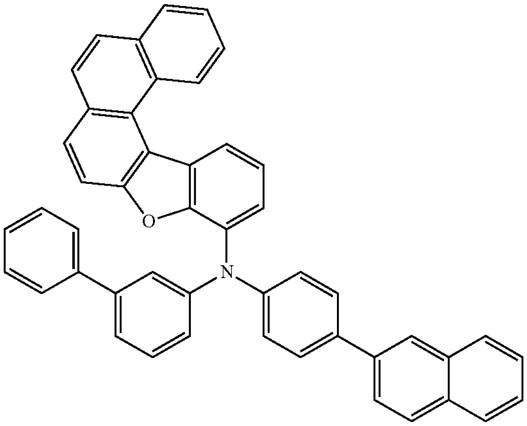
H2-216
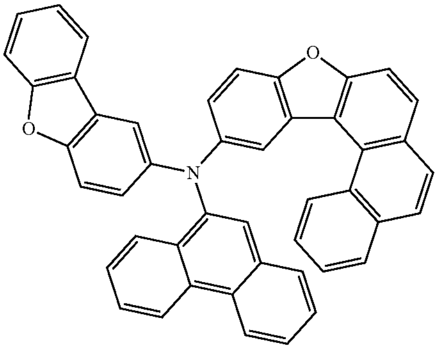
H2-217
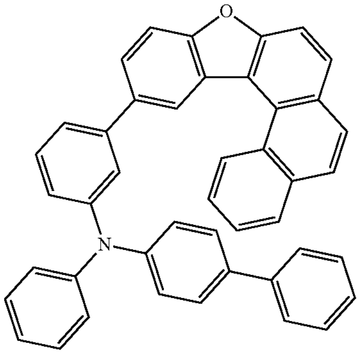
H2-218
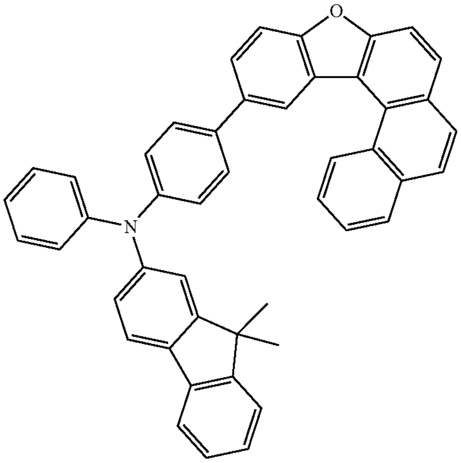

-continued
H2-219
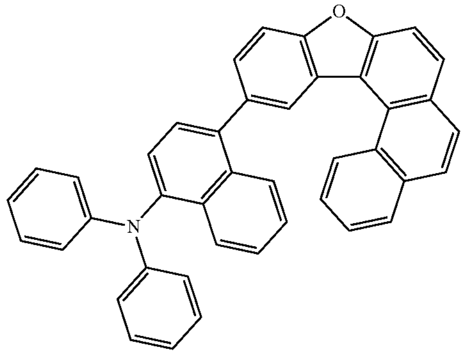
H2-220
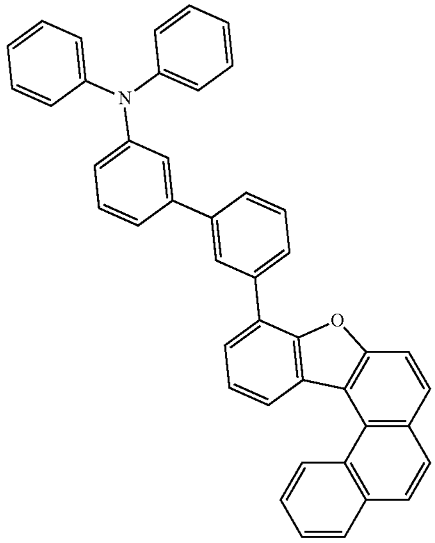
H2-221
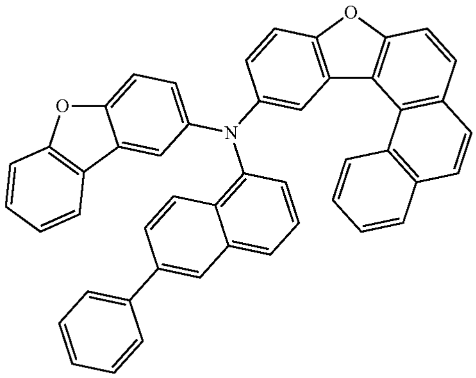
-continued
H2-222
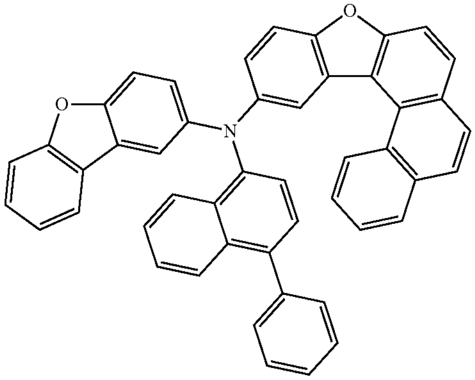
H2-223
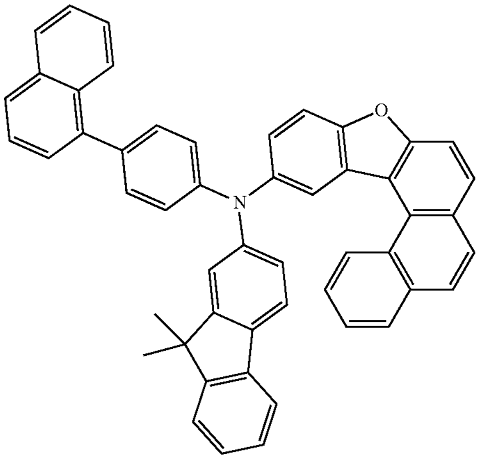
H2-224
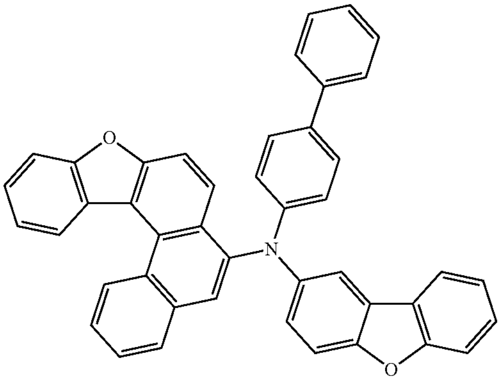
H2-225
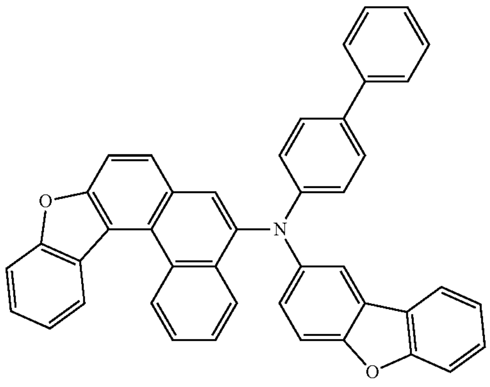

-continued
H2-226
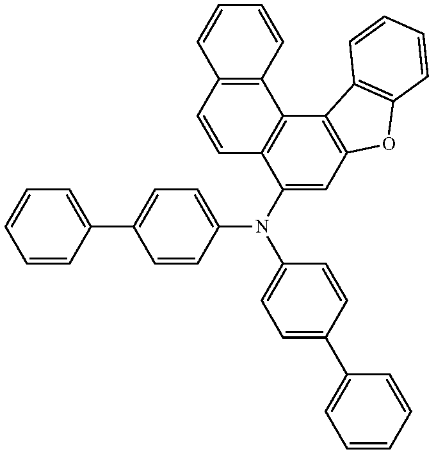
H2-227
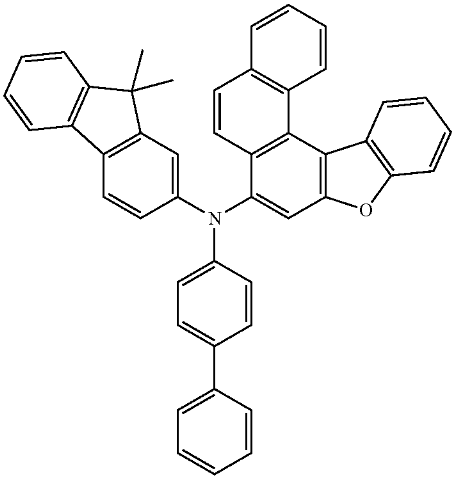
H2-228
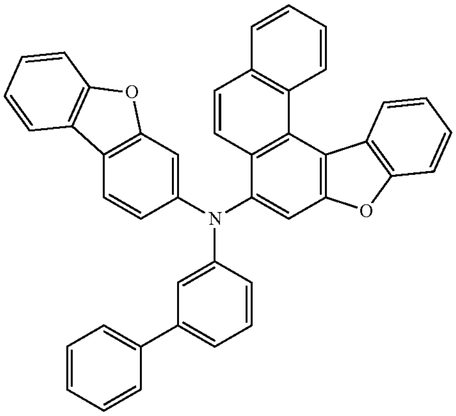
-continued
H2-229
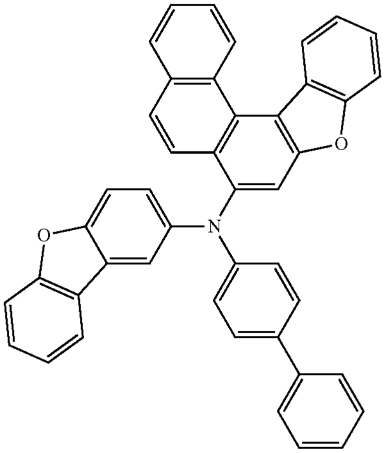
H2-230
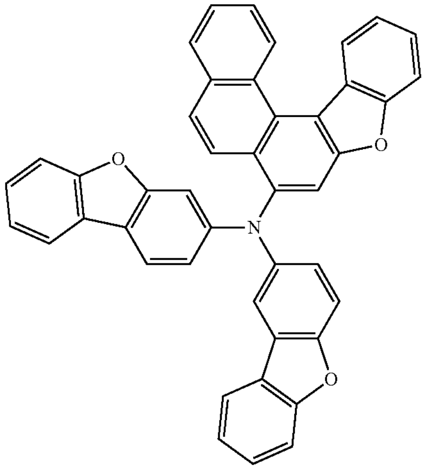
H2-231
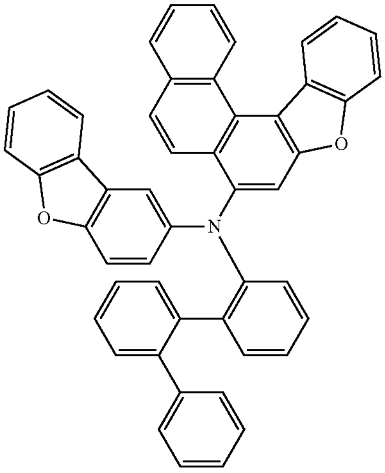

-continued
H2-232
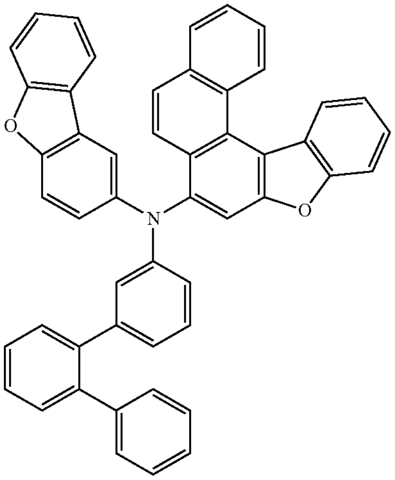
H2-233
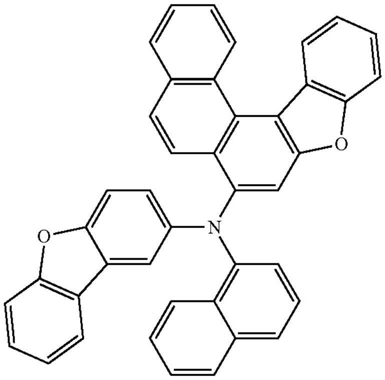
H2-234
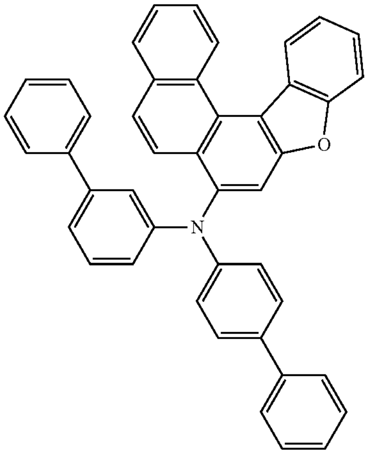
-continued
H2-235
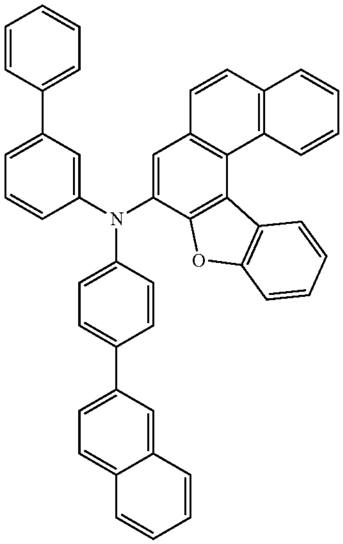
H2-236
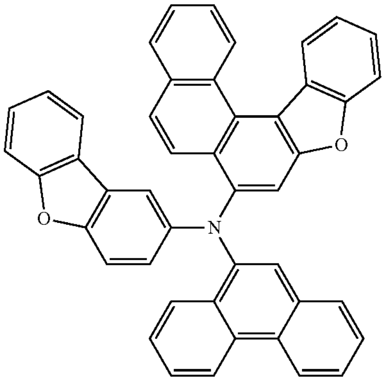
H2-237
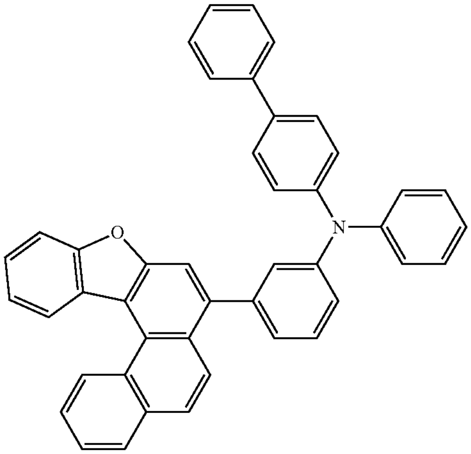

-continued
H2-238
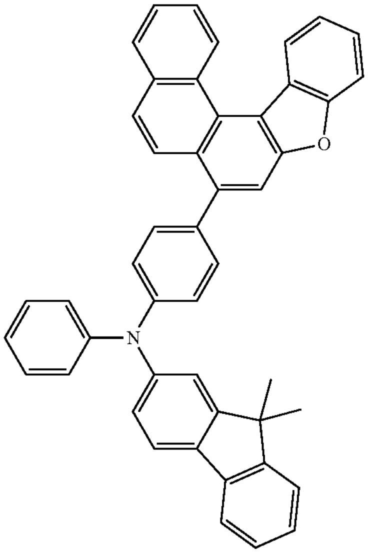
H2-239
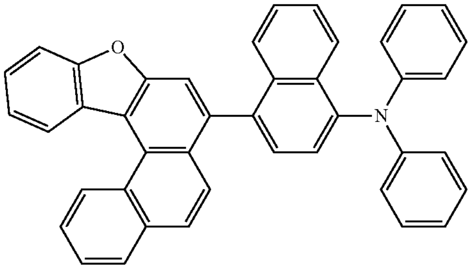
H2-240
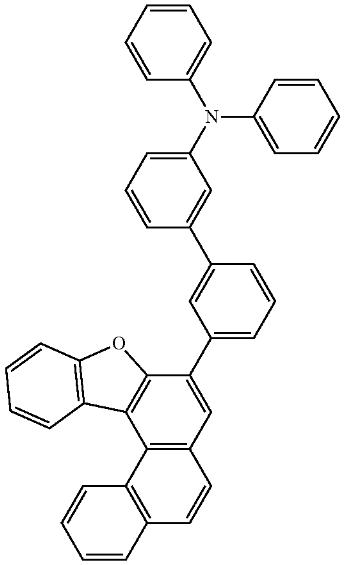
-continued
H2-241
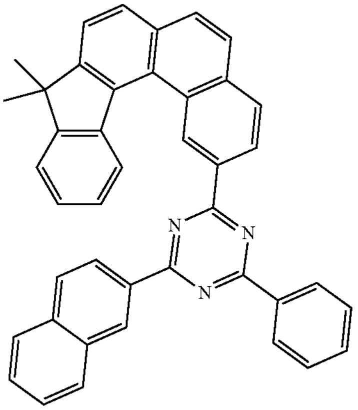
H2-242
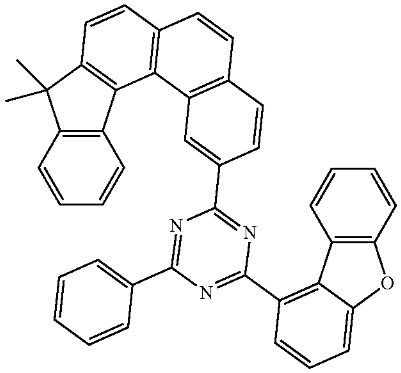
H2-243
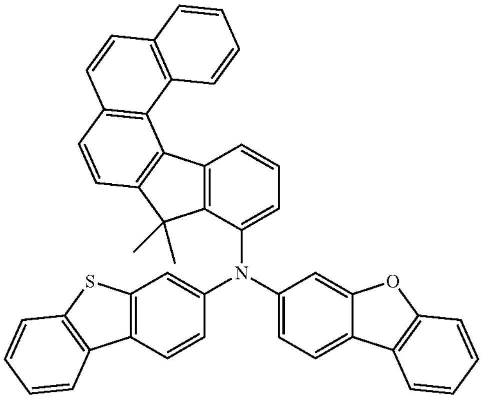
H2-244
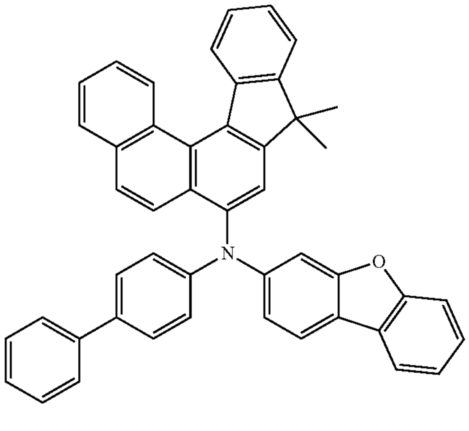

-continued
H2-245
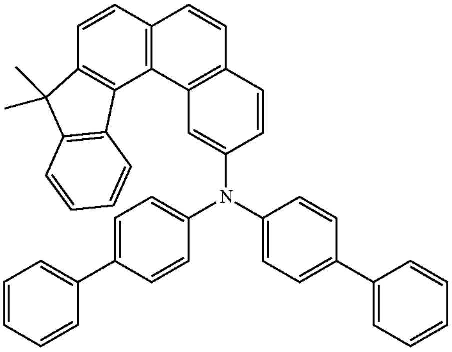
H2-246
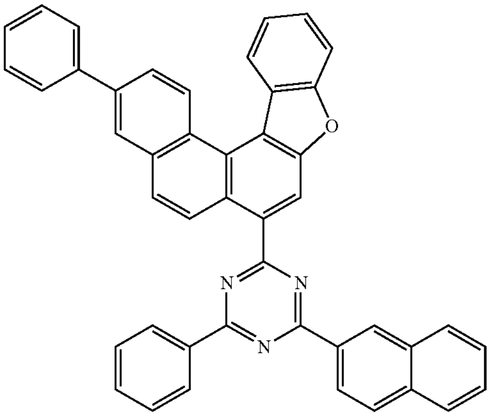
H2-247
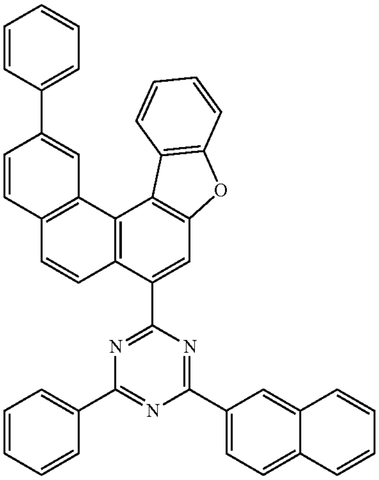
-continued
H2-248
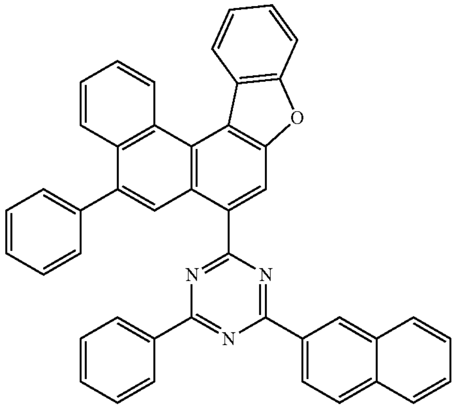
H2-249
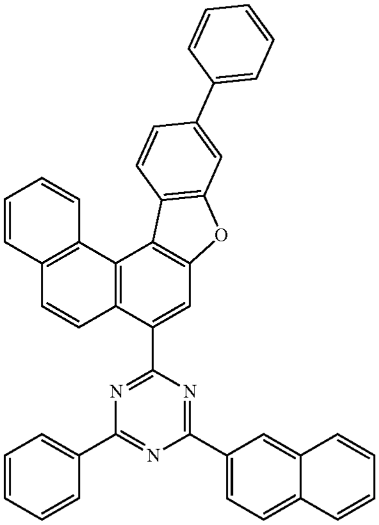
H2-250
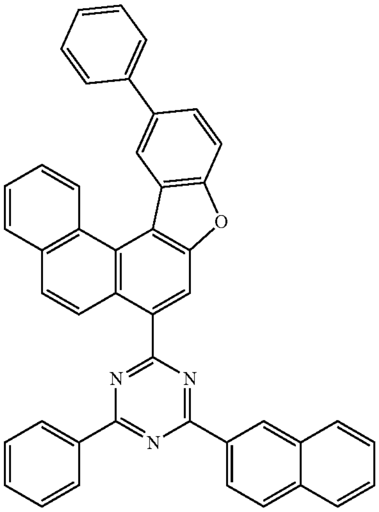

-continued
H2-251
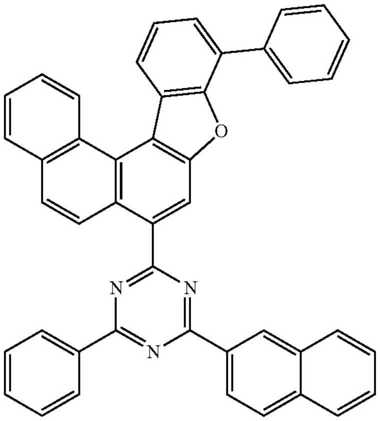
H2-252
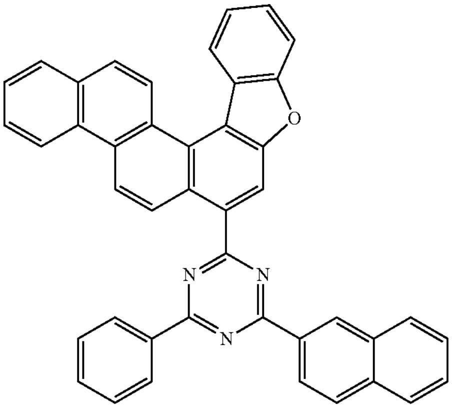
H2-253
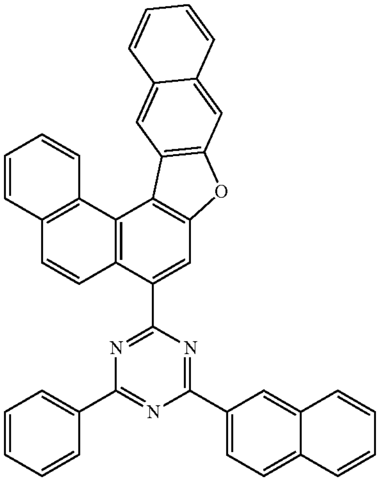
-continued
H2-254
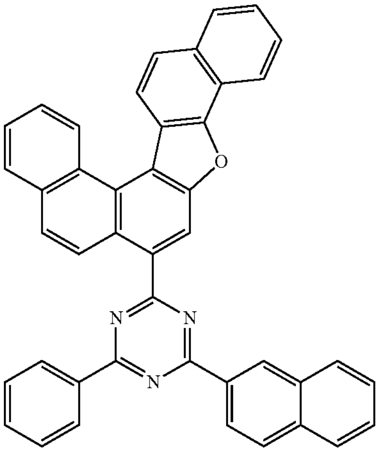
H2-255
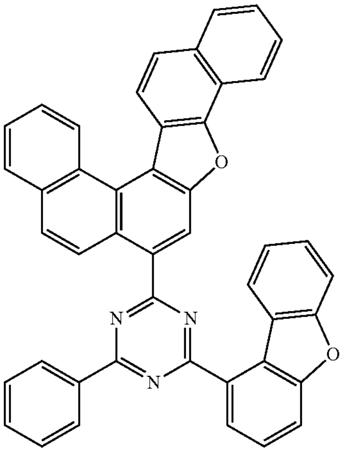
H2-256
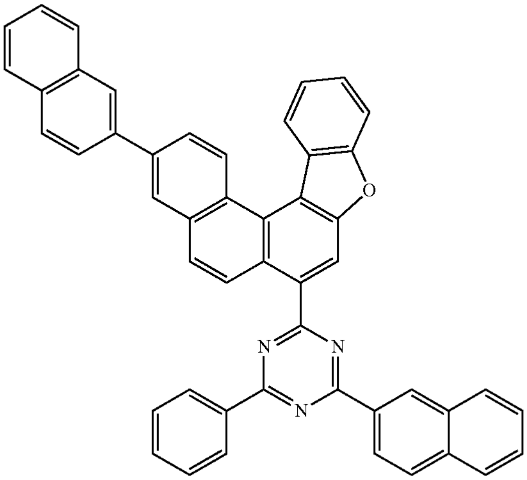

-continued
H2-257
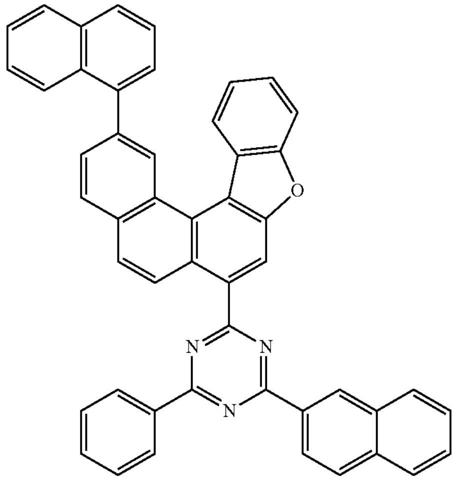
H2-258
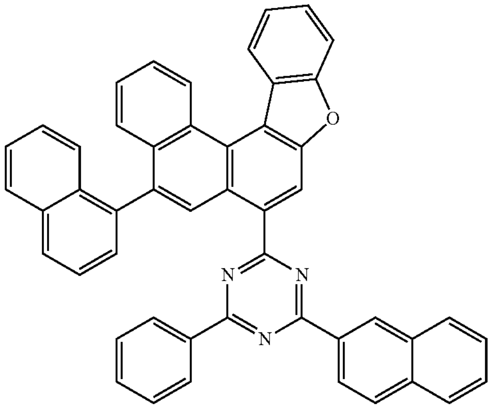
H2-259
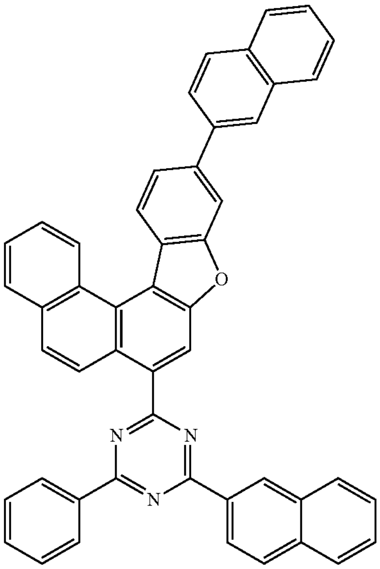
-continued
H2-260
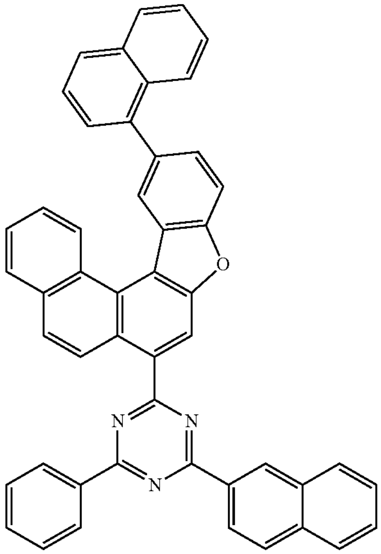
H2-261
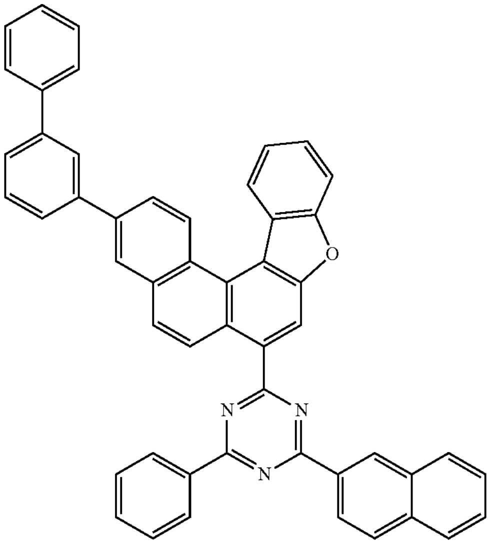

-continued
H2-262
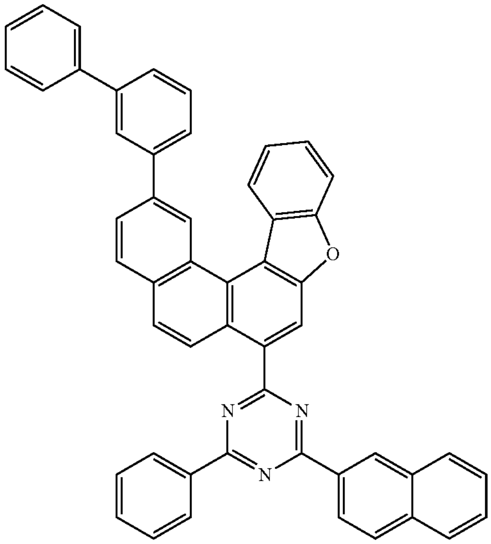
H2-263
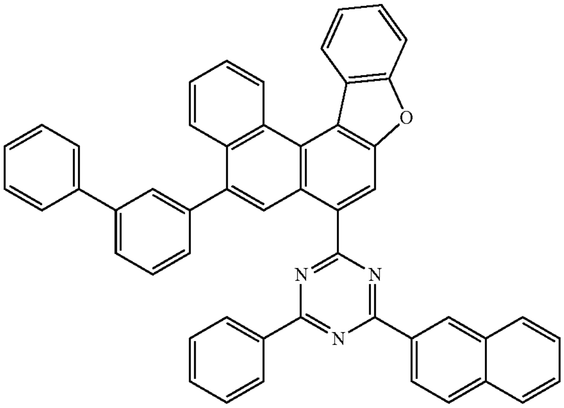
H2-264
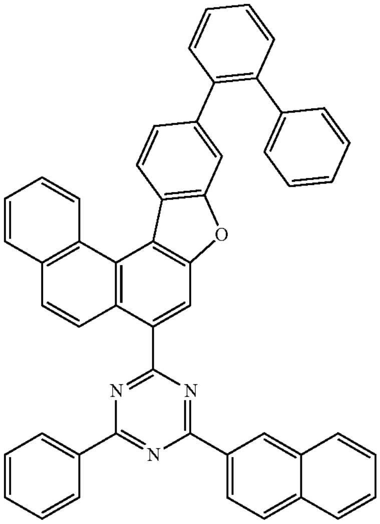
-continued
H2-265
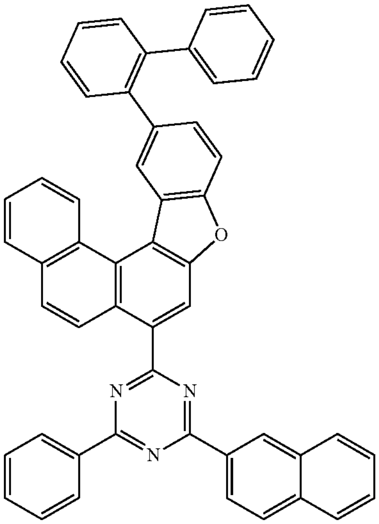
H2-266
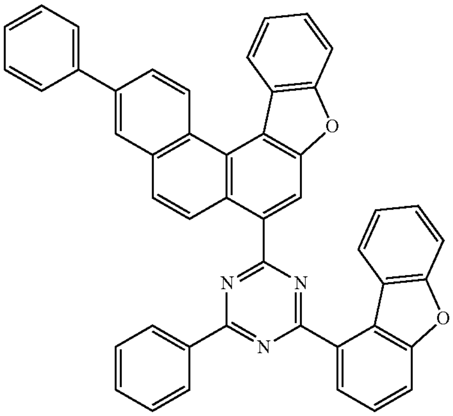
H2-267
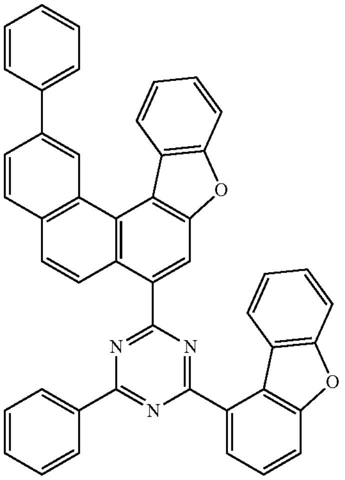

-continued
H2-268
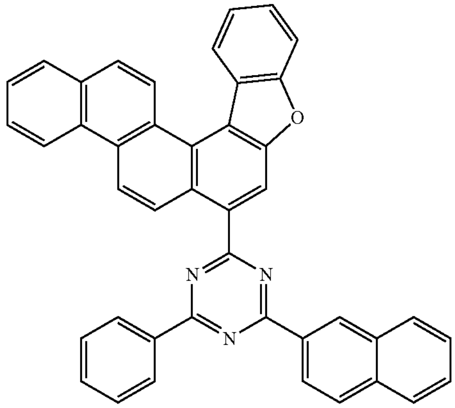
H2-269
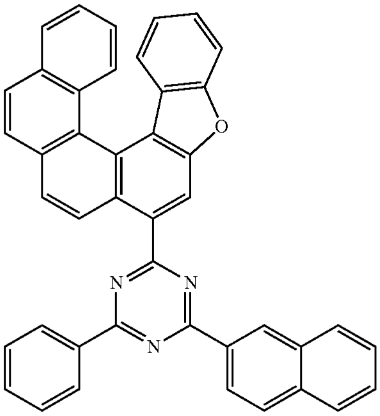
H2-270
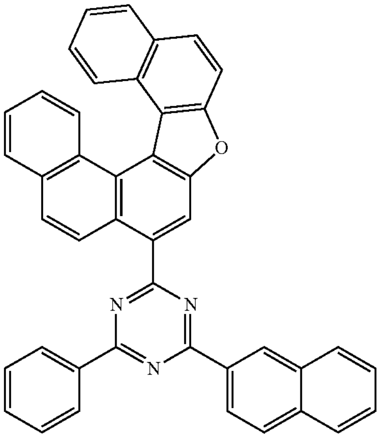
-continued
H2-271
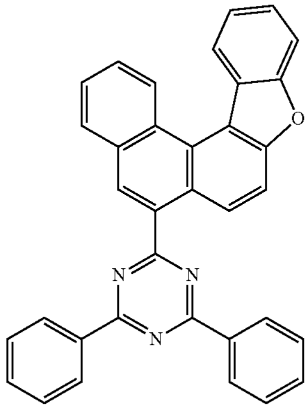
H2-272
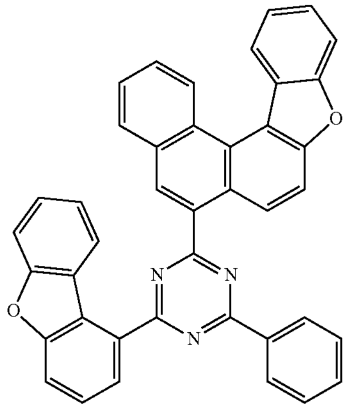
H2-273
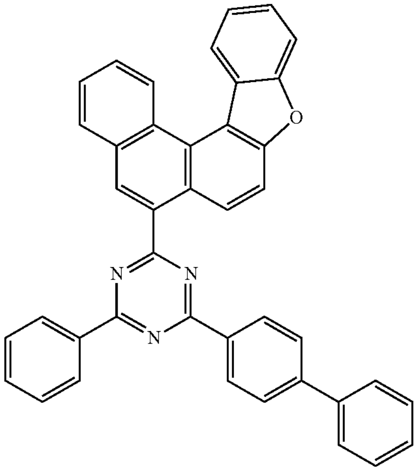

-continued
H2-274
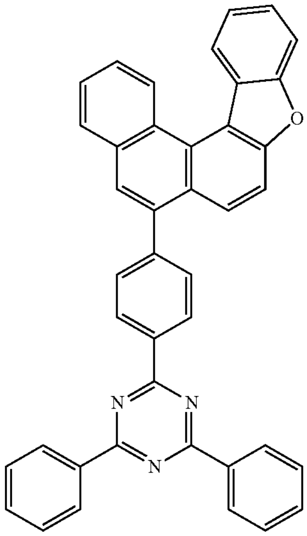
H2-275
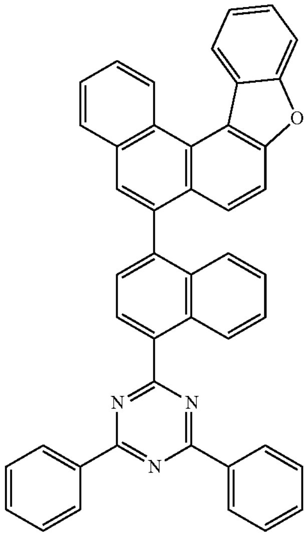
H2-276
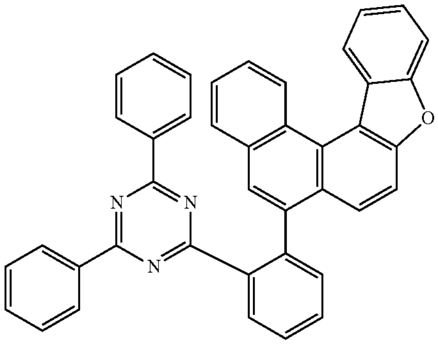
-continued
H2-277
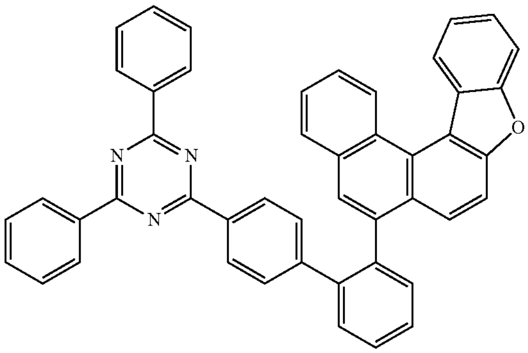
H2-278
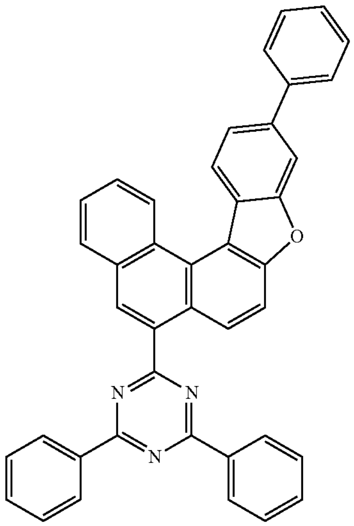
H2-279
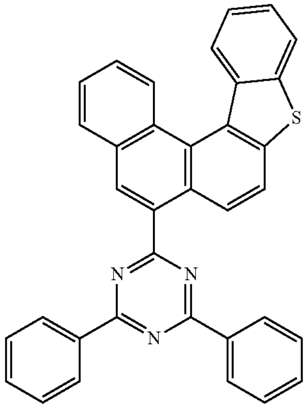

-continued
H2-280
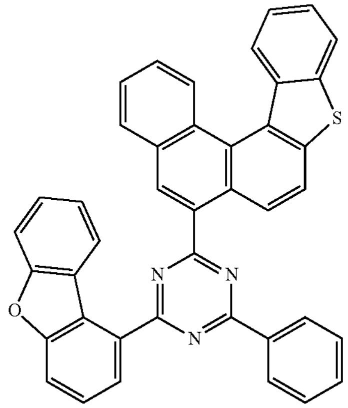
H2-281
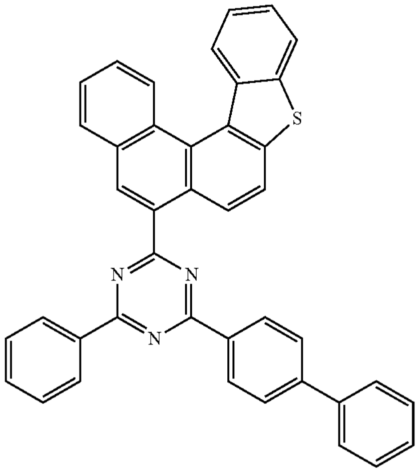
H2-282
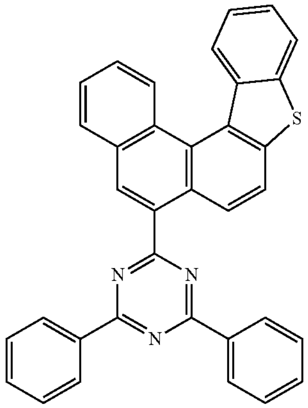
-continued
H2-283
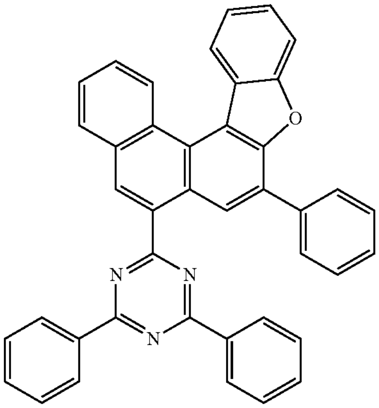
H2-284
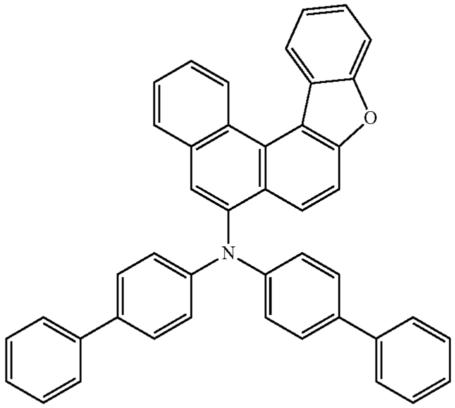
H2-285
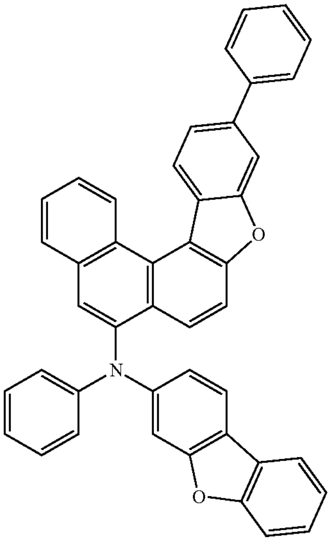

-continued
H2-286
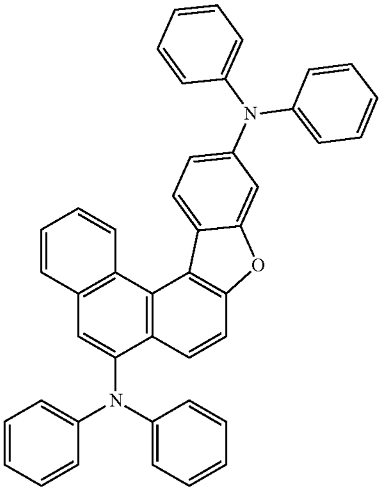
H2-287
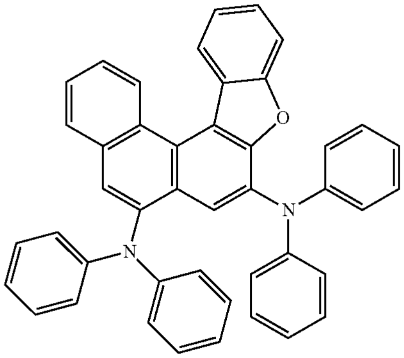
H2-288
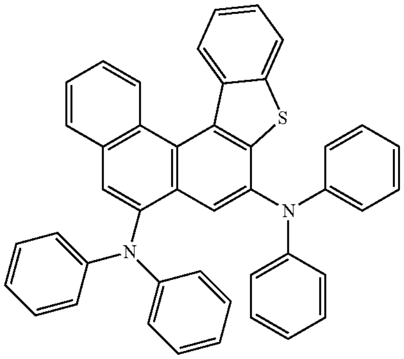
H2-289
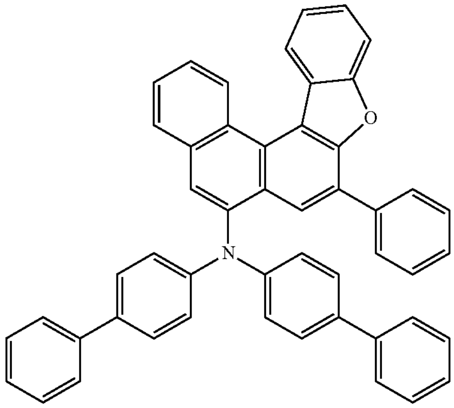
-continued
H2-290
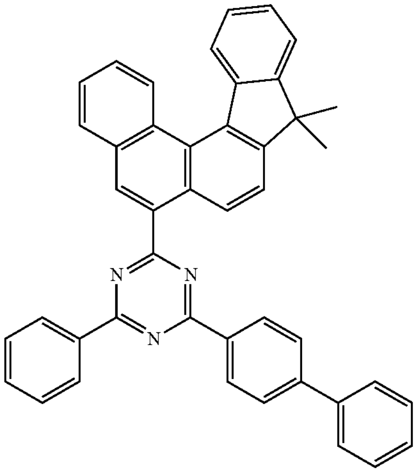
H2-291
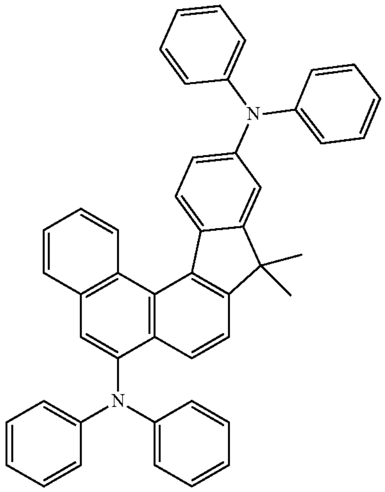
H2-292
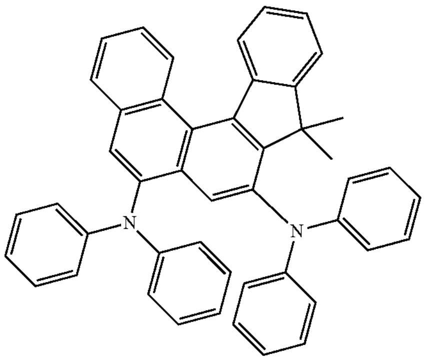

-continued

H2-293

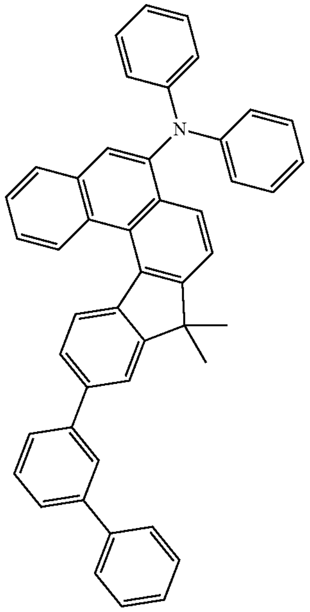

H2-294

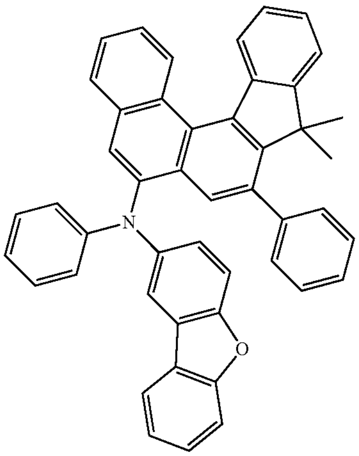

The combination of at least one of compounds H1-1 to H1-245 and at least one of compounds H2-1 to H2-294 may be used in an organic electroluminescent device.

The compound represented by formulas 1 and 2 according to the present disclosure may be prepared by a synthetic method known to one skilled in the art. For example, the compound represented by formula 1 according to the present disclosure may be prepared by referring to Korean Patent Application Laying-Open Nos. 2018-0099510 (published on Sep. 5, 2018), 2018-0012709 (published on Feb. 6, 2018), and 2020-0103524 (published on Sep. 2, 2020); and the compound represented by formula 2 according to the present disclosure may be prepared by referring to the following reaction schemes 1 to 4 and Korean Patent Application Laying-Open No. 2017-0043439 (published on Apr. 21, 2017), but is not limited thereto.

[Reaction Scheme 1]

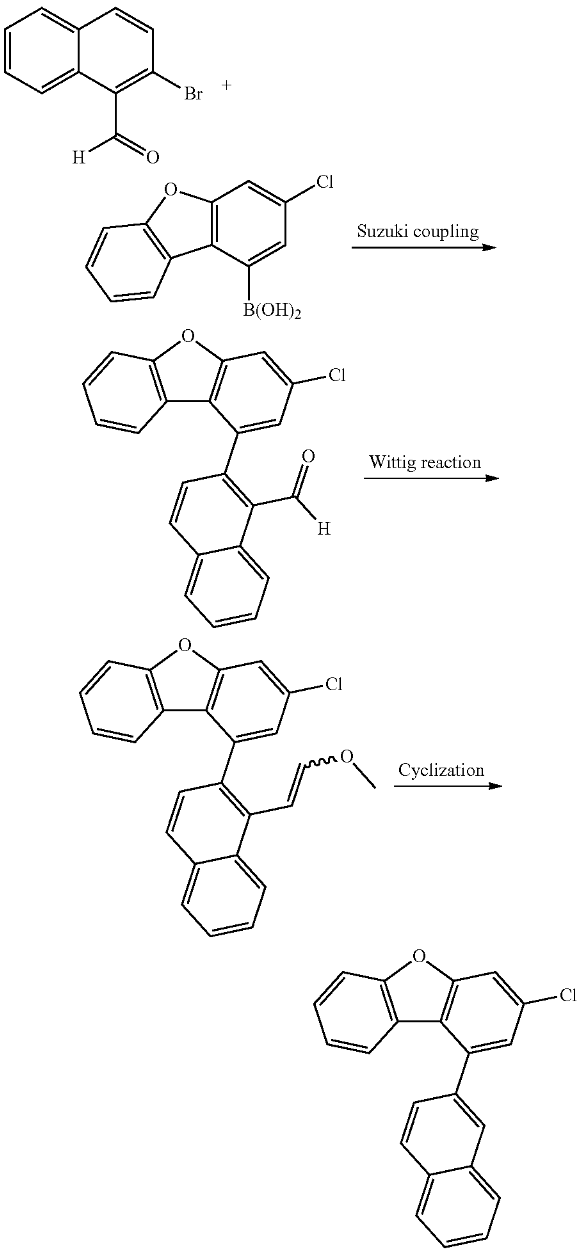

[Reaction Scheme 2]

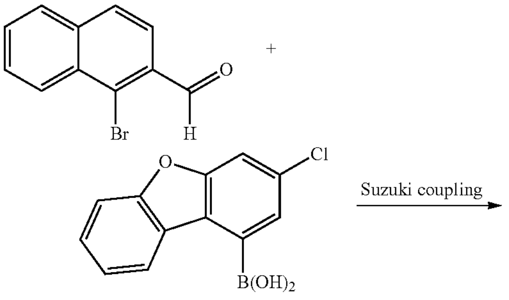

-continued
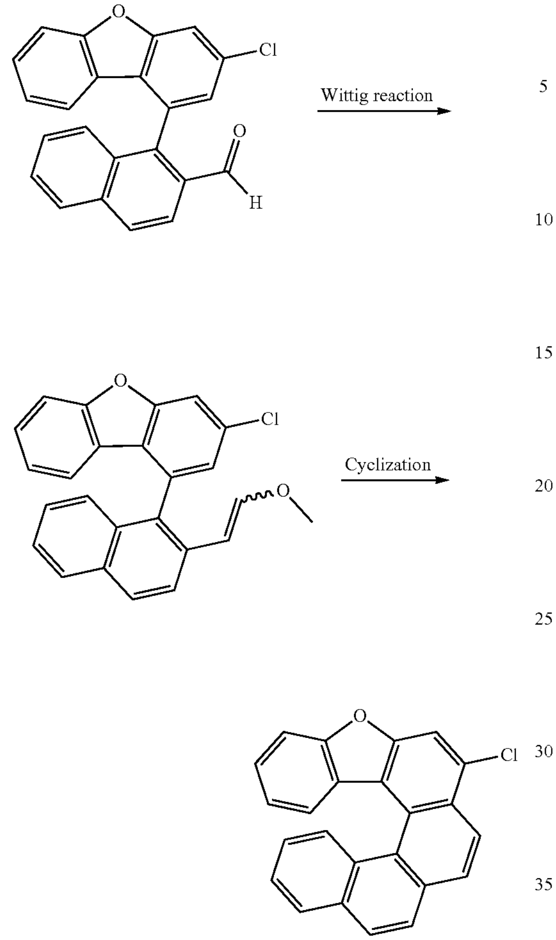
[Reaction Scheme 3]
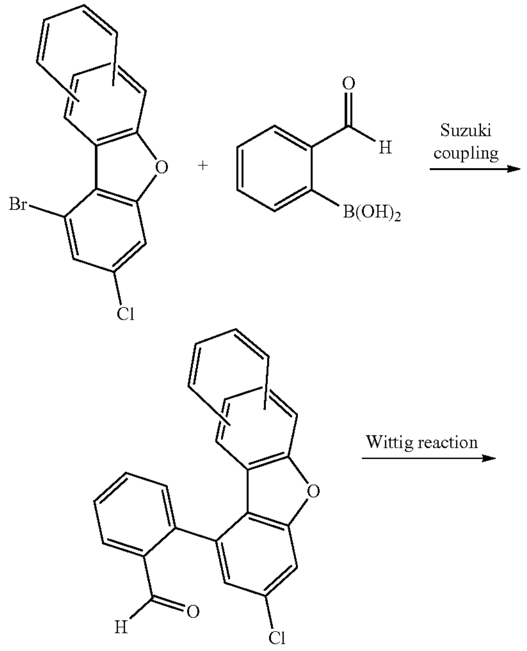
-continued
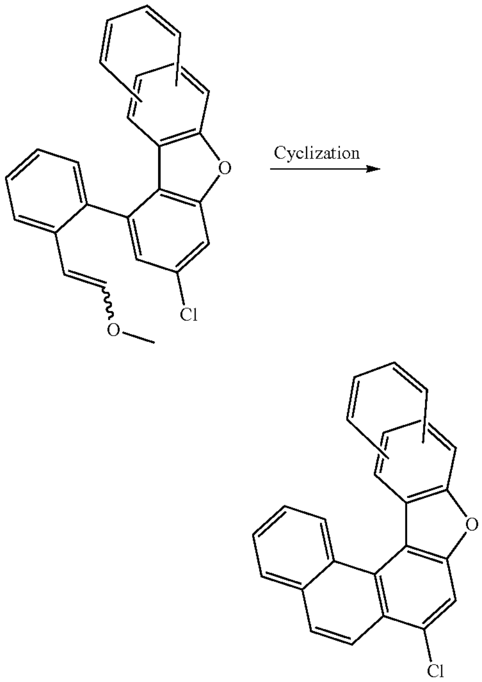
[Reaction Scheme 4]
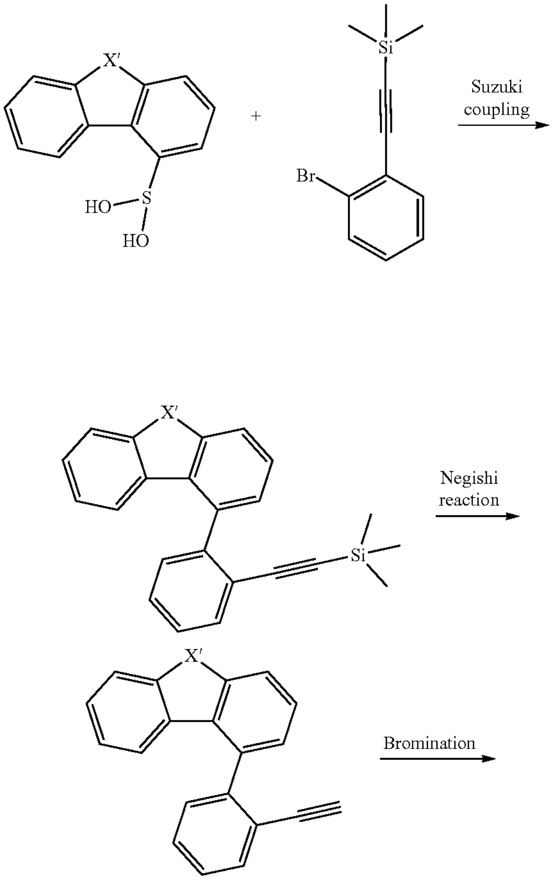

-continued

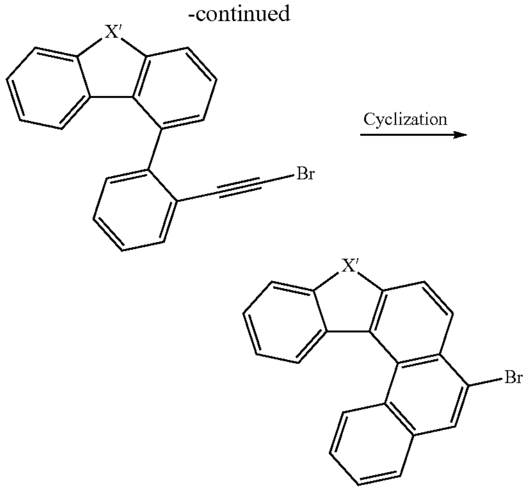

In reaction scheme 4, X' is as defined in formula 2.

Although illustrative synthesis examples of the compound represented by formulas 1 and 2 are described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, Wittig reaction, Negishi reaction, Bromination, and Phosphine-mediated reductive cyclization, etc., and the reactions above proceed even when substituents which are defined in formulas 1 and 2 above, but are not specified in the specific synthesis examples, are bonded.

The present disclosure provides an organic electroluminescent device comprising an anode, a cathode, and at least one light-emitting layer between the anode and cathode in which at least one light-emitting layer comprises a plurality of host materials of the present disclosure. The first host material and the second host material may be comprised in one light-emitting layer, or may be respectively comprised in different light-emitting layers. The ratio of the compound represented by formula 1 and the compound represented by formula 2 in the plurality of host materials is about 1:99 to about 99:1, preferably about 10:90 to about 90:10, more preferably about 30:70 to about 70:30. In addition, the compound represented by formula 1 and the compound represented by formula 2 may be combined by mixing them in a shaker, by dissolving them in a glass tube by heat, or by dissolving them in a solvent, etc. in the desired ration.

According to one embodiment of the present disclosure, the doping concentration of the dopant compound with respect to the host compound in the light-emitting layer may be less than about 20 wt %. The dopant comprised in the organic electroluminescent device of the present disclosure may be at least one phosphorescent or fluorescent dopant, and is preferably a phosphorescent dopant. The phosphorescent dopant material applied to the organic electroluminescent device of the present disclosure is not particularly limited, but may be a complex compound of a metal atom selected from iridium (Ir), osmium (Os), copper (Cu) and platinum (Pt), and preferably ortho-metallated complex compounds of a metal atom selected from iridium (Ir), osmium (Os), copper (Cu), and platinum (Pt), and more preferably ortho-metallated iridium complex compounds.

The dopant comprised in the organic electroluminescent device of the present disclosure may comprise a compound represented by the following formula 101, but is not limited thereto.

(101)

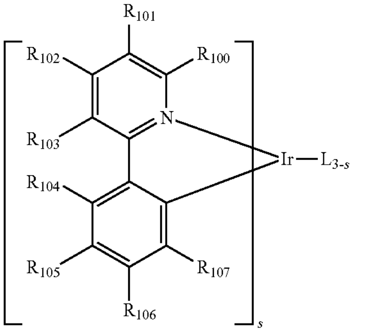

In formula 101,

L is selected from the following structures 1 to 3:

[Structure 1]

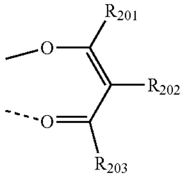

[Structure 2]

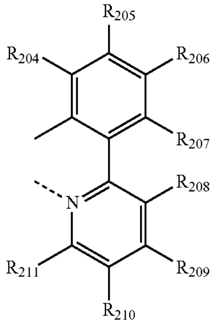

[Structure 3]

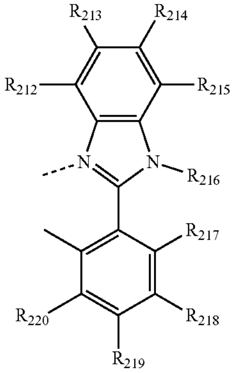

$R_{100}$ to $R_{103}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30) alkoxy; or may be linked to an adjacent substituent(s) to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent(s) to form a ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene;

$R_{201}$ to $R_{220}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, or a substituted or unsubstituted (C6-C30)aryl; or may be linked to an adjacent substituent(s) to form a substituted or unsubstituted ring(s); and s represents an integer of 1 to 3.

The specific examples of the dopant compound are as follows, but are not limited thereto.

D-1

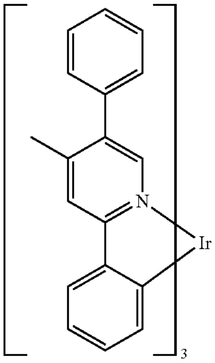

-continued

D-2

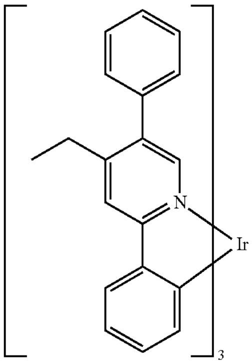

D-3

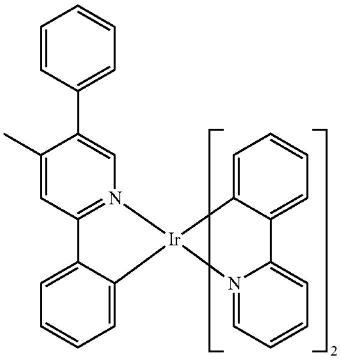

D-4

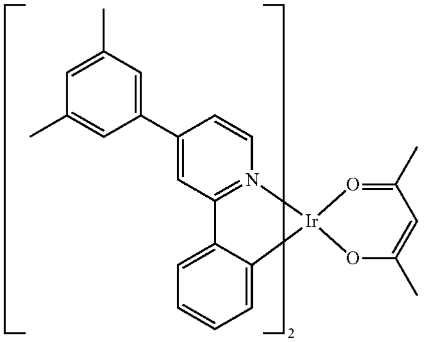

D-5

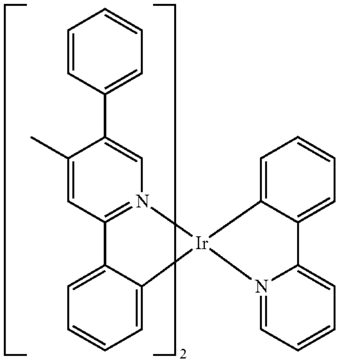

-continued
D-6
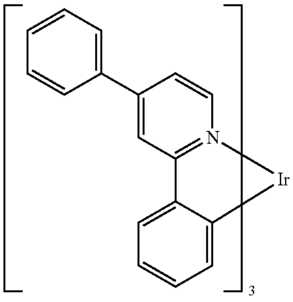
D-7
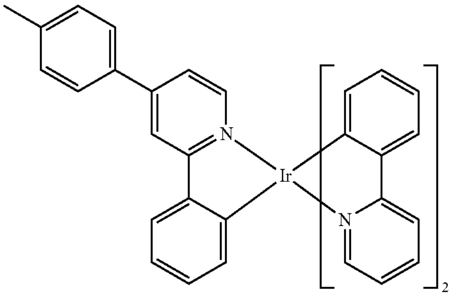
D-8
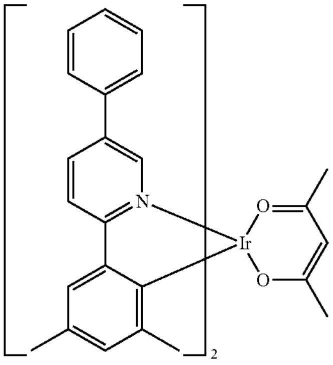
D-9
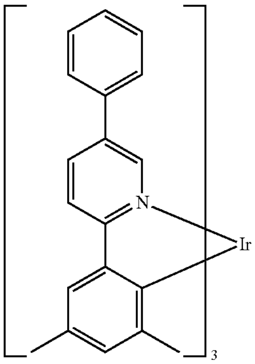
-continued
D-10
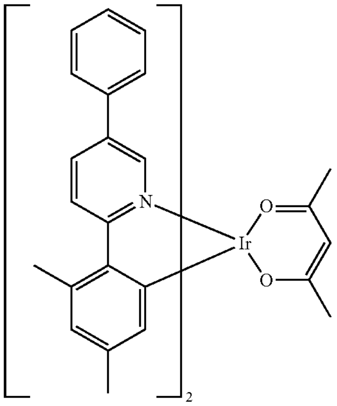
D-11
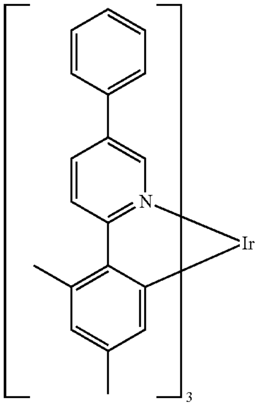
D-12
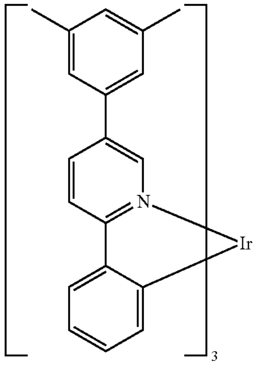
D-13
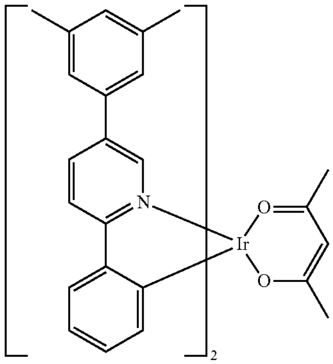

-continued
D-14
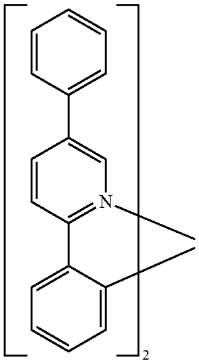
D-15
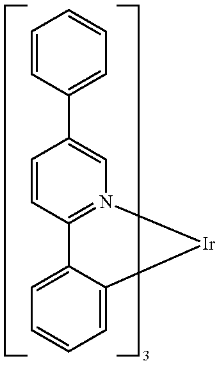
D-16
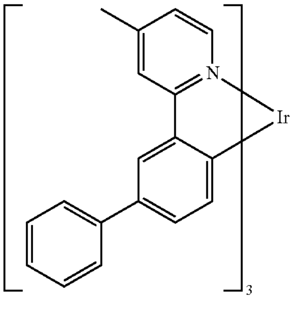
D-17
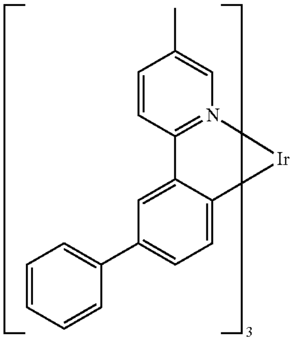
-continued
D-18
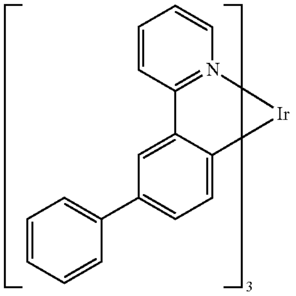
D-19
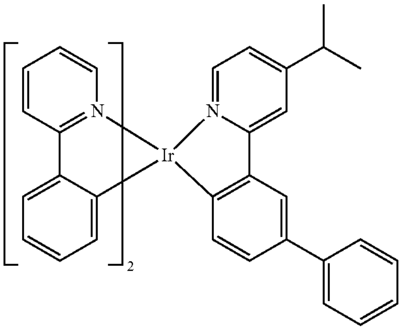
D-20
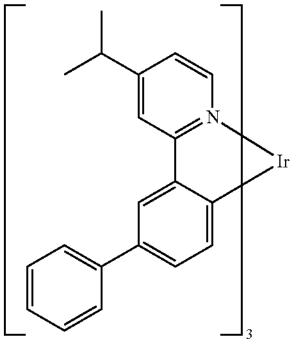
D-21
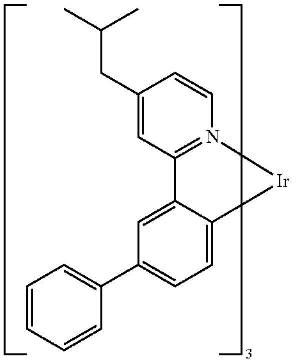

-continued
D-22
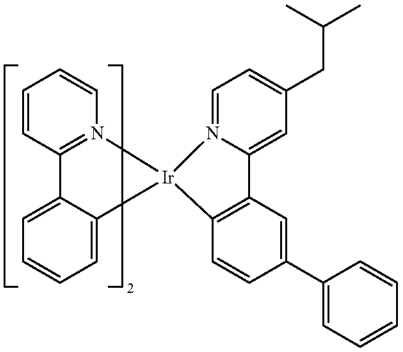
D-23
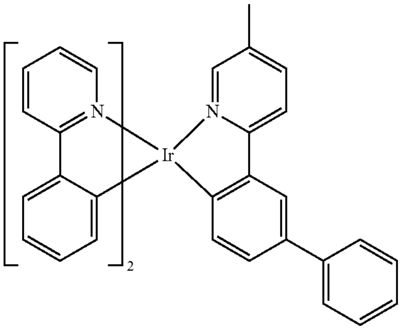
D-24
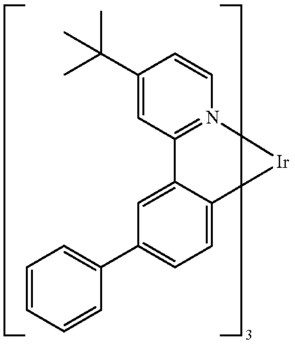
D-25
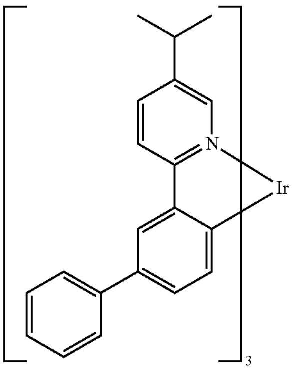
-continued
D-26
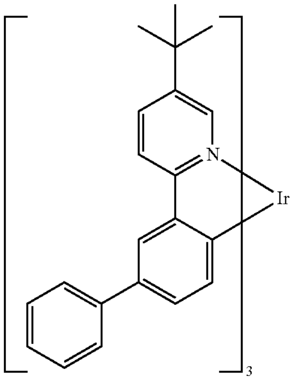
D-27
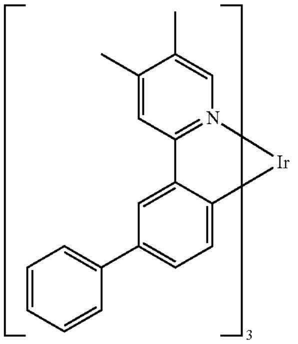
D-28
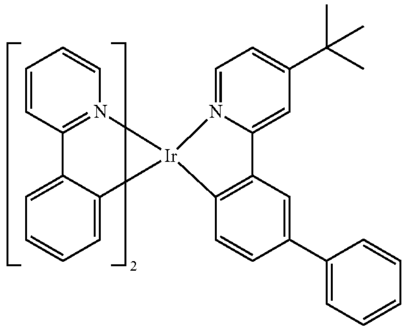
D-29
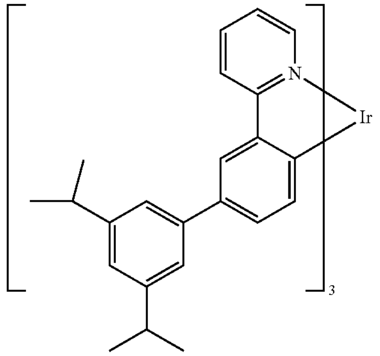

-continued
D-30
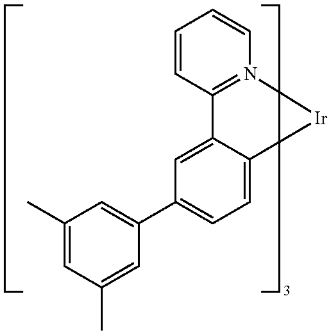
D-31
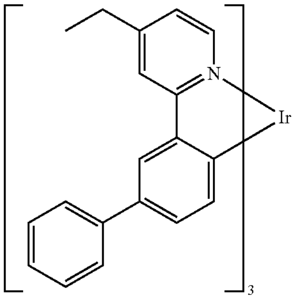
D-32
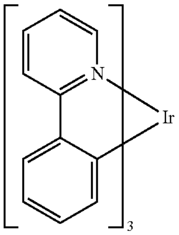
D-33
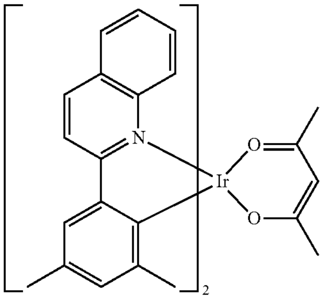
D-34
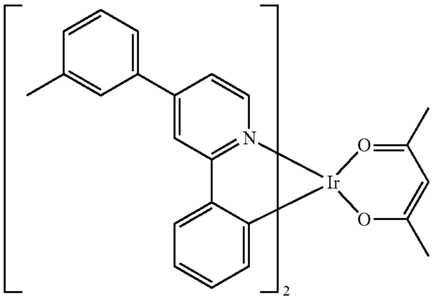
-continued
D-35
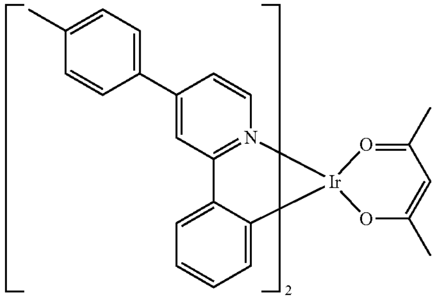
D-36
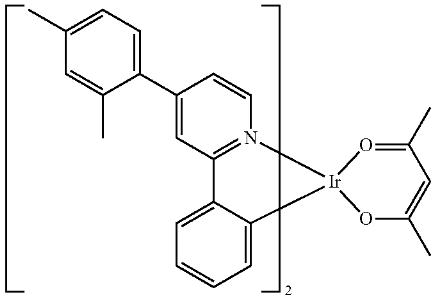
D-37
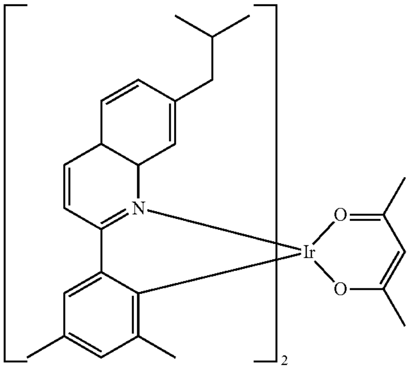
D-38
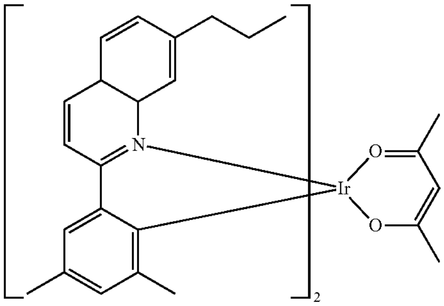

-continued
D-39
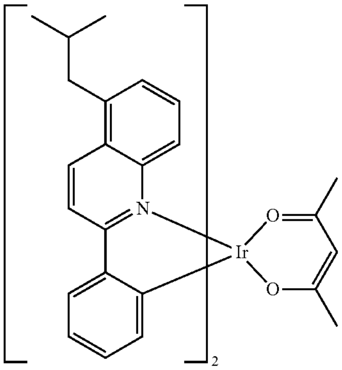
D-40
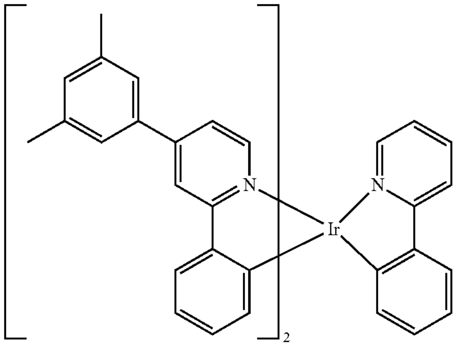
D-41
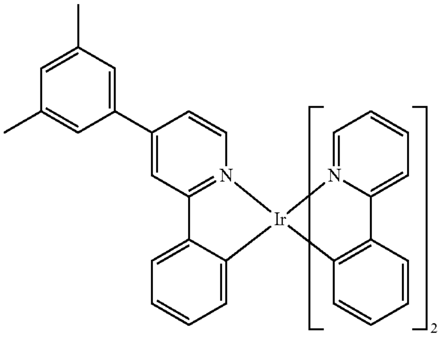
D-42
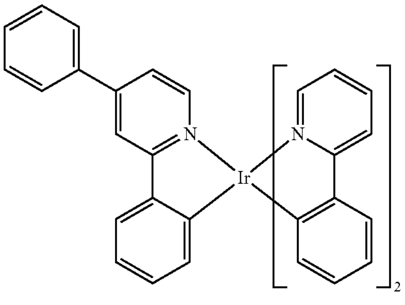
-continued
D-43
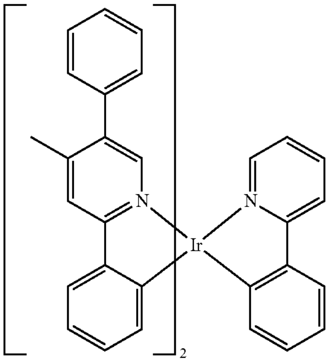
D-44
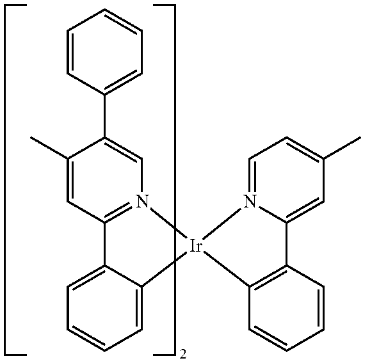
D-45
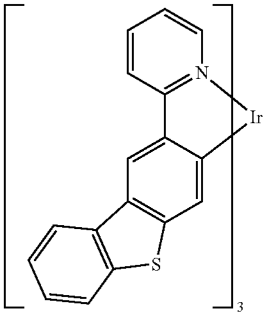
D-46
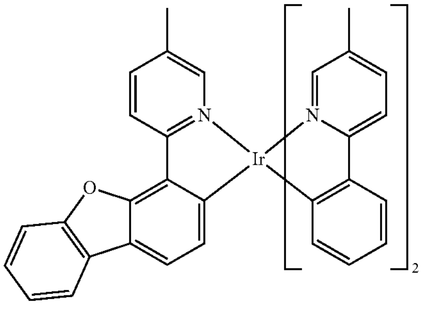

-continued
D-47
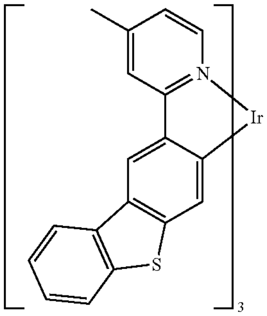
D-48
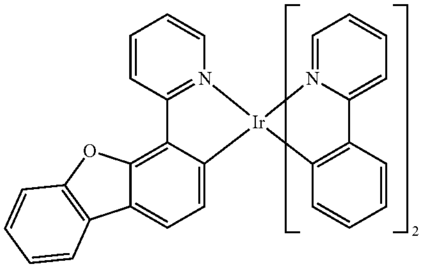
D-49
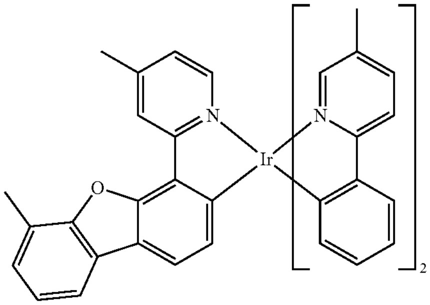
D-50
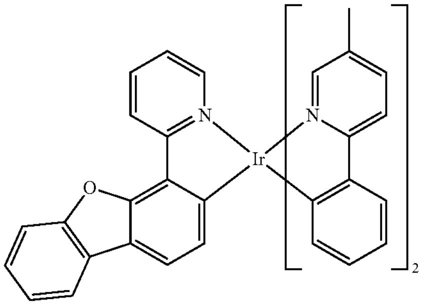
D-51
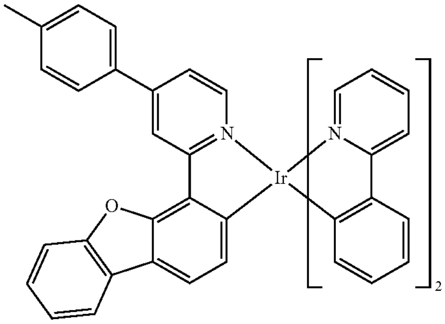
-continued
D-52
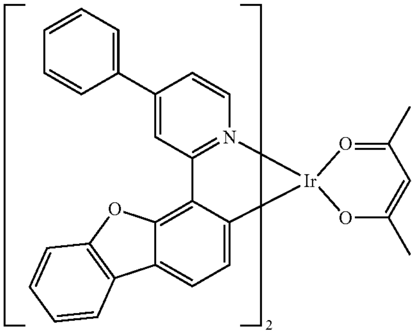
D-53
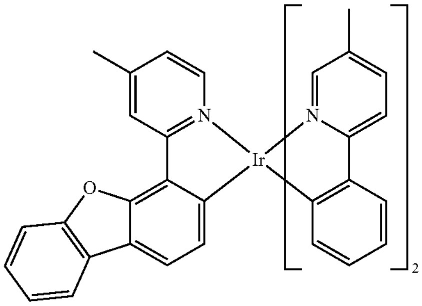
D-54
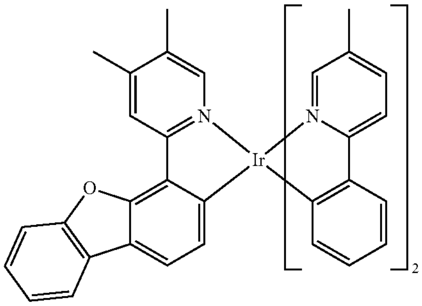
D-55
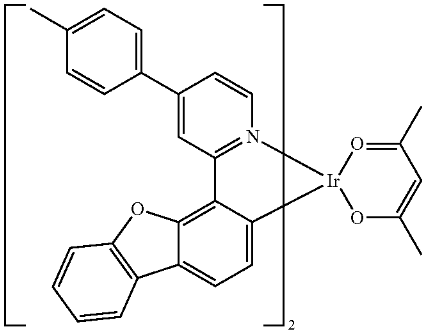
D-56
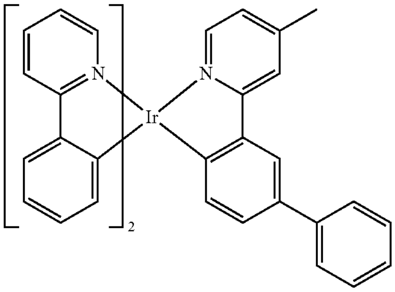

-continued
D-57
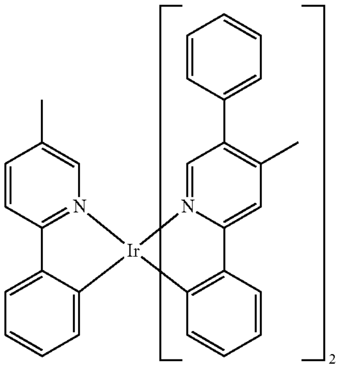
D-58
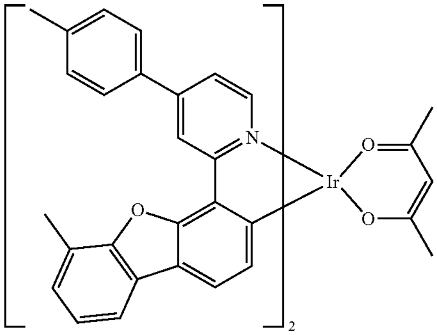
D-59
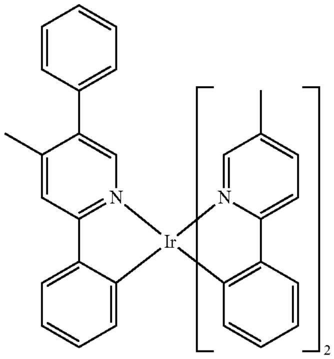
D-60
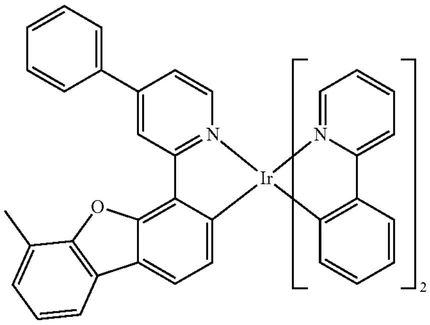
-continued
D-61
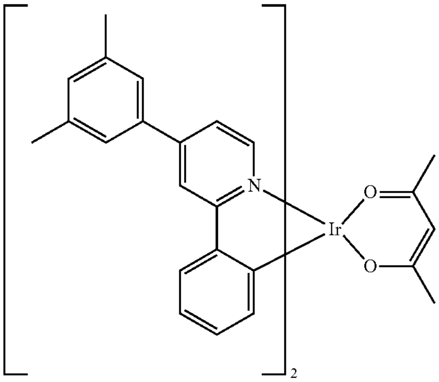
D-62
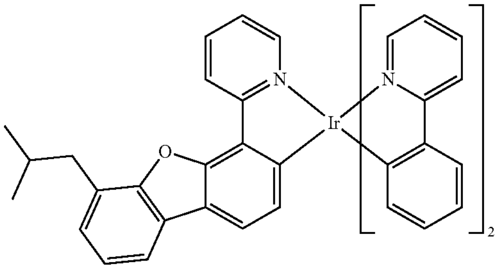
D-63
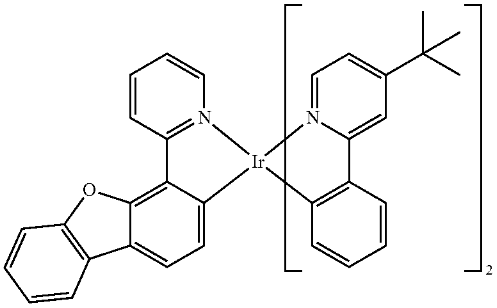
D-64
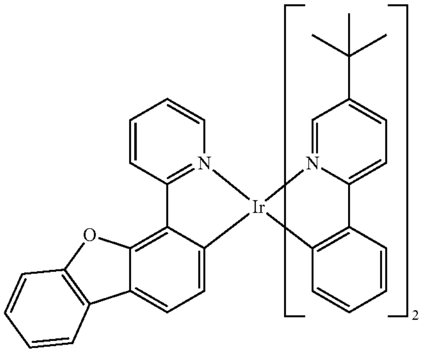

-continued
D-65
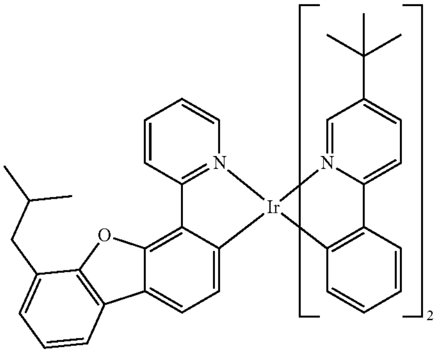
D-66
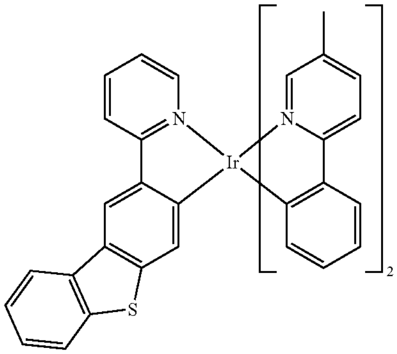
D-67
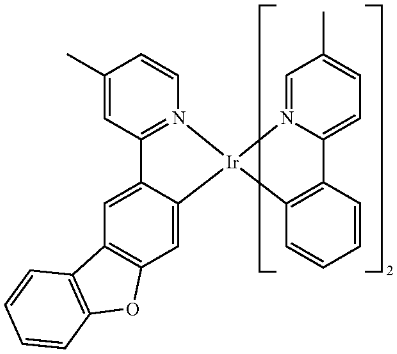
D-68
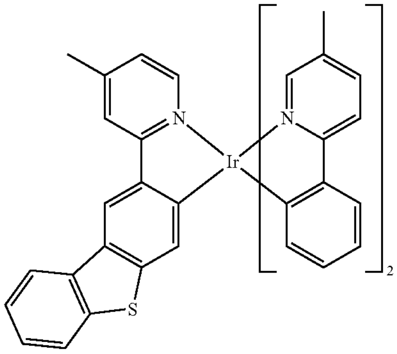
-continued
D-69
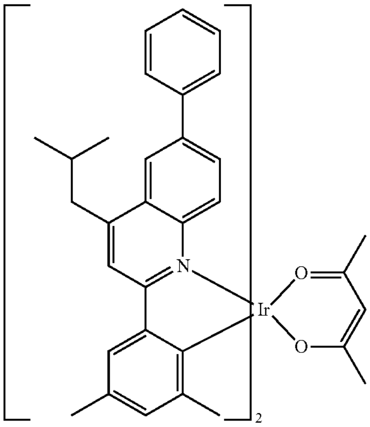
D-70
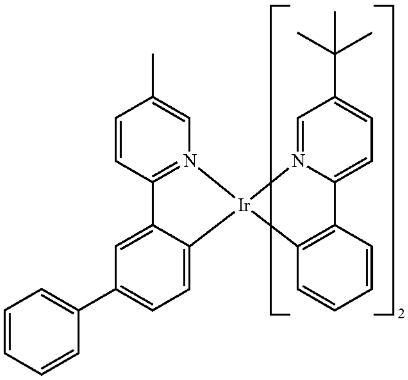
D-71
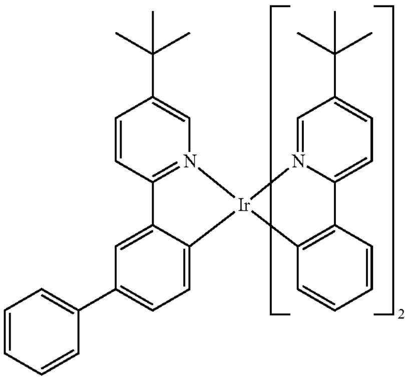
D-72
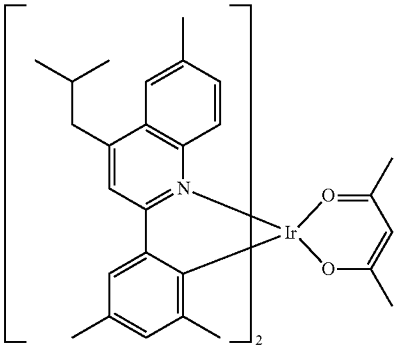

-continued
D-73
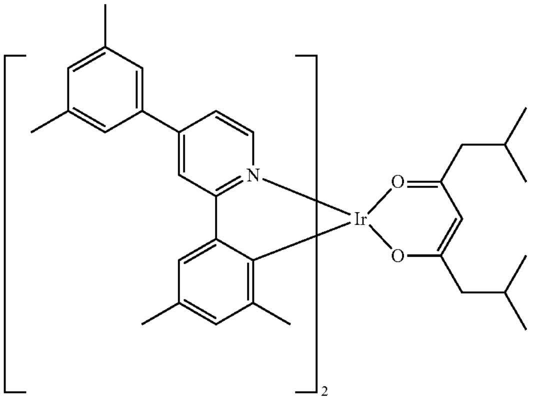
D-74
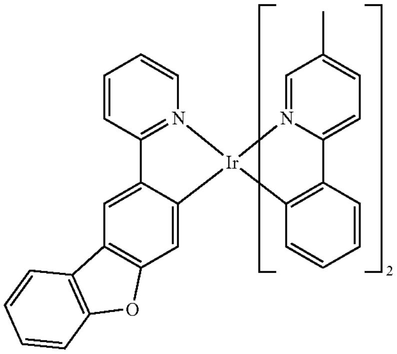
D-75
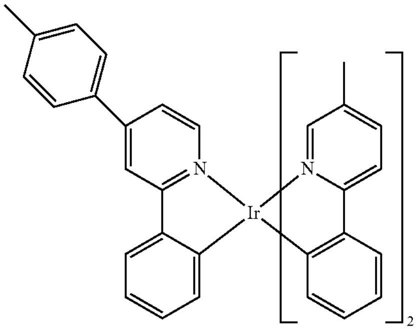
D-76
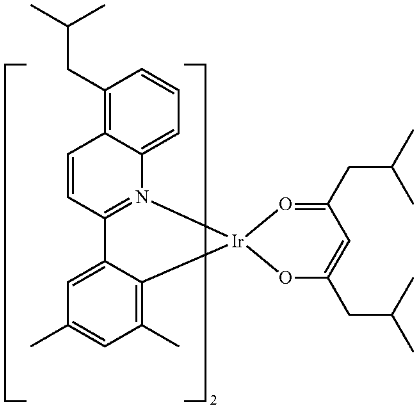
-continued
D-77
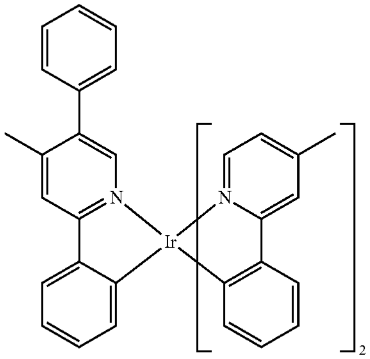
D-78
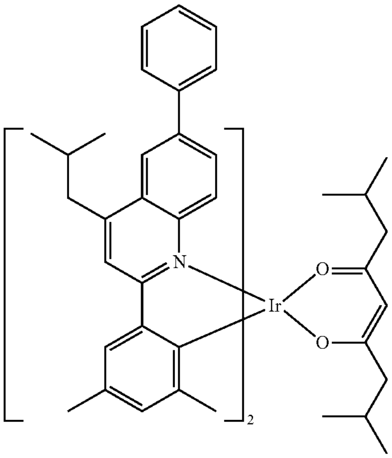
D-79
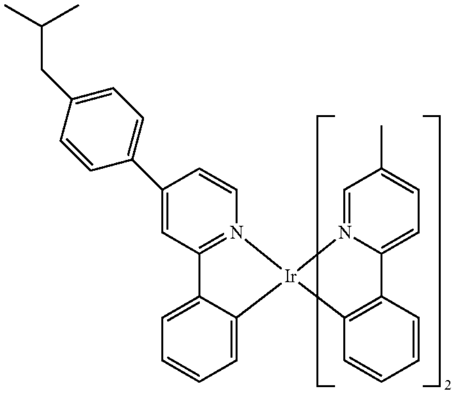
D-80
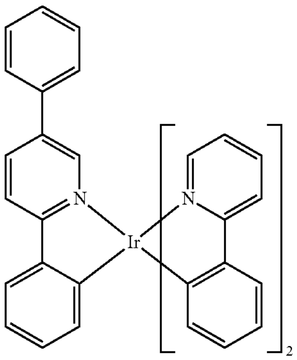

-continued
D-81
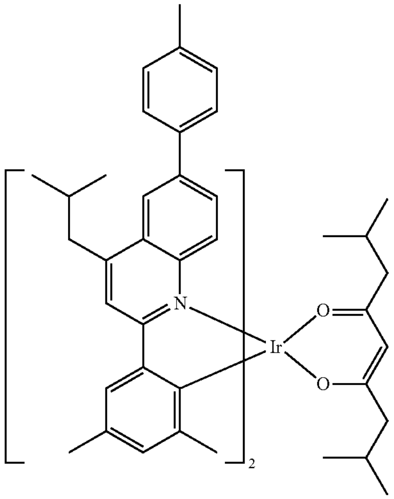
D-82
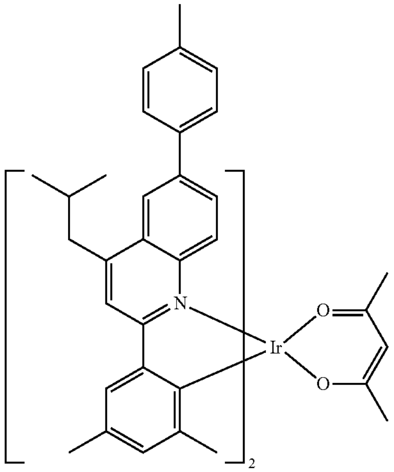
D-83
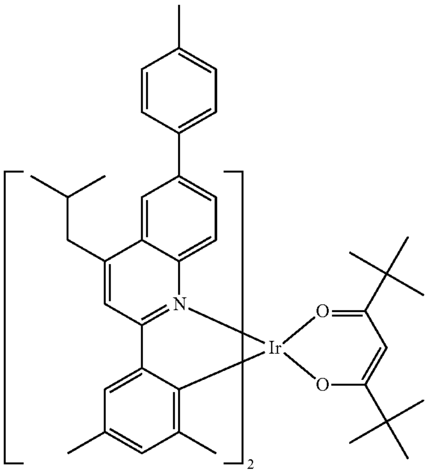
-continued
D-84
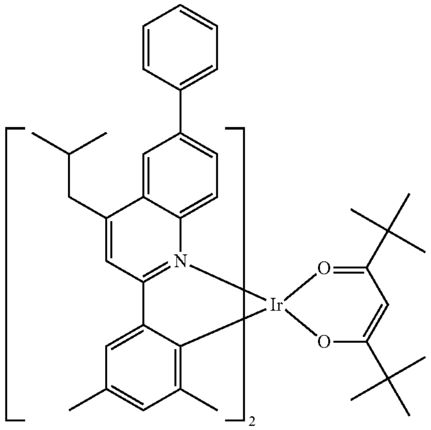
D-85
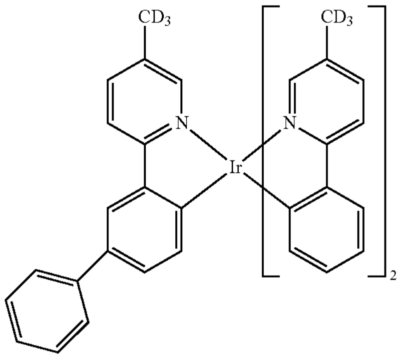
D-86
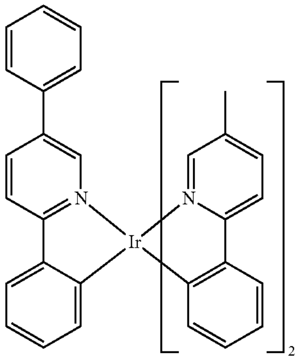
D-87
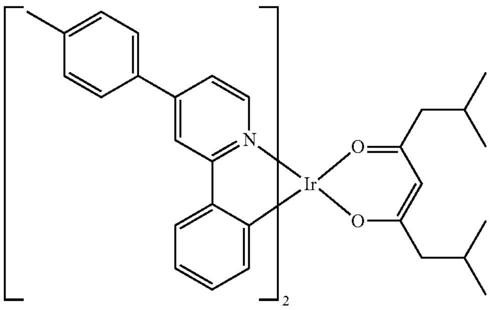

-continued
D-88
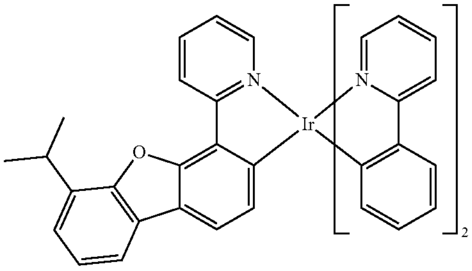
D-89
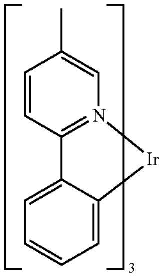
D-90
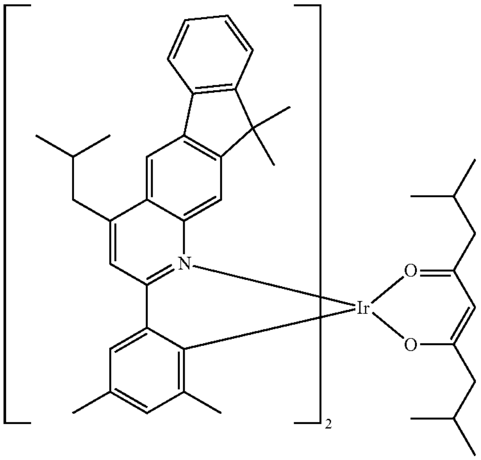
D-91
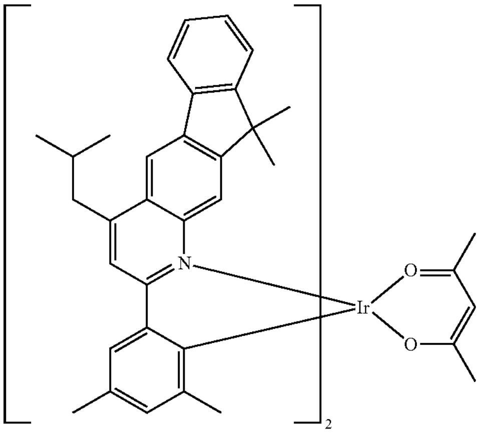
-continued
D-92
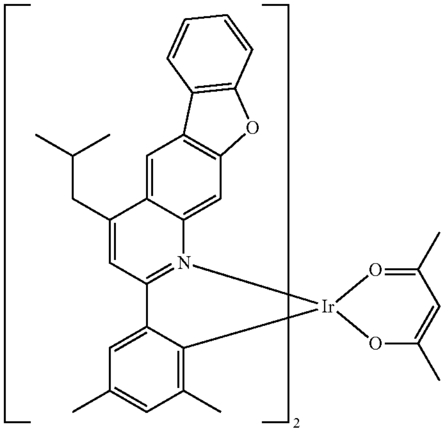
D-93
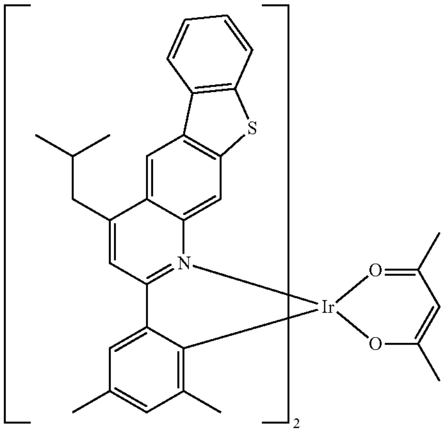
D-94
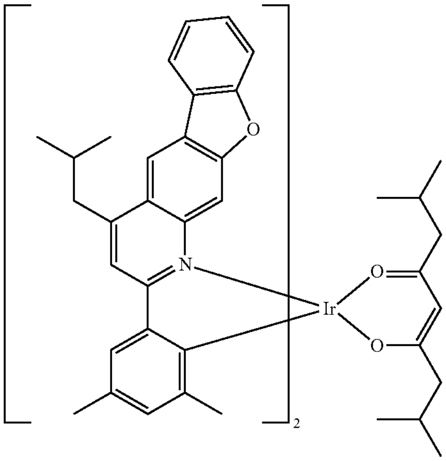

-continued
D-95
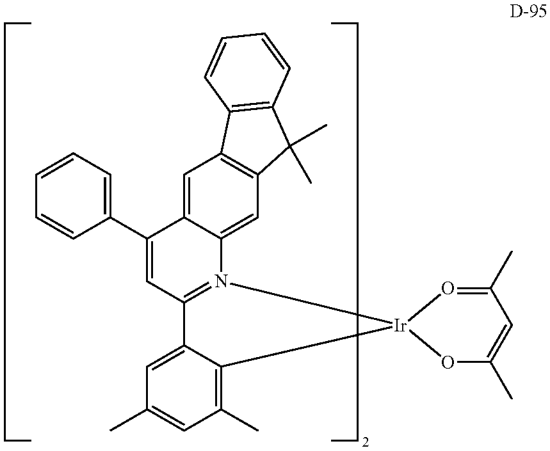
D-96
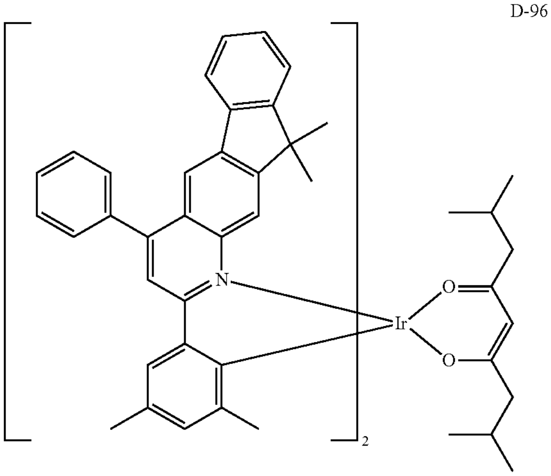
D-97
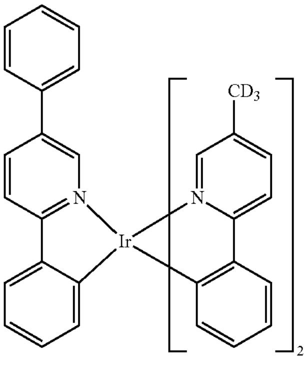
D-98
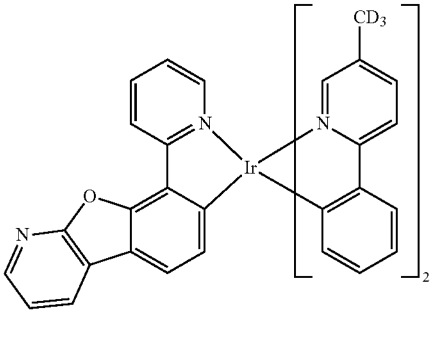
-continued
D-99
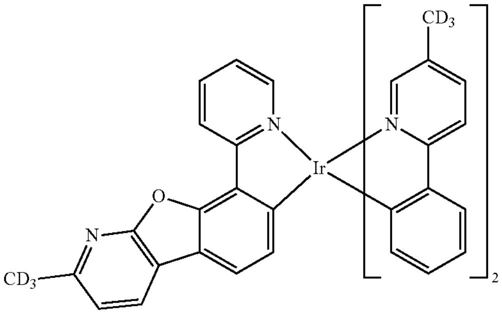
D-100
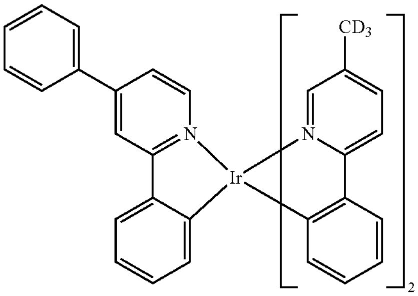
D-101
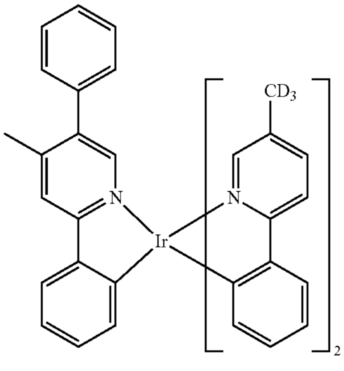
D-102
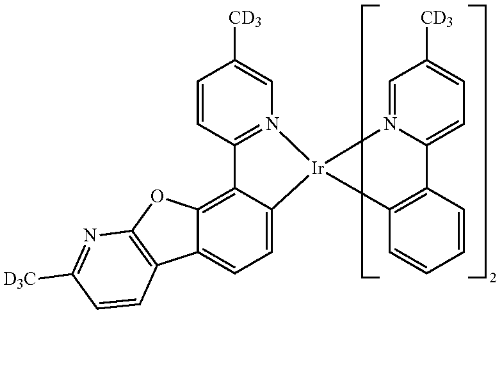

-continued
D-103
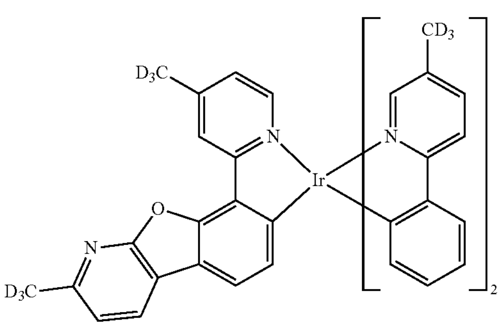
D-104
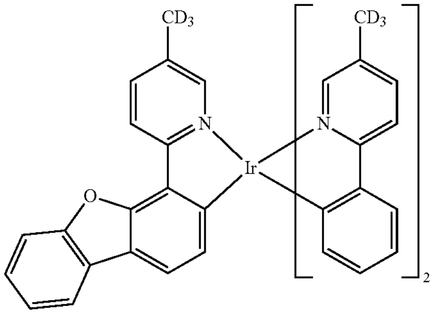
D-105
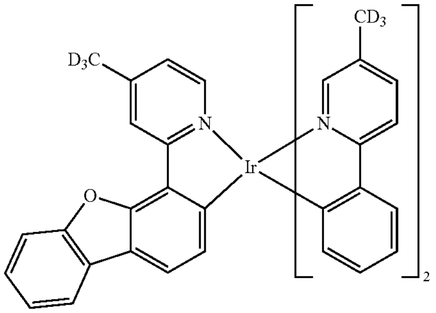
D-106
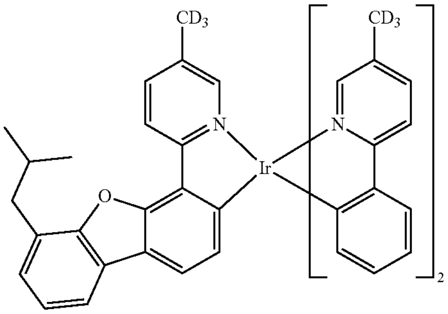
D-107
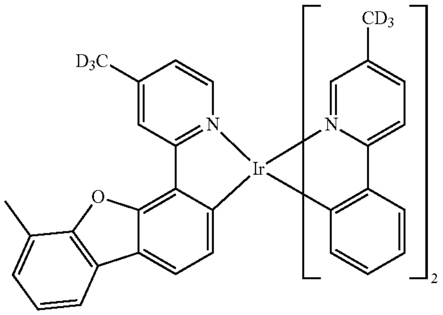
-continued
D-108
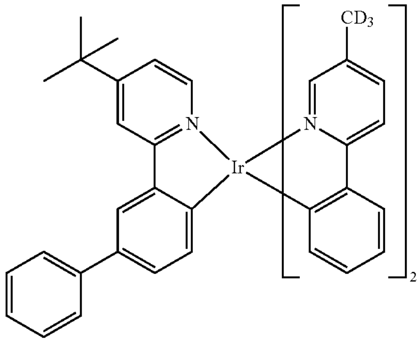
D-109
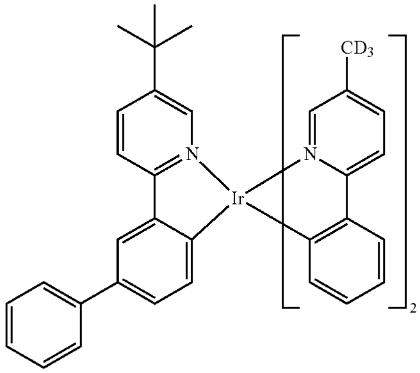
D-110
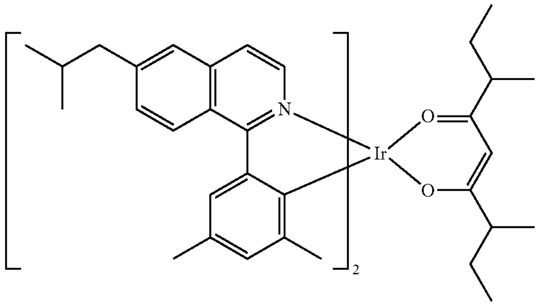
D-111
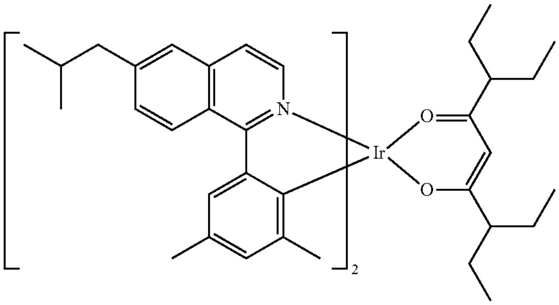

-continued
D-112
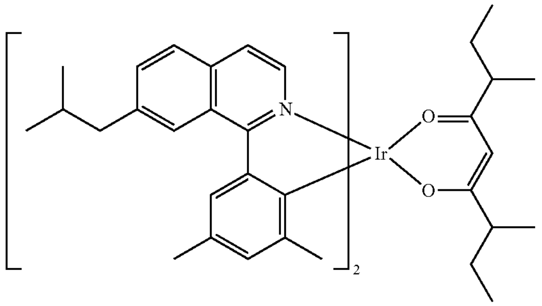
D-113
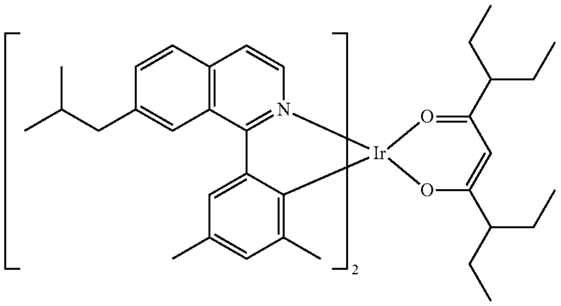
D-114
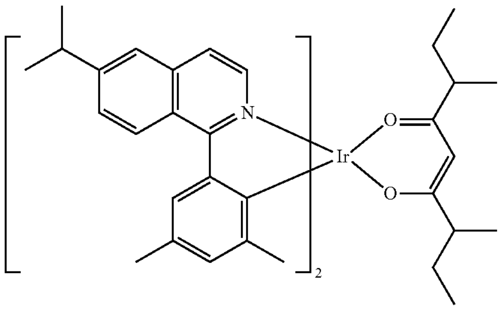
D-115
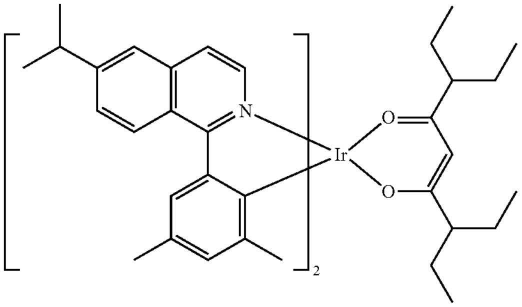
-continued
D-116
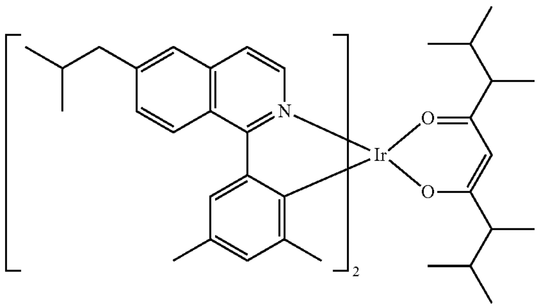
D-117
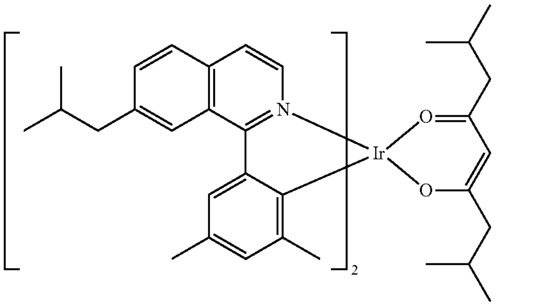
D-118
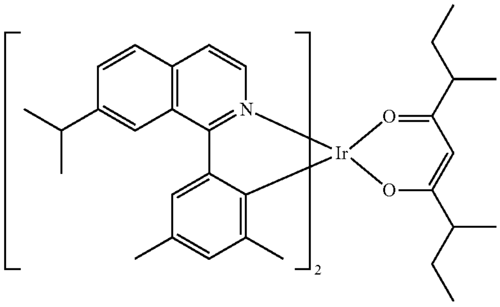
D-119
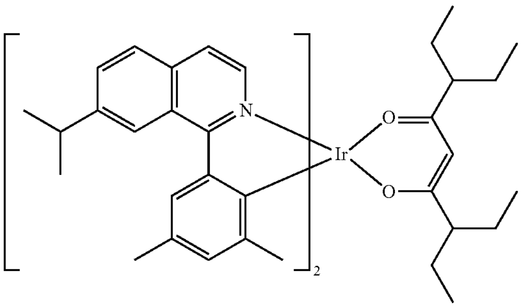

-continued
D-120
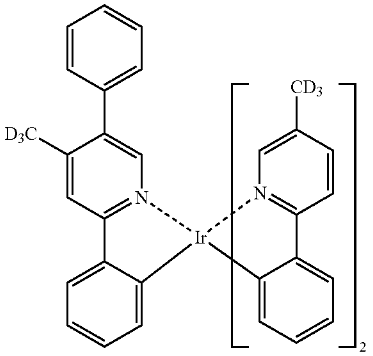
D-121
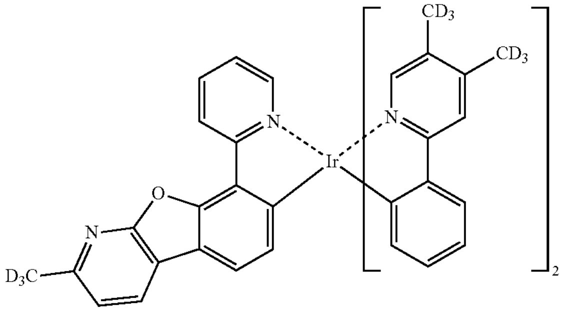
D-122
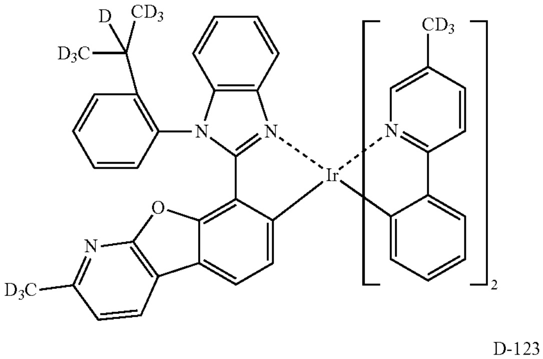
D-123
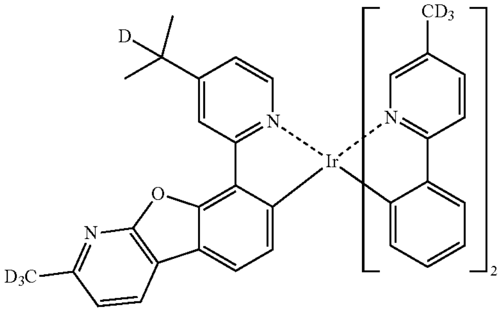
-continued
D-124
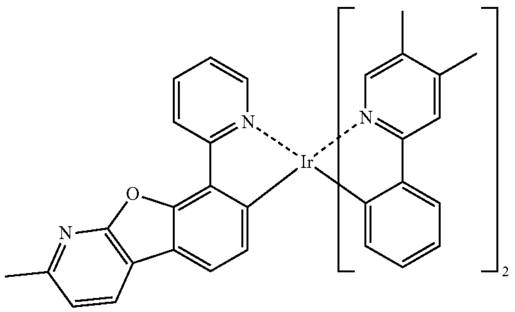
D-125
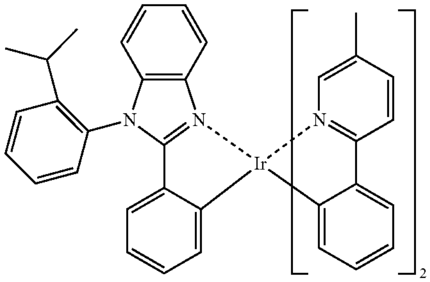
D-126
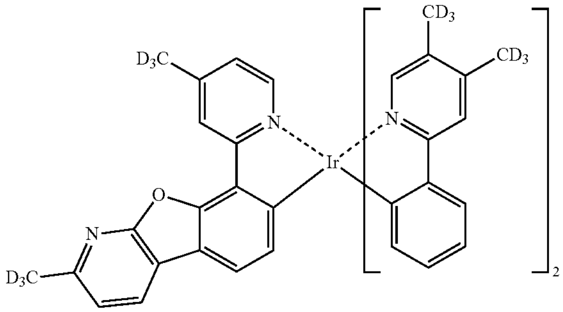
D-127
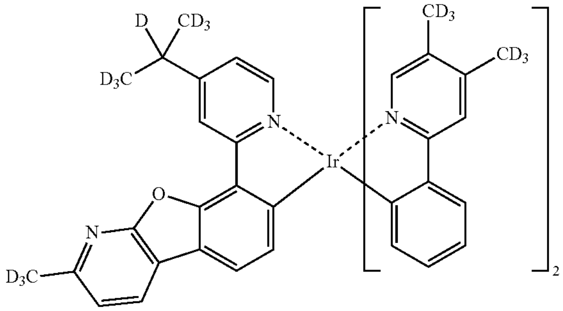
D-128
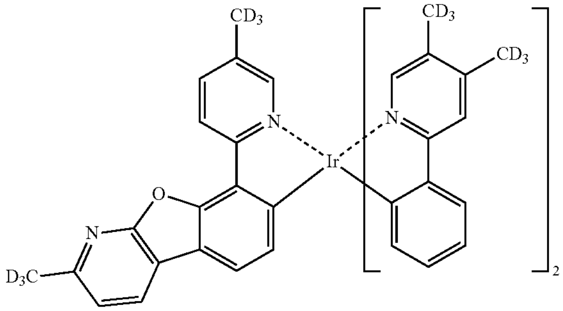

-continued
D-129
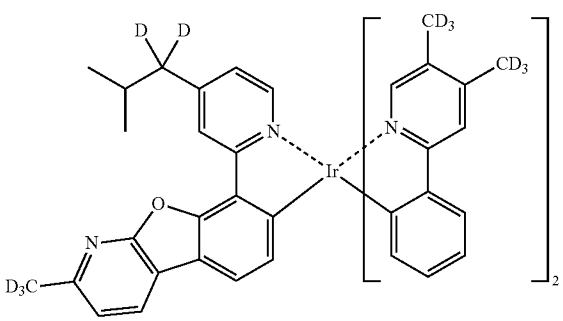
D-130
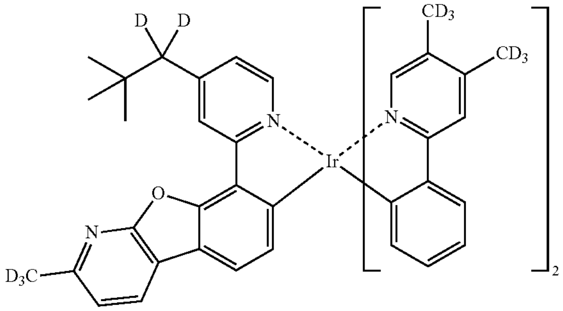
D-131
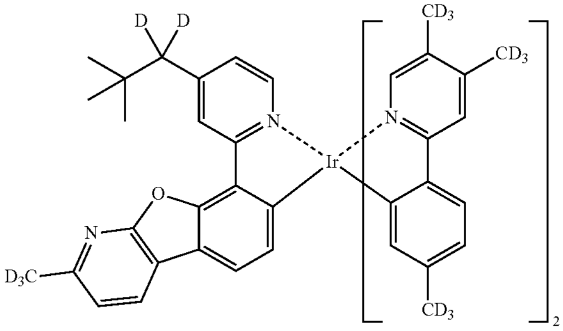
D-132
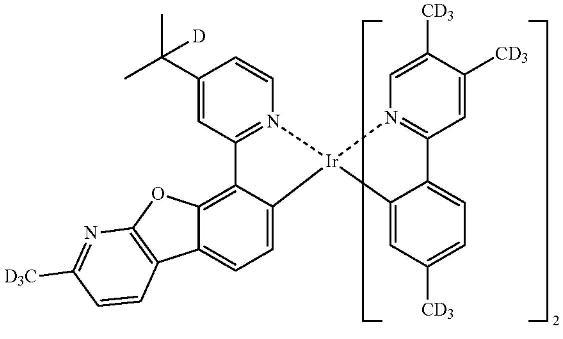
-continued
D-133
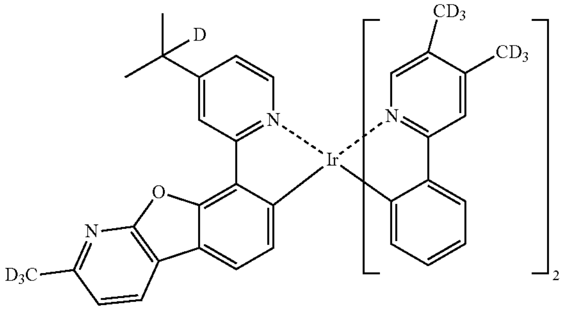
D-134
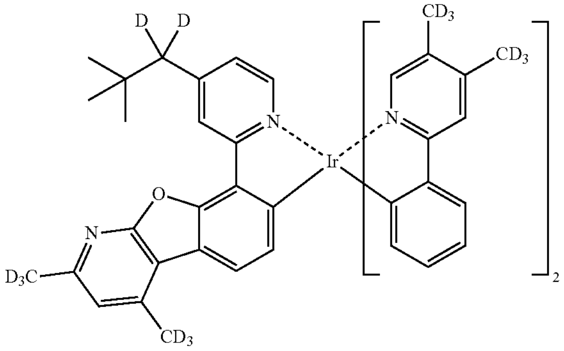
D-135
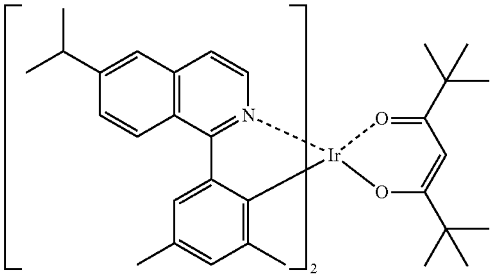
D-136
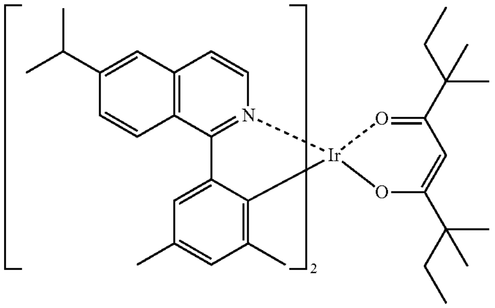
D-137
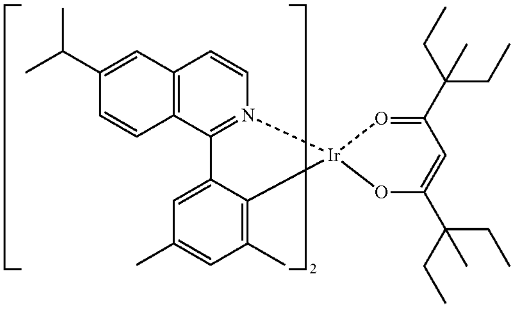

-continued
D-138
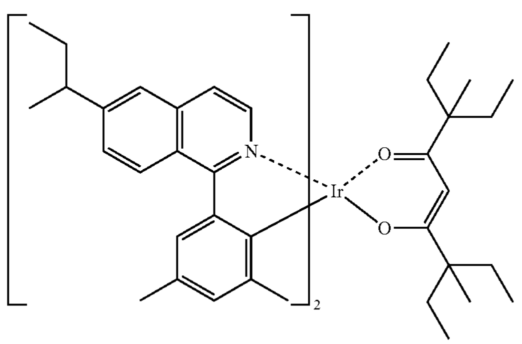
D-139
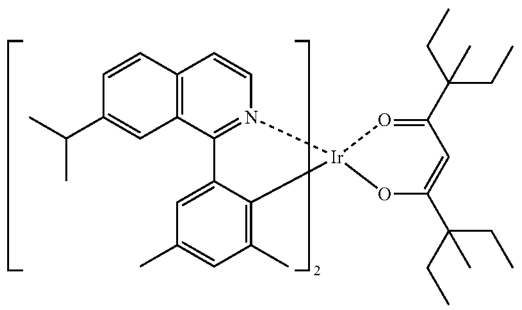
D-140
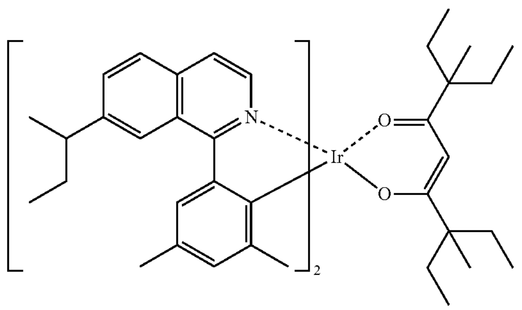
D1-141
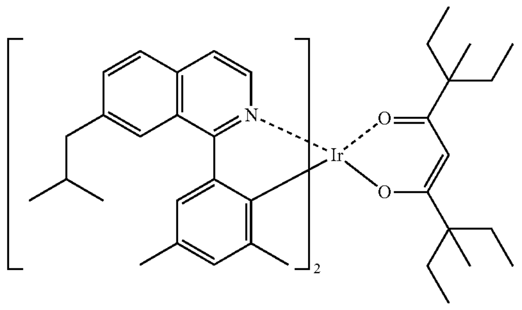
-continued
D-142
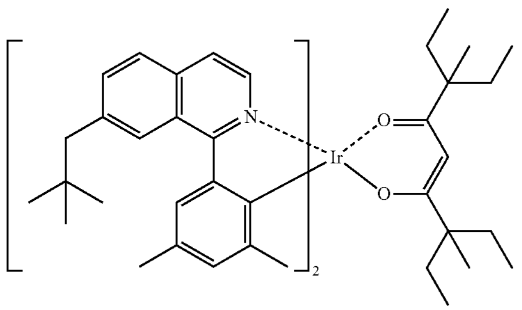
D-143
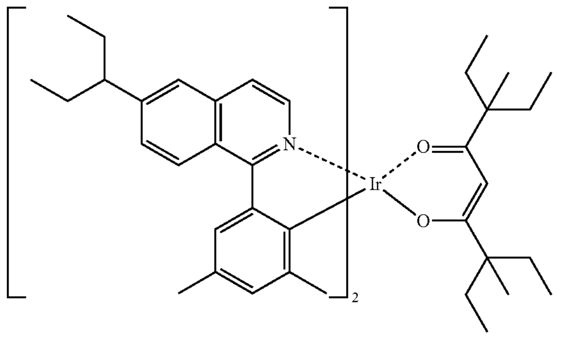
D-144
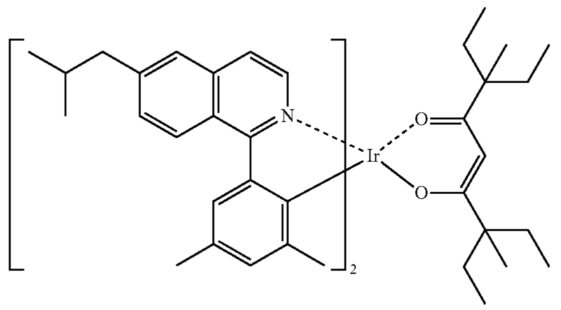
D-145
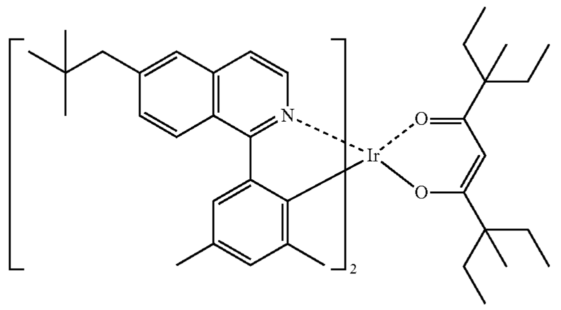

-continued

D-146

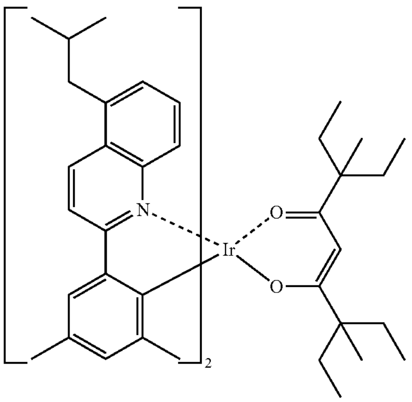

D-147

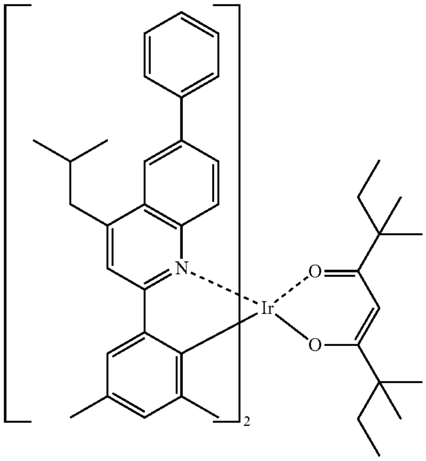

D-148

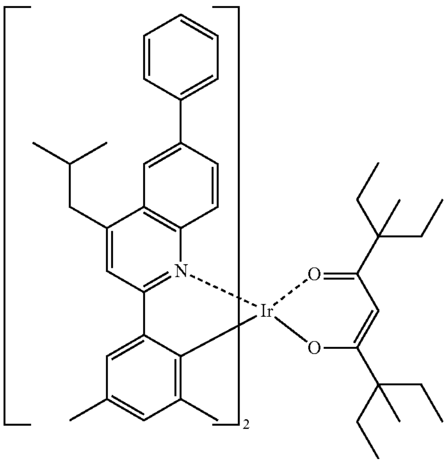

-continued

D-149

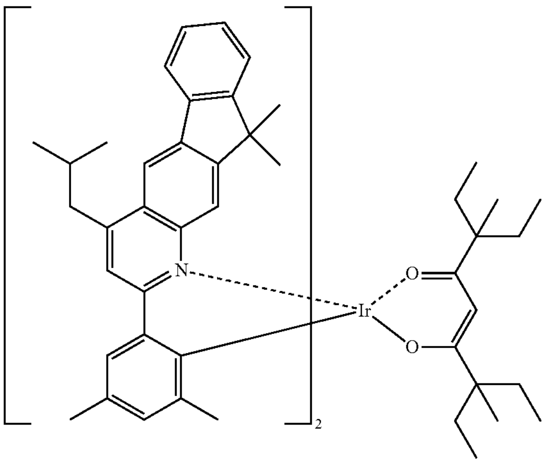

An organic electroluminescent device according to the present disclosure has an anode, a cathode, and at least one organic layer between the anode and the cathode. The organic layer comprises a light-emitting layer and may further comprise at least one layer selected from the group consisting of a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may be further configured as a plurality of layers.

The anode and the cathode may be respectively formed with a transparent conductive material, or a transflective or reflective conductive material. The organic electroluminescent device may be a top emission type, a bottom emission type, or a both-sides emission type, depending on the materials forming the anode and the cathode. In addition, the hole injection layer may be further doped with a p-dopant, and the electron injection layer may be further doped with an n-dopant.

The organic layer may further comprise at least one compound selected from the group consisting of arylamine-based compounds and styrylarylamine-based compounds.

Further, in the organic electroluminescent device of the present disclosure, the organic layer may further comprise at least one metal selected from the group consisting of metals of Group 1, metals of Group 2, transition metals of the 40 period, transition metals of the $5^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon and aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \le X \le 2$), $AlO_X$ ($1 \le X \le 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

In addition, preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers and emitting white light.

The organic electroluminescent compound or the organic electroluminescent material according to the present disclosure may be used as a light-emitting material for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. The organic electroluminescent material according to the present disclosure may also be used in an organic electroluminescent device comprising a quantum dot (QD).

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used. When the first and second host compounds of the present disclosure are used to form a film, a co-evaporation process or a mixture-evaporation process is carried out.

When using a wet film-forming method, a thin film can be formed by dissolving or diffusing materials forming each layer into any suitable solvent such as ethanol, chloroform, tetrahydrofuran, dioxane, etc. The solvent can be any one where the materials forming each layer can be dissolved or diffused, and where there are no problems in film-formation capability.

In addition, it is possible to produce a display system, for example, a display system for smart phones, tablets, notebooks, PCs, TVs, or cars; or a lighting system, for example an outdoor or indoor lighting system, by using the organic electroluminescent device of the present disclosure.

Hereinafter, the preparation method of the compounds according to the present disclosure and the properties thereof will be explained in detail with reference to the representative compounds of the present disclosure. However, the present disclosure is not limited by the following examples.

[Example 1] Preparation of Compound H1-1

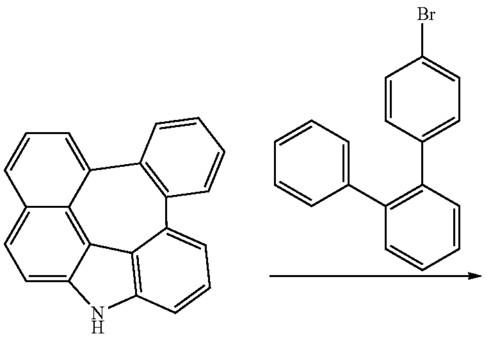

5

-continued

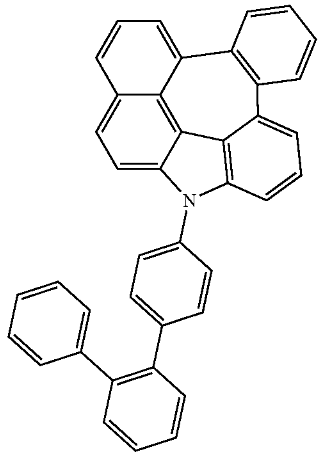

H1-1

Compound 5 (5 g, 17.16 mmol), 4-bromo-1,1':2',1"-terphenyl (5.3 g, 17.16 mmol), $Pd_2(dba)_3$ (0.8 g, 0.858 mmol), Sphos (0.7 g, 1.716 mmol), NaOt-Bu (5 g, 51.48 mmol), and 86 mL of o-xylene were added to a flask, dissolved, and then stirred under reflux for 2 hours. After completion of the reaction, the mixture was cooled to room temperature, and the resulting solid was filtered under reduced pressure. The filtered solid was dissolved in $CHCl_3$, extracted with MC/Hex, and separated by column chromatography to obtain compound H1-1 (2.4 g, yield: 26%).

$^1H$ NMR (DMSO-$d_6$) δ: 7.92-7.88 (m, 1H), 7.87-7.83 (m, 1H), 7.79 (d, J=9.1 Hz, 1H), 7.74 (t, J=8.3 Hz, 2H), 7.59-7.54 (m, 2H), 7.53-7.49 (m, 2H), 7.48-7.41 (m, 6H), 7.38 (d, J=2.3 Hz, 1H), 7.36 (d, J=2.1 Hz, 2H), 7.34-7.31 (m, 2H), 7.30-7.25 (m, 2H), 7.21-7.17 (m, 2H), 7.12 (dd, J=8.1, 0.6 Hz, 1H)

[Example 2] Preparation of Compound H1-122

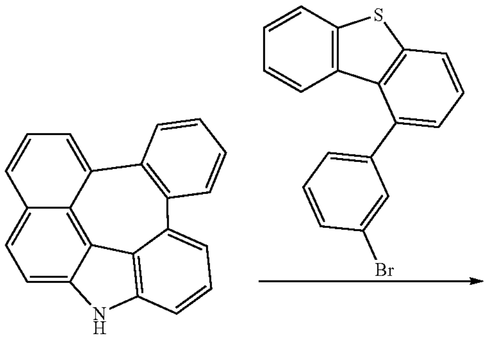

5

-continued

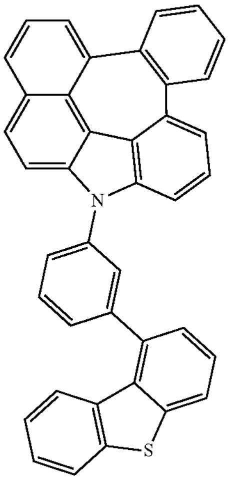

H1-122

Compound 5 (5 g, 17.16 mmol), 1-(3-bromophenyl) dibenzo[b,d]thiophene (7 g, 20.59 mmol), CuI (0.16 g, 0.858 mmol), ethylenediamine (EDA) (1 g, 17.16 mmol), $K_3PO_4$ (9.1 g, 42.90 mmol), and 90 mL of o-xylene were added to a flask, dissolved, and then stirred under reflux for 2 hours. After completion of the reaction, the mixture was cooled to room temperature, and the resulting solid was filtered under reduced pressure. The filtered solid was dissolved in $CHCl_3$, extracted with MC/Hex, and separated by column chromatography to obtain compound H1-122 (2.2 g, yield: 22%).

$^1H$ NMR (DMSO-$d_6$) δ: 8.09 (dd, J=8.0, 1.1 Hz, 1H), 8.04 (ddd, J=8.0, 1.1, 0.7 Hz, 1H), 7.92-7.87 (m, 2H), 7.85-7.82 (m, 1H), 7.80 (ddd, J=8.0, 2.1, 1.2 Hz, 1H), 7.78-7.71 (m, 3H), 7.68-7.63 (m, 2H), 7.60-7.52 (m, 3H), 7.48-7.38 (m, 5H), 7.36-7.24 (m, 4H)

[Example 3] Preparation of Compound H1-16

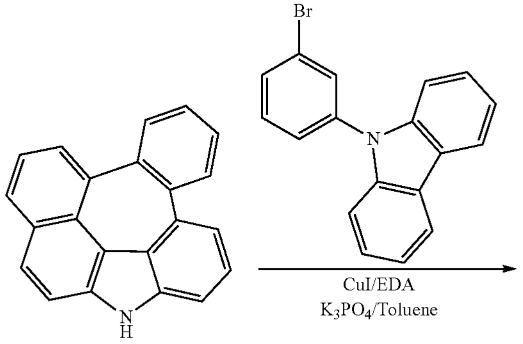

5

-continued

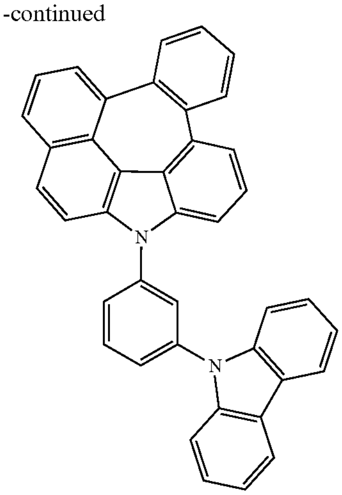

H1-16

In a flask, 70 mL of toluene was added dropwise to compound 5 (4.0 g, 14 mmol), 9-(3-bromophenyl)-9H-carbazole (4.87 g, 15 mmol), CuI (1.307 g, 7 mmol), EDA (1.647 g, 27 mmol), and $K_3PO_4$ (5.83 g, 27 mmol), and then the mixture was stirred under reflux at 180° C. for 4 hours. After completion of the reaction, the mixture was extracted with ethyl acetate, dried with magnesium sulfate, and then separated by column chromatography. Thereafter, methanol was added to the residue, and the resulting solid was filtered under reduced pressure to obtain compound H1-16 (2.3 g, yield: 31.5%).

$^1$H NMR (600 MHz, DMSO-d6, δ) 8.27 (d, J=7.8 Hz, 2H), 8.01 (t, J=8.0 Hz, 1H), 7.95-7.92 (m, 1H), 7.91-7.84 (m, 4H), 7.83 (d, J=6.9 Hz, 1H), 7.81-7.77 (m, 2H), 7.66 (d, J=8.9 Hz, 1H), 7.63-7.57 (m, 3H), 7.51-7.44 (m, 5H), 7.44-7.40 (m, 2H), 7.35-7.30 (m, 2H)

[Example 4] Preparation of Compound H1-120

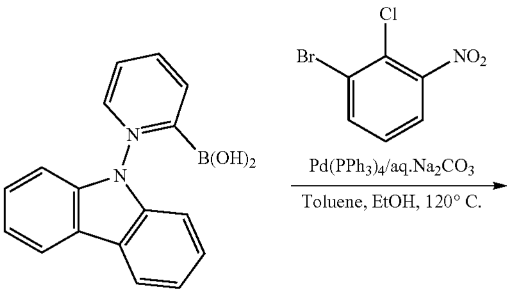

S1

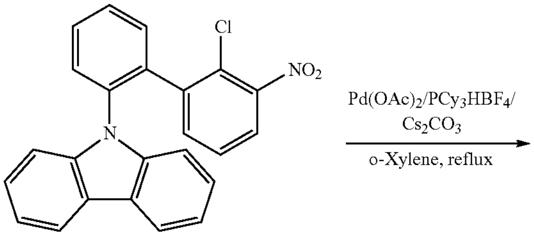

S2

-continued

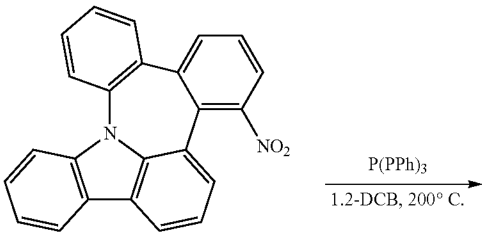

S3

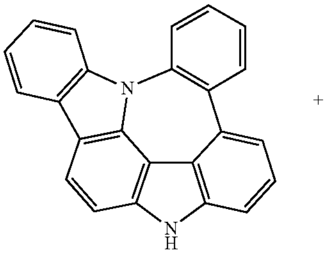

S4

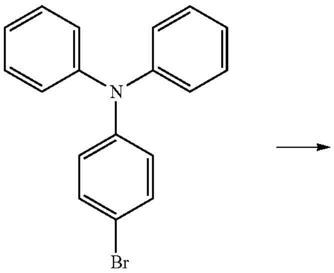

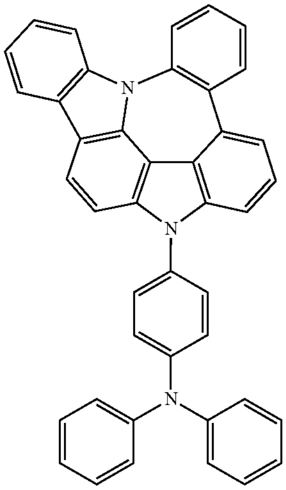

H1-120

1) Synthesis of Compound S2

Compound S1 (36 g, 125.38 mmol), 3-bromo-2-chloronitrobenzene (27 g, 113.98 mmol), tetrakis(trphenylphosphine)palladium (4 g, 3.42 mmol), sodium carbonate (30 g, 285.95 mmol), 570 mL of toluene, 140 mL of ethanol, and 140 mL of distilled water were added to a reaction vessel, and then stirred under reflux at 120° C. for 3 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound S2 (30 g, yield: 66%).

2) Synthesis of Compound S3

Compound S2 (27 g, 68.20 mmol), palladium(II)acetate (1.5 g, 6.82 mmol), tricyclohexylphosphonium tetrafluoroborate (5.0 g, 13.64 mmol), cesium carbonate (66 g, 204.60 mmol), and 340 mL of o-xylene were added to a reaction vessel, and then stirred under reflux for 2 hours. After completion of the reaction, the mixture was washed with distilled water, and the organic layer was extracted with ethyl acetate. The extracted organic layer was dried with magnesium sulfate, and then the solvent was removed using a rotary evaporator. Thereafter, the residue was purified by column chromatography to obtain compound S3 (24.8 g, yield: 100%).

3) Synthesis of Compound S4

Compound S3 (24.8 g, 68.20 mmol), triethylphosphite (176 mL, 0.4 M), and 341 mL of 1,2-dichlorobenzene (DCB) were added to a reaction vessel, and then stirred at 200° C. for 4 hours. After completion of the reaction, the mixture was distilled under reduced pressure, and triethylphosphite was removed. Subsequently, the result was washed with distilled water, and the organic layer extracted with ethyl acetate. The extracted organic layer was dried with magnesium sulfate, and then the solvent was removed using a rotary evaporator. Thereafter, the residue was purified by column chromatography to obtain compound S4 (16.4 g, yield: 70%).

4) Synthesis of Compound H1-120

Compound S4 (5.0 g, 15.2 mmol), 4-bromo-N,N-diphenylaniline (5.4 g, 16.7 mmol), $Pd_2(dba)_3$ (0.7 g, 0.76 mmol), Sphos (0.6 g, 1.52 mmol), NaOtBu (2.9 g, 30.4 mmol), and 80 mL of o-xylene were added to a flask, dissolved, and then stirred under reflux for 4 hours. After completion of the reaction, the mixture was cooled to room temperature, and stirred at room temperature. Subsequently, the solid formed by addition of MeOH was filtered under reduced pressure, extracted with MC/Hex, and separated by column chromatography to obtain compound H1-120 (4.0 g, yield: 46%).

| Compound | MW | M.P. |
|---|---|---|
| H1 -120 | 573.7 | 317° C. |

[Example 5] Preparation of Compound H1-121

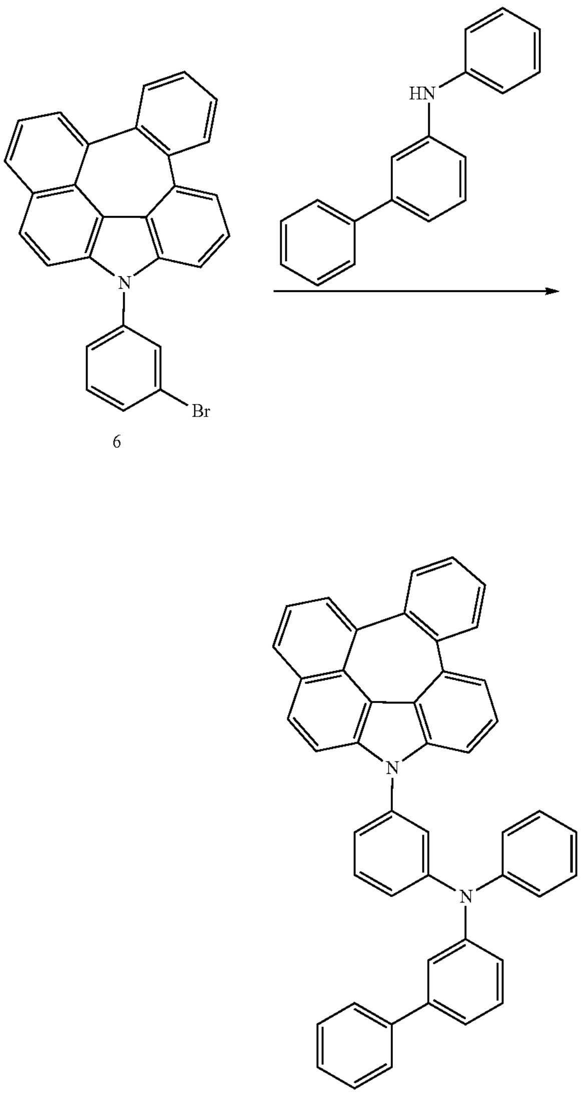

6

H1-121

Compound 6 (14.0 g, 31.4 mmol), N-phenyl-[1,1'-biphenyl]-3-amine (7.78 g, 31.7 mmol), $Pd_2(dba)_3$ (1.44 g, 1.57 mmol), $t\text{-}Bu_3P$ (635 mg, 3.14 mmol), and t-BuONa (6.04 g, 62.8 mmol), and 160 mL of toluene were added to a flask, dissolved, and then stirred under reflux for 2 hours. After completion of the reaction, the mixture was cooled to room temperature, and extracted with distilled water and ethyl acetate. The organic layer was distilled under reduced pressure, extracted with MC/Hex, and separated by column chromatography to obtain compound H1-121 (14.6 g, yield: 76%).

| Compound | MW | M.P. |
|---|---|---|
| H1-121 | 610.7 | 141° C. |

[Example 6] Preparation of Compound H1-119

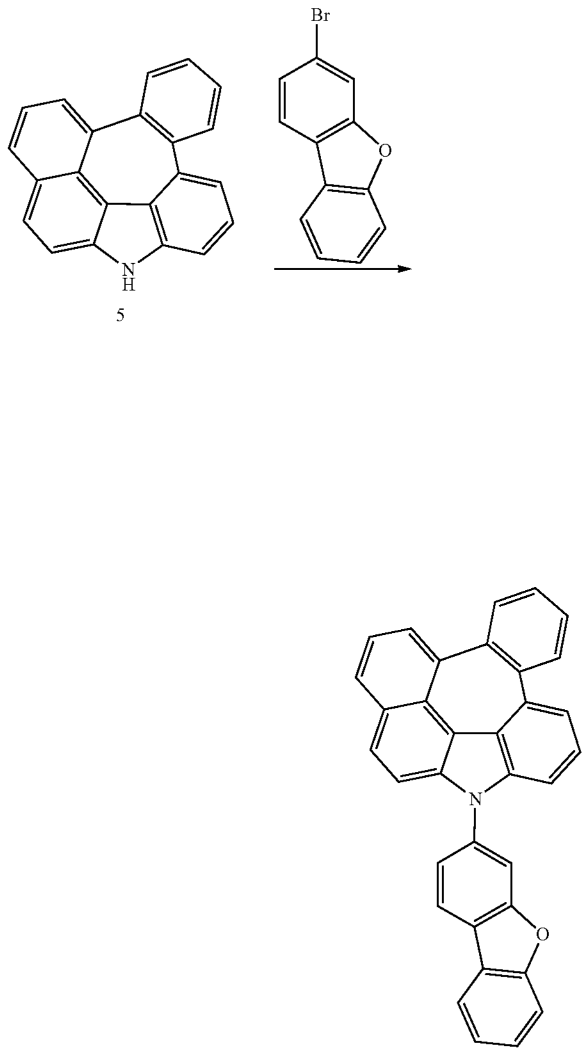

5

H1-119

Compound 5 (10 g, 34.3 mmol), 3-bromodibenzo[b,d]furan (12.7 g, 51.45 mmol), CuI (3.3 g, 17.15 mmol), ethylenediamine (EDA) (4.6 mL, 68.8 mmol), $K_3PO_4$ (21.8 g, 102.9 mmol), and 170 mL of toluene were added to a flask, dissolved, and then stirred under reflux for 12 hours. After completion of the reaction, the mixture was cooled to room temperature, and stirred at room temperature. Subsequently, the solid formed by addition of MeOH was filtered under reduced pressure, extracted with MC/Hex, and separated by column chromatography to obtain compound H1-119 (8.3 g, yield: 53%).

| Compound | MW | M.R |
|---|---|---|
| H1-119 | 457.53 | 255.4° C. |

[Example 7] Preparation of Compound H1-12

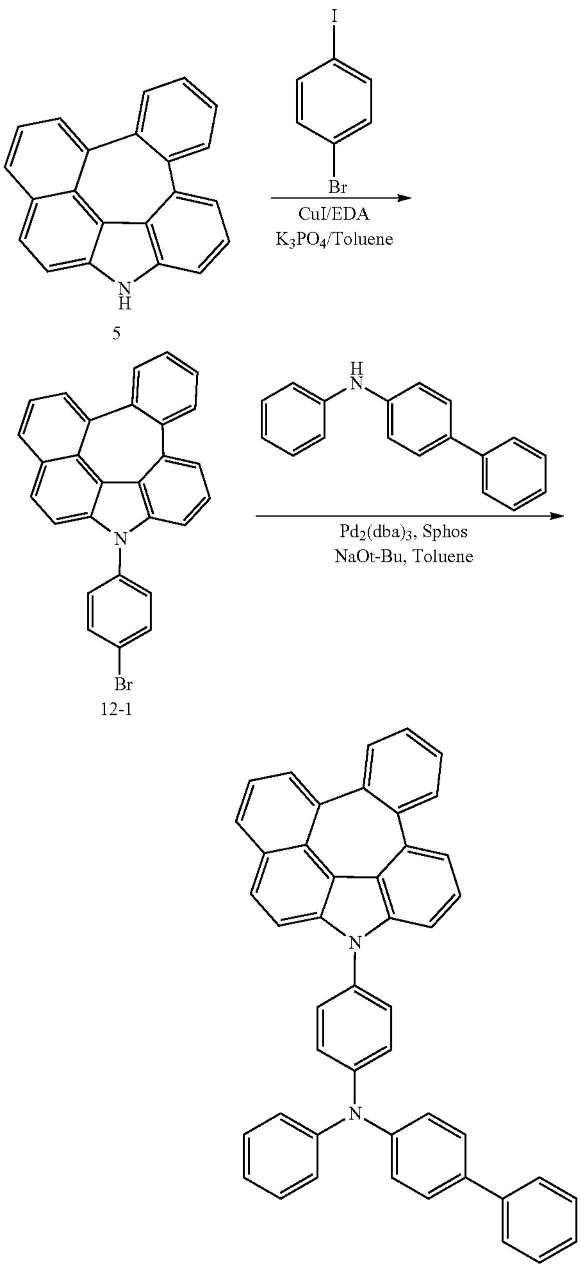

5

12-1

H1-12

1) Synthesis of Compound 12-1

Compound 5 (10.0 g, 34.3 mmol), 1-bromo-4-iodobenzene (14.6 g, 51.5 mmol), CuI (3.28 g, 17.2 mmol), EDA (4.12 g, 68.6 mmol), $K_3PO_4$ (14.6 g, 68.6 mmol), and 170 mL of toluene were added to a flask, and then stirred under reflux at 145° C. for 3 hours. After completion of the reaction, the solid was extracted with MC, and dried with $MgSO_4$, and separated by column chromatography. Subsequently, MeOH was added to the residue, and the resulting solid was filtered under reduced to obtain compound H12-1 (9.0 g, yield: 59%).

2) Synthesis of Compound H1-12

Compound 12-1 (5.0 g, 11 mmol), N-phenyl-[1,1'-biphenyl]-4-amine (3.3 g, 13 mmol), $Pd_2(dba)_3$ (0.513 g, 0.56 mmol), Sphos (0.460 g, 1 mmol), NaOt-Bu (2.691 g, 28 mmol), and 60 mL of toluene were added to a flask, and then stirred under reflux at 100° C. for half an hour. After completion of the reaction, the solid was extracted with MC, and dried with $MgSO_4$, and then separated by column chromatography. Subsequently, MeOH was added to the residue, and the resulting solid was filtered under reduced pressure to obtain compound H1-12 (1.3 g, yield: 19%).

| Compound | MW | M.P. |
|---|---|---|
| H1-12 | 610.76 | 168° C. |

[Example 8] Preparation of Compound H1-35

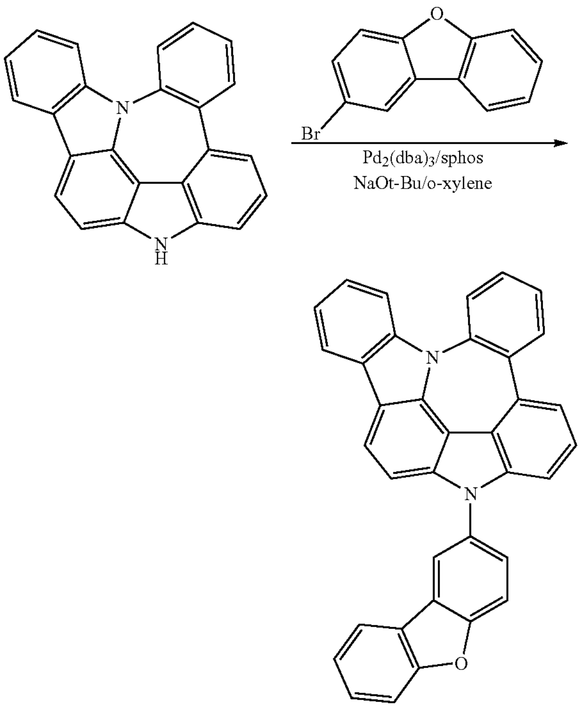

H1-35

14H-7b,14-diazadibenzo[3,4:5,6]azuleno[7,8,1-lma]fluorene (5.0 g, 15.1 mmol), 2-bromodibenzo[b,d]furan (4.1 g, 16.6 mmol), $Pd_2(dba)_3$ (0.691 g, 0.755 mmol), Sphos (0.620 g, 1.51 mmol), NaOtBu (3.63 g, 37.8 mmol), and 75 mL of o-xylene were added to a flask, dissolved, and then stirred under reflux for 6 hours. After completion of the reaction, the mixture was cooled to room temperature and stirred. The solid formed by addition of MeOH was filtered under reduced pressure, extracted with MC/Hex, and separated by column chromatography to obtain compound H1-35 (1.9 g, yield: 25%).

| Compound | MW | M.P. |
|---|---|---|
| H1-35 | 496.56 | 280° C. |

[Example 9] Preparation of Compound H1-36

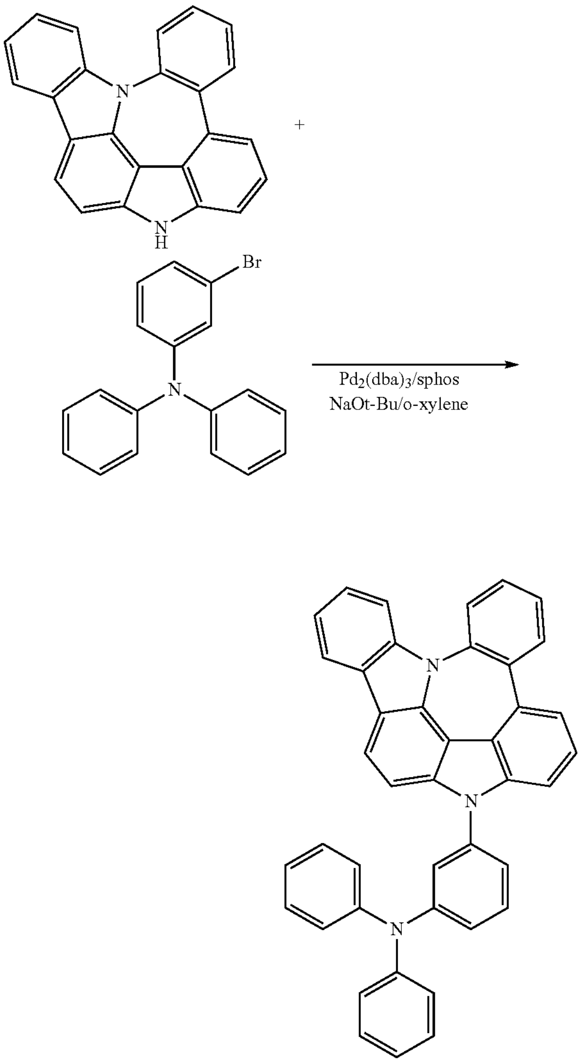

H1-36

14H-7b,14-diazadibenzo[3,4:5,6]azuleno[7,8,1-lma]fluorene (5.0 g, 15.1 mmol), 3-bromo-N,N-diphenylaniline (5.4 g, 16.6 mmol), $Pd_2(dba)_3$ (0.693 g, 0.757 mmol), Sphos (0.621 g, 1.51 mmol), NaOt-Bu (3.64 g, 37.8 mmol), and 60 mL of o-xylene were added to a flask, dissolved, and then stirred under reflux at 190° C. for an hour. After completion of the reaction, the mixture was cooled to room temperature, and separated by silica filter to obtain compound H1-36 (6.3 g, yield: 72.6%).

| Compound | MW | M.P. | Color |
| --- | --- | --- | --- |
| H1-36 | 573.70 | 230.4° c. | greenish yellow |

[Example 10] Preparation of Compound H1-14

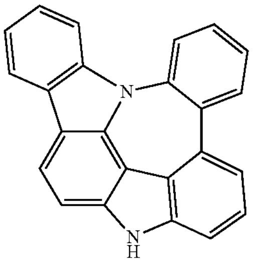

1

+

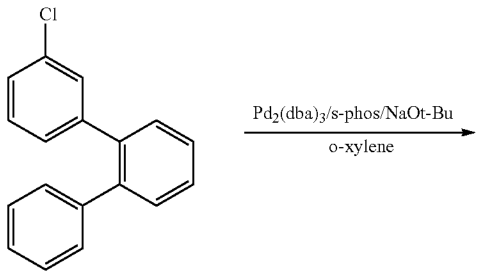

2

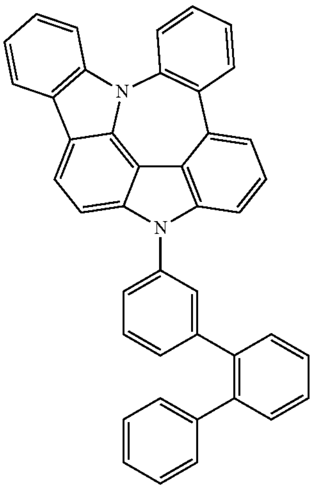

H1-14

Compound 1 (5 g, 15.13 mmol), compound 2 (4 g, 15.13 mmol), $Pd_2(dba)_3$ (0.7 g, 0.756 mmol), NaOt-Bu (4.3 g, 45.40 mmol), s-phos (0.6 g, 1.513 mmol), and 75 mL of o-xylene were added to a flask, dissolved, and then stirred under reflux for an hour and 20 minutes. After completion of the reaction, the mixture was cooled to room temperature, and methanol was added dropwise. Thereafter, the mixture was filtered, dissolved with MC, and separated by column chromatography to obtain compound H1-14 (3.1 g, yield: 36%).

| Compound | MW | M.P. |
| --- | --- | --- |
| H1-14 | 538.7 | 245.2° C. |

[Example 11] Preparation of Compound H2-9

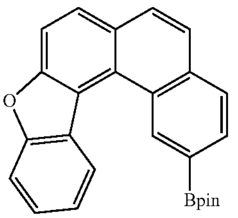

2

+

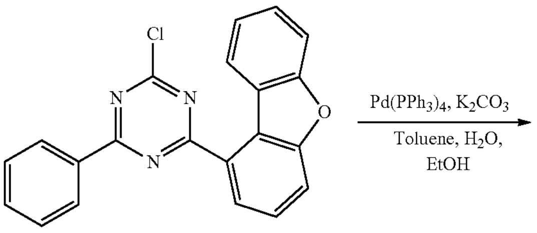

3

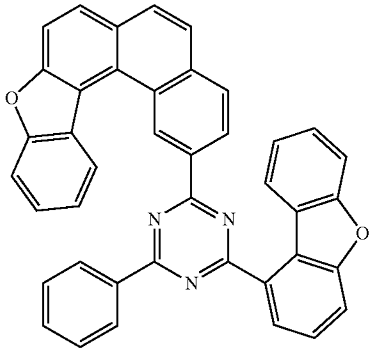

H2-9

Compound 2 (5.0 g, 12.7 mmol), compound 3 (5.5 g, 15.3 mmol), $K_2CO_3$ (3.5 g, 25.4 mmol), and $Pd(PPh_3)_4$ (0.73 g, 0.63 mmol) were added to a flask, dissolved in 39 mL of toluene, 10 mL of ethanol, and 13 mL of water, and then stirred under reflux at 130° C. for 6 hours. After completion of the reaction, the organic layer was extracted with ethyl acetate, the residual moisture was dried with magnesium sulfate, and the residue was separated by column chromatography to obtain compound H2-9 (4.4 g, yield: 20%).

| Compound | MW | M.P. |
|---|---|---|
| H2-9 | 589.65 | 318° C. |

[Example 12] Preparation of Compound H2-2

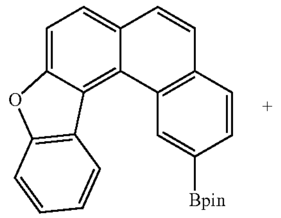

2

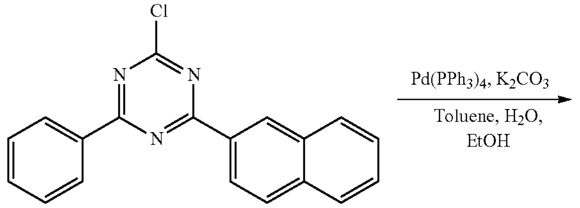

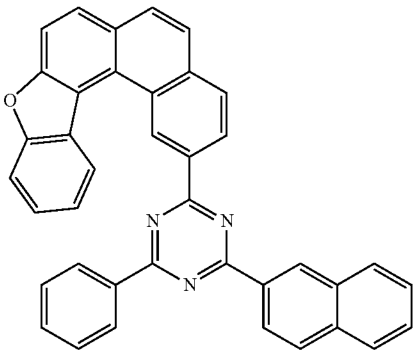

H2-2

Compound 2 (5.0 g, 12.7 mmol), 2-chloro-4-(naphthalen-2-yl)-6-phenyl-1,3,5-triazine (4.8 g, 15.2 mmol), $K_2CO_3$ (3.5 g, 25.4 mmol), and $Pd(PPh_3)_4$ (0.73 g, 0.63 mmol) were added to a flask, dissolved in 39 mL of toluene, 10 mL of ethanol, and 13 mL of water, and then stirred under reflux at 130° C. for 6 hours. After completion of the reaction, the organic layer was extracted with ethyl acetate, the residual moisture was dried with magnesium sulfate, and the residue was separated by column chromatography to obtain compound H2-2 (4.4 g, yield: 20%).

| Compound | MW | M.P. |
|---|---|---|
| H2-2 | 549.62 | 229° C. |

[Example 13] Preparation of Compound H2-191

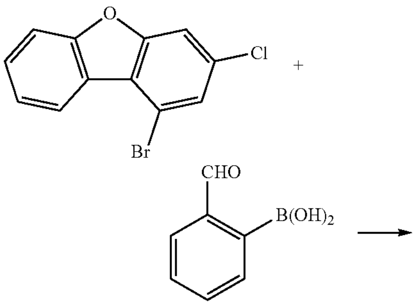

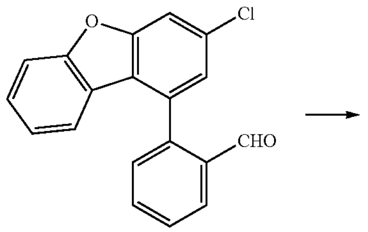

4

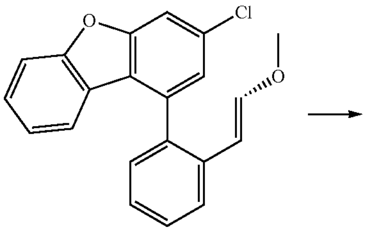

5

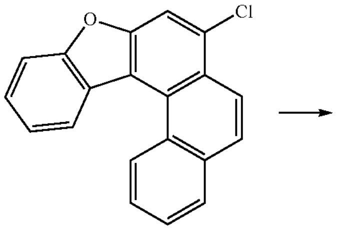

6

-continued

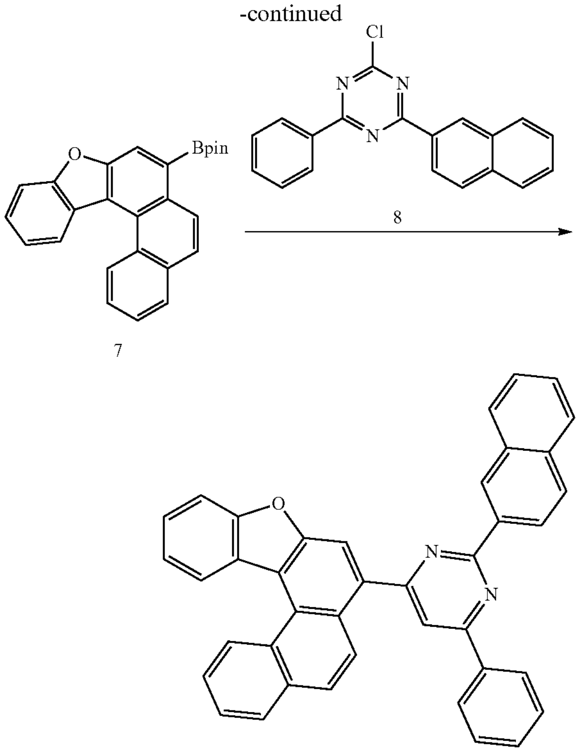

7

8

H2-191

1) Synthesis of Compound 4

1-bromo-3-chlorodibenzo[b,d]furan (39.2 g, 139.3 mmol), (2-formylphenyl)boronic acid (52.2 g, 348.1 mmol), tetrakis(triphenylphosphine)palladium(0) (16.1 g, 13.9 mmol), $Cs_2CO_3$ (136.1 g, 418 mmol), 840 mL of toluene, 160 mL of ethanol, and 210 mL of distilled water were added to a reaction vessel, and the mixture was stirred at 140° C. for 5 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound 4 (32.1 g, yield: 75%).

2) Synthesis of Compound 5

Compound 4 (31.6 g, 103 mmol), (methoxymethyl)triphenylphosphonium chloride (45.9 g, 133.9 mmol), and 515 mL of tetrahydrofuran were added, and the reaction mixture was stirred for 10 minutes. Subsequently, potassium tert-butoxide (1 M in THF, 150 mL) was slowly added dropwise at 0° C. The temperature was raised slowly, and the mixture was stirred at room temperature for 3 hours. After completion of the reaction by adding distilled water, the organic layer was extracted with ethyl acetate. The extracted organic layer was dried with magnesium sulfate, and then the solvent was removed using a rotary evaporator. Thereafter, the residue was purified by column chromatography to obtain compound 5 (31.2 g, yield: 90%).

3) Synthesis of Compound 6

Compound 5 (29.8 g, 89.0 mmol), 22.4 mL of borontrifluoride etherate, and 890 mL of methylene chloride (MC) were added to a reaction vessel, and the mixture was stirred for 3 hours. After completion of the reaction, the organic layer was extracted with methylene chloride (MC) together with water. The extracted organic layer was dried with magnesium sulfate, and then the solvent was removed using a rotary evaporator. Thereafter, the residue was purified by column chromatography to obtain compound 6 (24.2 g, yield: 90%).

4) Synthesis of Compound 7

Compound 6 (18.0 g, 59.5 mmol), bis(pinacolato)diboron (19.7 g, 77.3 mmol), tris(dibenzylideneacetone)dipalladium (0) (2.8 g, 2.9 mmol), 2-dicyclohexylphosphino-2',6'-dimethoxybiphenyl (SPhos) (2.4 g, 5.9 mmol), potassium acetate (17.5 g, 178.5 mmol), and 300 mL of 1,4-dioxane were added to a reaction vessel, and then stirred at 150° C. for 6 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound 7 (1.84 g, yield: 78%).

5) Synthesis of Compound H2-191

Compound 7 (4.0 g, 10.1 mmol), compound 8 (3.9 g, 12.2 mmol), tetrakis(triphenylphosphine)palladium(0) (0.6 g, 0.51 mmol), potassium carbonate (2.8 g, 20.2 mmol), 30 mL of toluene, 7 mL of ethanol, and 10 mL of distilled water were added to a reaction vessel, and the mixture was stirred at 130° C. for 6 hours. After completion of the reaction, methanol was added dropwise to the mixture, and the resulting solid was filtered, and purified by column chromatography to obtain compound H2-191 (4.5 g, yield: 81%).

| Compound | MW | M.P. |
|---|---|---|
| H2-191 | 549.6 | 228° C. |

[Example 14] Preparation of Compound H2-192

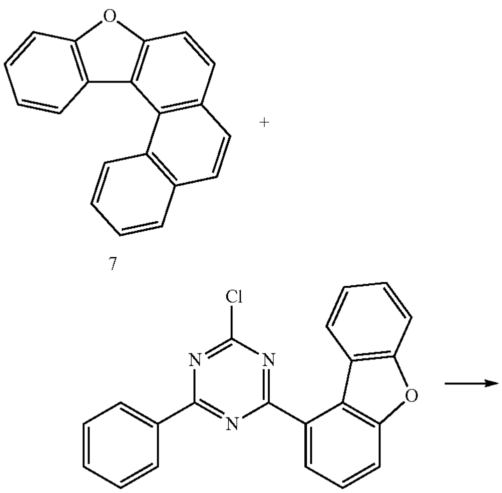

7

-continued

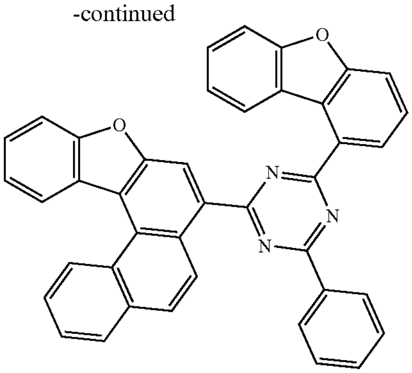

H2-192

Compound 7 (4.0 g, 10.1 mmol), 2-chloro-4-(dibenzo[b,d]furan-1-yl)-6-phenyl-1,3,5-triazine (4.4 g, 12.2 mmol), tetrakis(triphenylphosphine)palladium(0) (0.6 g, 0.5 mmol), potassium carbonate (2.8 g, 20.2 mmol), 30 mL of toluene, 7 mL of ethanol, and 10 mL of distilled water were added to a reaction vessel, and then stirred at 130° C. for 6 hours. After completion of the reaction, methanol was added dropwise to the mixture, and the resulting solid was filtered. The resulting solid was purified by column chromatography to obtain compound H2-192 (3.13 g, yield: 53%).

| Compound | MW | M.P. |
| --- | --- | --- |
| H2-192 | 589.6 | 250° C. |

[Example 15] Preparation of Compound H2-229

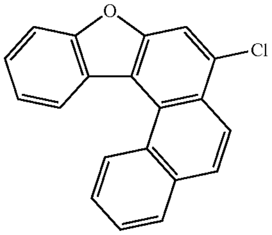

+

6

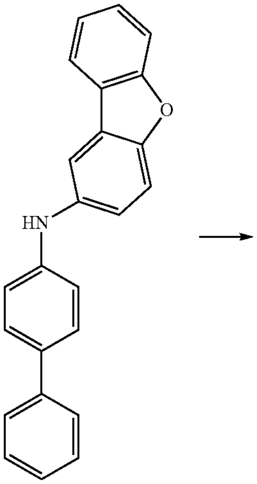

-continued

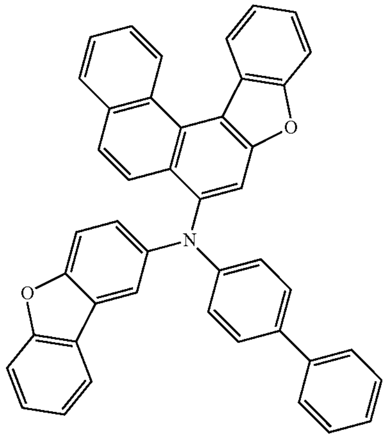

H2-229

Compound 6 (4.0 g, 13.2 mmol), N-([1,1'-biphenyl]-4-yl)dibenzo[b,d]furan-2-amine (4.4 g, 13.2 mmol), $Pd(OAc)_2$ (0.15 g, 0.66 mmol), $P(tert\text{-}Bu)_3$ (0.65 mL, 1.32 mmol), sodium tert-butoxide (2.5 g, 26.4 mmol), and 66 mL of xylene were added to a reaction vessel, and the mixture was stirred at 165° C. for 5 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound H2-229 (4.9 g, yield: 61%).

| Compound | MW | M.P. |
| --- | --- | --- |
| H2-229 | 601.7 | 200° C. |

[Example 16] Preparation of Compound H2-171

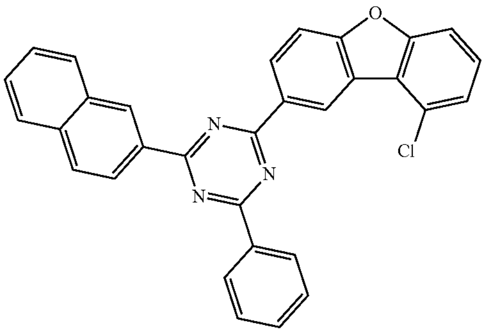

+

A

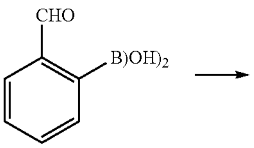

-continued

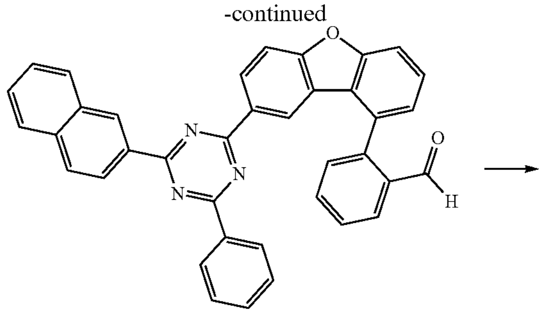

B

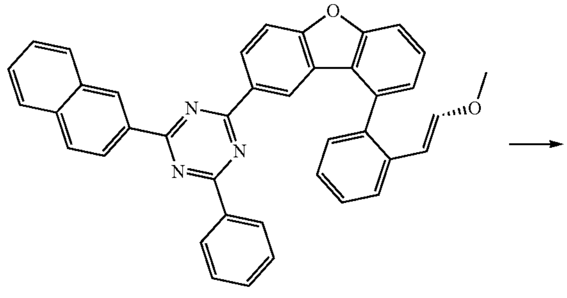

C

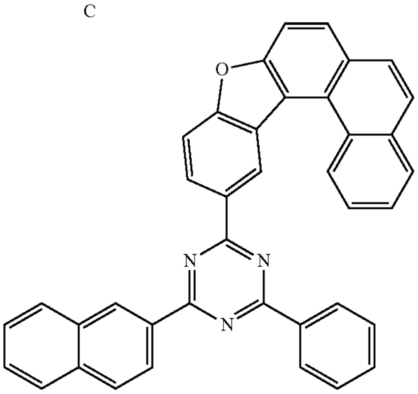

H2-171

1) Synthesis of Compound B

Compound A (5.0 g, 10.3 mmol), (2-formylphenyl)boronic acid (2.3 g, 15.5 mmol), $Pd_2(dba)_3$ (0.47 g, 0.52 mmol), 2-dicyclohexylphosphino-2',6'-dimethoxybiphenyl (SPhos) (0.43 g, 1.03 mmol), $K_3PO_4$ (5.5 g, 25.8 mmol), and 52 mL of xylene were added to a reaction vessel, and then stirred at 165° C. for 6 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound B (4.55 g, yield: 80%).

2) Synthesis of Compound C

Compound B (4.55 g, 8.22 mmol), (methoxymethyl) triphenylphosphonium chloride (3.66 g, 10.7 mmol), and 41 mL of tetrahydrofuran were added to a reaction vessel, and then the reaction mixture was stirred for 10 minutes. Subsequently, 11 mL of potassium tert-butoxide (1 M in THF) was slowly added dropwise at 0° C. The temperature was raised slowly, and the mixture was stirred at room temperature for 3 hours. After completion of the reaction by adding distilled water, the organic layer was extracted with ethyl acetate. The extracted organic layer was dried with magnesium sulfate, and then the solvent was removed using a rotary evaporator. Thereafter, the residue was purified by column chromatography to obtain compound C (3.06 g, yield: 64%).

3) Synthesis of Compound H2-171

Compound C (2.3 g, 3.95 mmol), Eaton's reagent (0.23 mL), and 23 mL of chlorobenzene were added to a reaction vessel, and then refluxed for 2 hours. After completion of the reaction, the mixture was cooled to room temperature, and the organic layer was extracted with methylene chloride (MC). The extracted organic layer was dried with magnesium sulfate, and then the solvent was removed using a rotary evaporator. Thereafter, the residue was purified by column chromatography to obtain compound H2-171 (1.93 g, yield: 89%).

| Compound | MW | M.P. |
|---|---|---|
| H2-171 | 549.62 | 204° C. |

[Example 17] Preparation of Compound H2-242

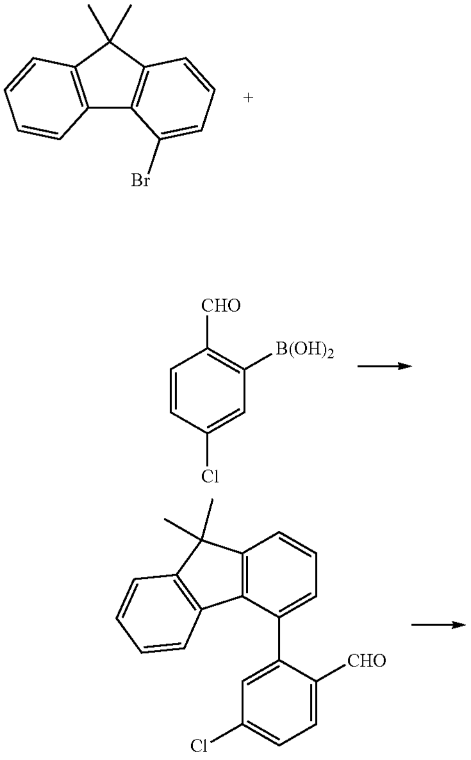

9

-continued

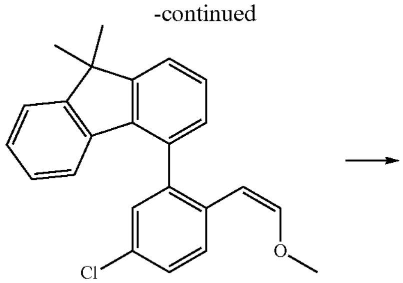

10

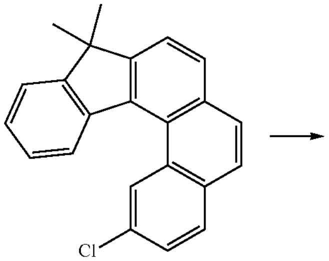

11

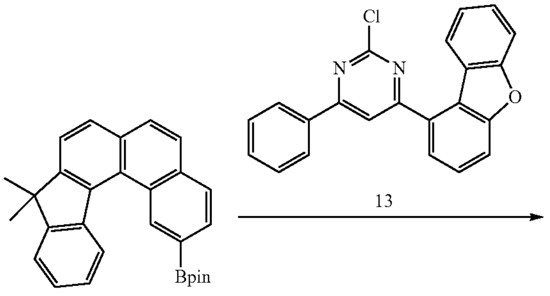

12

13

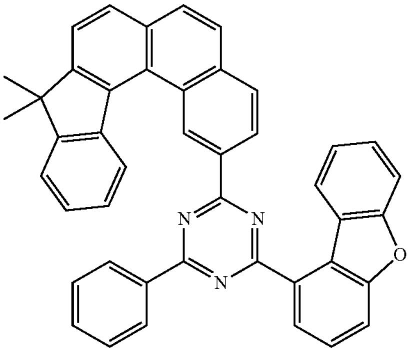

H2-242

1) Synthesis of Compound 9

4-bromo-9,9-dimethyl-9H-fluorene (50 g, 183 mmol), (5-chloro-2-formylphenyl)boronic acid (40.5 g, 219 mmol), tetrakis(triphenylphosphine) palladium(0) (10.6 g, 9.15 mmol), potassium carbonate (63 g, 457 mmol), 690 mL of toluene, 180 mL of ethanol, and 230 mL of distilled water were added to a reaction vessel, and then stirred at 140° C. for 5 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound 9 (40.3 g, yield: 66%).

2) Synthesis of Compound 10

Compound 9 (40.3 g, 121 mmol), (methoxymethyl)triphenylphosphonium chloride (53.9 g, 157.4 mmol), and 600 mL of tetrahydrofuran were added to a reaction vessel, and then the reaction mixture was stirred for 10 minutes. Subsequently, 162 mL of potassium tert-butoxide (1 M in THF) was slowly added dropwise at 0° C. The temperature was raised slowly and the mixture was stirred at room temperature for 3 hours. After completion of the reaction by adding distilled water to the reaction solution, the organic layer was extracted with ethyl acetate. The extracted organic layer was dried with magnesium sulfate, and then the solvent was removed using a rotary evaporator. Thereafter, the residue was purified by column chromatography to obtain compound 10 (39 g, yield: 89%).

3) Synthesis of Compound 11

Compound 10 (38 g, 105.3 mmol), 26.5 mL of boron trifluoride etherate, and 1000 mL of methylenechloride (MC) were added to a reaction vessel, and then stirred for 3 hours. After completion of the reaction, the organic layer was extracted with methylene chloride (MC) together with water. The extracted organic layer was dried with magnesium sulfate, and then the solvent was removed using a rotary evaporator. Thereafter, the residue was purified by column chromatography to obtain compound 11 (23.2 g, yield: 67%).

4) Synthesis of Compound 12

Compound 11 (19.1 g, 58.1 mmol), bis(pinacolato)diboron (19.1 g, 75.5 mmol), tris(dibenzylideneacetone)dipalladium(0) (2.7 g, 2.9 mmol), 2-dicyclohexylphosphino-2',6'-dimethoxybiphenyl (SPhos) (2.4 g, 5.81 mmol), potassium acetate (17.1 g, 174.3 mmol), and 290 mL of 1,4-dioxane were added to a reaction vessel, and then stirred at 150° C. for 6 hours. After completion of the reaction, the mixture was cooled to room temperature and the organic layer was extracted with ethyl acetate. The extracted organic layer was dried with magnesium sulfate, and then the solvent was removed using a rotary evaporator. Thereafter, the residue was purified by column chromatography to obtain compound 12 (12.7 g, yield: 52%).

5) Synthesis of Compound H2-242

Compound 12 (4 g, 9.5 mmol), compound 13 (4.1 g, 11.4 mmol), tetrakis(triphenylphosphine)palladium(0) (0.55 g, 0.48 mmol), potassium carbonate (2.6 g, 19.0 mmol), toluene (30 mL), ethanol (7 mL), and distilled water (10 mL) were added to a reaction vessel, and then stirred at 130° C. for 6 hours. After completion of the reaction, methanol was added dropwise to the mixture, and the resulting solid was filtered. The resulting solid was purified by column chromatography to obtain compound H2-242 (4.73 g, yield: 80%).

| Compound | MW | M.P. |
|---|---|---|
| H2-242 | 615.7 | 237° C. |

[Example 18] Preparation of Compound H2-241

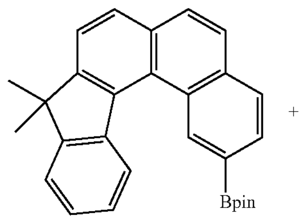

12

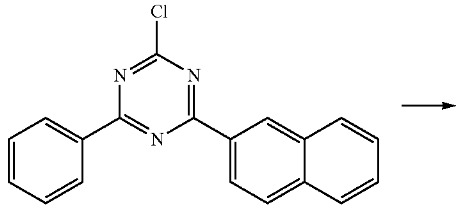

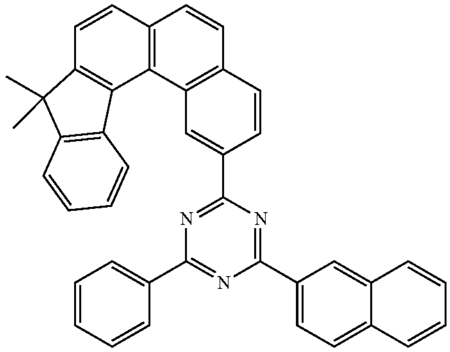

H2-241

Compound 12 (5.0 g, 11.9 mmol), 2-chloro-4-(naphthalen-2-yl)-6-phenyl-1,3,5-triazine (4.5 g, 14.3 mmol), tetrakis (triphenylphosphine)palladium(0) (0.7 g, 0.6 mmol), potassium carbonate (3.3 g, 23.8 mmol), 36 mL of toluene, 10 mL of ethanol, and 12 mL of distilled water were added to a reaction vessel, and then stirred at 130° C. for 6 hours. After completion of the reaction, methanol was added dropwise to the mixture, and the resulting solid was filtered. The resulting solid was purified by column chromatography to obtain compound H2-241 (3.64 g, yield: 53%).

| Compound | MW | M.P. |
|---|---|---|
| H2-241 | 575.7 | 209° C. |

[Example 19] Preparation of Compound H2-57

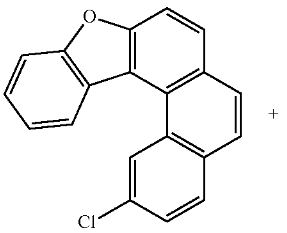

14

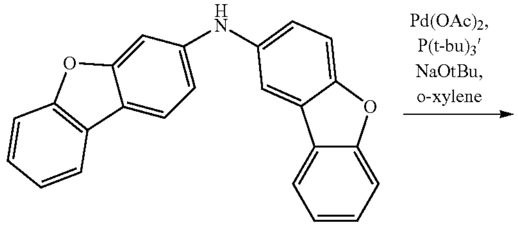

15

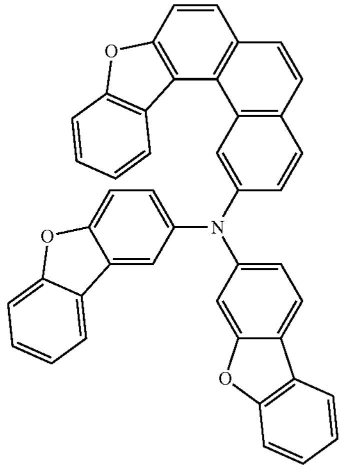

H2-57

Compound 14 (5.0 g, 16.5 mmol), compound 15 (5.7 g, 16.5 mmol), $Pd(OAc)_2$ (0.19 g, 0.82 mmol), $P(t\text{-}Bu)_3$ (0.82 mL, 1.65 mmol), NaOtBu (3.2 g, 33.0 mmol), and 83 mL of o-xylene were added to a flask, dissolved, and then stirred under reflux for 2 hours. After completion of the reaction, the mixture was extracted with $EA/H_2O$, and separated by column chromatography to obtain compound H2-57 (4.46 g, yield: 43%).

| Compound | MW | M.P. |
|---|---|---|
| H2-57 | 615.69 | 239° C. |

[Example 20] Preparation of Compound H2-52

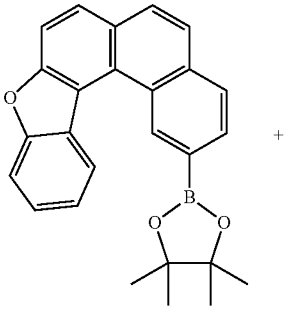

16

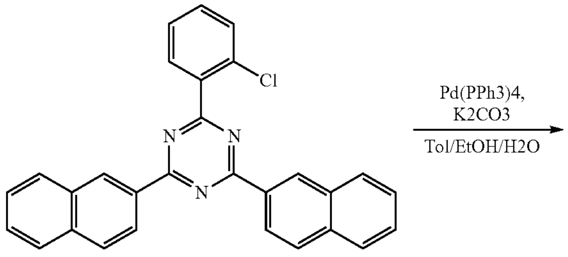

17

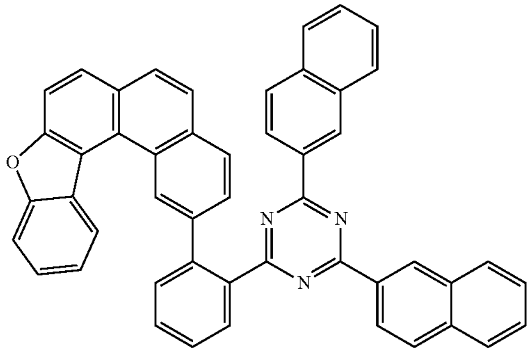

H2-52

Compound 16 (4 g, 10.14 mmol), compound 17 (4.3 g, 10.14 mmol), $Pd(PPh_3)_4$ (586 mg, 0.507 mmol), $K_2CO_3$ (2.8 g, 20.29 mmol), 50 mL of toluene, 12 mL of EtOH, and 13 mL of $H_2O$ were added to a flask, dissolved, and then stirred under reflux at 140° C. for 6 hours. After completion of the reaction, the mixture was cooled to room temperature, and the resulting solid was filtered under reduced pressure. The resulting solid was dissolved in $CHCl_3$, separated with $SiO_2$ filter, and recrystallized with o-xylene and o-dichlorobenzene (o-DCB) to obtain compound H2-52 (5.8 g, yield: 65%).

| Compound | MW | M.P. |
|---|---|---|
| H2-52 | 675.7 | 270.8° C. |

[Example 21] Preparation of Compound H2-166

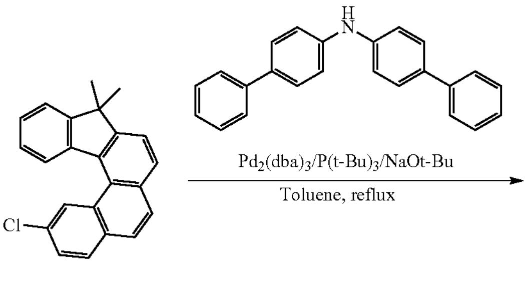

11

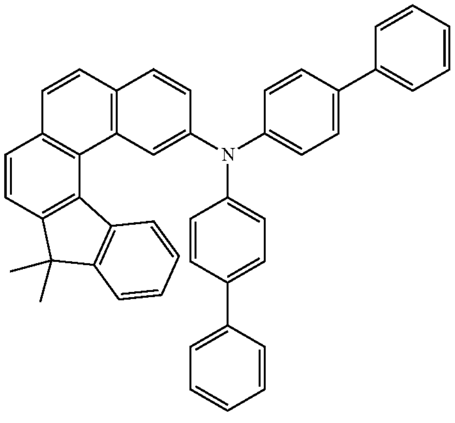

H2-166

Compound 11 (3.3 g, 10.04 mmol), di([1,1'-biphenyl]-4-yl)amine (3.2 g, 10.04 mmol), tris(dibenzylideneacetone) dipalladium(0) (0.5 g, 0.50 mmol), tri-tert-butylphosphine (0.5 mL, 1.04 mmol), sodium tert-butoxide (1.5 g, 15.06 mmol), and 50 mL of toluene were added to a flask, and then stirred under reflux for 4 hours. After the reaction mixture was cooled to room temperature, the solid was filtered and washed with ethyl acetate. The filtrate was distilled under reduced pressure and purified by column chromatography to obtain compound H2-166 (3.2 g, yield: 52%).

| Compound | MW | M.P. |
|---|---|---|
| H2-166 | 613.79 | 213° C. |

[Example 22] Preparation of Compound H2-230

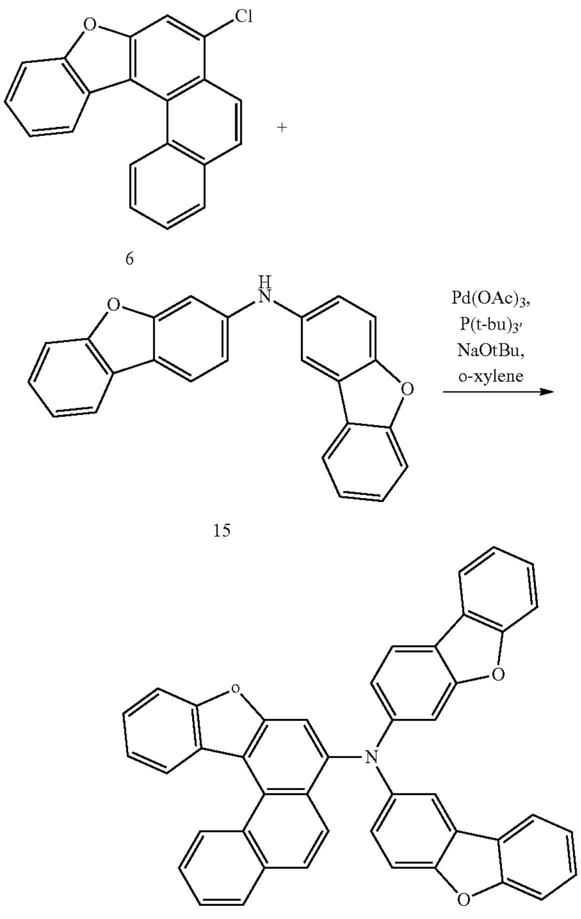

6

15

H2-230

Compound 6 (2.14 g, 7.1 mmol), compound 15 (2.5 g, 7.1 mmol), $Pd(OAc)_2$ (0.08 g, 0.36 mmol), tri-tert-butylphosphine (0.35 mL, 0.71 mmol), sodium tert-butoxide (1.4 g, 14.2 mmol), and 36 mL of o-xylene were added to a reaction vessel, and then stirred at 165° C. for 6 hours. After completion of the reaction, the mixture was cooled to room temperature, and the organic layer was extracted with ethyl acetate. The extracted organic layer was dried with magnesium sulfate, and then the solvent was removed using a rotary evaporator. Thereafter, the residue was purified by column chromatography to obtain compound H2-230 (2.0 g, yield: 12%).

| Compound | MW |
|---|---|
| H2-230 | 615.69 |

Hereinafter, the luminous efficiency and lifetime properties of the organic electroluminescent device (OLED) according to the present disclosure will be explained in detail. However, the following examples merely illustrate the properties of an OLED according to the present disclosure, but the present disclosure is not limited to the following examples.

Device Examples 1 to 7: Producing OLEDs by Co-Evaporating the First Host Compound and the Second Host Compound According to the Present Disclosure OLEDs according to the present disclosure were produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was used after storage in isopropyl alcohol. The ITO substrate was then mounted on a substrate holder of a vacuum vapor deposition apparatus. Compound HI-1 shown in Table 2 was introduced into a cell of the vacuum vapor deposition apparatus, and compound HT-1 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm. Next, compound HT-1 was deposited on the hole injection layer to form a first hole transport layer having a thickness of 80 nm. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: Each of the first host compound and the second host compound shown in Table 1 below were introduced into two cells of the vacuum vapor deposition apparatus as hosts, and compound D-39 was introduced into another cell as a dopant. The two host materials were evaporated at a rate of 1:1 while simultaneously evaporating the dopant material at different rates, and the dopant was deposited in a doping amount of 3 wt % based on the total amount of the hosts and dopant to form a light-emitting layer having a thickness of 40 nm on the second hole transport layer. Next, compound ET-1 and compound EI-1 were deposited at a weight ratio of 50:50 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, OLEDs were produced. All the materials used for producing the OLEDs were purified by vacuum sublimation at 10$ torr.

Comparative Examples 1 to 3: Producing OLEDs Comprising Comparative Compound as a Host OLEDs were produced in the same manner as in Device Examples 1 to 7, except that the second host compound of Table 1 below was used alone as a host of the light emitting layer.

The driving voltage, luminous efficiency, and light-emitting color at a luminance of 1,000 nit, and the time taken for the intensity of light to decrease from 100% to 95% at a luminance of 10,000 nit (lifetime: T95) of the OLEDs produced in Device Examples 1 to 7 and Comparative Examples 1 to 3 are provided in Table 1 below.

TABLE 1

| | First Host | Second Host | Driving Voltage [V] | Luminous Efficiency [cd/A] | Light-Emitting Color | Lifetime T95 [hr] |
|---|---|---|---|---|---|---|
| Device Example 1 | H1-35 | H2-192 | 3.0 | 36.1 | Red | 321 |
| Device Example 2 | H1-36 | H2-192 | 2.9 | 36.2 | Red | 202 |
| Device Example 3 | H1-14 | H2-192 | 3.0 | 34.2 | Red | 414 |
| Device Example 4 | H1-11 | H2-192 | 3.0 | 33.6 | Red | 368 |
| Device Example 5 | H1-14 | H2-171 | 3.2 | 30.5 | Red | 138 |
| Device Example 6 | H1-11 | H2-171 | 3.2 | 34.1 | Red | 151 |
| Device Example 7 | H1-11 | H2-172 | 3.1 | 33.3 | Red | 298 |
| Comparative Example 1 | — | H2-192 | 3.1 | 25.5 | Red | 40 |
| Comparative Example 2 | — | H2-172 | 3.3 | 18.2 | Red | 10 |
| Comparative Example 3 | — | H2-171 | 3.3 | 26.6 | Red | 5 |

From Table 1 above, it can be confirmed that the OLEDs comprising the specific combinations of the compounds according to the present disclosure as host materials exhibit low driving voltage and high luminous efficiency, and in particular, the lifetime is significantly improved, compared to the OLEDs using the a single host material (Comparative Example 1 to 3).

The compounds used in the Device Examples and the Comparative Examples are shown in Table 2 below.

TABLE 2

| | |
|---|---|
| Hole Injection Layer/ Hole Transport Layer | 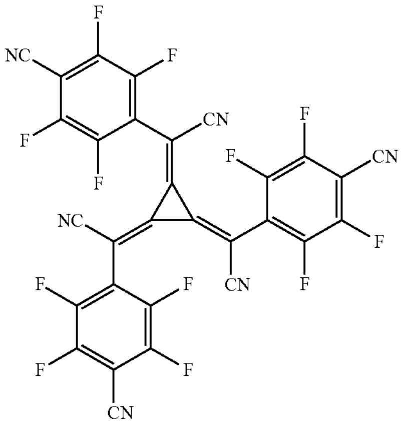 HI-1 |

TABLE 2-continued

| | |
|---|---|
| | 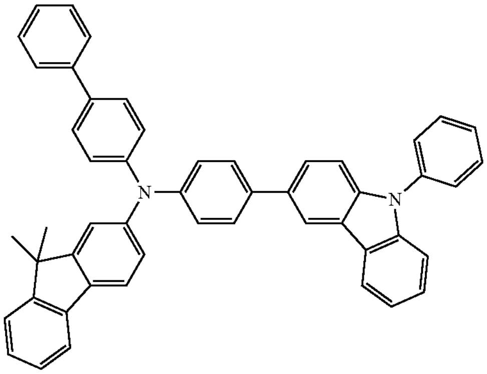 HT-1 |
| | 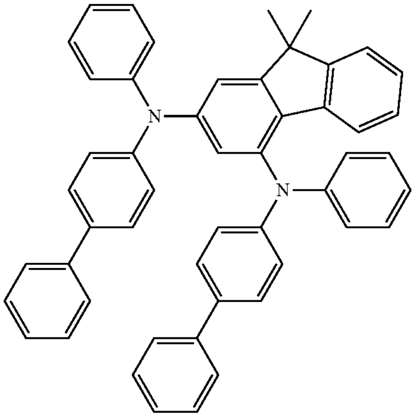 HT-2 |
| Light-Emitting Layer | 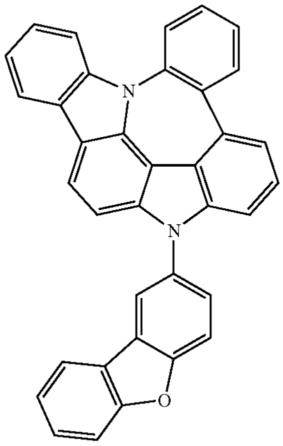 H1-35 |

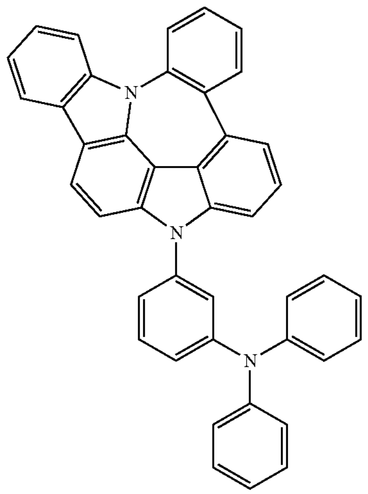
H1-36
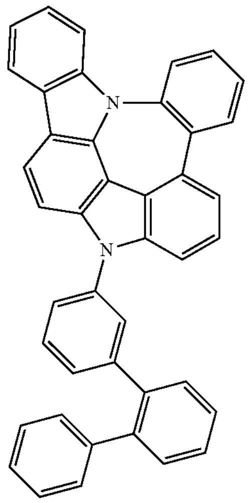
H1-14
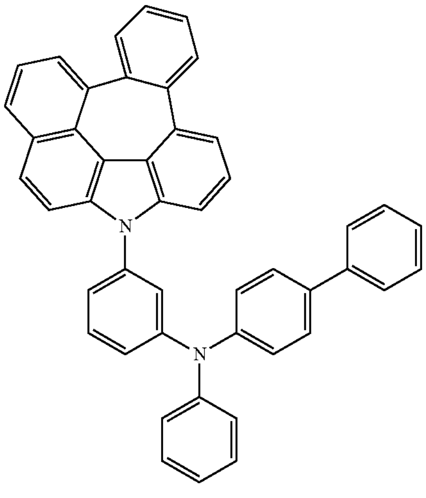
H1-11
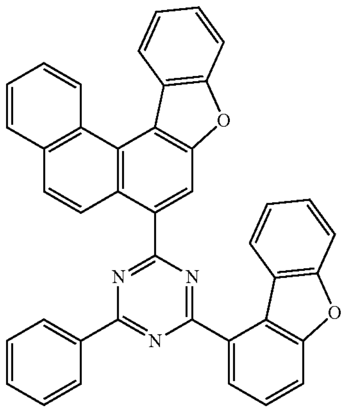
H2-192
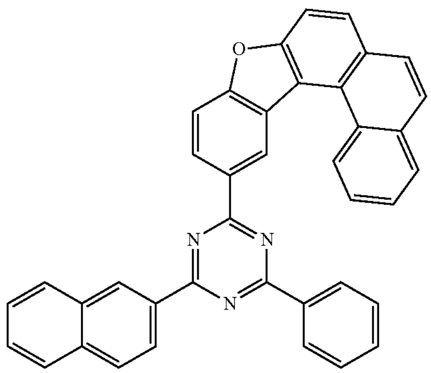
H2-171
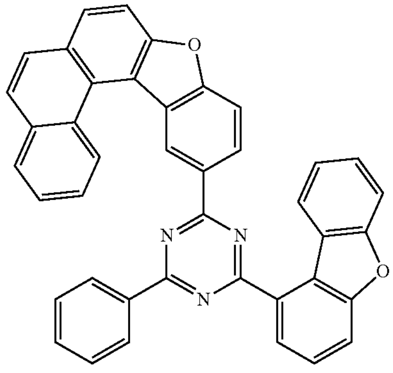
H2-172

TABLE 2-continued

| | |
|---|---|
| | 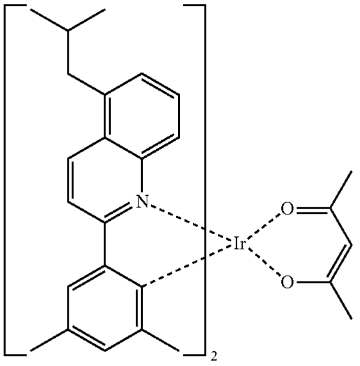<br>D-39 |
| Electron Transport Layer/ Electron Injection Layer | 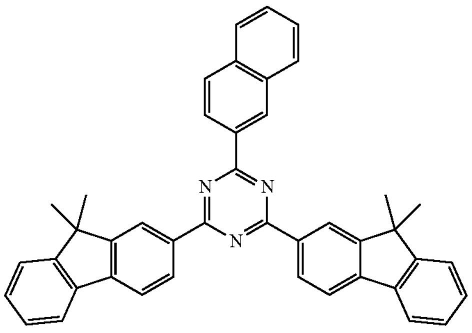<br>ET-1 |
| | 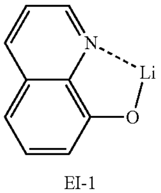<br>EI-1 |

The invention claimed is:

1. A plurality of host materials comprising a first host material comprising the compound represented by formula 1, and a second host material comprising the compound represented by formula 2:

(1)

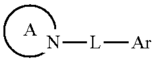

in formula 1,

L represents a single bond, a substituted or unsubstituted (C1-C30)alkylene, a substituted or unsubstituted (C3-C30)cycloalkylene, a substituted or unsubstituted (C6-C30)arylene, or a substituted or unsubstituted (3-to 30-membered)heteroarylene;

Ar represents deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3-to 7-membered)heterocycloalkyl, a substituted or unsubstituted (C6-C30) aryl, a substituted or unsubstituted (3-to 30-membered) heteroaryl, $—NR_{11}R_{12}$, or $—SiR_{13}R_{14}R_{15}$;

$R_{11}$ to $R_{15}$, each independently, represent a substituted or unsubstituted (C1-C30)alkyl, a substituted or unsubstituted (C6-C30)aryl, or a substituted or unsubstituted (3-to 30-membered)heteroaryl; and

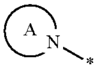

is represented by the following formula 1-1 or 1-2:

(1-1)

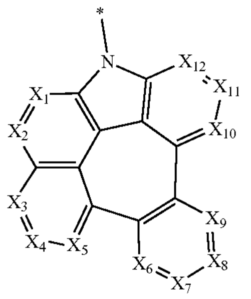

(1-2)

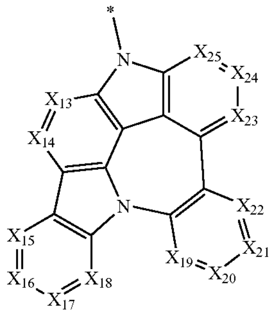

in formulas 1-1 and 1-2, $X_1$ to $X_{25}$, each independently, represent —N═ or $—C(R_a)═$;

$R_a$, each independently, represent hydrogen, deuterium, a halogen, a cyano, a substituted or unsubstituted (C1-C30)alkyl, a substituted or unsubstituted (C6-C30)aryl, a substituted or unsubstituted (3-to 30-membered)heteroaryl, a substituted or unsubstituted (C3-C30)cycloalkyl, a substituted or unsubstituted (C1-C30) alkoxy, a substituted or unsubstituted tri (C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C2-C30) alkenylamino, a substituted or unsubstituted mono- or di-(C6-C30)arylamino, a substituted or unsubstituted mono- or di-(3-to 30-membered)heteroarylamino, a substituted or unsubstituted (C1-C30)alkyl(C2-C30) alkenylamino, a substituted or unsubstituted (C1-C30) alkyl(C6-C30)arylamino, a substituted or unsubstituted (C1-C30)alkyl (3-to 30-membered)heteroarylamino, a substituted or unsubstituted (C2-C30) alkenyl (C6-C30)arylamino, a substituted or unsubstituted (C2-C30) alkenyl (3-to 30-membered)heteroarylamino, or a substituted or unsubstituted (C6-C30)aryl (3-to 30-membered)heteroarylamino, or the adjacent $R_a$'s may be linked to each other to form a ring(s), and where if there is a plurality of $R_a$, each of $R_a$ may be the same or different from each other; with the provisos that:

$R_a$ in $X_5$ is not linked to the adjacent $R_a$ in $X_6$ to form a ring(s);

$R_a$ in $X_9$ is not linked to the adjacent $R_a$ in $X_{10}$ to form a ring(s);

$R_a$ in $X_{18}$ is not linked to the adjacent $R_a$ in $X_{19}$ to form a ring(s); and $R_a$ in $X_{22}$ is not linked to the adjacent $R_a$ in $X_{23}$ to form a ring(s); and (2)

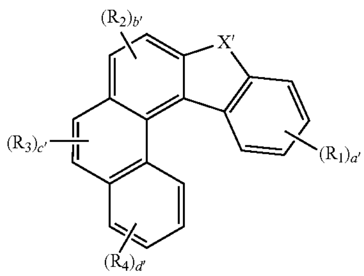

in formula 2,

X' represents O, S, or $CR_5R_6$;

$R_1$ to $R_4$, each independently, represent hydrogen, deuterium, a cyano, a substituted or unsubstituted (C1-C30) alkyl, a substituted or unsubstituted (C3-C30)cycloalkyl, a substituted or unsubstituted (C3-C30) cycloalkenyl, a substituted or unsubstituted (3-to 7-membered)heterocycloalkyl, a substituted or unsubstituted (C6-C30)aryl, a substituted or unsubstituted (3-to 30-membered)heteroaryl, $-L_3-NR_{16}R_{17}$, or $—SiR_{18}R_{19}R_{20}$; or may be linked to adjacent substituent(s) to form a ring(s);

wherein, at least one of $R_1$ to $R_4$ represents a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3-to 7-membered) heterocycloalkyl, a substituted or unsubstituted (C6-C30)aryl, a substituted or unsubstituted (3-to 30-membered)heteroaryl, $-L_3-NR_{16}R_{17}$, or $—SiR_{18}R_{19}R_{20}$;

$L_3$ represents a single bond, a substituted or unsubstituted (C6-C30)arylene, or a substituted or unsubstituted (3-to 30-membered)heteroarylene;

$R_5$ and $R_6$, each independently, represent a substituted or unsubstituted (C1-C30)alkyl, a substituted or unsubstituted (C6-C30)aryl, or a substituted or unsubstituted (3-to 30-membered)heteroaryl, or $R_5$ and $R_6$ may be linked to each other to form a ring(s);

$R_{16}$ to $R_{20}$, each independently, represent a substituted or unsubstituted (C1-C30)alkyl, a substituted or unsubstituted (C6-C30)aryl, or a substituted or unsubstituted (3-to 30-membered)heteroaryl; and a' and d', each independently, represent an integer of 1 to 4, b' and c', each independently, represent an integer of 1 or 2, and where if each of a' to d' is an integer of 2 or more, each of $R_1$ to each of $R_4$ may be the same or different from each other.

2. The plurality of host materials according to claim 1, wherein formula 1-1 is represented by the following formula 1-1-1:

(1-1-1)

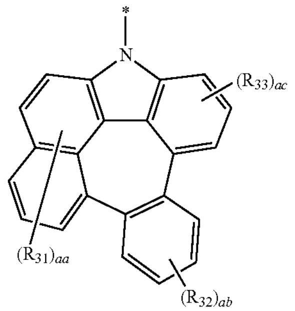

in formula 1-1-1, $R_{31}$ to $R_{33}$, each independently, are the same as the definition of $R_a$, with the provisos that:

$R_{31}$ is not linked to the adjacent $R_{32}$ to form a ring(s); and $R_{32}$ is not linked to the adjacent $R_{33}$ to form a ring(s); and aa represents an integer of 1 to 5, ab represents an integer of 1 to 4, ac represents an integer of 1 to 3, and where if aa, ab, and ac are an integer of 2 or more, each of $R_{31}$, each of $R_{32}$, and each of $R_{33}$ may be the same or different from each other.

3. The plurality of host materials according to claim 1, wherein formula 1-2 is represented by the following formula 1-2-1:

(1-2-1)

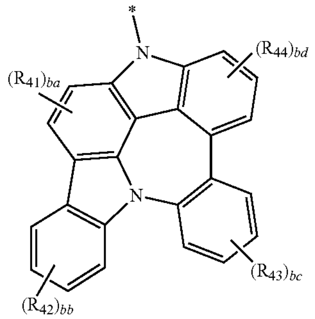

in formula 1-2-1, $R_{41}$ to $R_{44}$, each independently, are the same as the definition of $R_a$, with the provisos that:

$R_{42}$ is not linked to the adjacent $R_{43}$ to form a ring(s); and $R_{43}$ is not linked to the adjacent $R_{44}$ to form a ring(s); and ba represents an integer of 1 or 2, bb and bc, each independently, represent an integer of 1 to 4, bd represents an integer of 1 to 3, and where if ba, bb, bc, and bd are an integer of 2 or more, each of $R_{41}$, each of $R_{42}$, each of $R_{43}$, and each of $R_{44}$ may be the same or different from each other.

4. The plurality of host materials according to claim 1, in formula 2, at least one of $R_1$ to $R_4$ is-$L_2$-HAr or $-L_3-NR_{16}R_{17}$;

$L_2$ represents a single bond, a substituted or unsubstituted (C6-C30)arylene, or a substituted or unsubstituted (3-to 30-membered)heteroarylene;

HAr represents a substituted or unsubstituted (3-to 30-membered)heteroaryl comprising at least one of N, O and S; and $L_3$, $R_{16}$, and $R_{17}$, each independently, are as defined in claim 1.

5. The plurality of host materials according to claim 1, wherein the compound represented by formula 2 is represented by any one of the following formulas 2-1 to 2-4:

(2-1)

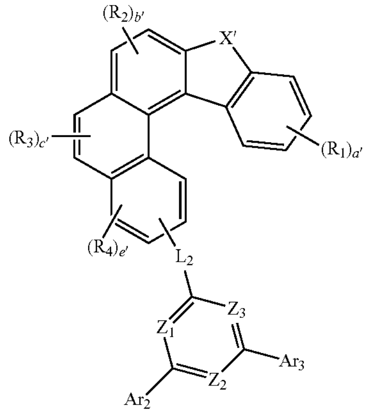

(2-2)

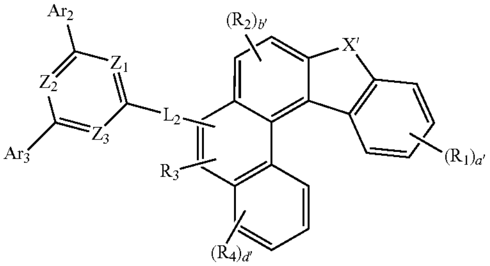

(2-3)

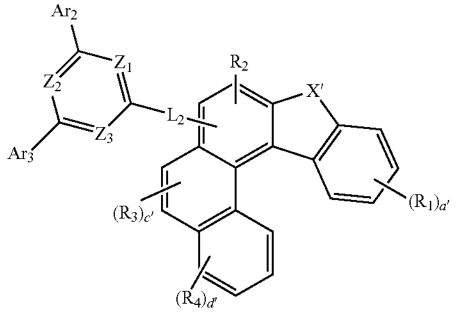

(2-4)

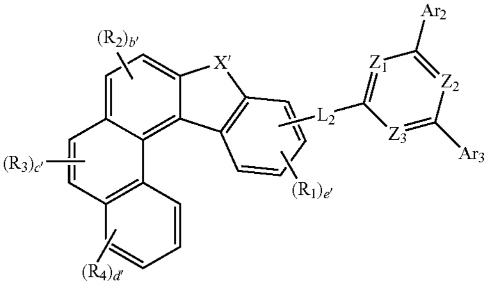

in formulas 2-1 to 2-4,

X', $R_1$ to $R_4$, and a' to d' are as defined in claim 1;

$L_2$, each independently, represents a single bond, a substituted or unsubstituted (C6-C30)arylene, or a substituted or unsubstituted (3-to 30-membered)heteroarylene;

$Z_1$ to $Z_3$, each independently, represent N or CH, provided that at least one of $Z_1$ to $Z_3$ is N;

$Ar_2$ and $Ar_3$, each independently, represent a substituted or unsubstituted (C6-C30)aryl, or a substituted or unsubstituted (3-to 30-membered)heteroaryl; and e', each independently, represents an integer of 1 to 3, and where if each of e' is an integer of 2 or more, each of $R_1$ and each of $R_4$ may be the same or different from each other.

6. The plurality of host materials according to claim 1, wherein the compound represented by formula 2 is represented by any one of the following formulas 2-5 to 2-8:

(2-5)

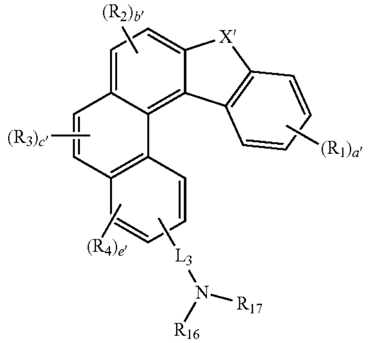

(2-6)

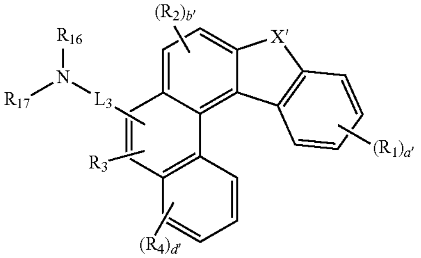

(2-7)

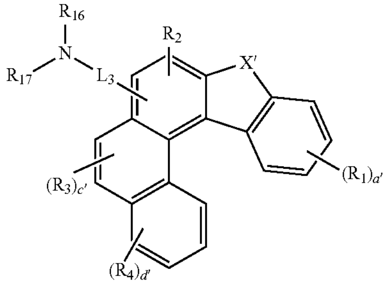

(2-8)

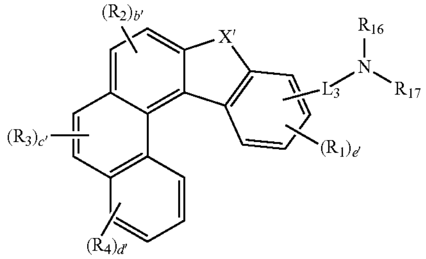

in formulas 2-5 to 2-8,

X', $L_3$, $R_1$ to $R_4$, $R_{16}$, $R_{17}$, and a' to d' are as defined in claim 1; and e', each independently, represents an integer of 1 to 3, and where if each of e' is an integer of 2 or more, each of $R_1$ and each of $R_4$ may be the same or different from each other.

7. The plurality of host materials according to claim 1, wherein the compound represented by formula 1 is at least one selected from the group consisting of the following compounds:
H1-1
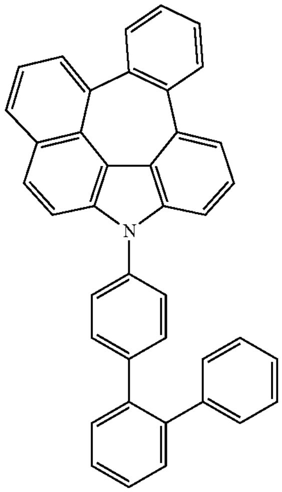
H1-2
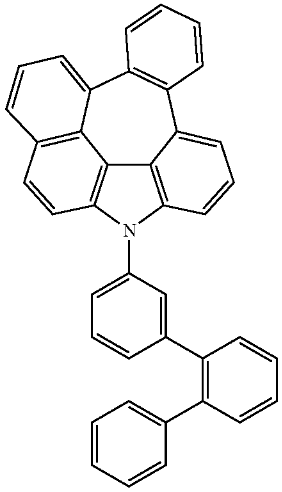
H1-3
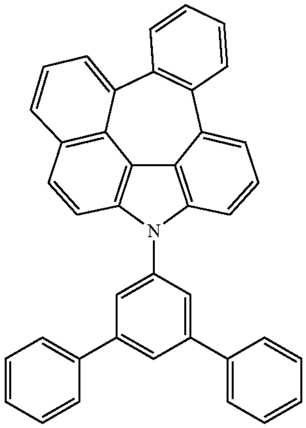
-continued
H1-4
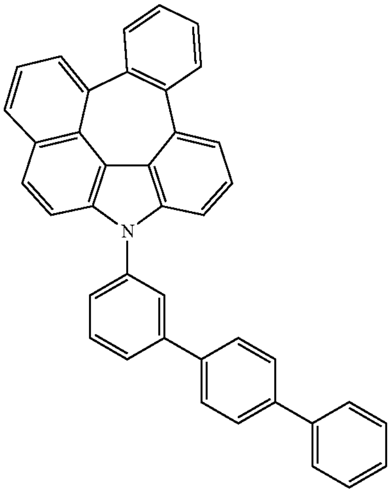
H1-5
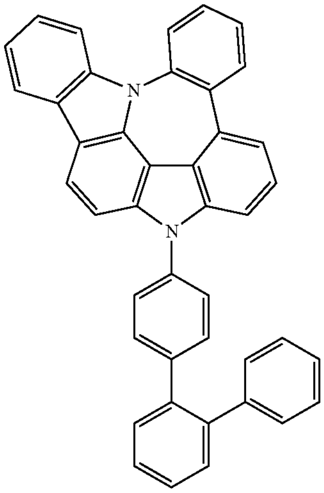
H1-6
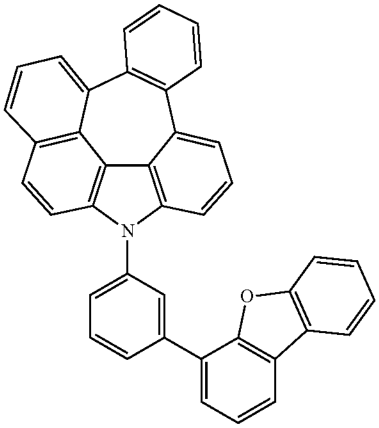

-continued
H1-7
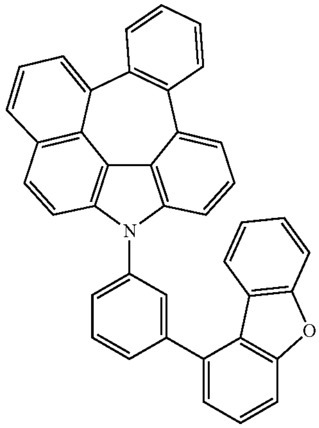
H1-8
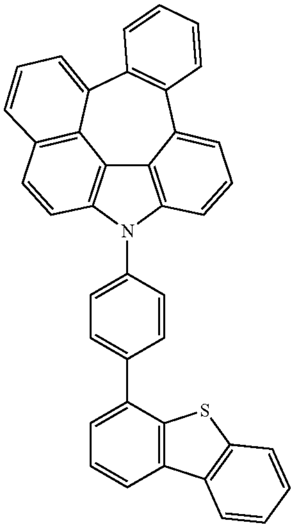
H1-9
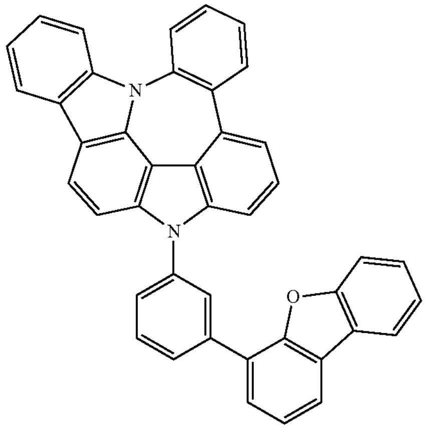
-continued
H1-10
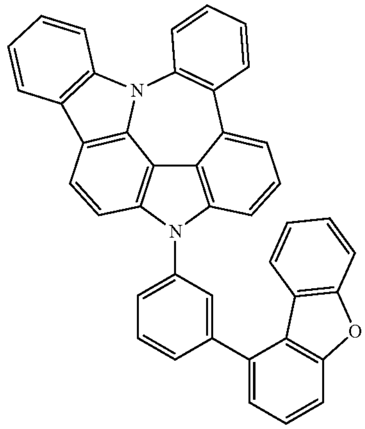
H1-11
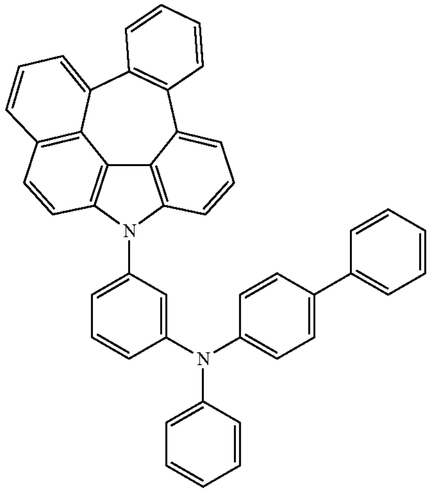
H1-12
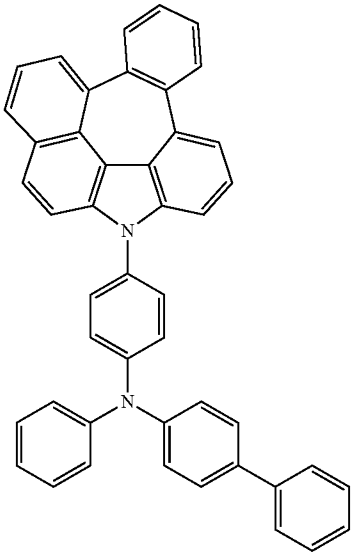

-continued
H1-13
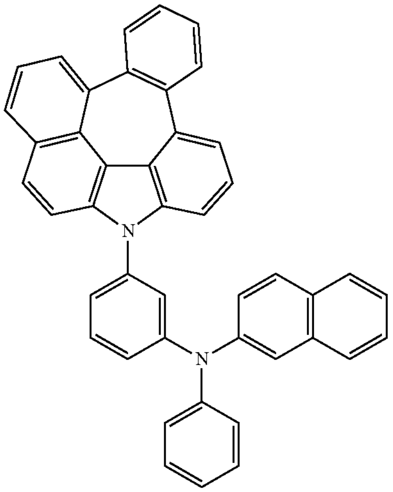
H1-14
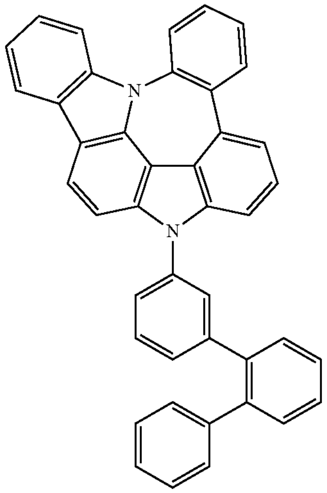
H1-15
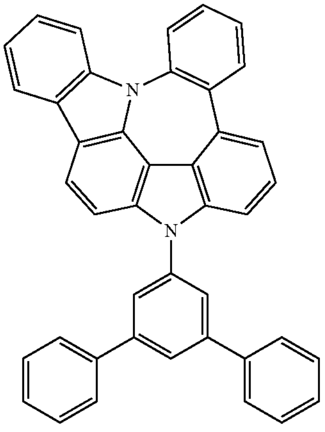
-continued
H1-16
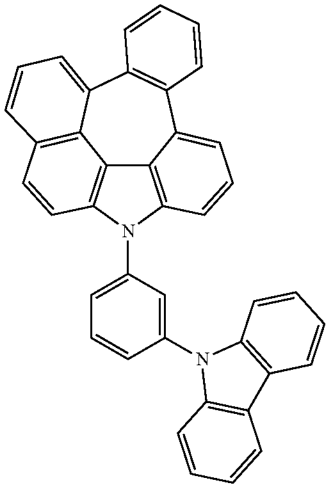
H1-17
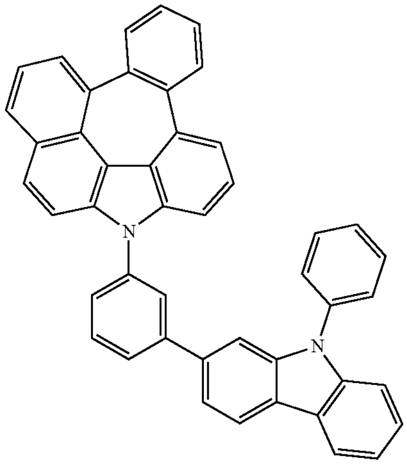
H1-18
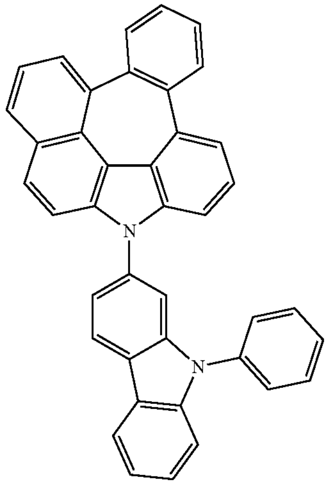

-continued
H1-19
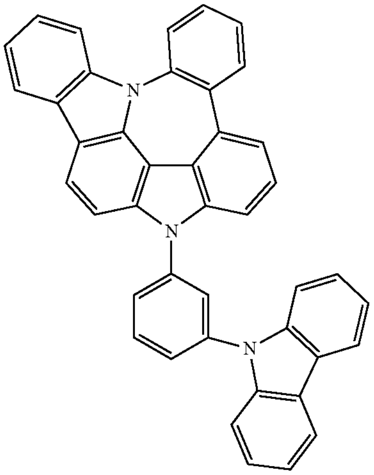
H1-20
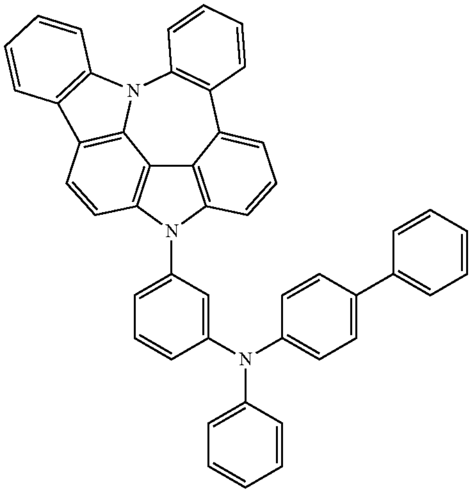
H1-21
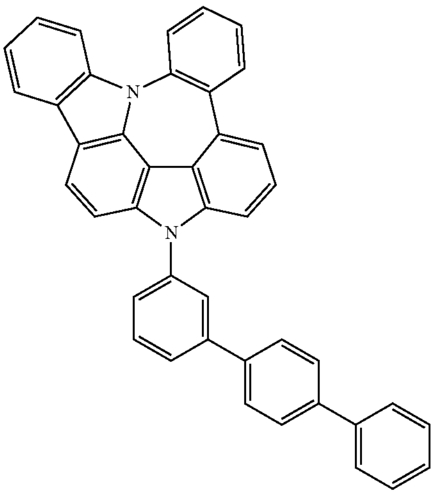
-continued
H1-22
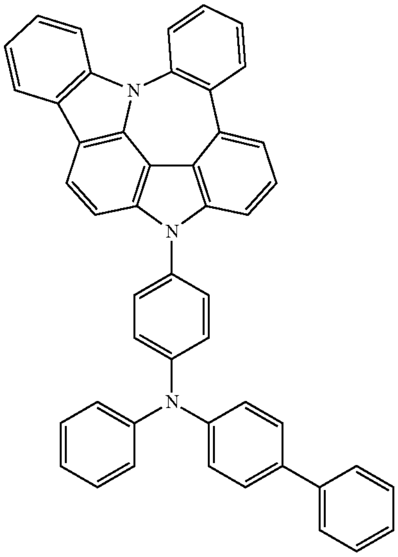
H1-23
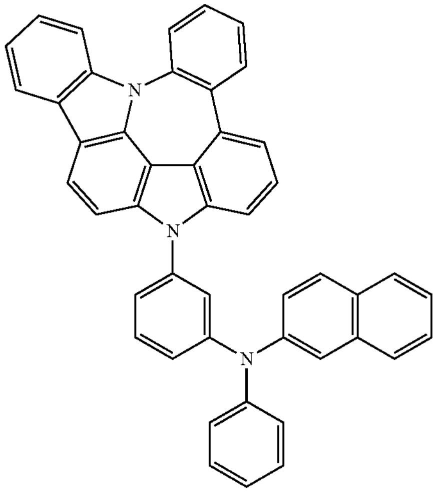
H1-24
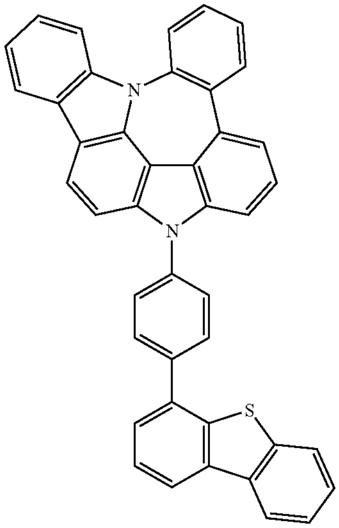

H1-25
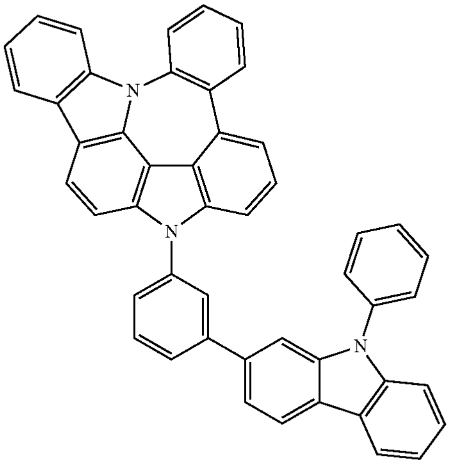
H1-26
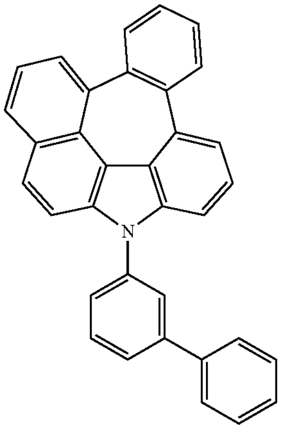
H1-27
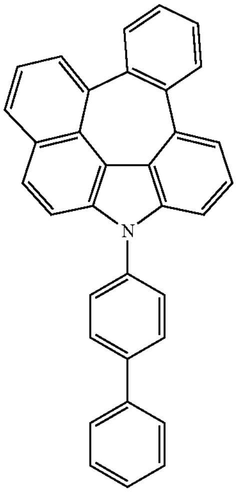
H1-28
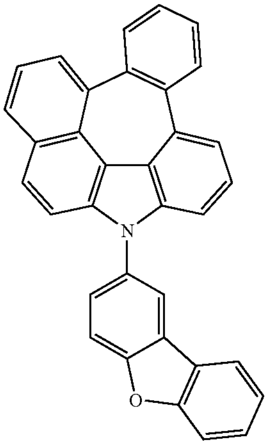
H1-29
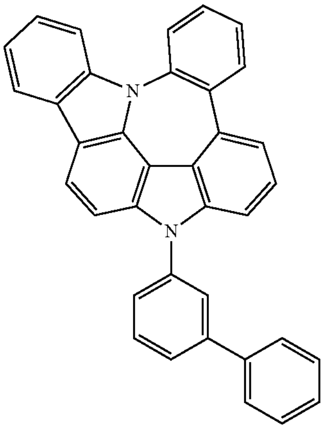
H1-30
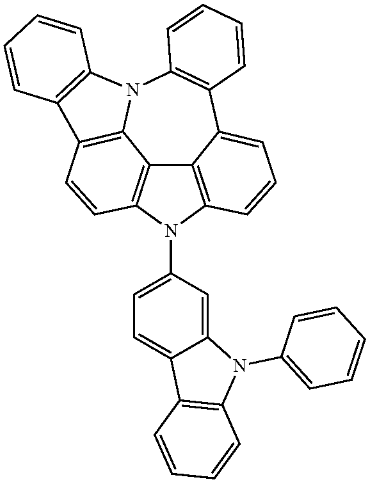

-continued
H1-31
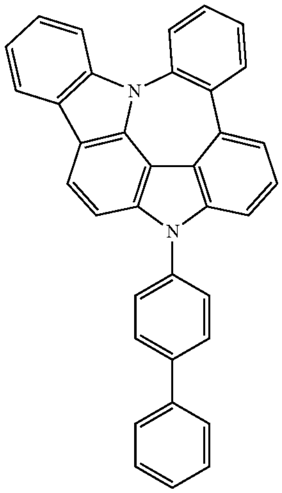
H1-32
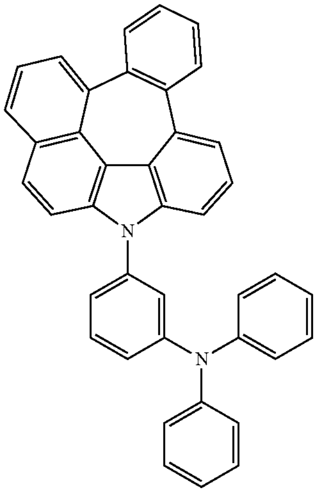
H1-33
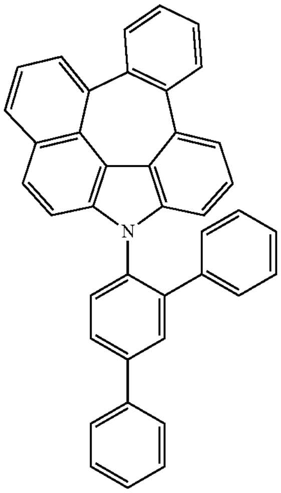
-continued
H1-34
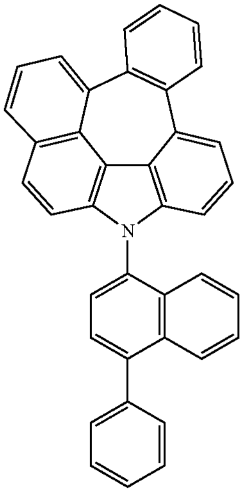
H1-35
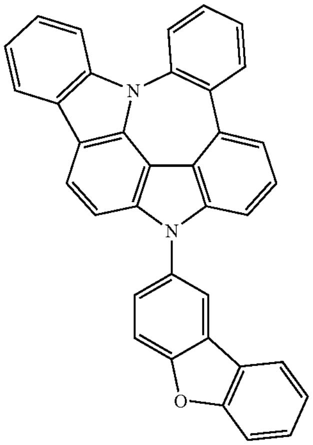
H1-36
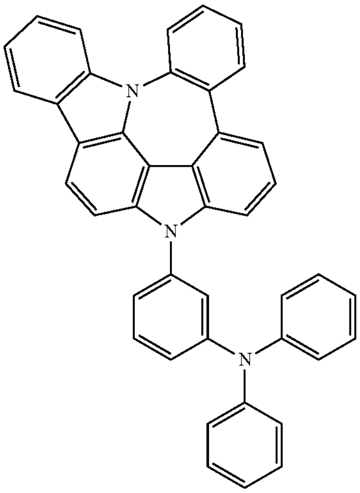

-continued
H1-37
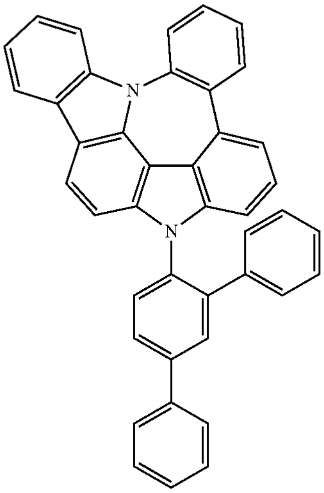
H1-38
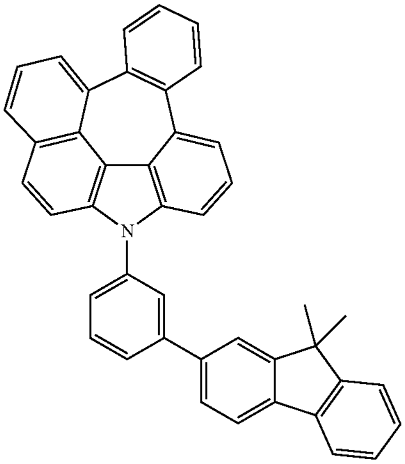
H1-39
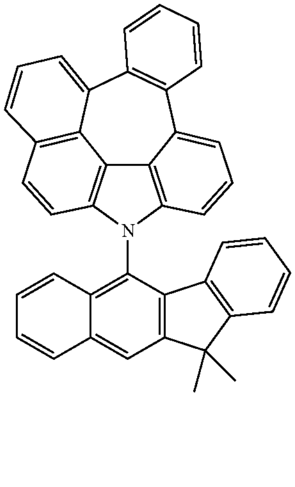
-continued
H1-40
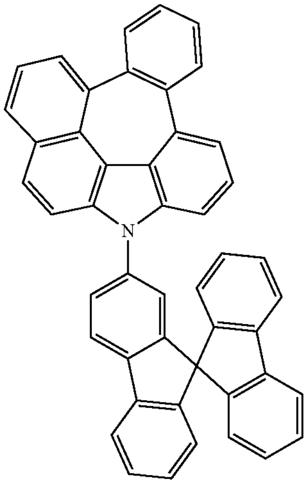
H1-41
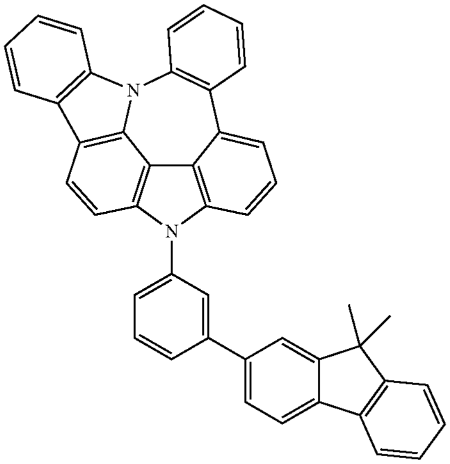
H1-42
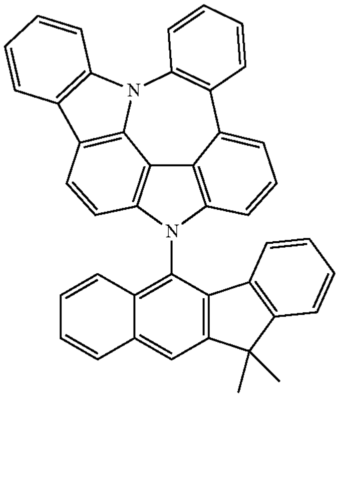

-continued
H1-43
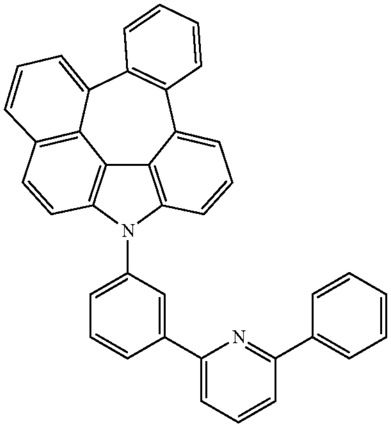
H1-44
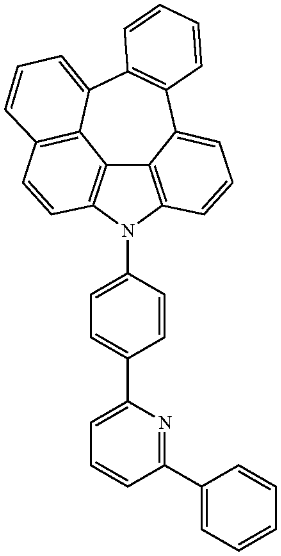
H1-45
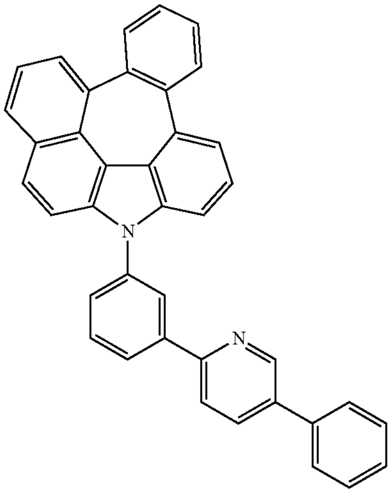
-continued
H1-46
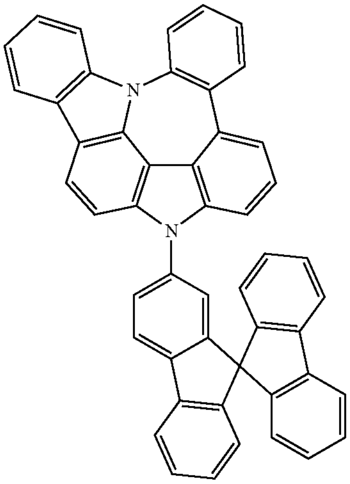
H1-47
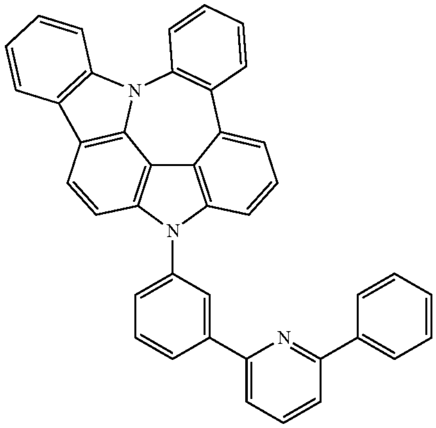
H1-48
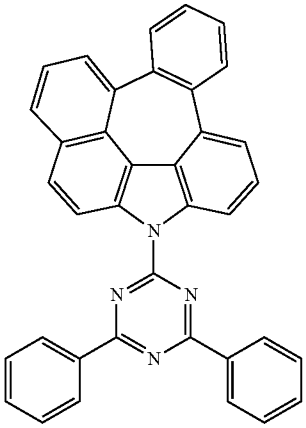

-continued
H1-49
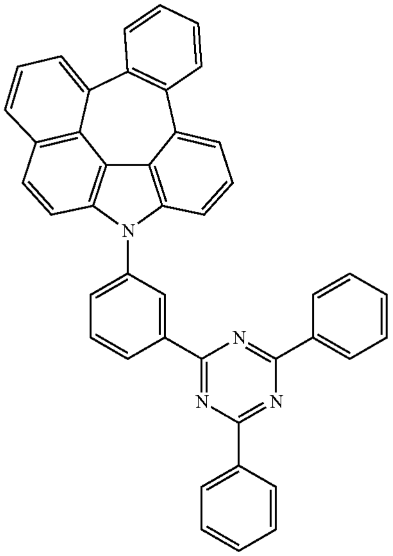
H1-50
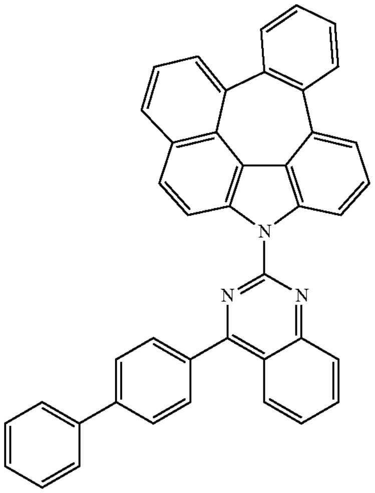
H1-51
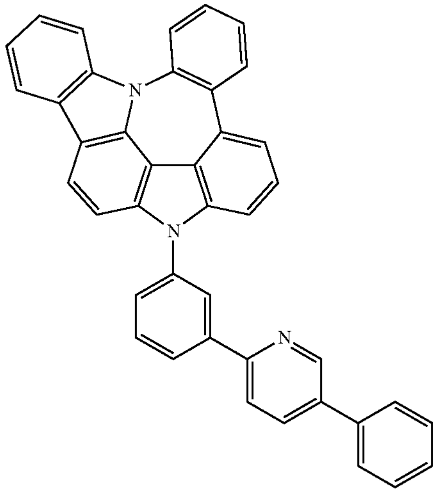
-continued
H1-52
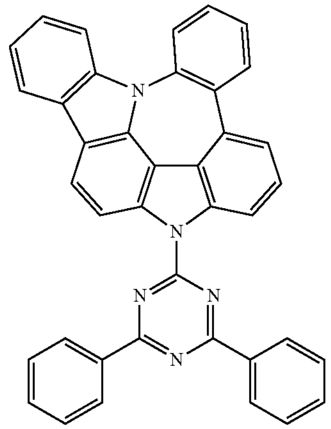
H1-53
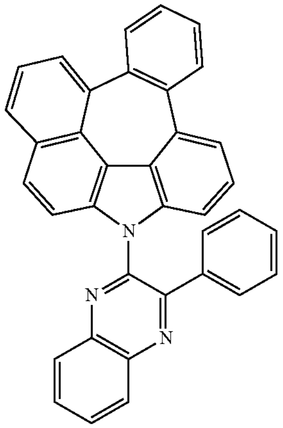
H1-54
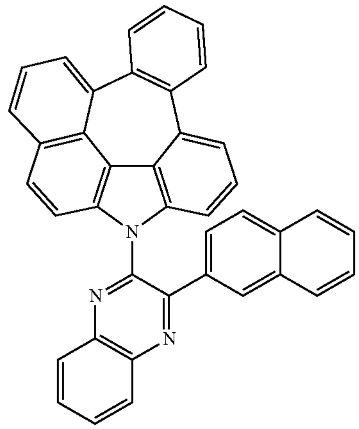

H1-55
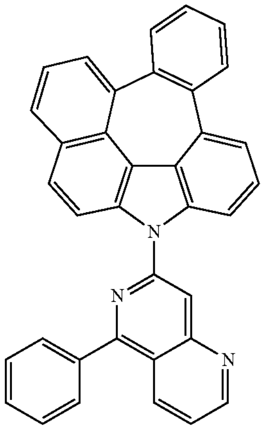
H1-56
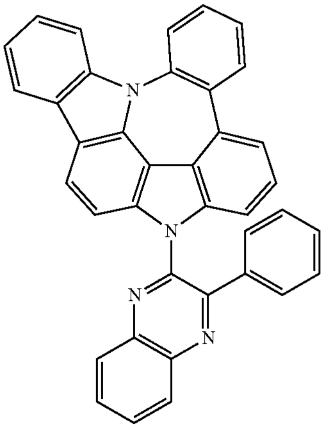
H1-57
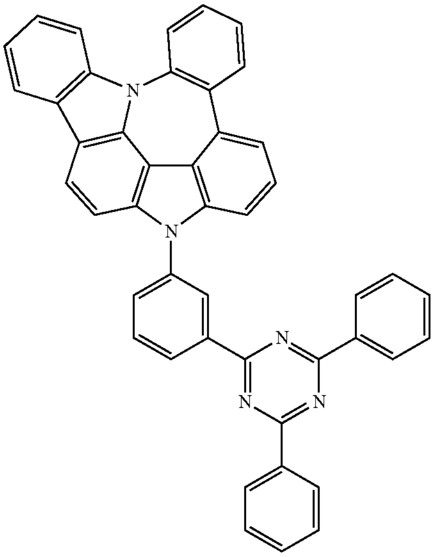
H1-58
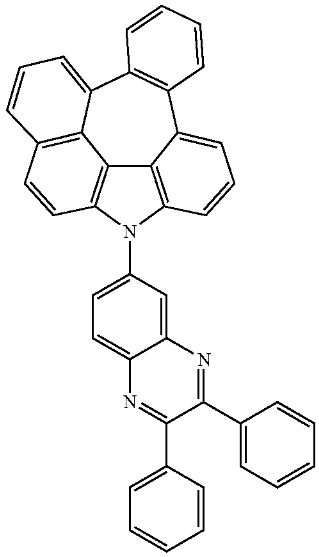
H1-59
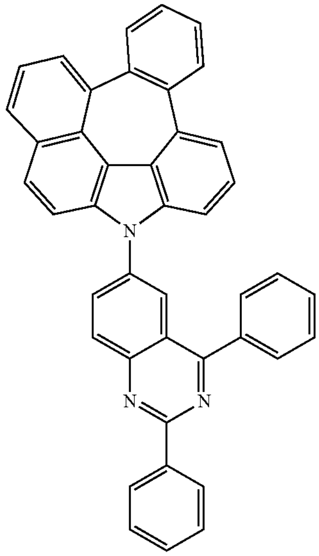
H1-60
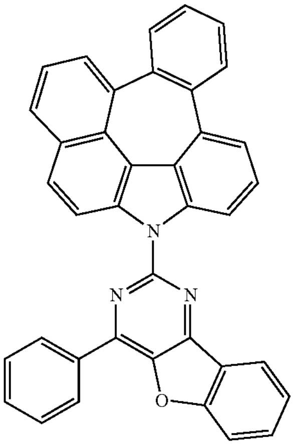

-continued
H1-61
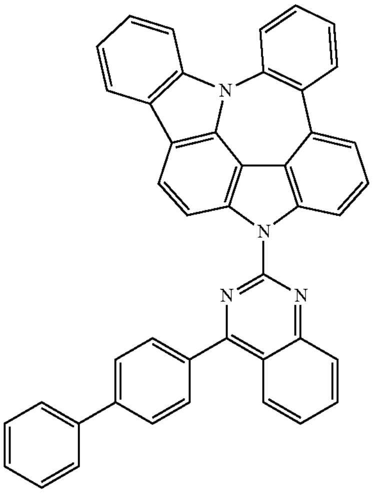
H1-62
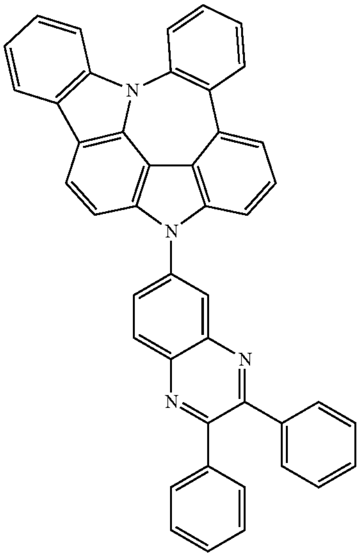
H1-63
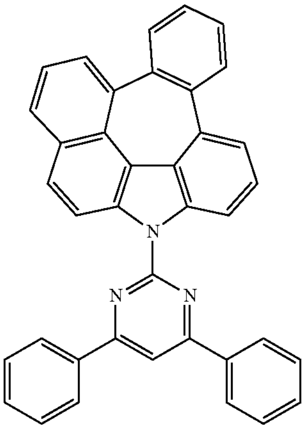
-continued
H1-64
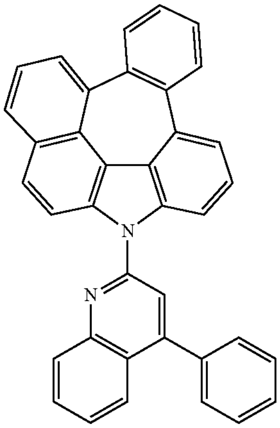
H1-65
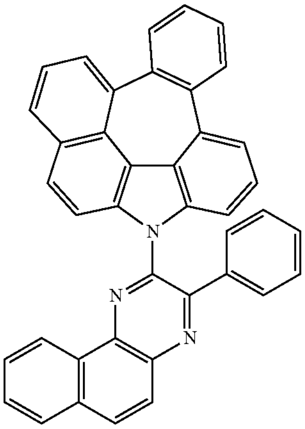
H1-66
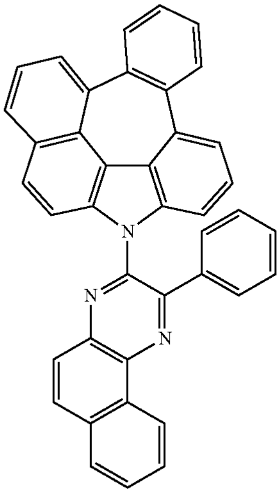

-continued
H1-67
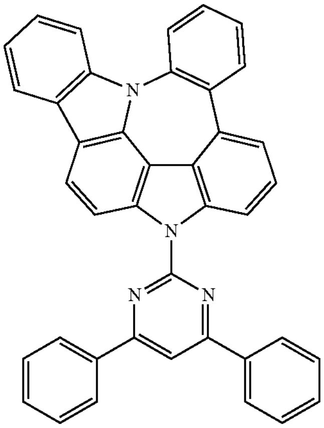
H1-68
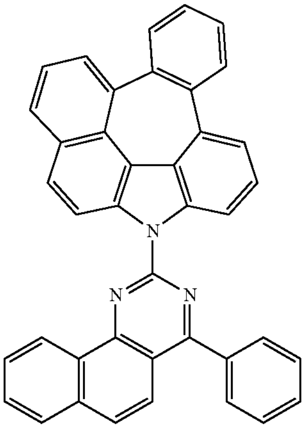
H1-69
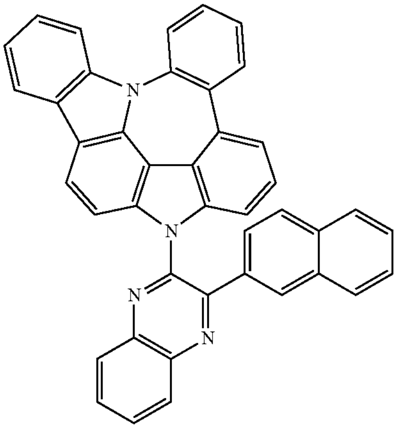
-continued
H1-70
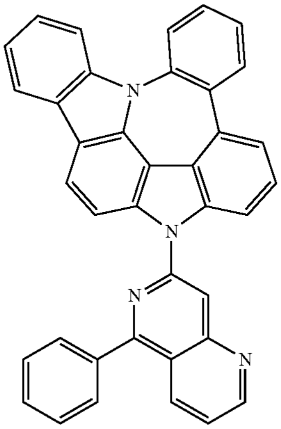
H1-71
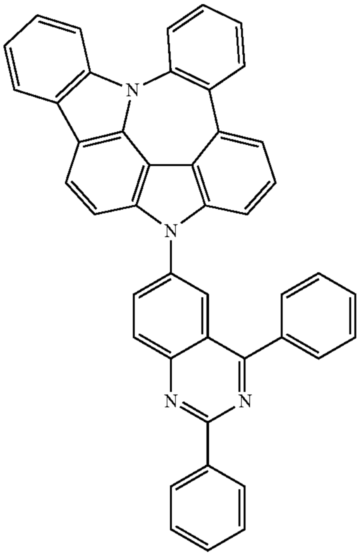
H1-72
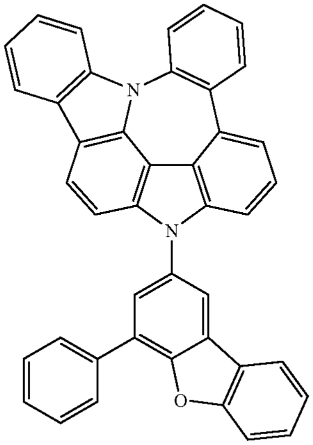

-continued
H1-73
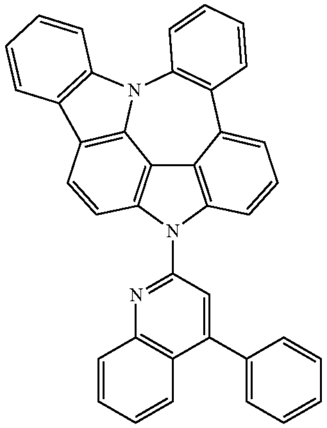
H1-74
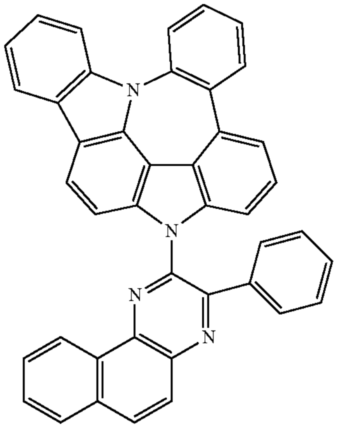
H1-75
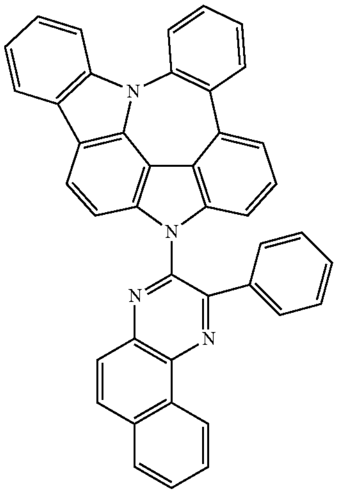
-continued
H1-76
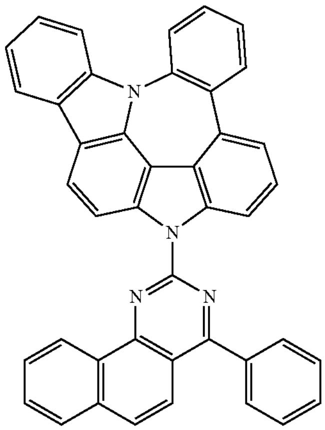
H1-77
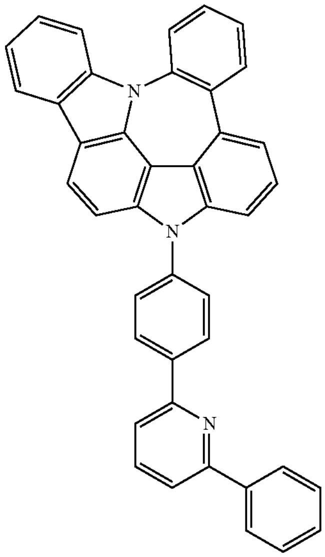
H1-78
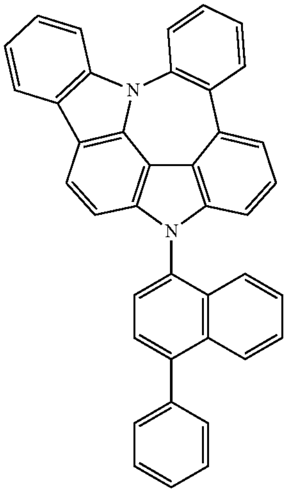

-continued
H1-79
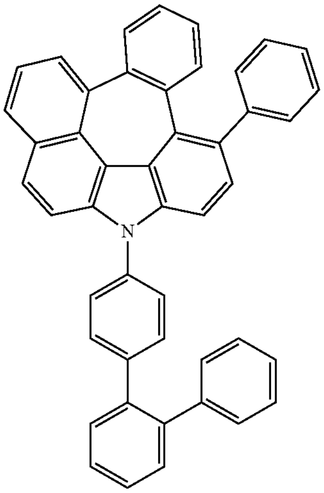
H1-80
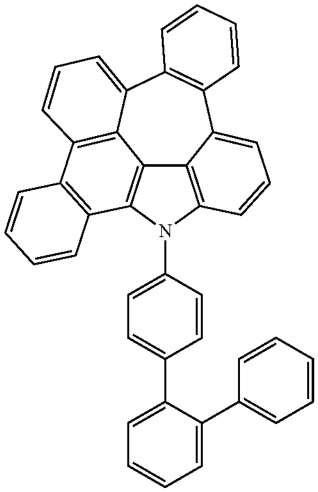
H1-81
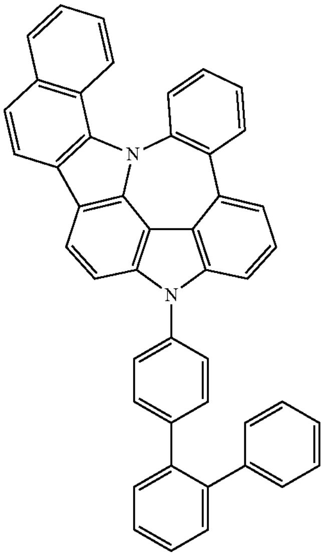
-continued
H1-82
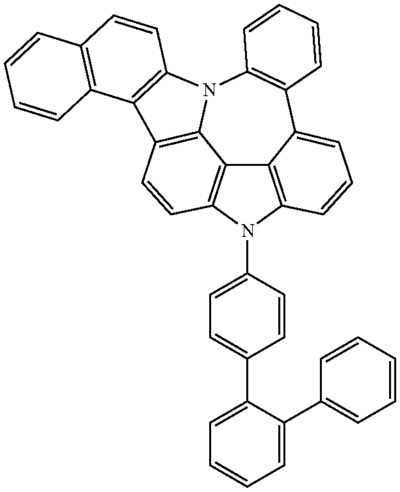
H1-83
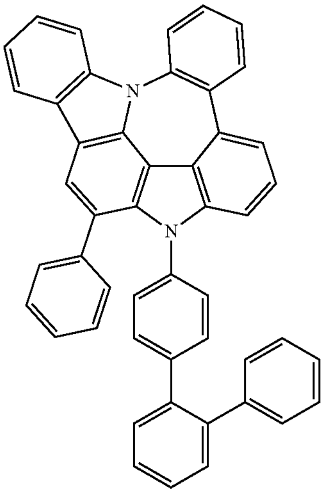
H1-84
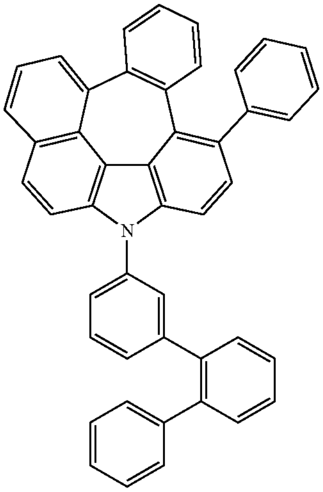

-continued
H1-85
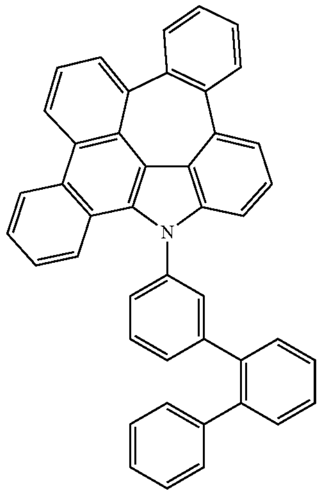
H1-86
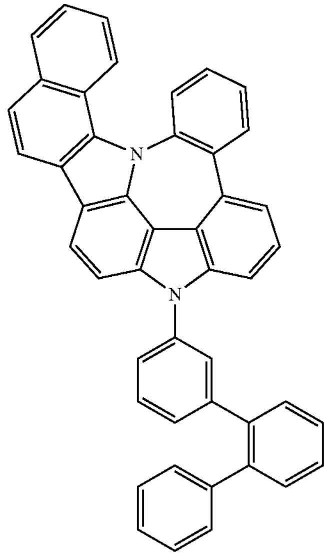
H1-87
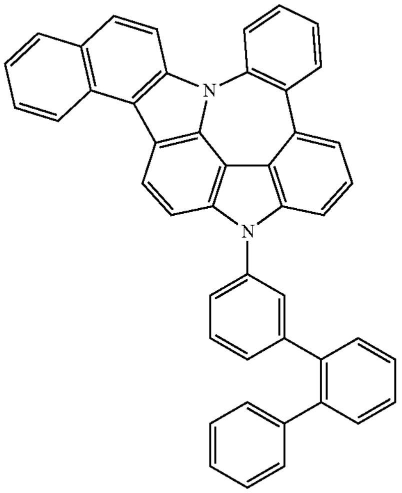
-continued
H1-88
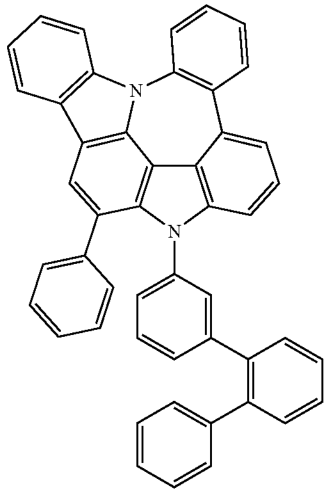
H1-89
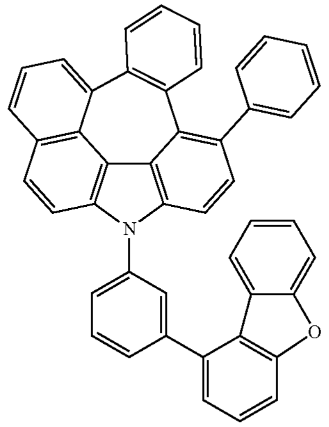
H1-90
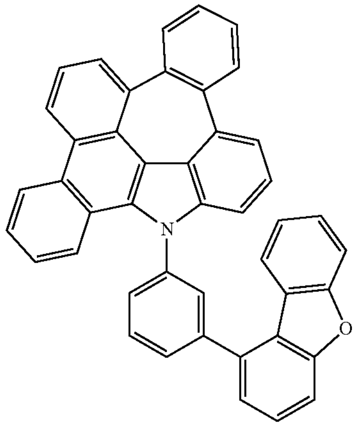

-continued
H1-91
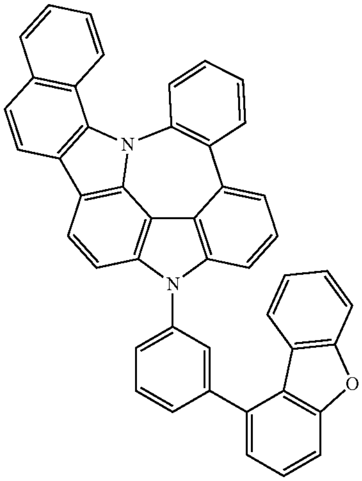
H1-92
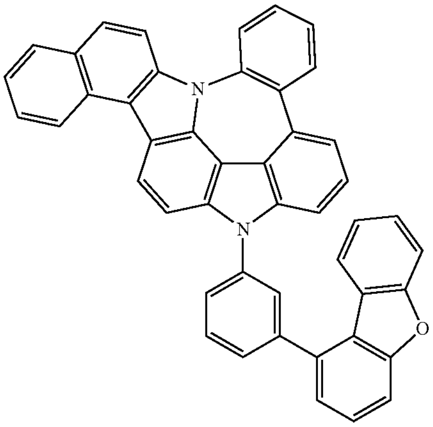
H1-93
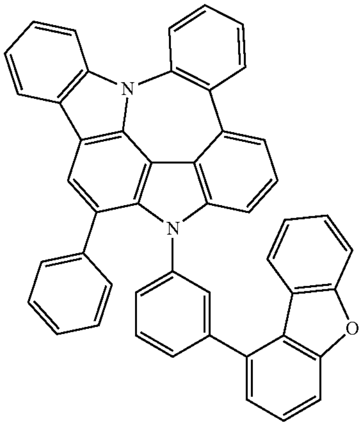
-continued
H1-94
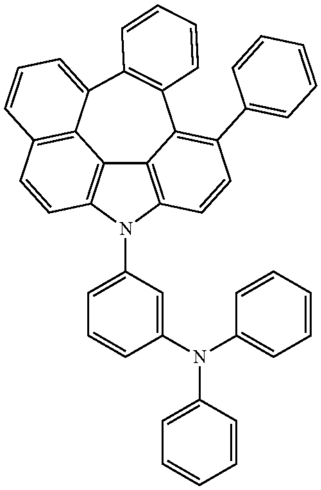
H1-95
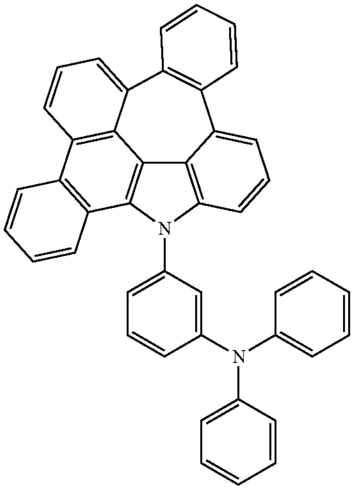
H1-96
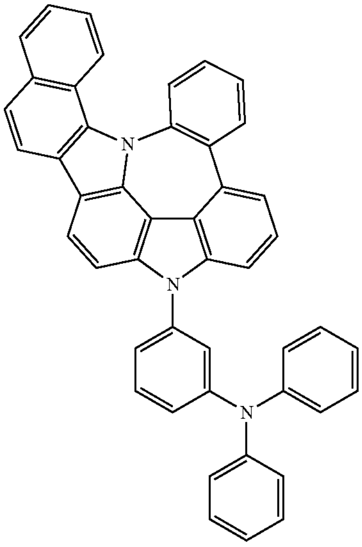

-continued
H1-97
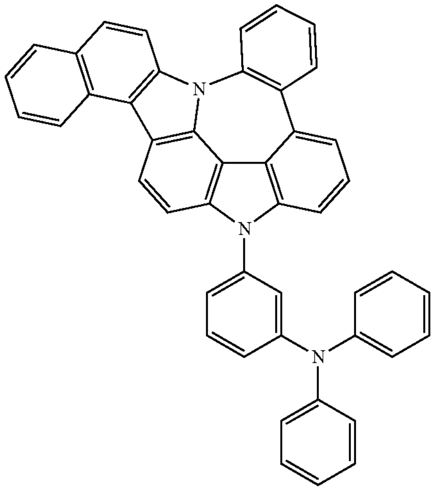
H1-98
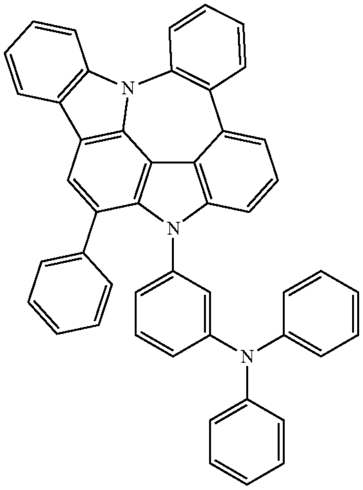
H1-99
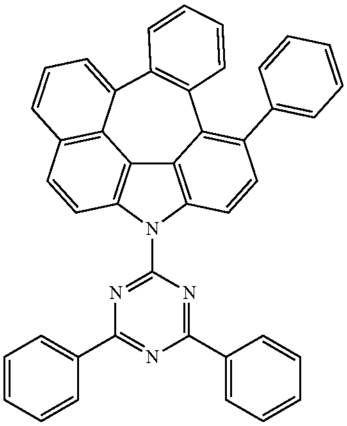
-continued
H1-100
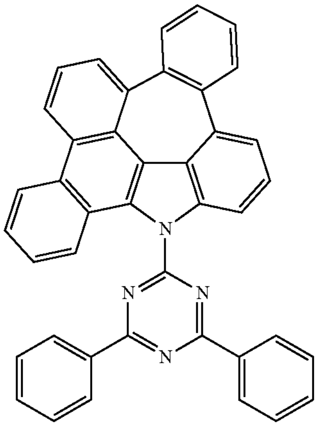
H1-101
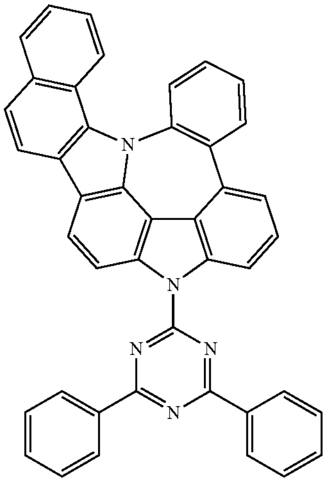
H1-102
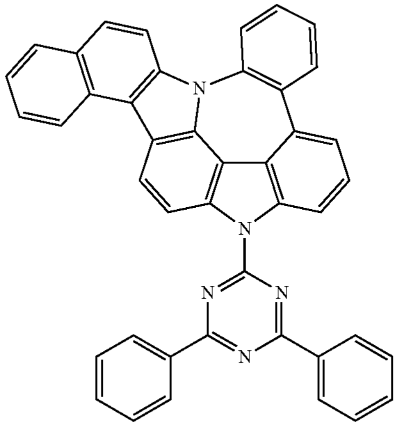

-continued
H1-103
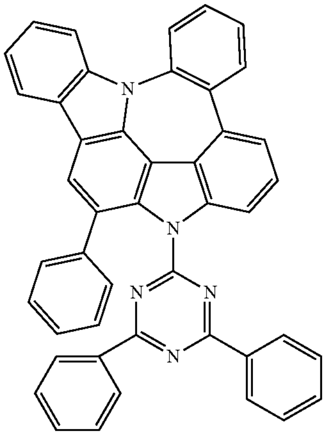
H1-104
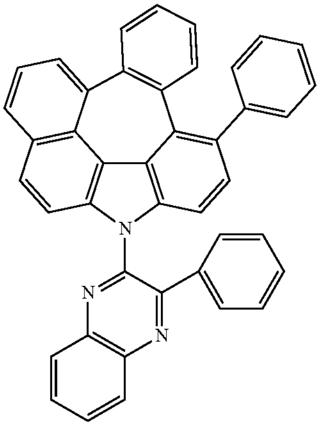
H1-105
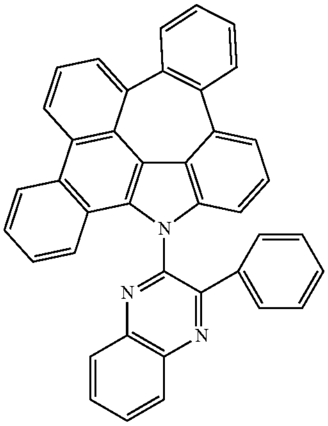
-continued
H1-106
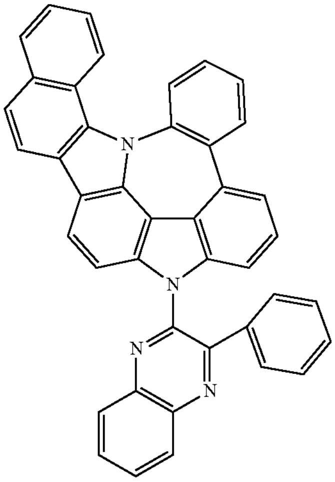
H1-107
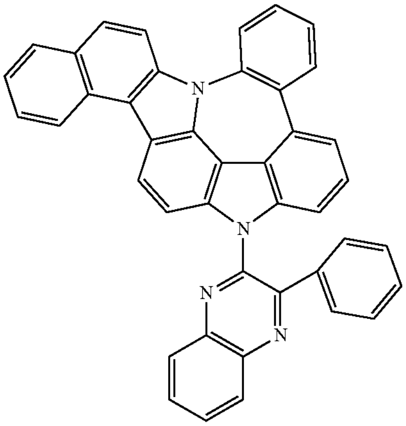
H1-108
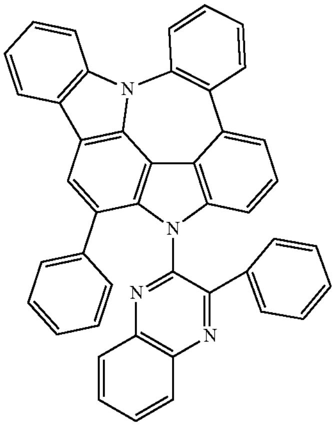

-continued
H1-109
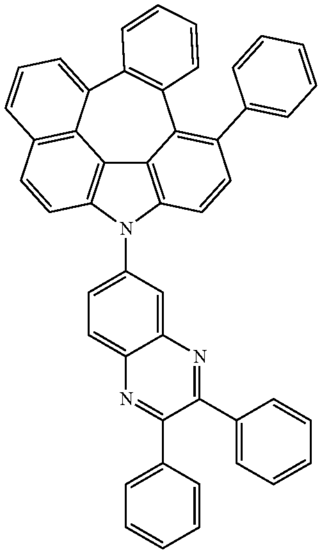
H1-110
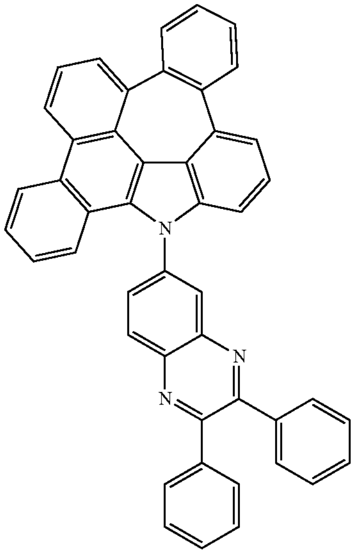
-continued
H1-111
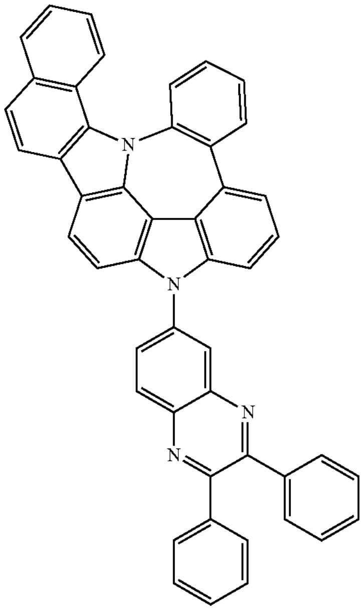
H1-112
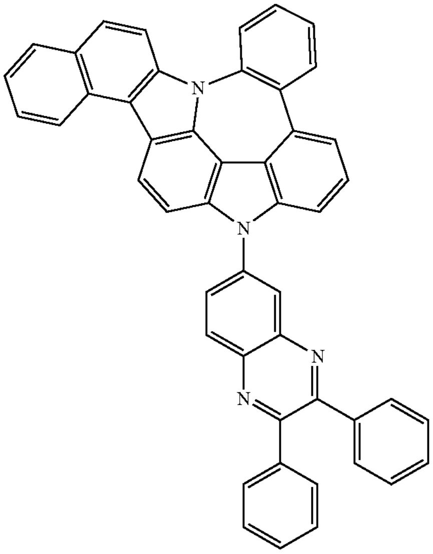

H1-113
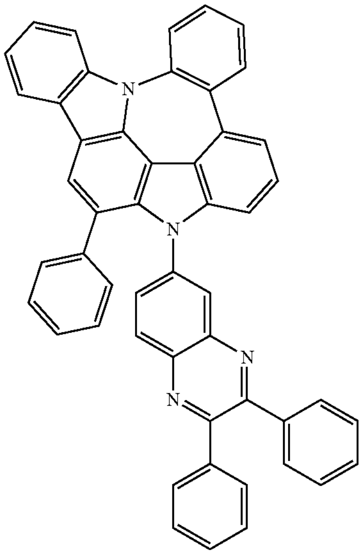
H1-114
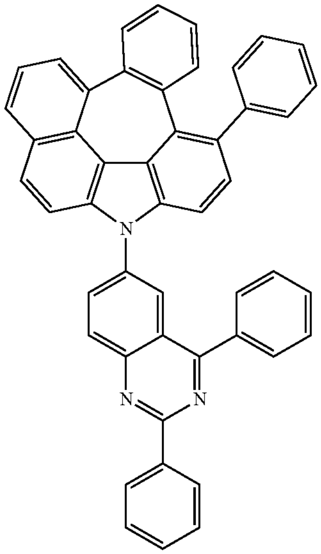
H1-115
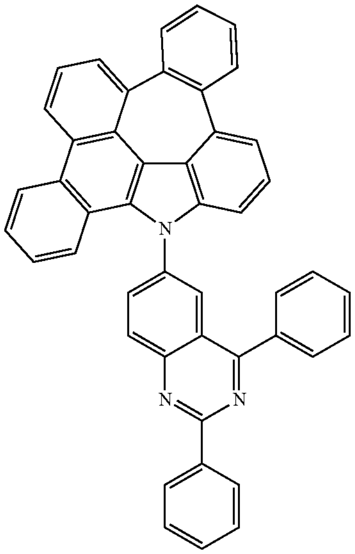
H1-116
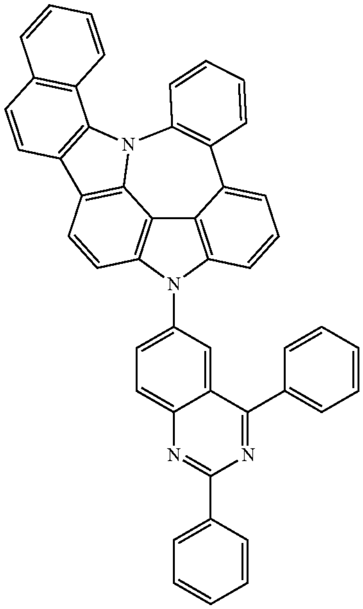
H1-117
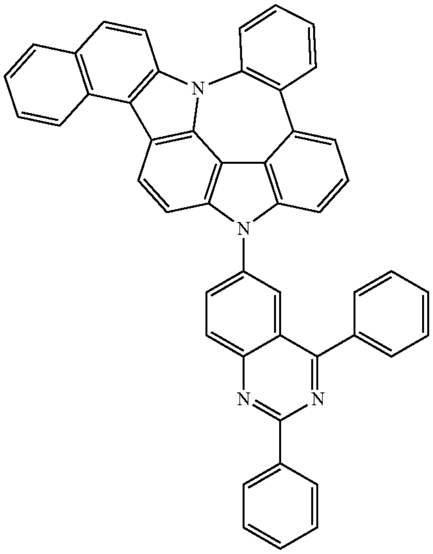

-continued
H1-118
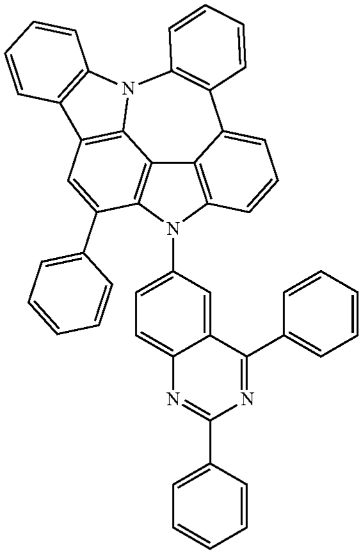
H1-119
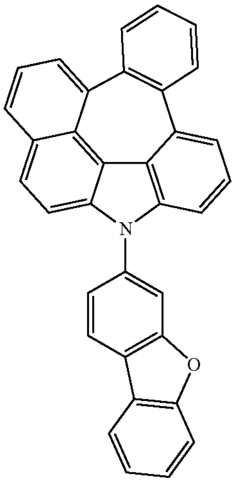
H1-120
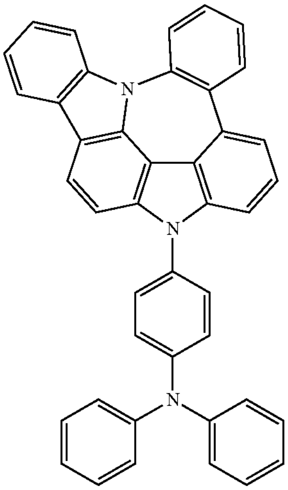
-continued
H1-121
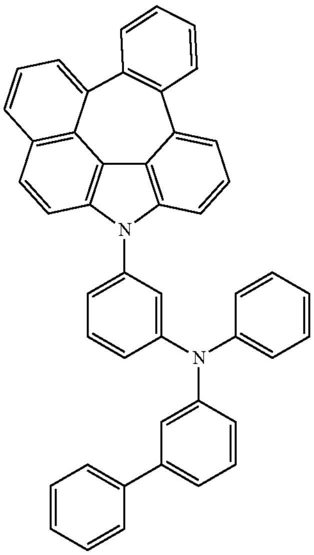
H1-122
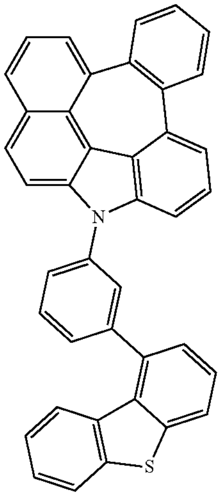
and
H1-245
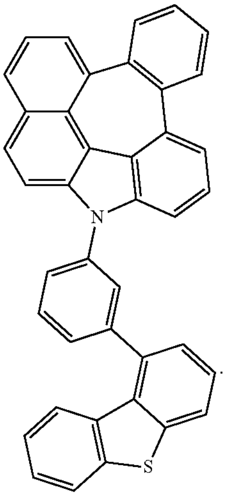
.
8. The plurality of host materials according to claim 1, wherein the compound represented by formula 2 is at least one selected from the group consisting of the following compounds:

H2-1
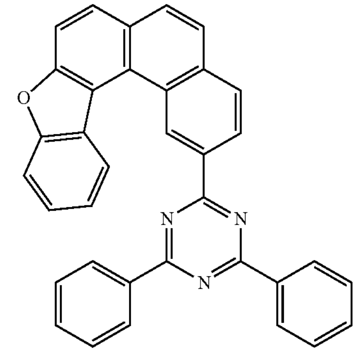
H2-2
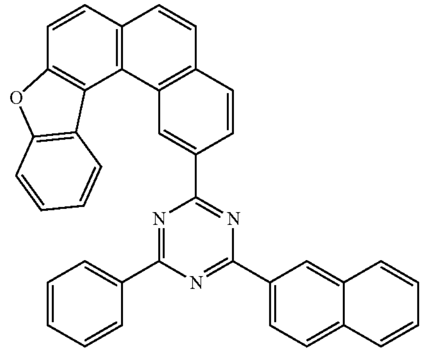
H2-3
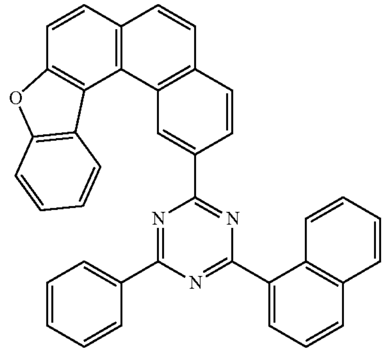
H2-4
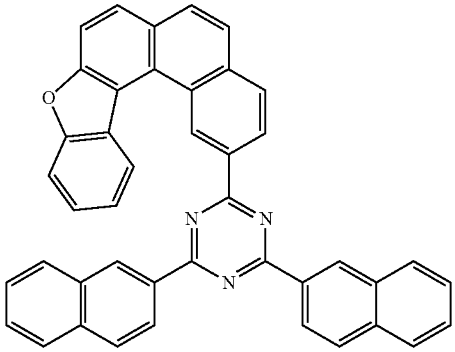
-continued
H2-5
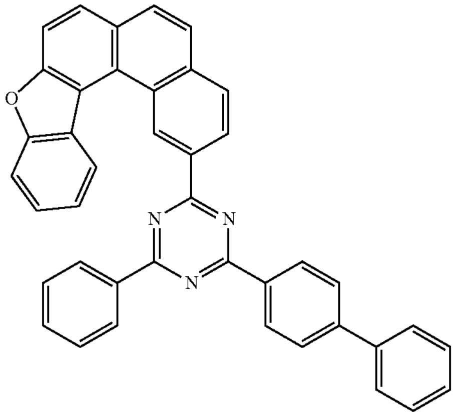
H2-6
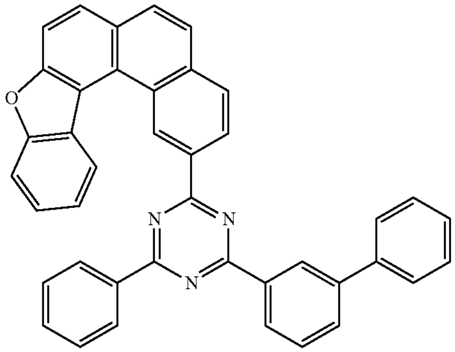
H2-7
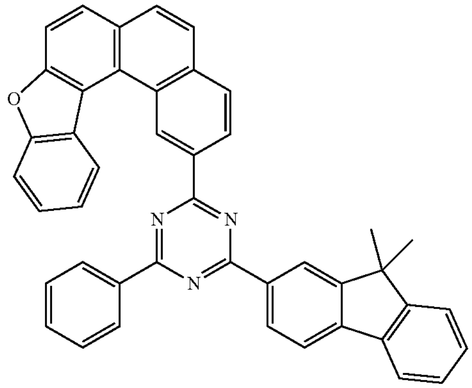
H2-8
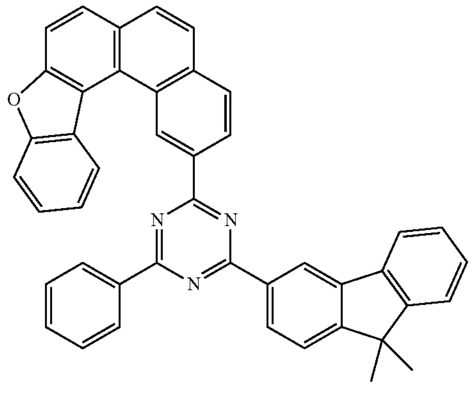

-continued
H2-9
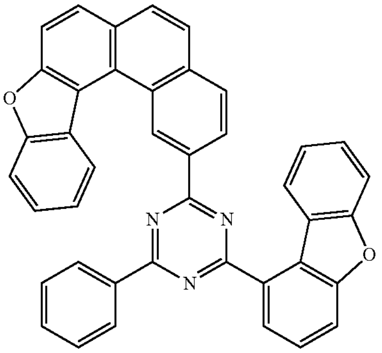
H-10
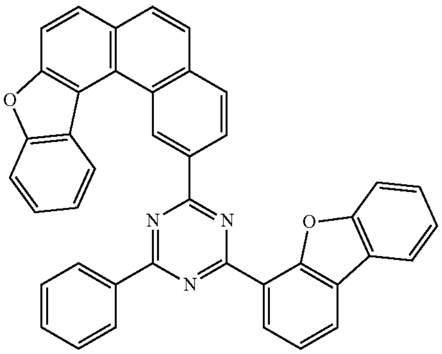
H2-11
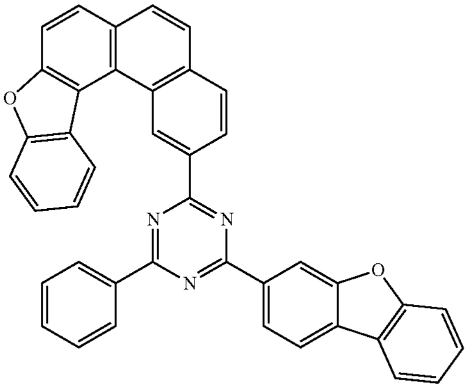
H2-12
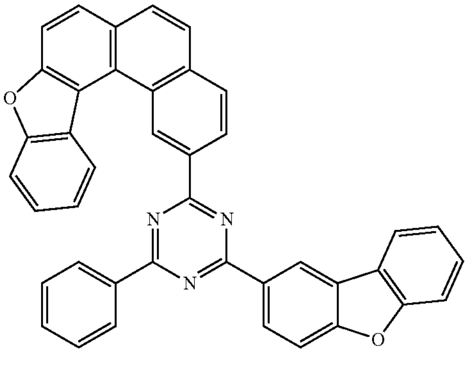
-continued
H2-13
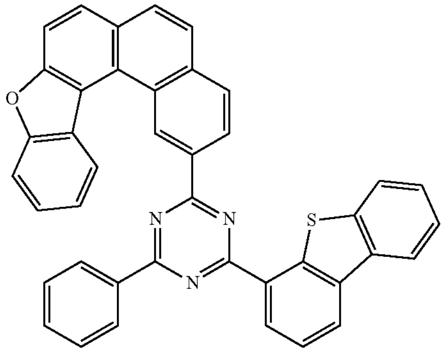
H2-14
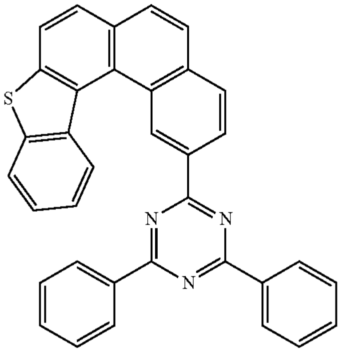
H2-15
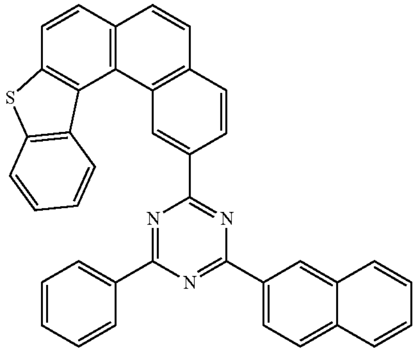
H2-16
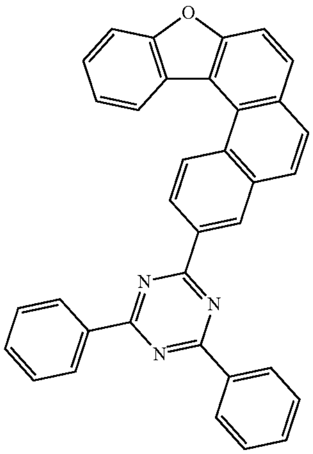

-continued
H2-17
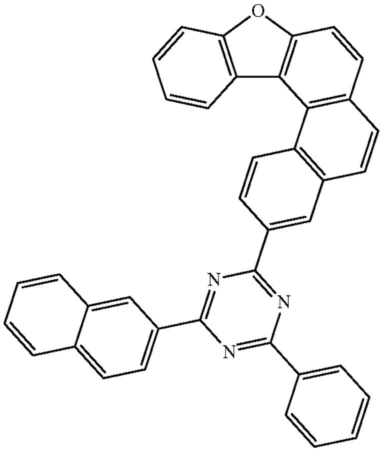
H2-18
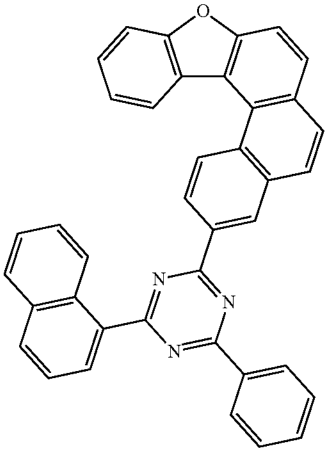
H2-19
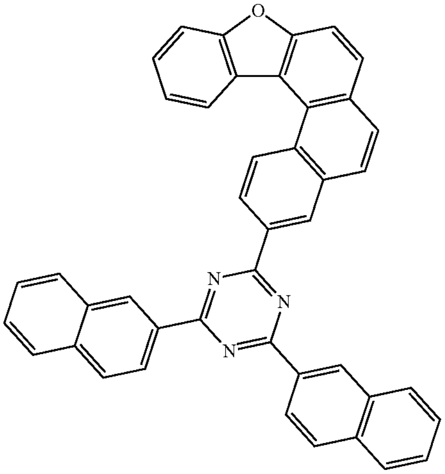
-continued
H2-20
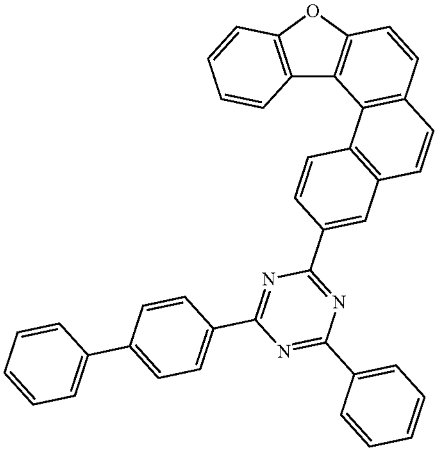
H2-21
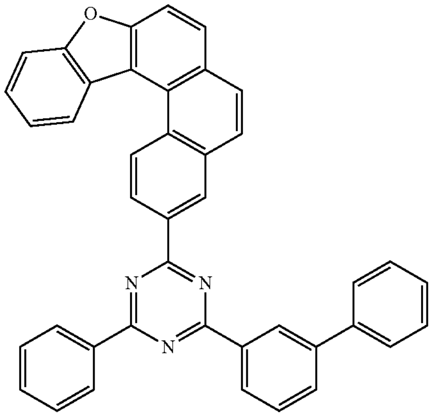
H2-22
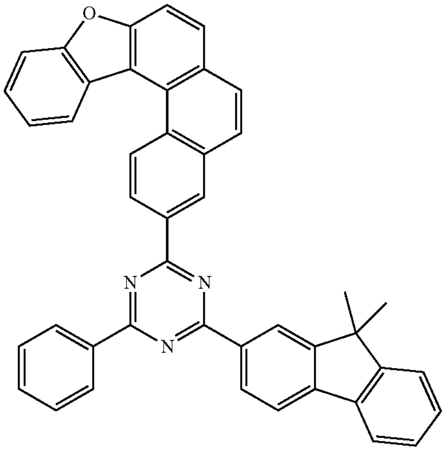

-continued
H2-23
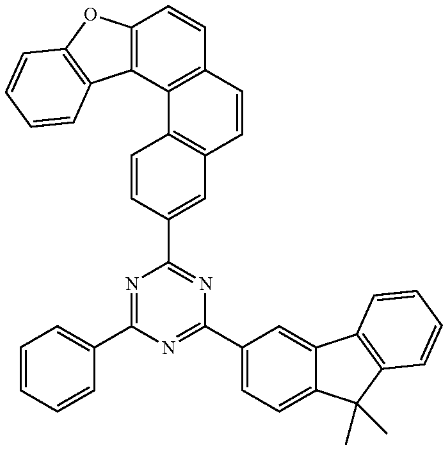
H2-24
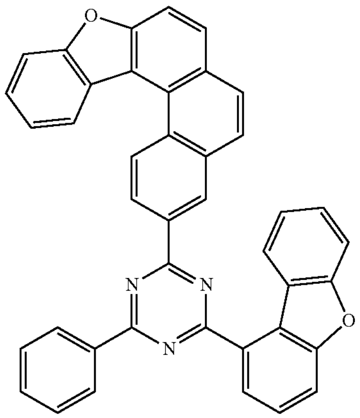
H2-25
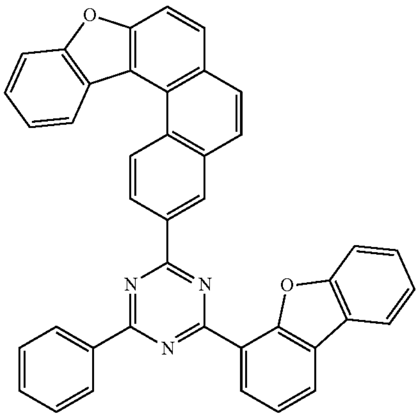
-continued
H2-26
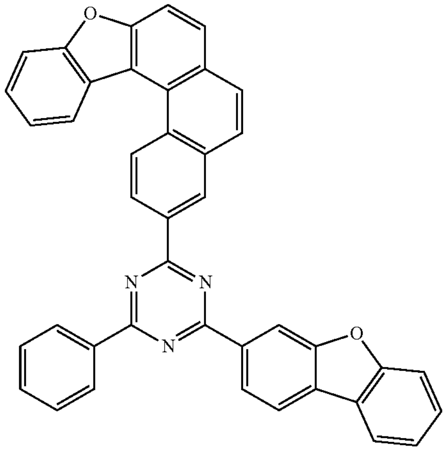
H2-27
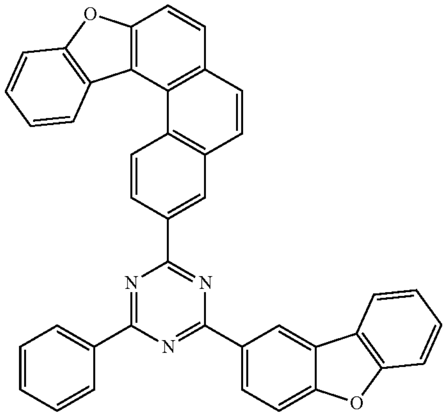
H2-28
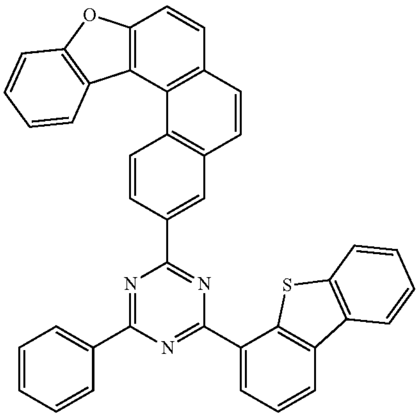

-continued
H2-29
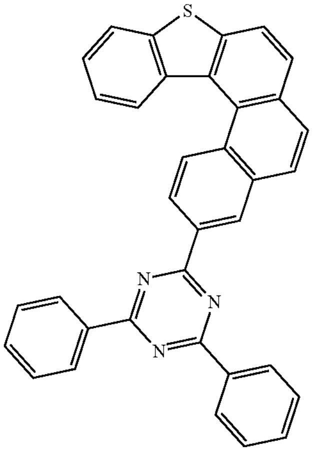
H2-30
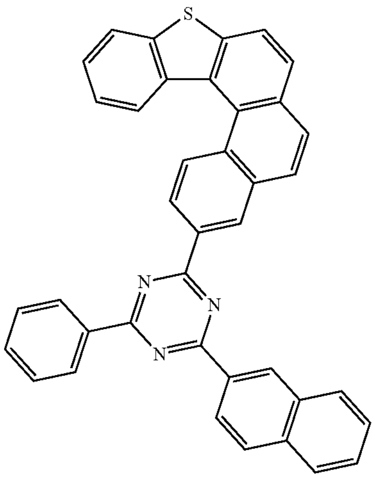
H2-31
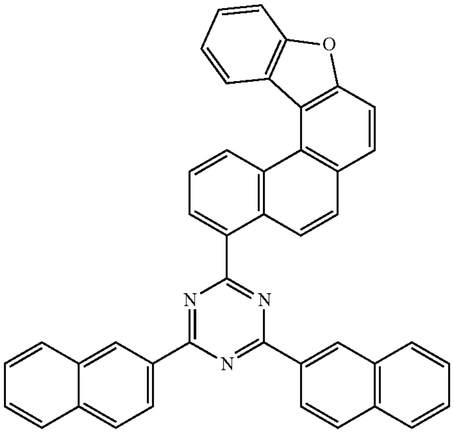
-continued
H2-32
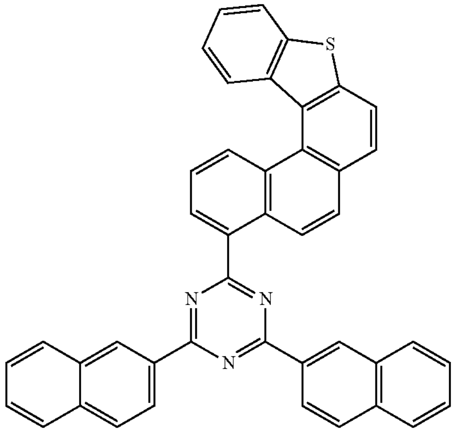
H2-33
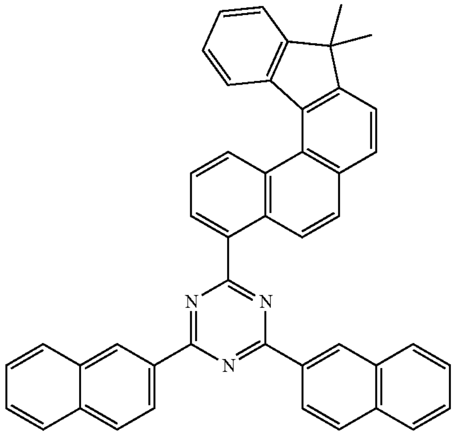
H2-34
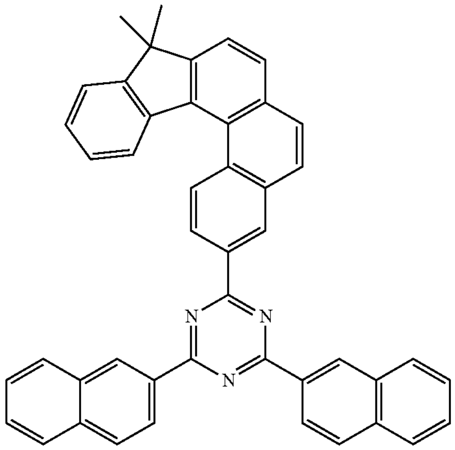

-continued
H2-35
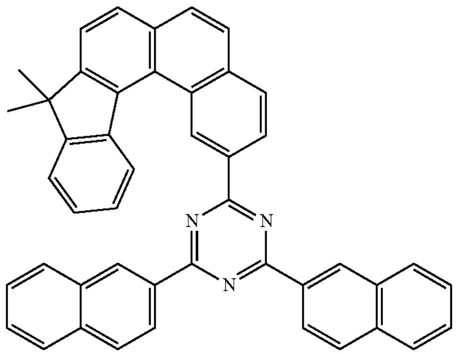
H2-36
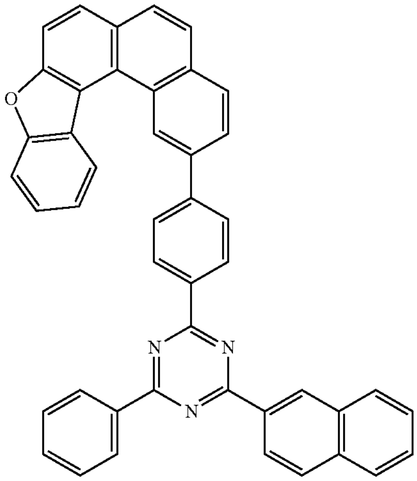
H2-37
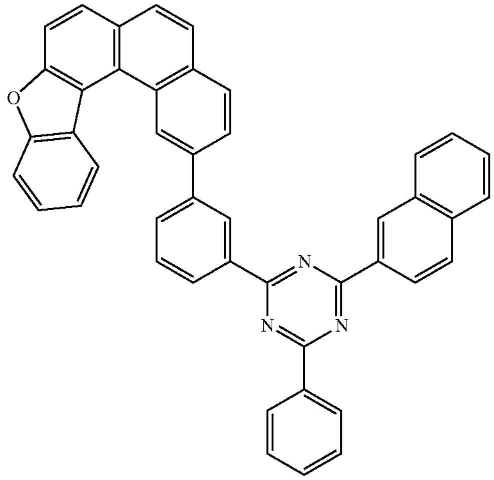
-continued
H2-38
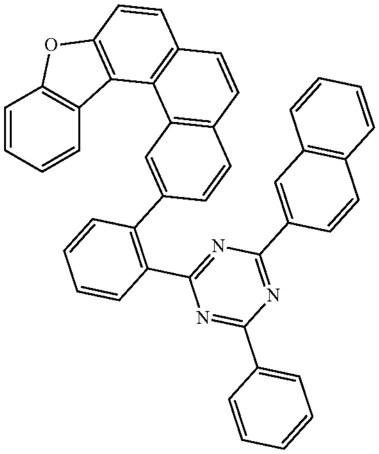
H2-39
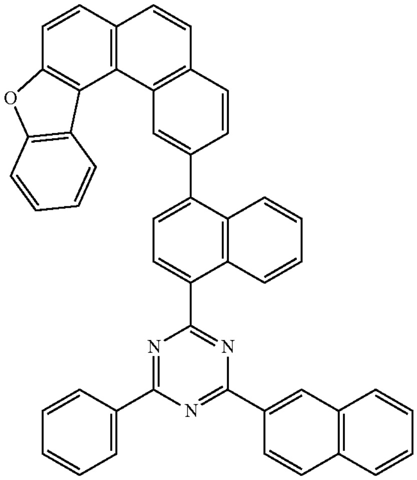
H2-40
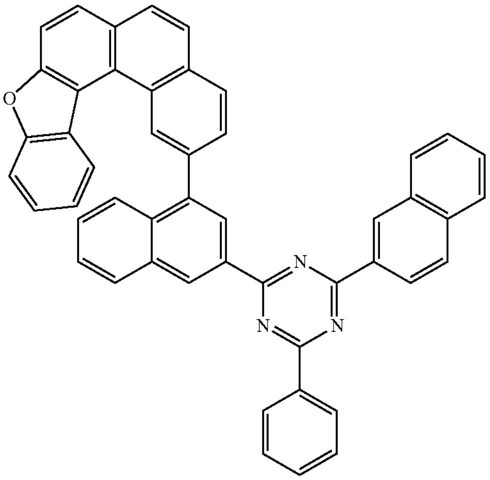

-continued
H2-41
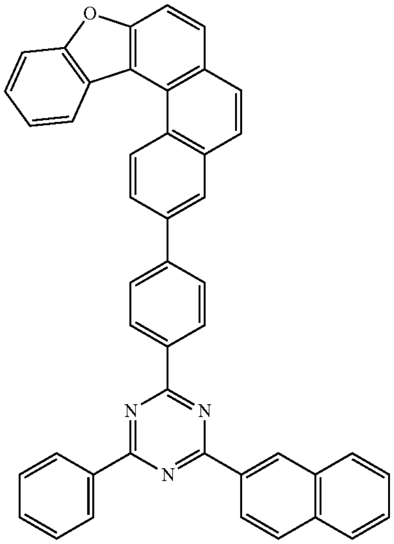
H2-42
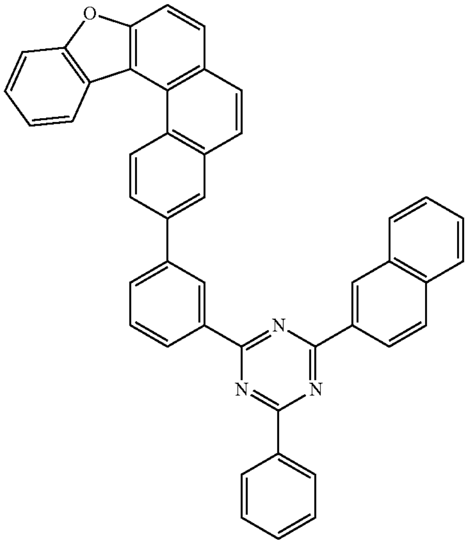
H2-43
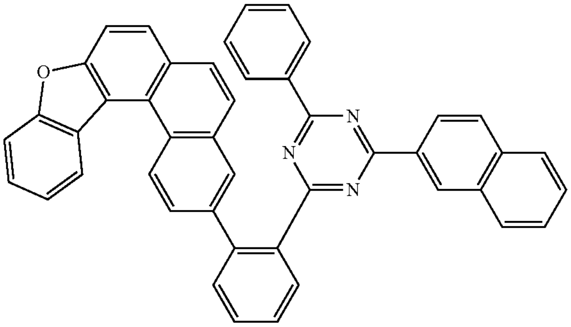
-continued
H2-44
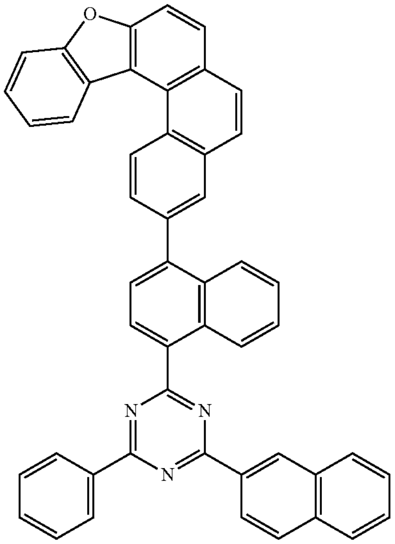
H2-45
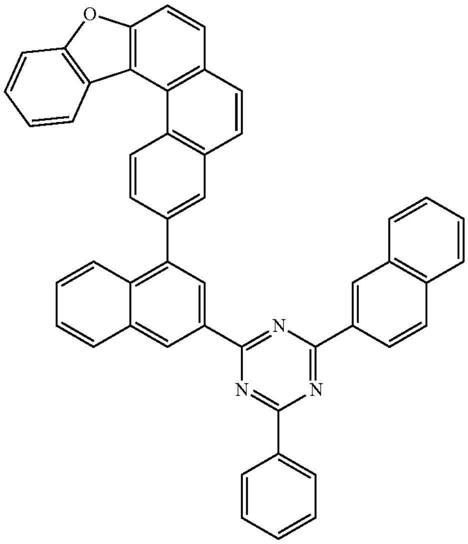
H2-46
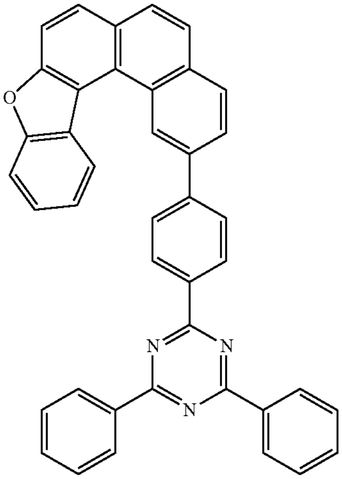

-continued
H2-47
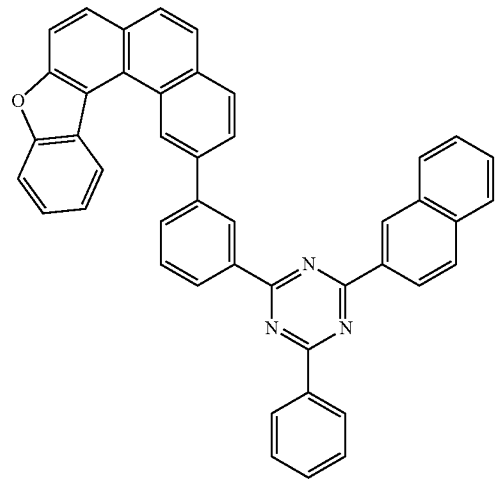
H2-48
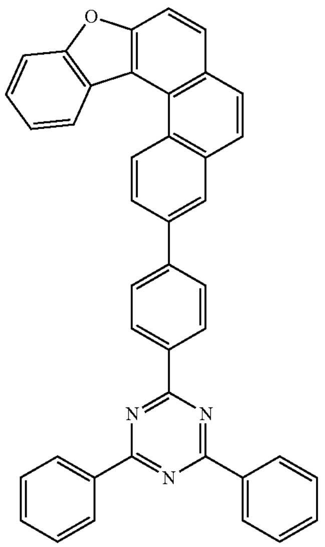
H2-49
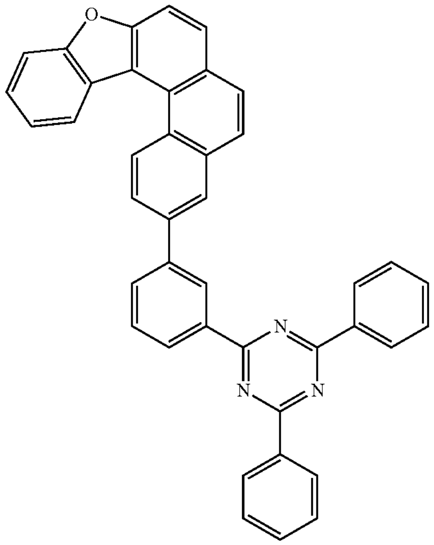
-continued
H2-50
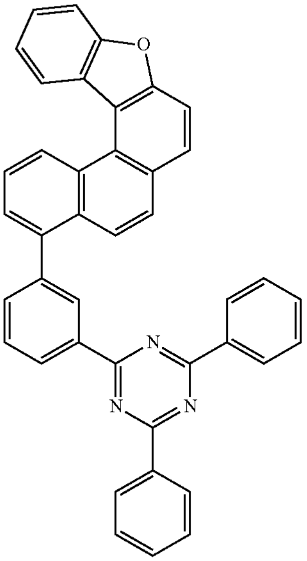
H2-51
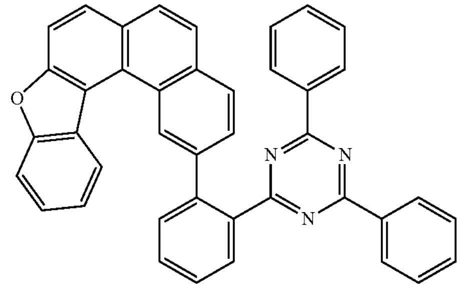
H2-52
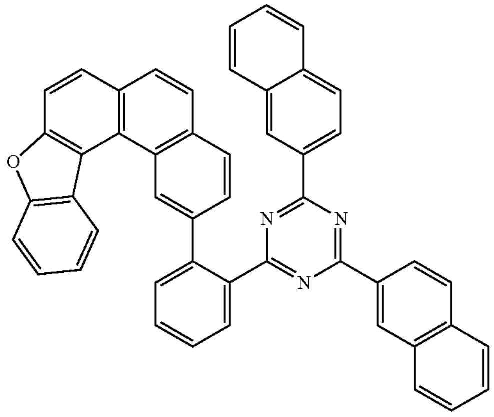

-continued
H2-53
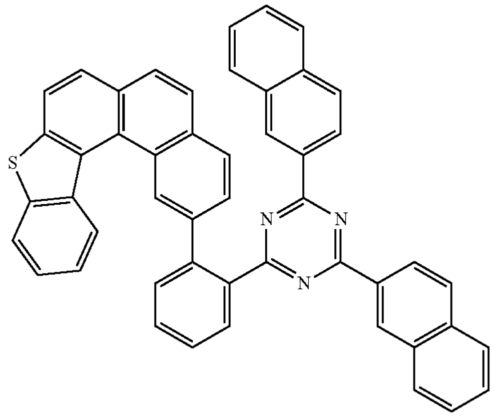
H2-54
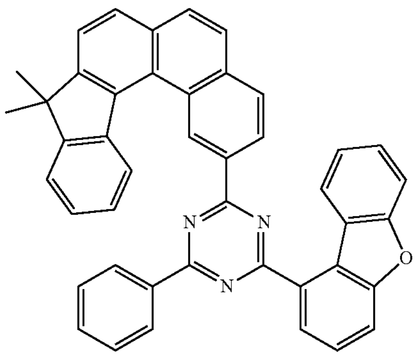
H2-55
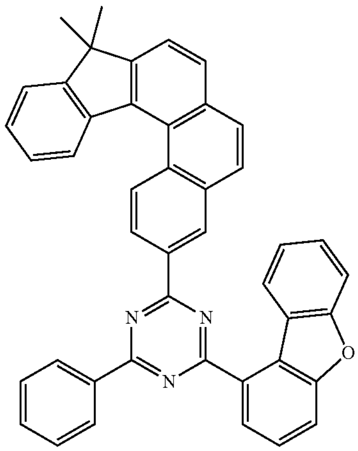
-continued
H2-56
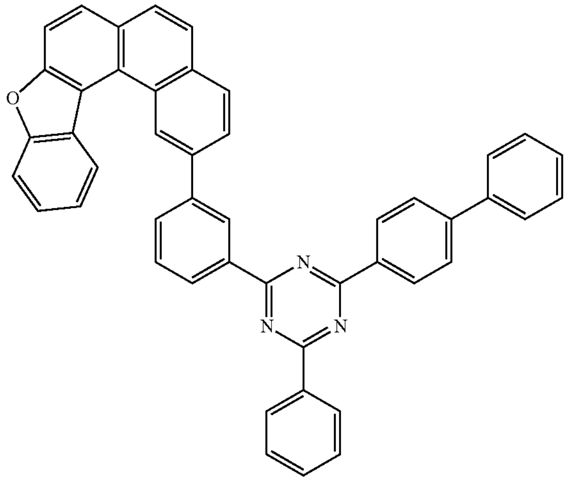
H2-57
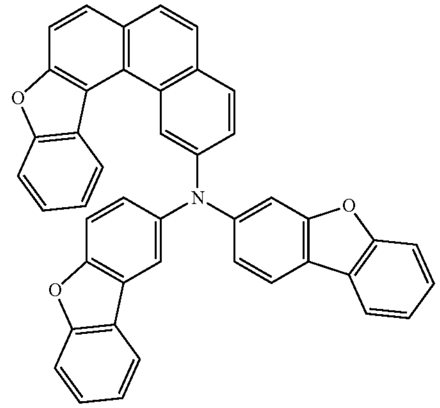
H2-58
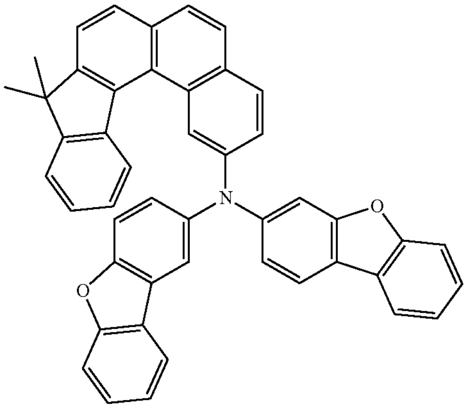

-continued
H2-59
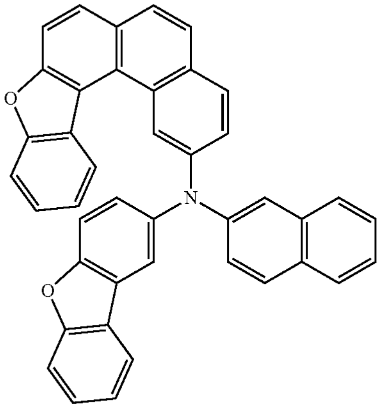
H2-60
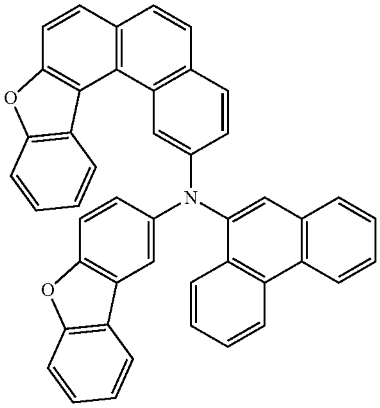
H2-61
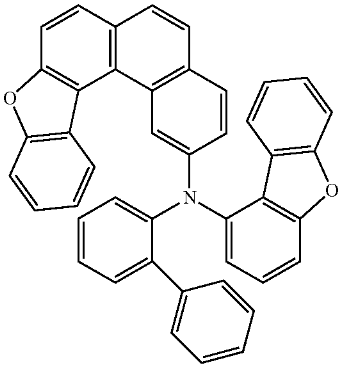
H2-62
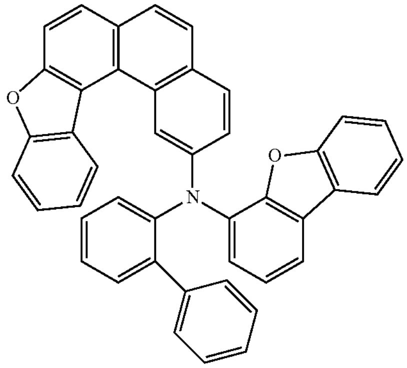
-continued
H2-63
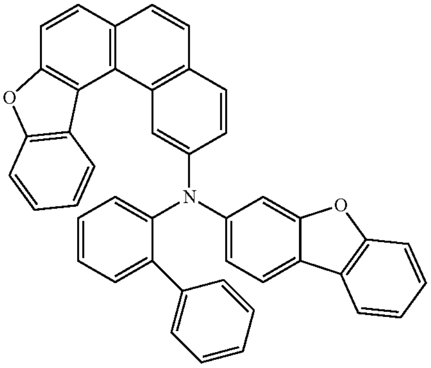
H2-64
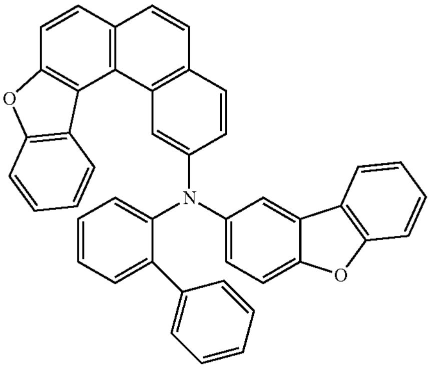
H2-65
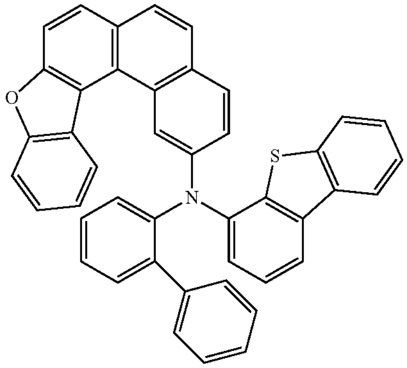
H2-66
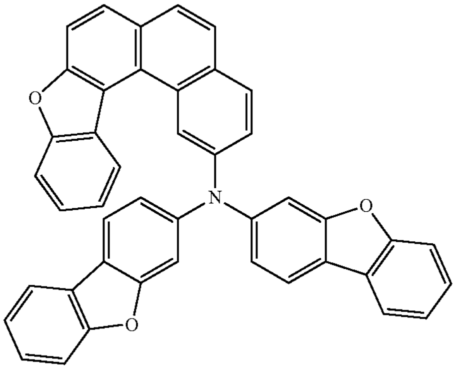

-continued
H2-67
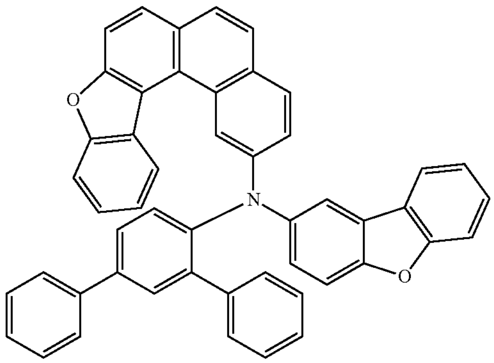
H2-68
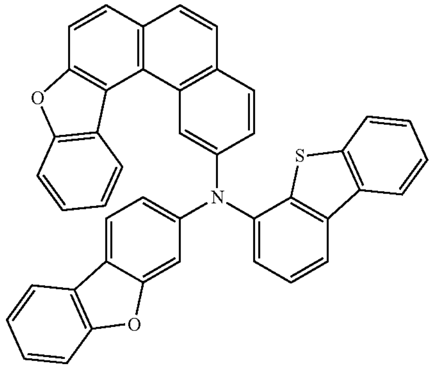
H2-69
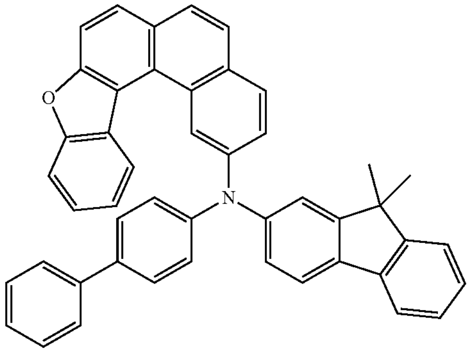
H2-70
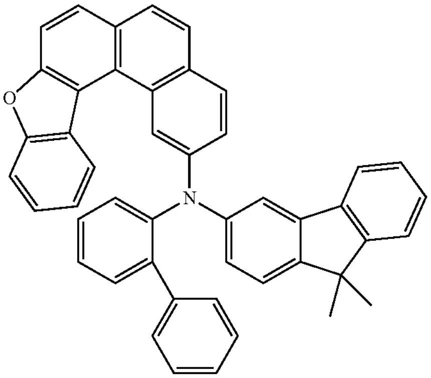
-continued
H2-71
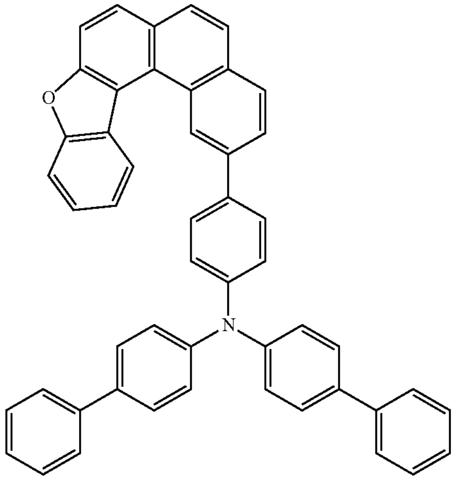
H2-72
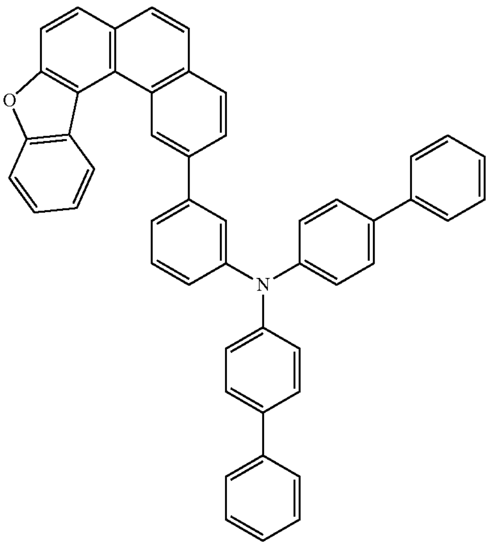
H2-73
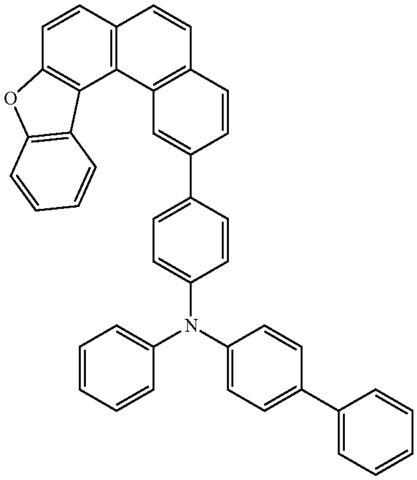

-continued
H2-74
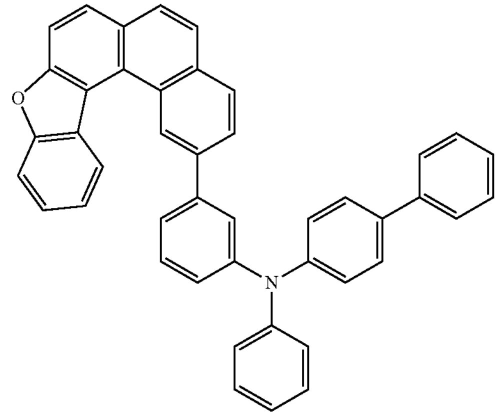
H2-75
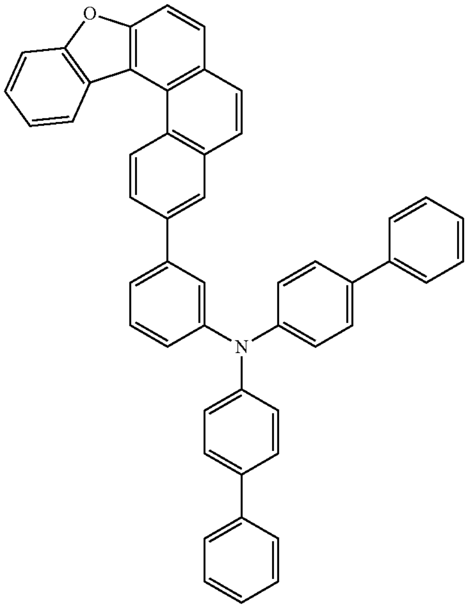
H2-76
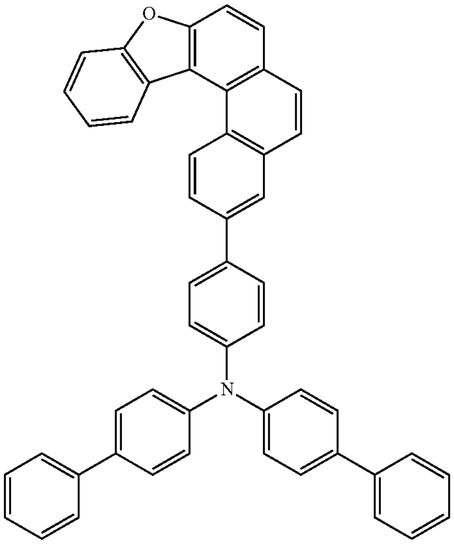
-continued
H2-77
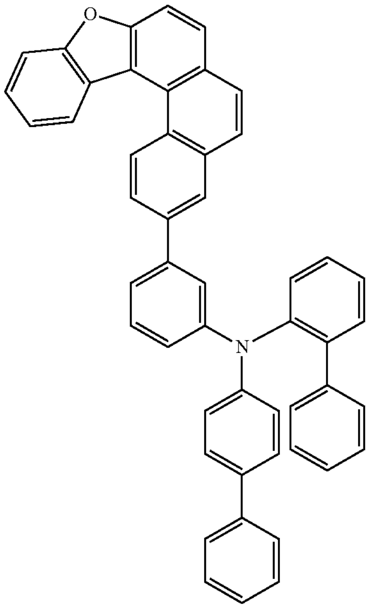
H2-78
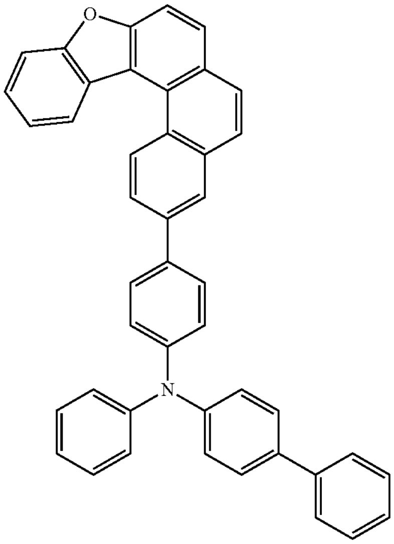
H2-79
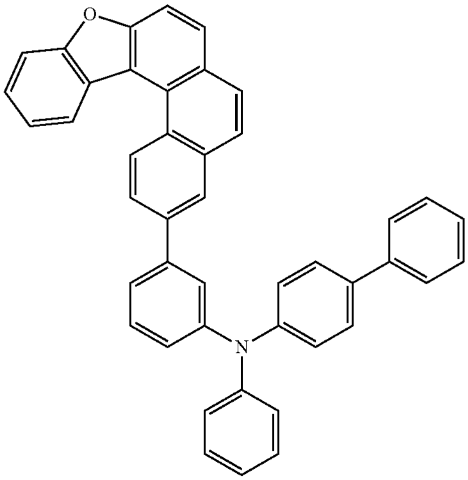

-continued
H2-80
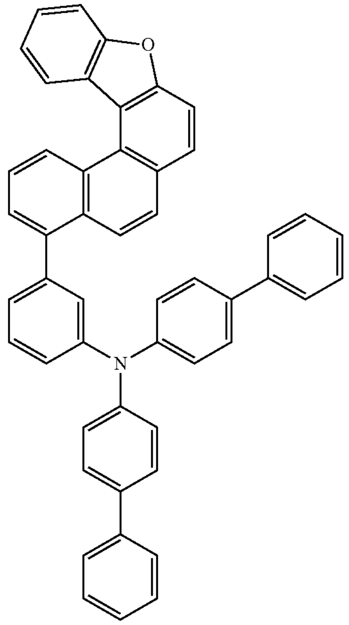
H2-81
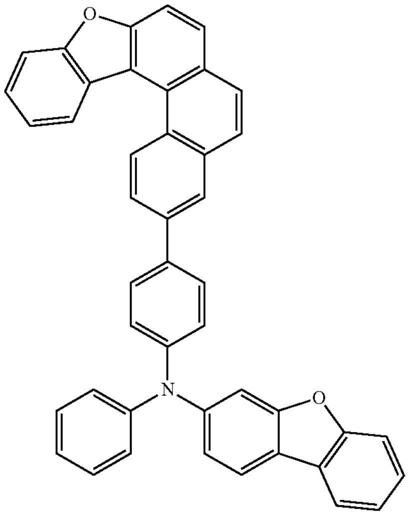
H2-82
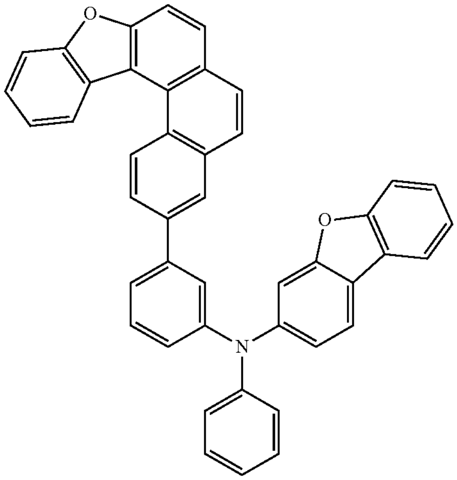
-continued
H2-83
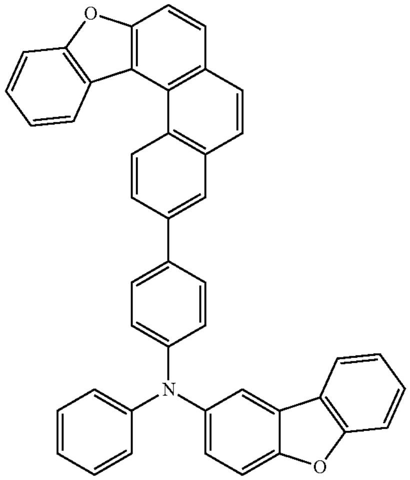
H2-84
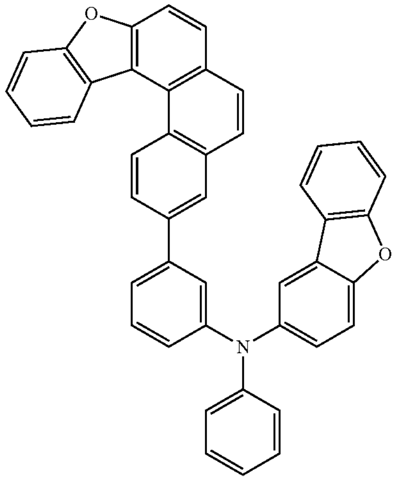
H2-85
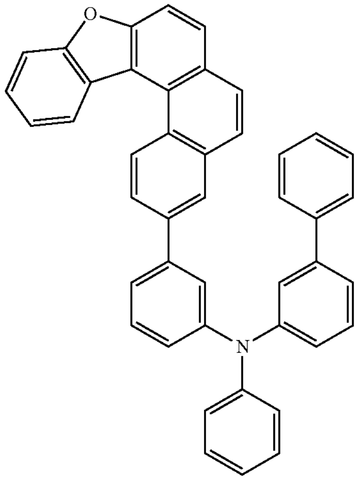

-continued
H2-86
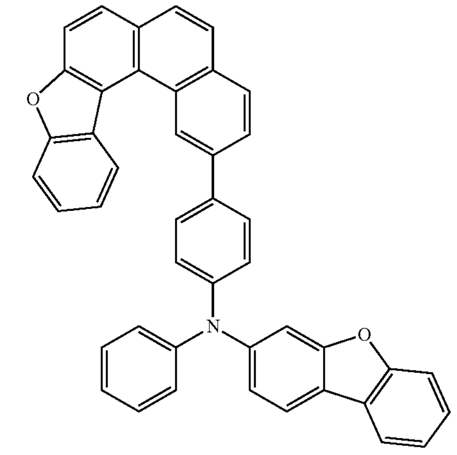
H2-87
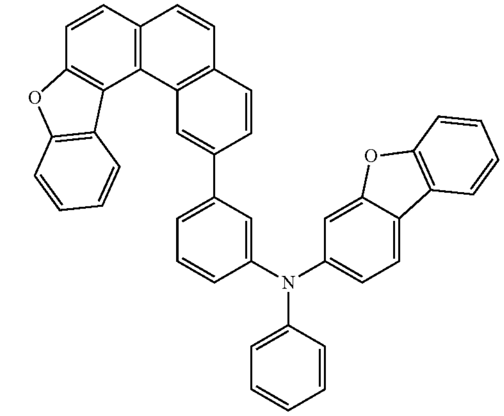
H2-88
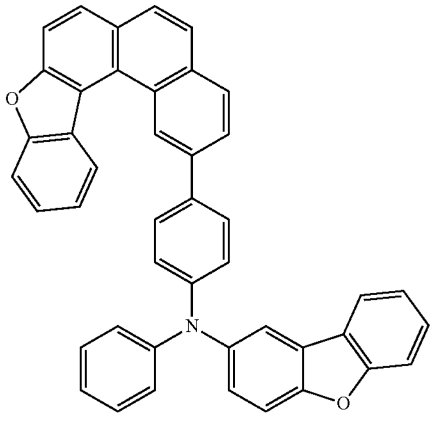
-continued
H2-89
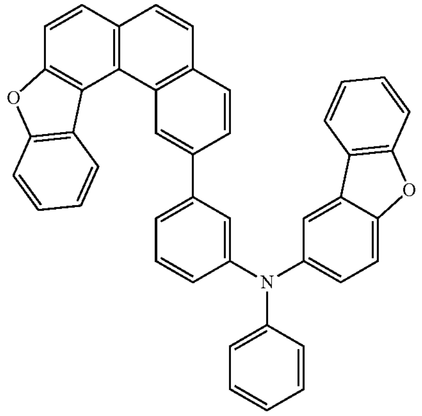
H2-90
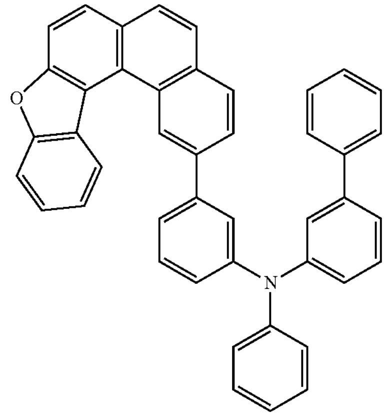
H2-91
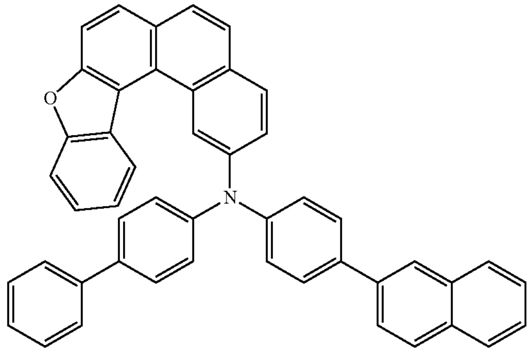
H2-92
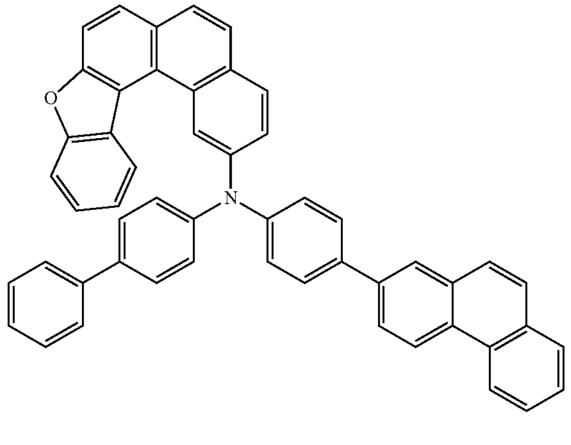

-continued
H2-93
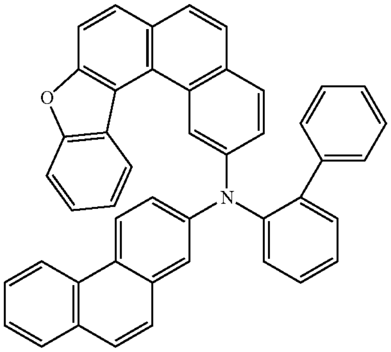
H2-94
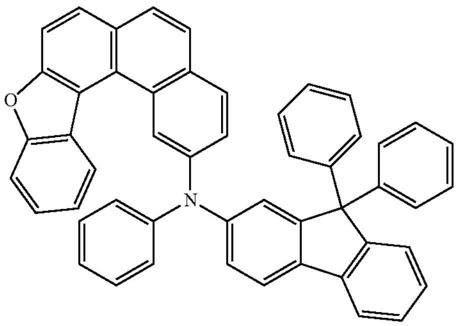
H2-95
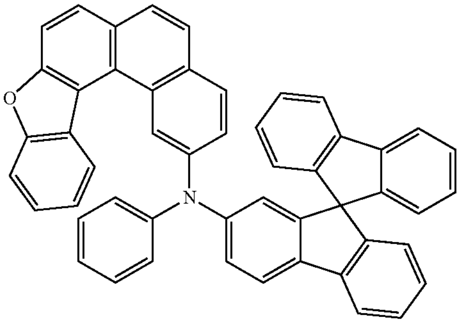
H2-96
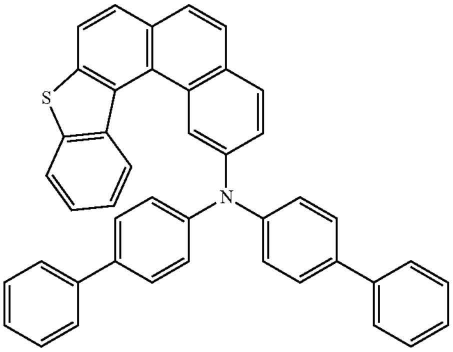
-continued
H2-97
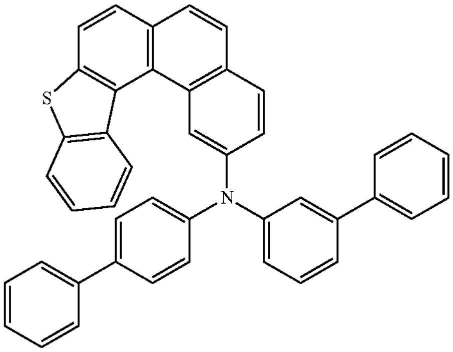
H2-98
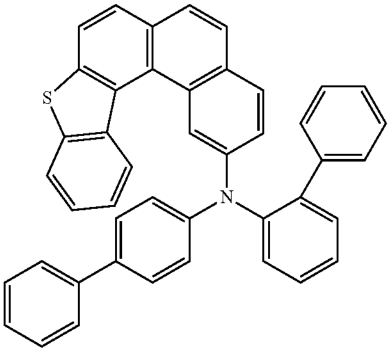
H2-99
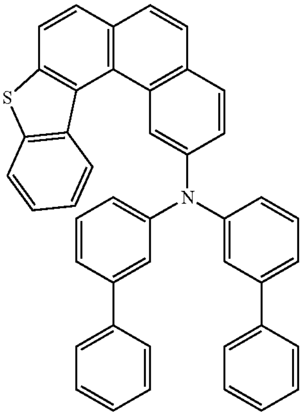
H2-100
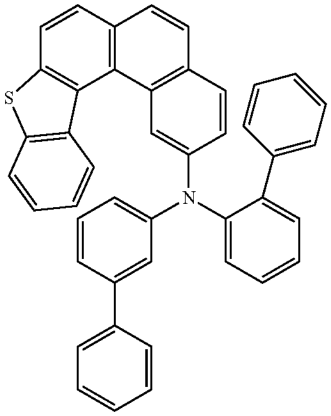

-continued
H2-101
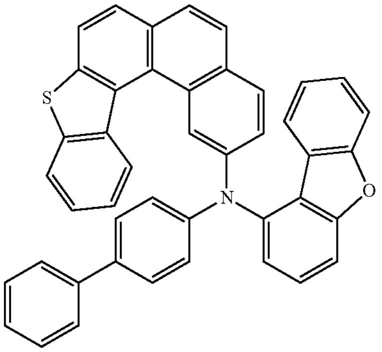
H2-102
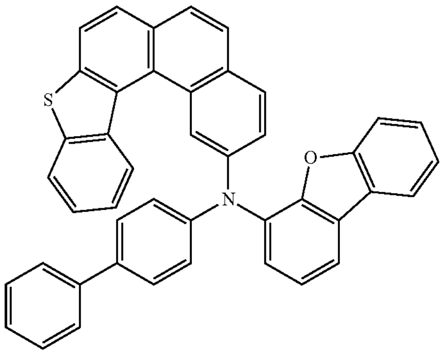
H2-103
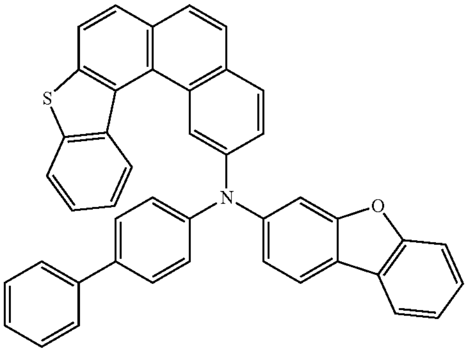
H2-104
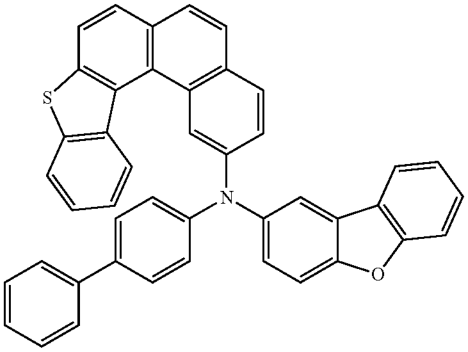
-continued
H2-105
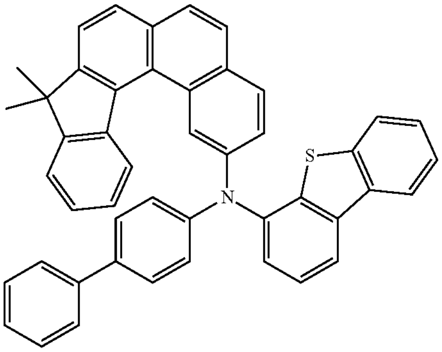
H2-106
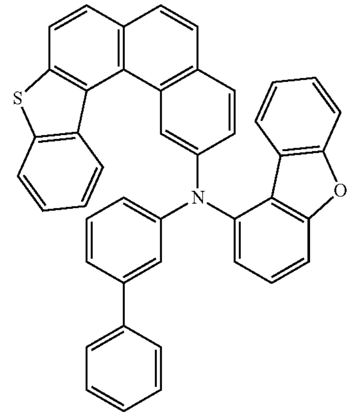
H2-107
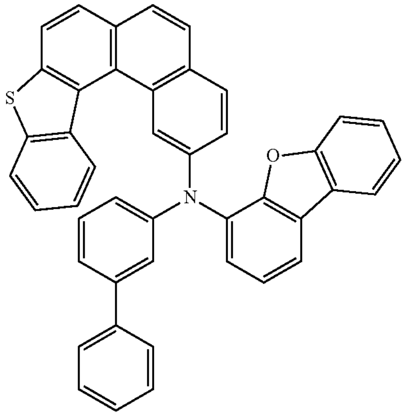
H2-108
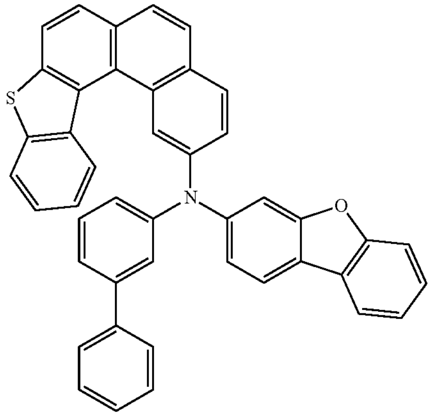

-continued
H2-109
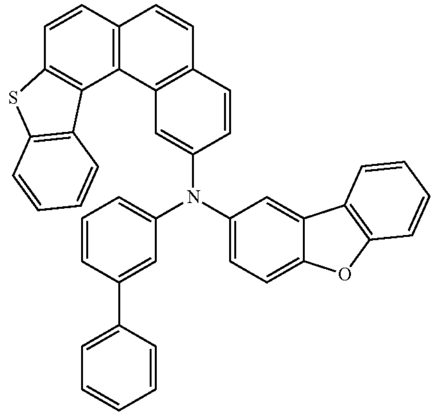
H2-110
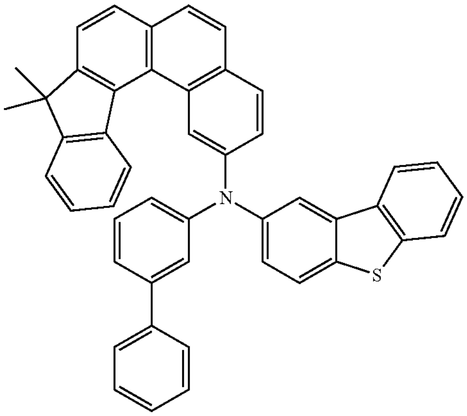
H2-111
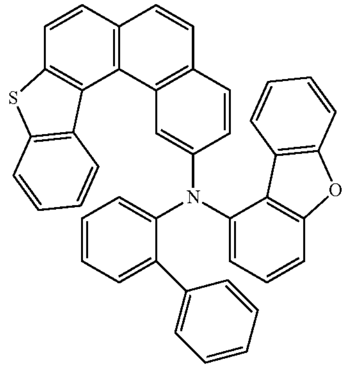
H2-112
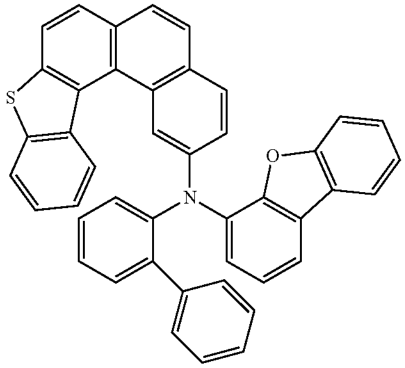
-continued
H2-113
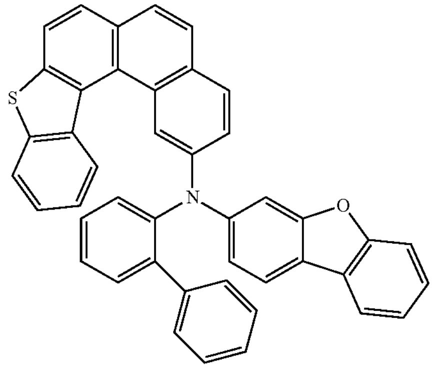
H2-114
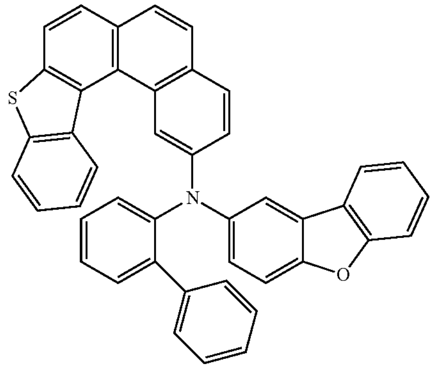
H2-115
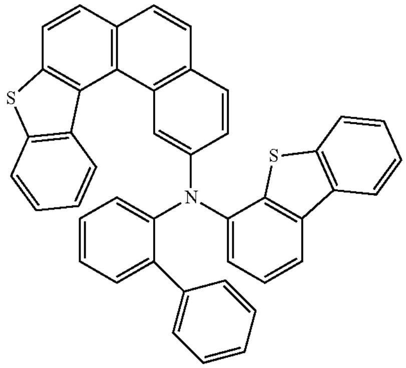
H2-116
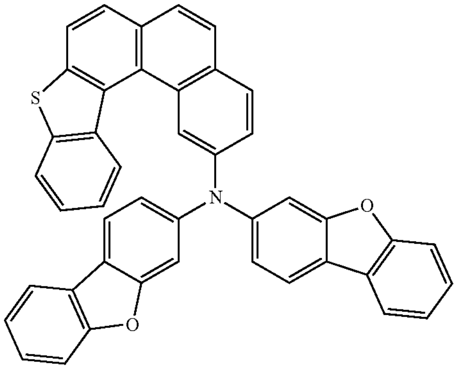

-continued
H2-117
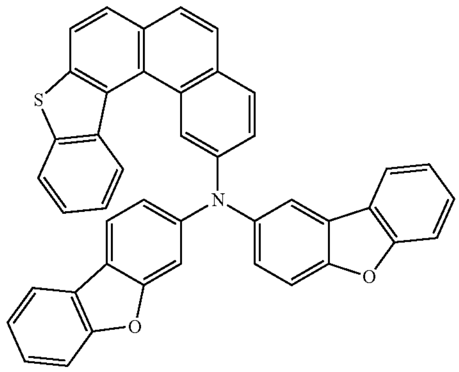
H2-118
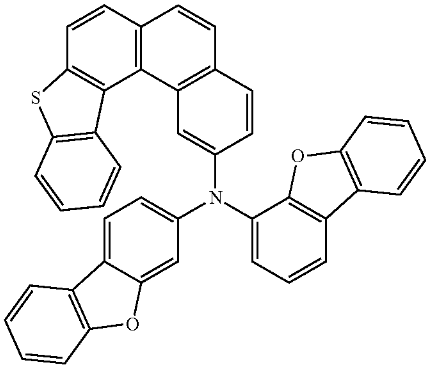
H2-119
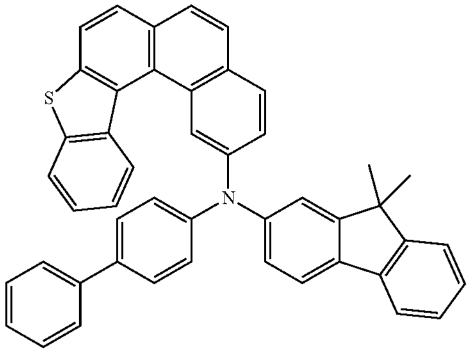
H2-120
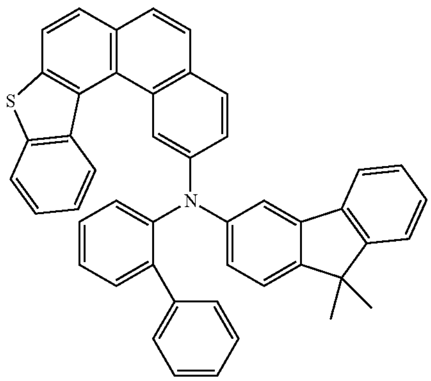
-continued
H2-121
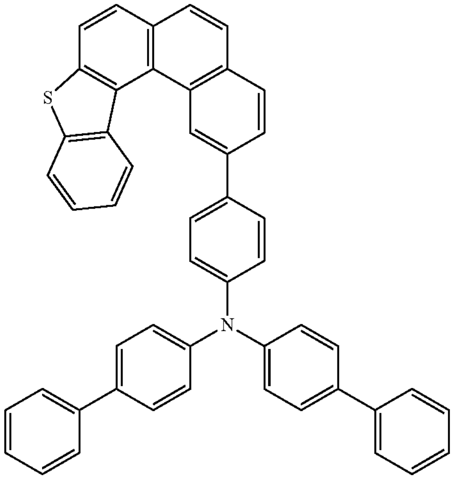
H2-122
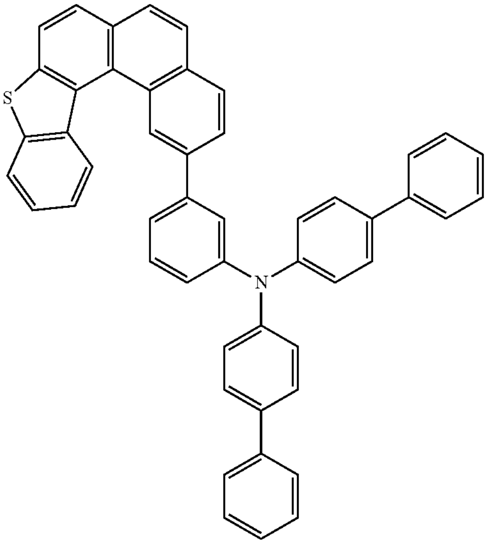
H2-123
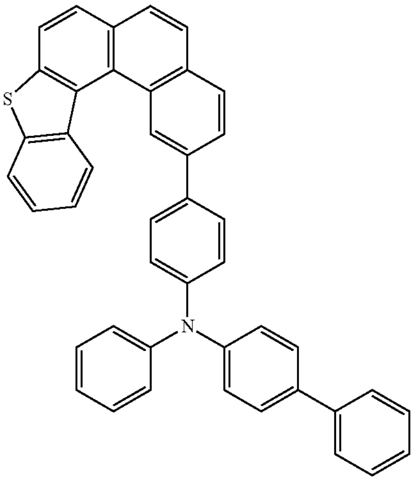

-continued
H2-124
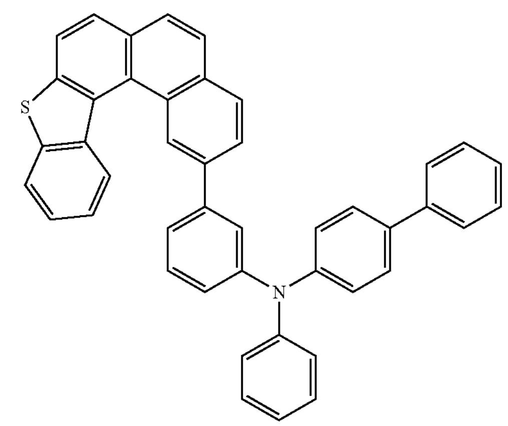
H2-125
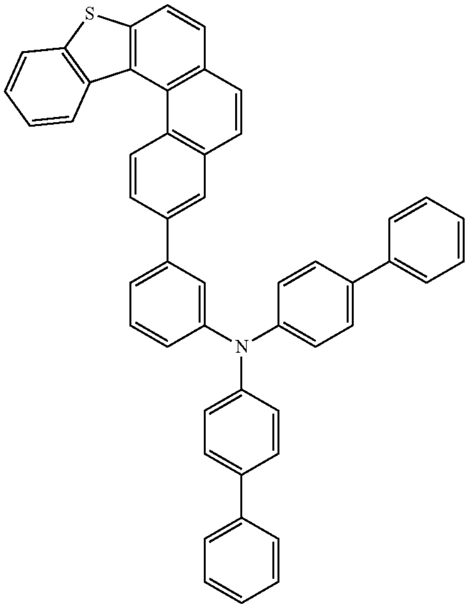
H2-126
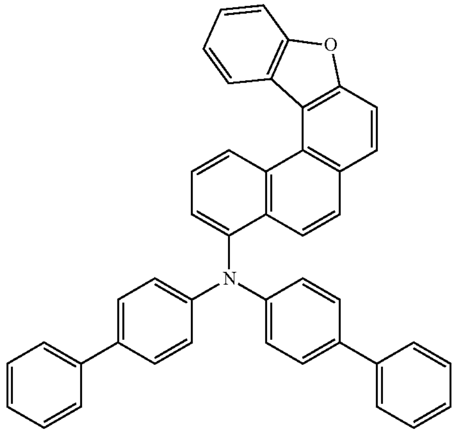
-continued
H2-127
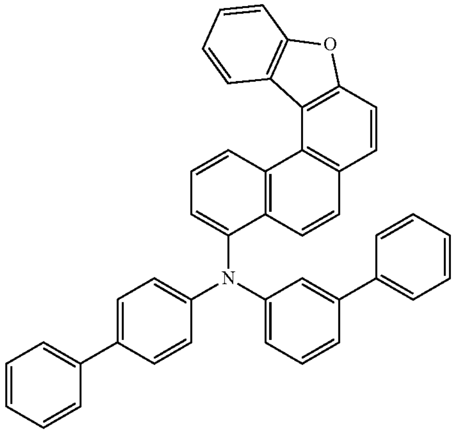
H2-128
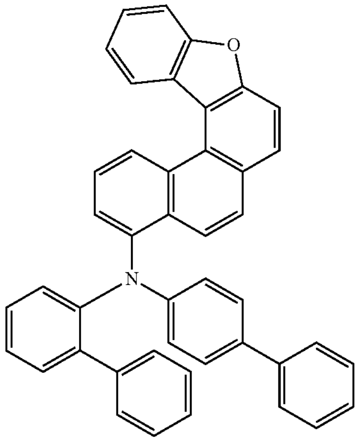
H2-129
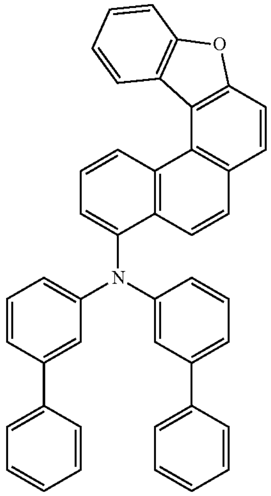

-continued
H2-130
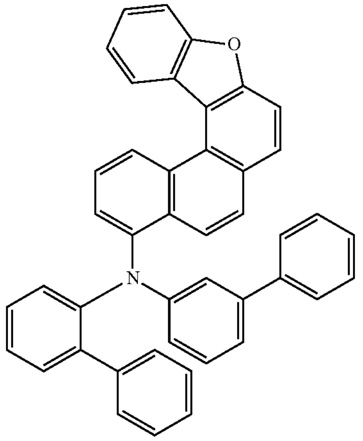
H2-131
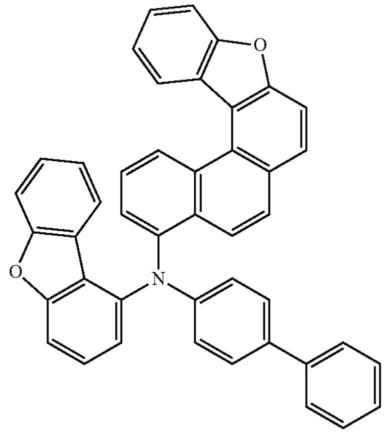
H2-132
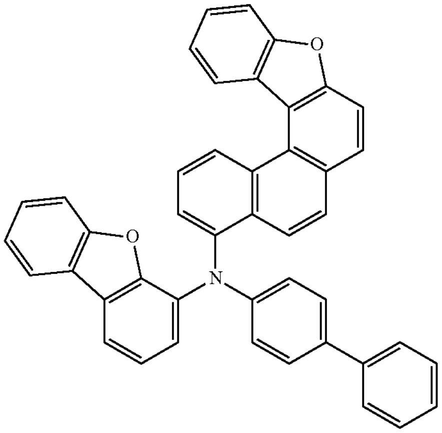
-continued
H2-133
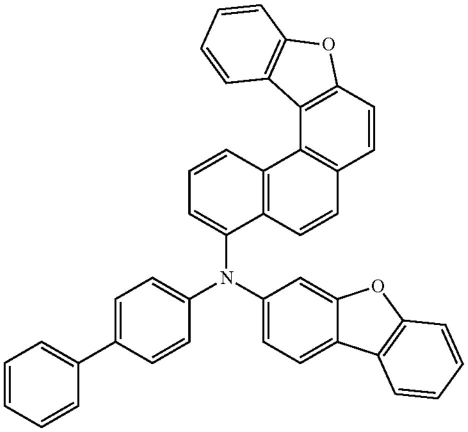
H2-134
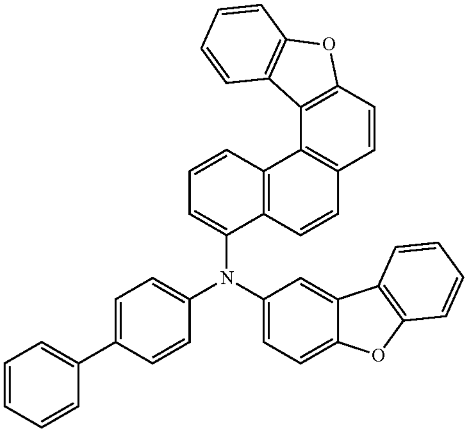
H2-135
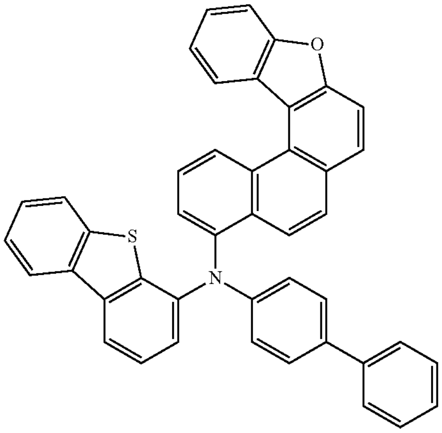

-continued
H2-136
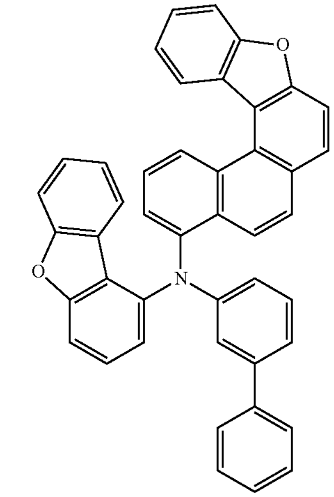
H2-137
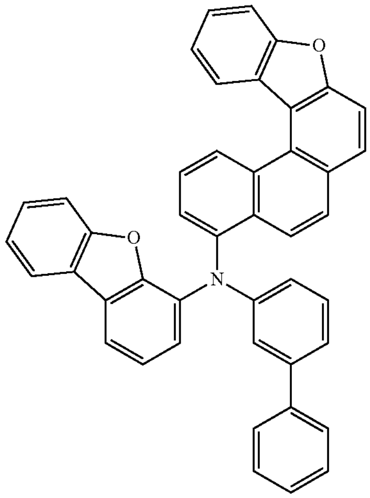
H2-138
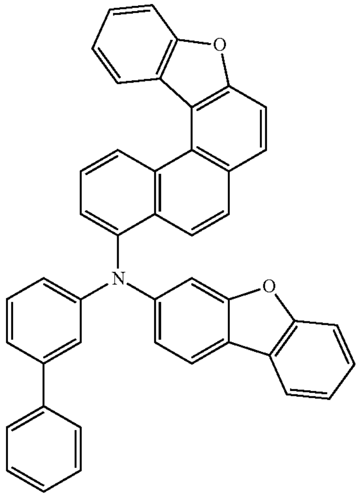
-continued
H2-139
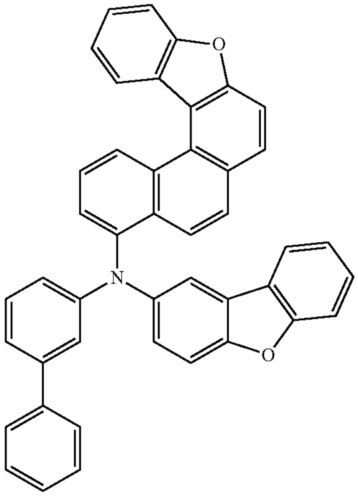
H2-140
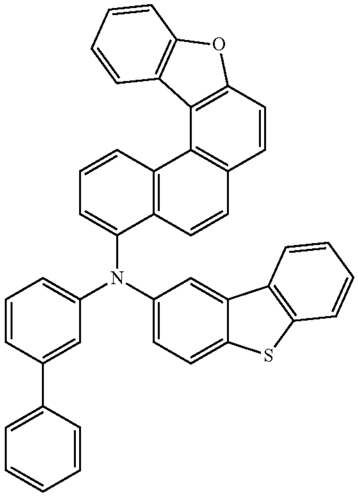
H2-141
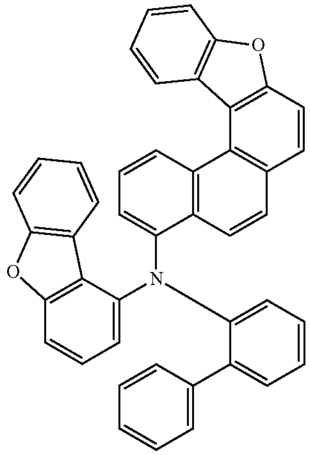

-continued
H2-142
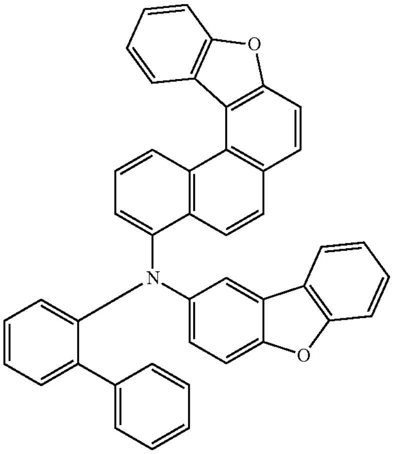
H2-143
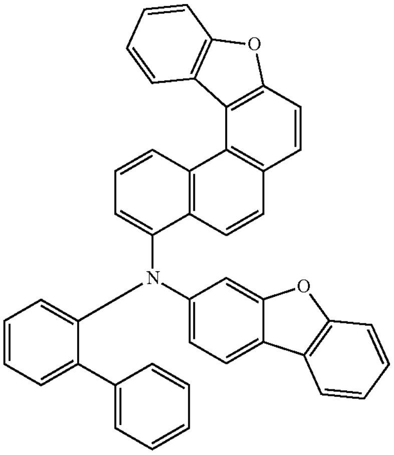
H2-144
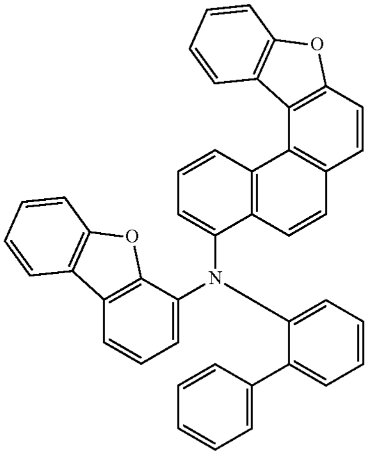
-continued
H2-145
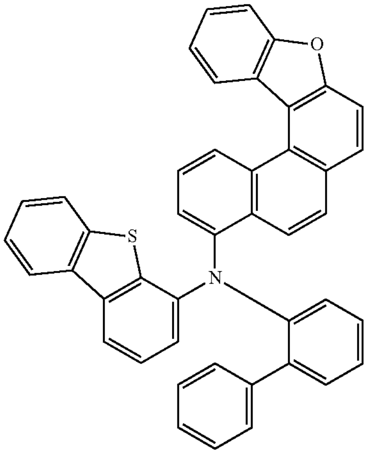
H2-146
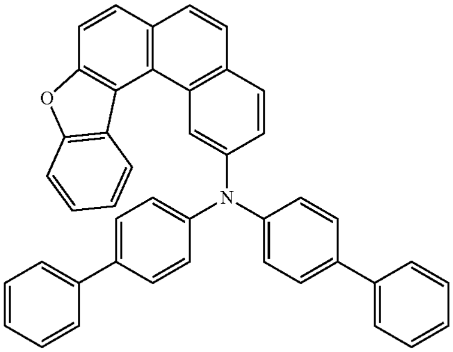
H2-147
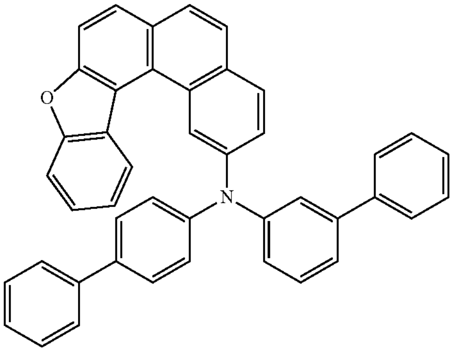
H2-148
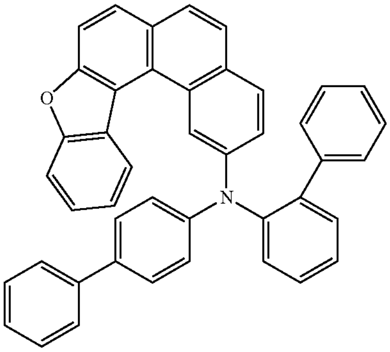

-continued
H2-149
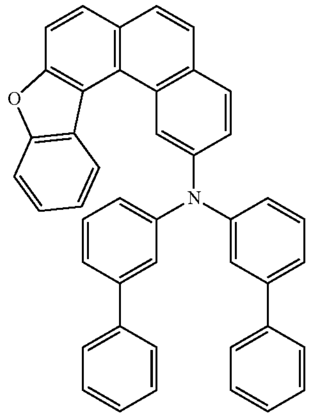
H2-150
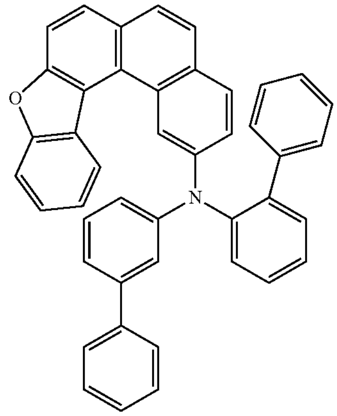
H2-151
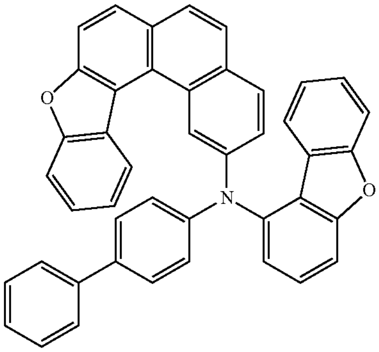
H2-152
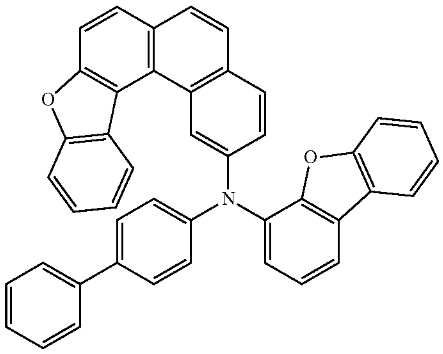
-continued
H2-153
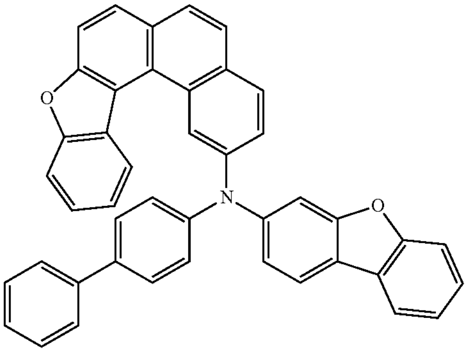
H2-154
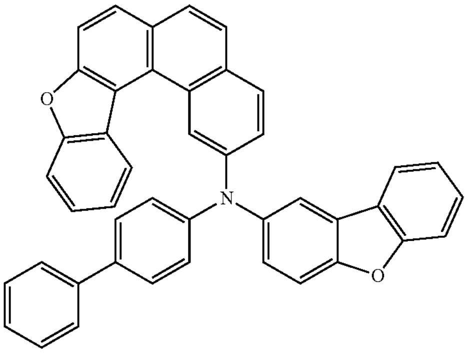
H2-155
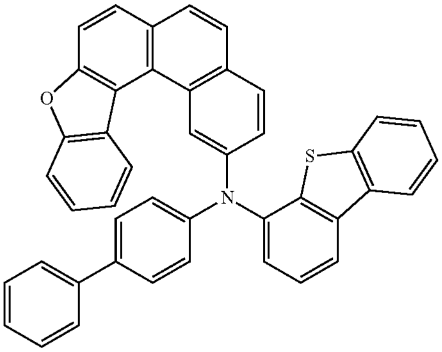
H2-156
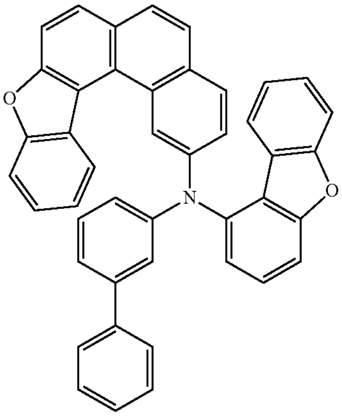

-continued
H2-157
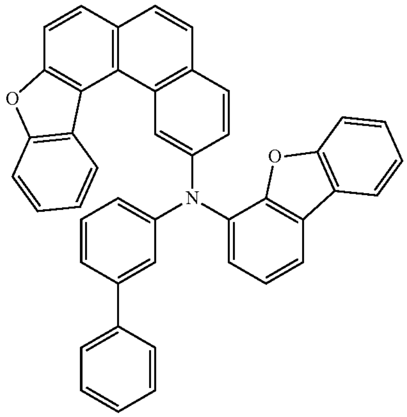
H2-158
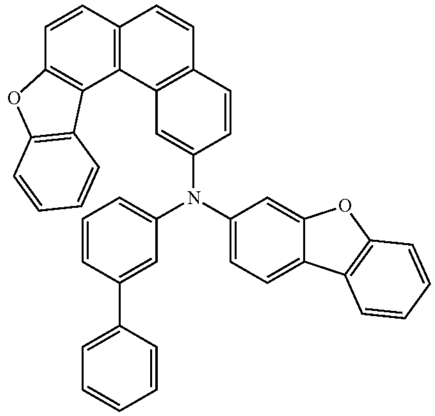
H2-159
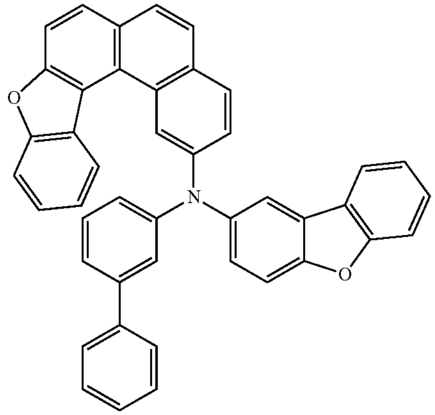
-continued
H2-160
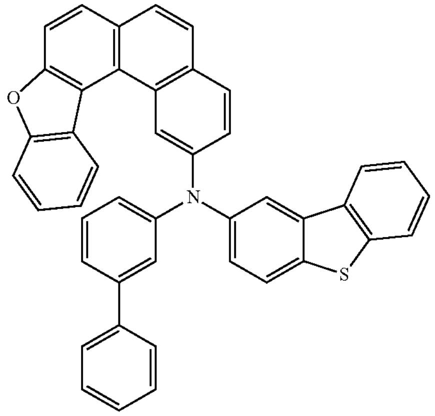
H2-161
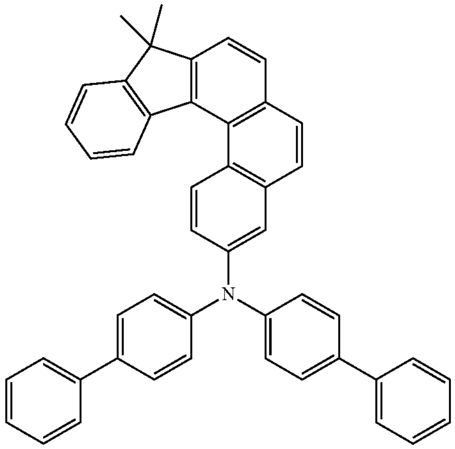
H2-162
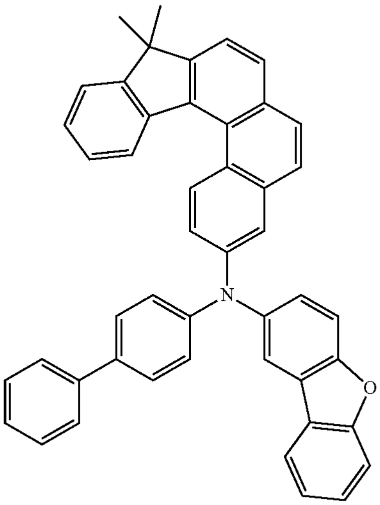

-continued
H2-163
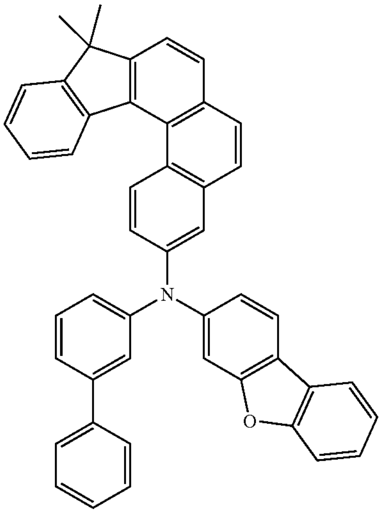
H2-164
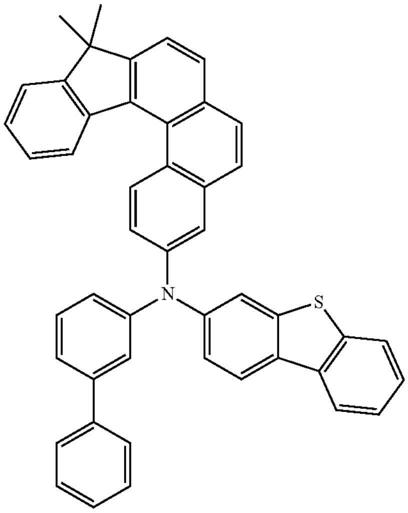
H2-165
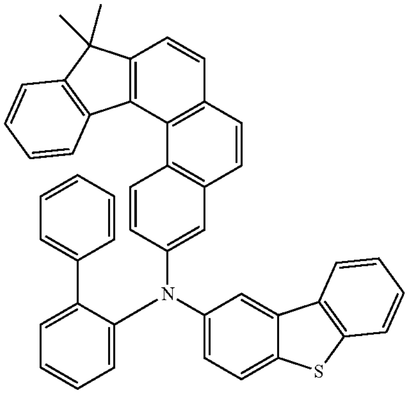
-continued
H2-166
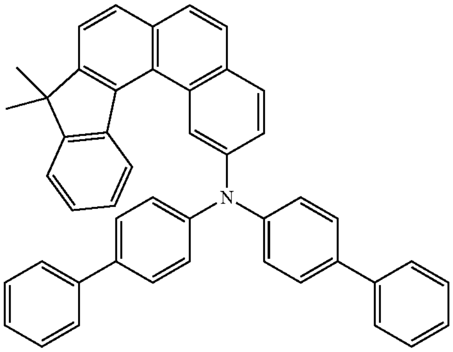
H2-167
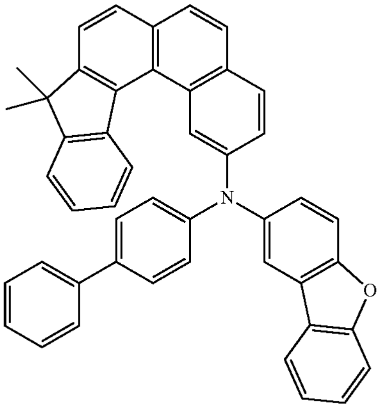
H2-168
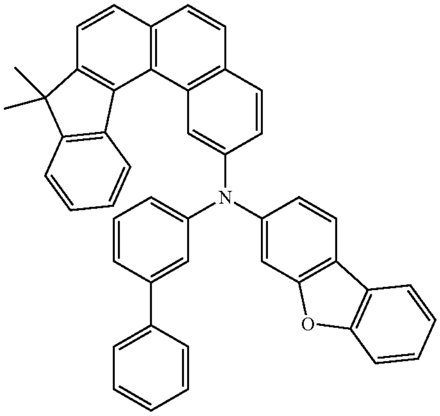
H2-169
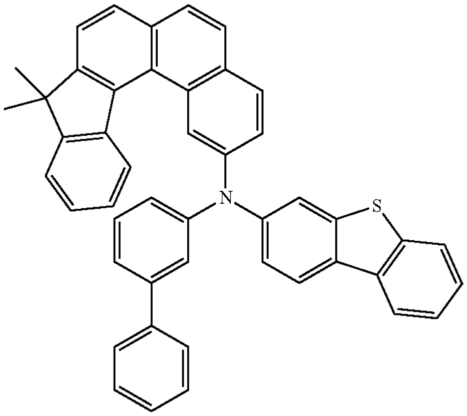

-continued
H2-170
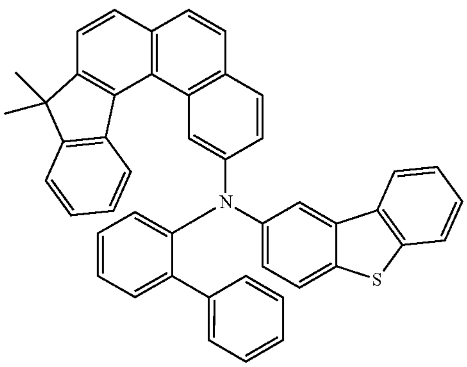
H2-171
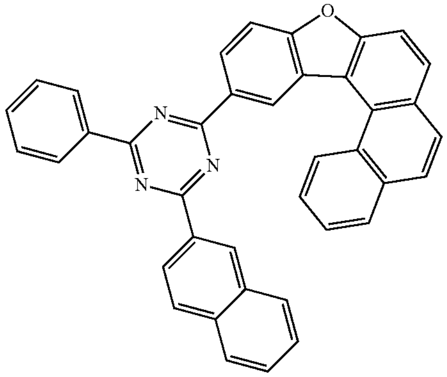
H2-172
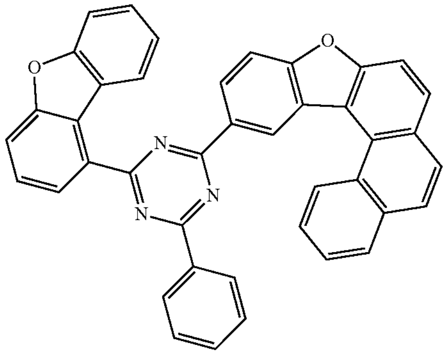
H2-173
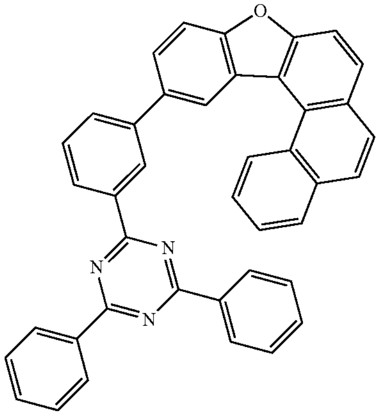
-continued
H2-174
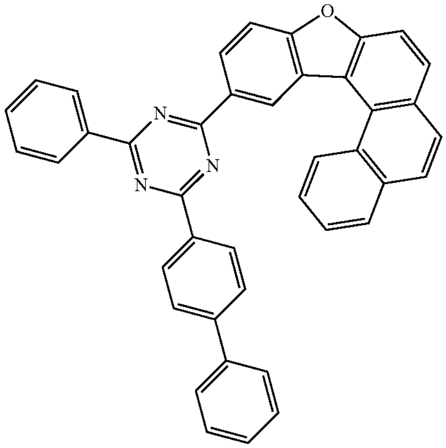
H2-175
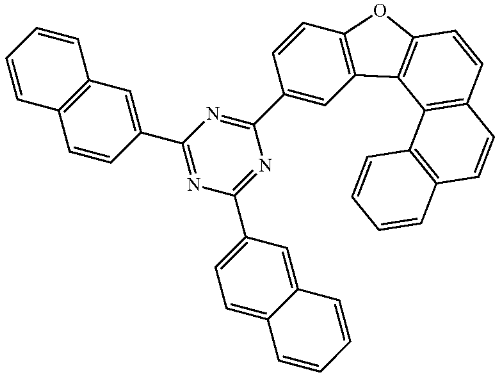
H2-176
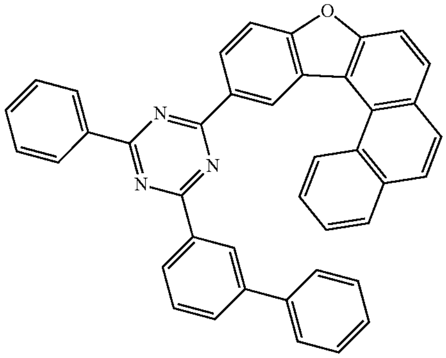

-continued
H2-177
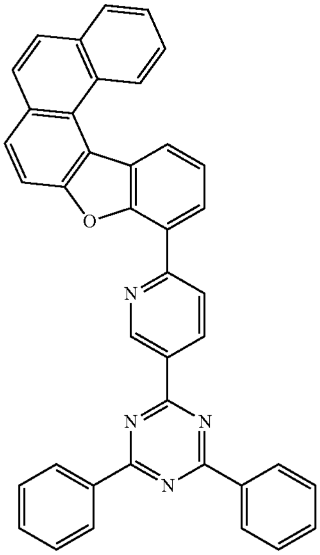
H2-178
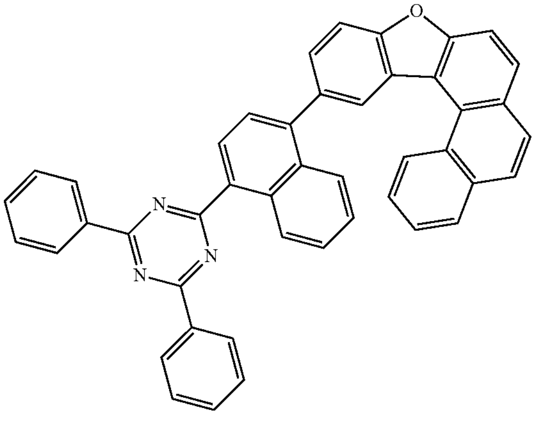
H2-179
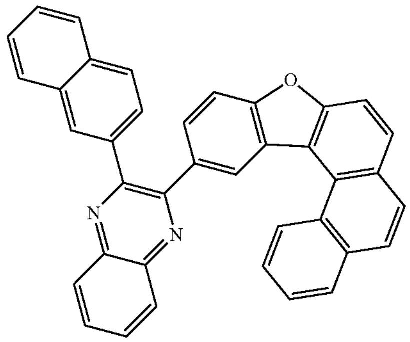
-continued
H2-180
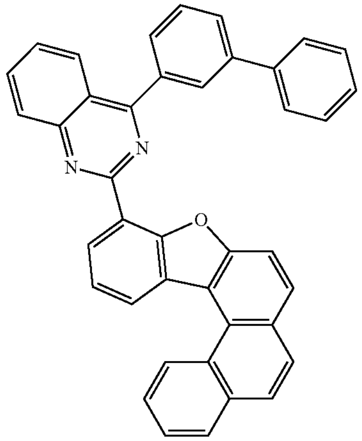
H2-181
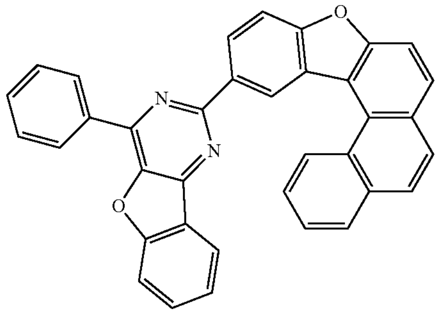
H2-182
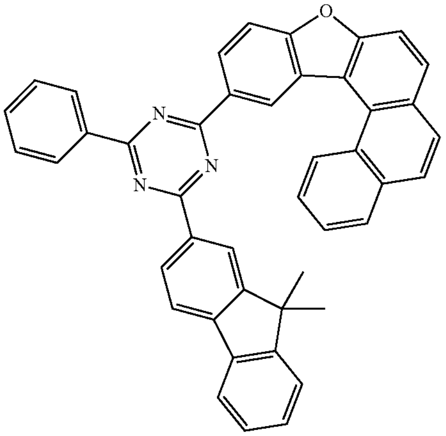
H2-183
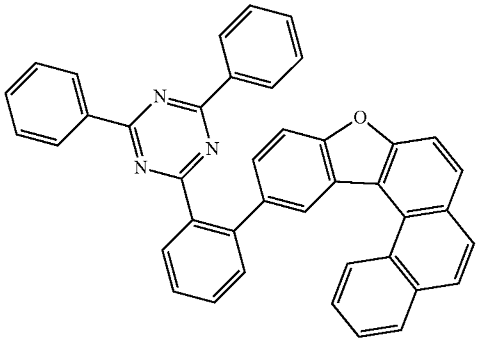

-continued
H2-184
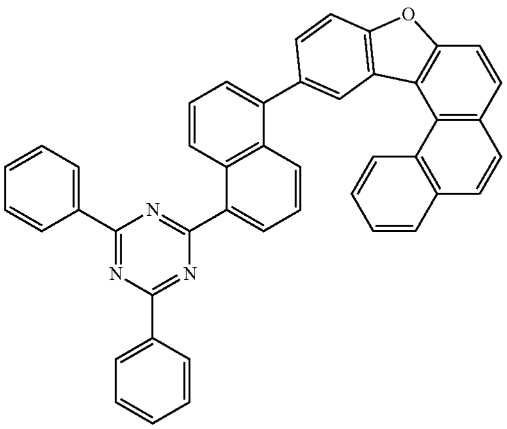
H2-185
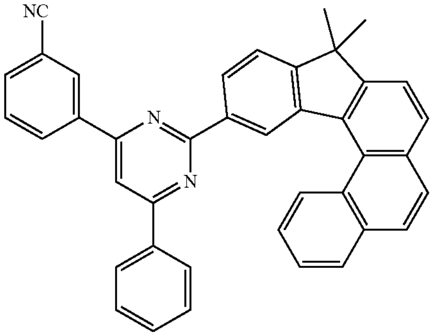
H2-186
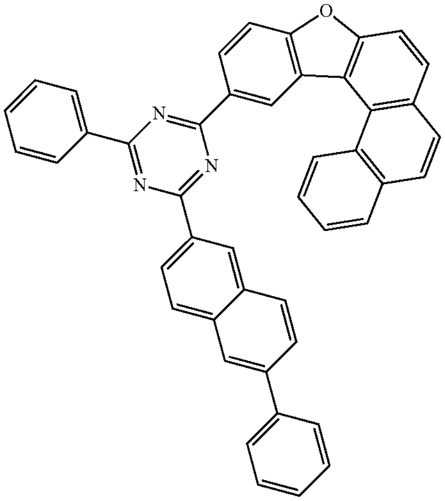
-continued
H2-187
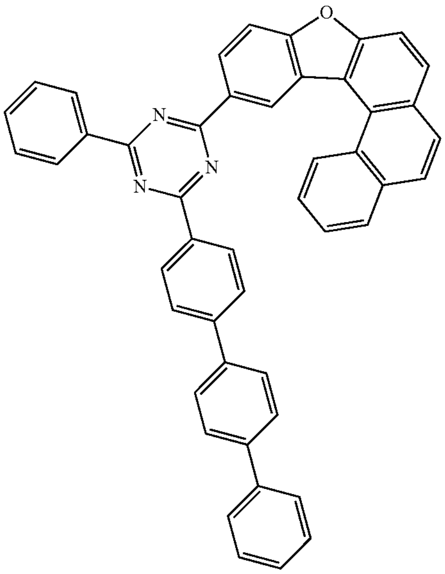
H2-188
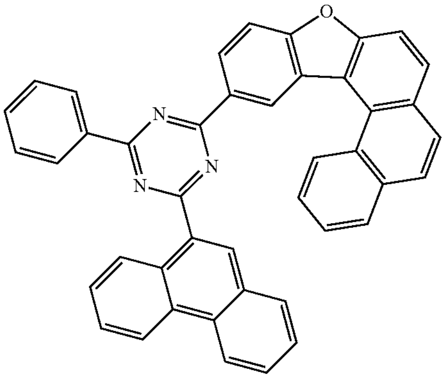
H2-189
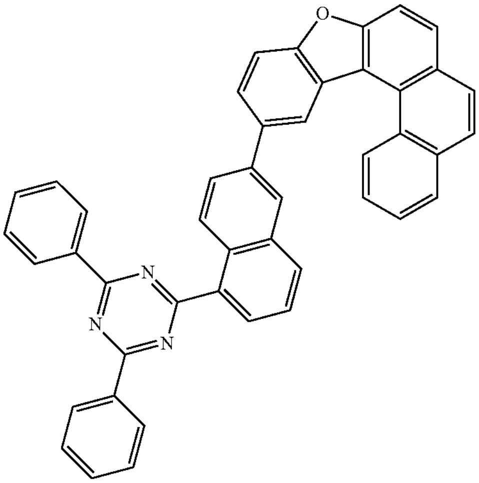

-continued
H2-190
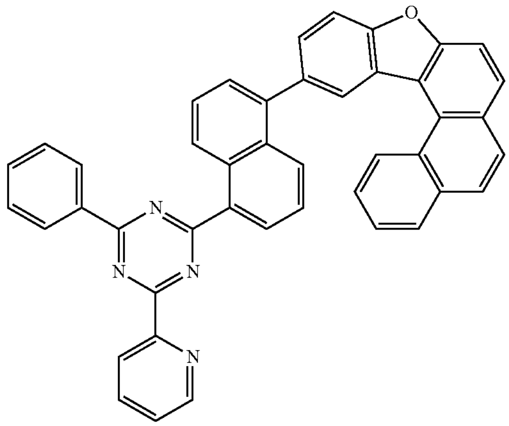
H2-191
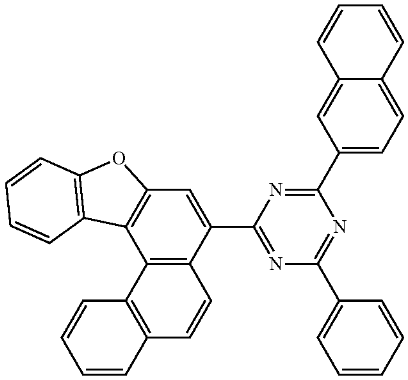
H2-192
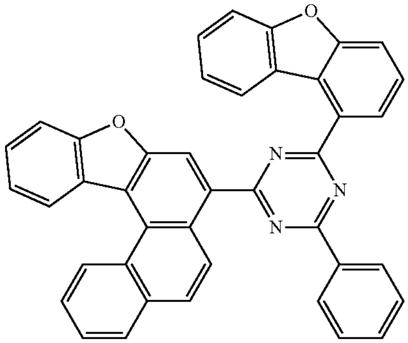
H2-193
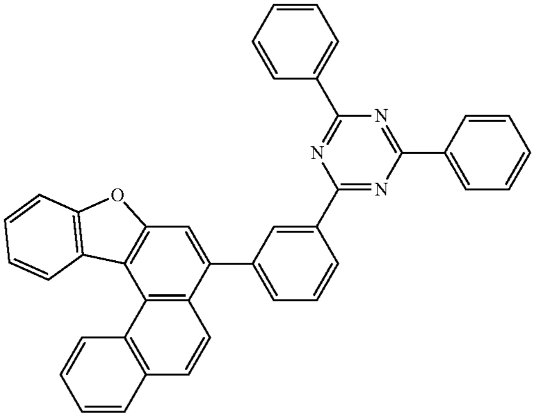
-continued
H2-194
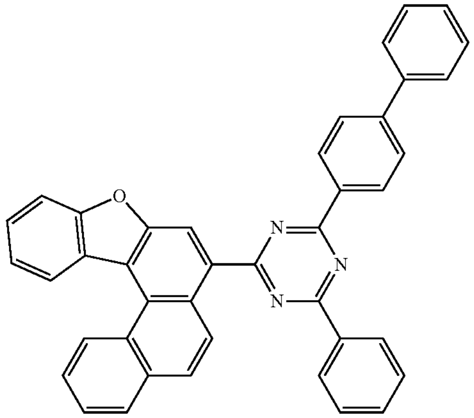
H2-195
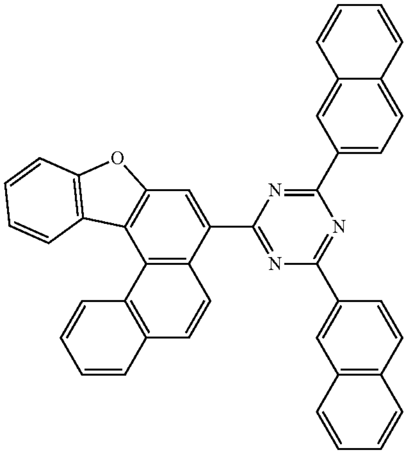
H2-196
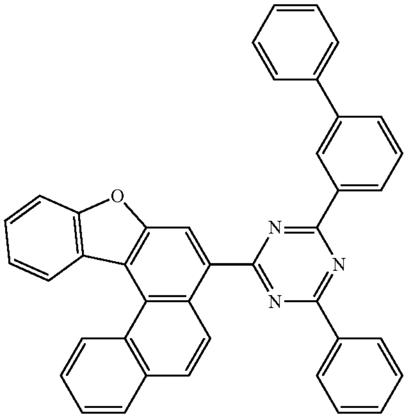

-continued
H2-197
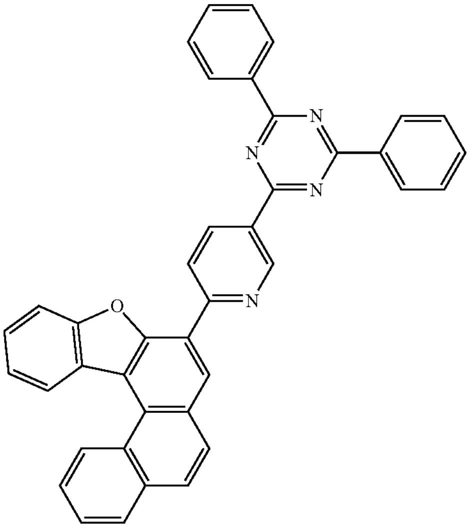
H2-198
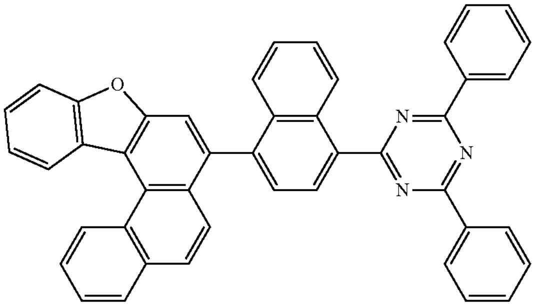
H2-199
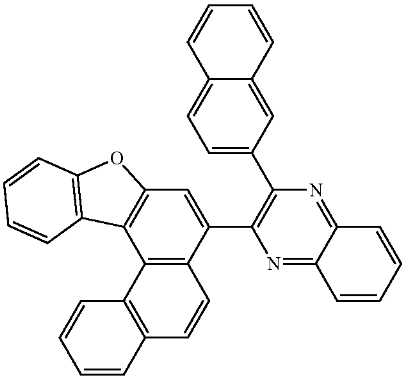
H2-200
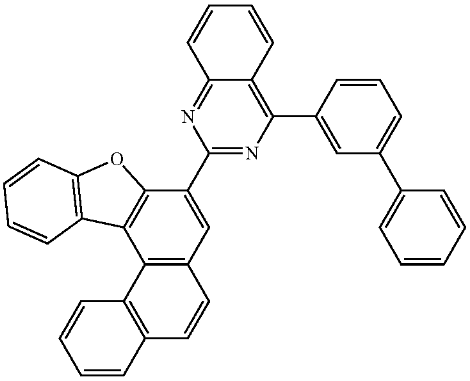
-continued
H2-201
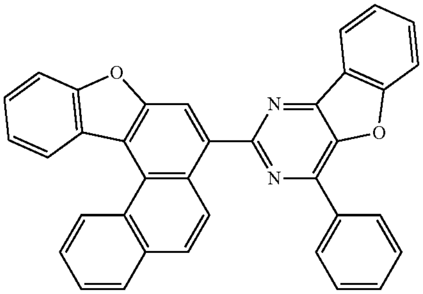
H2-202
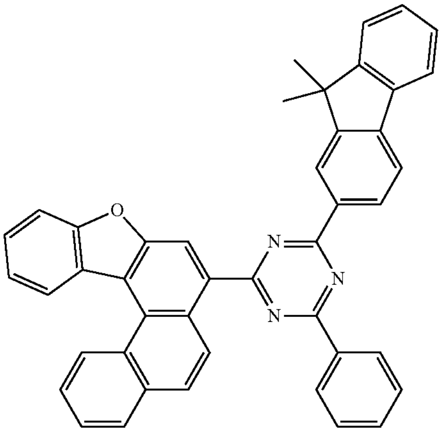
H2-203
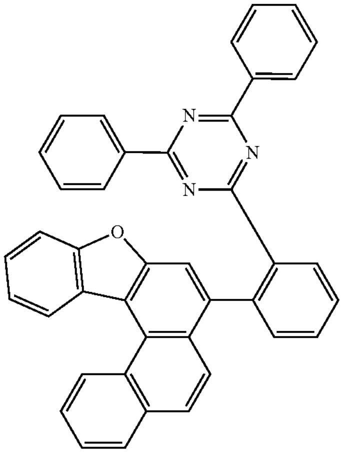

-continued
H2-204
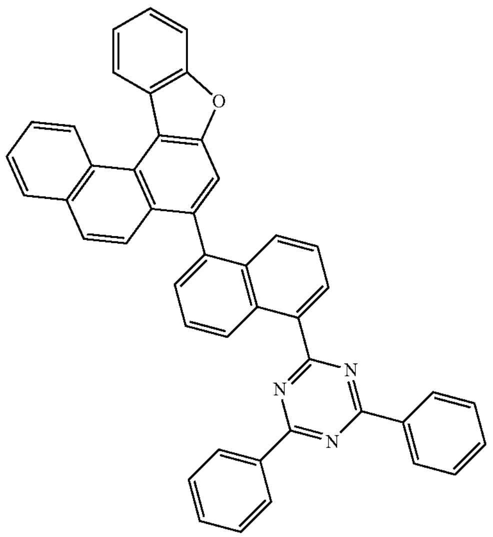
H2-205
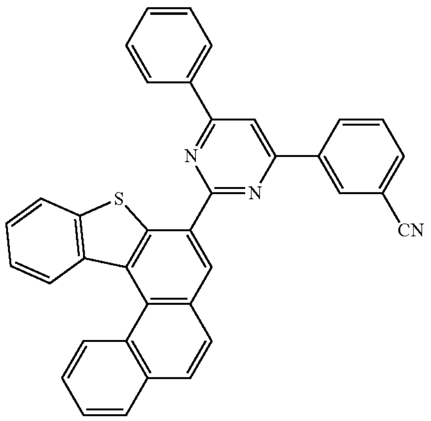
H2-206
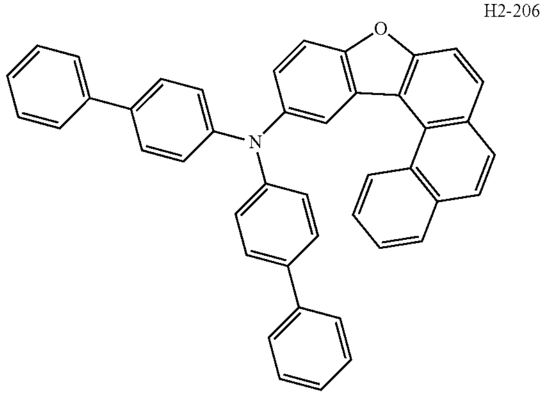
-continued
H2-207
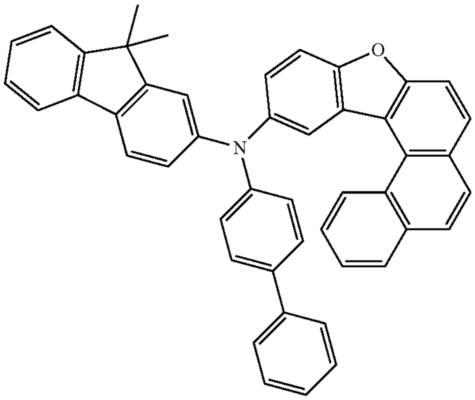
H2-208
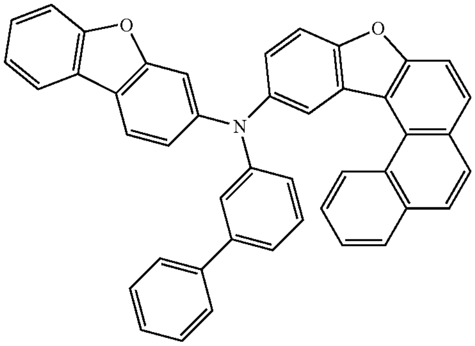
H2-209
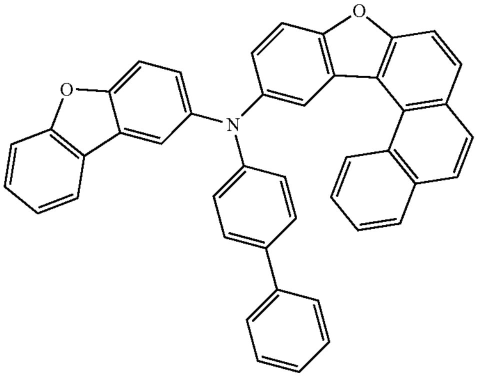
H2-210
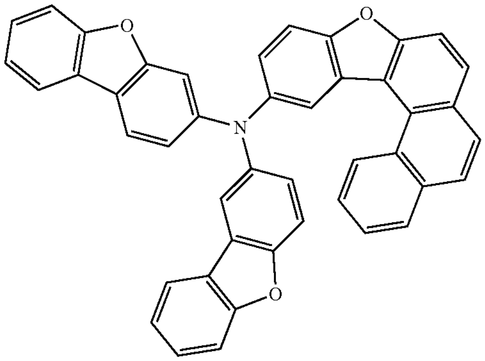

-continued
H2-211
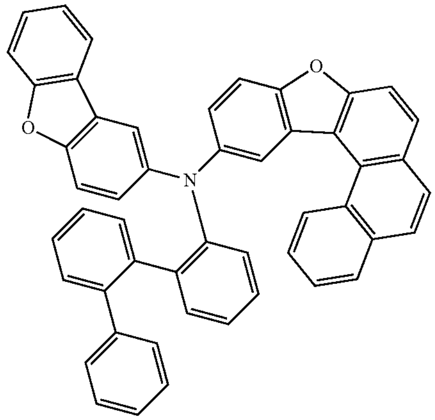
H2-212
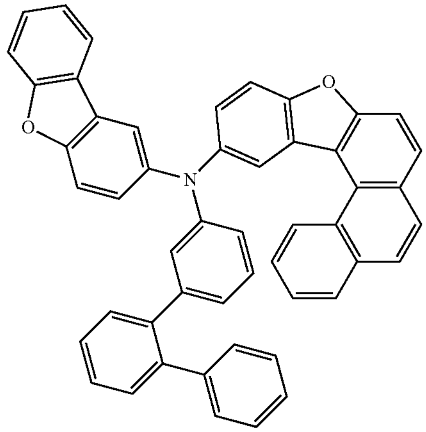
H2-213
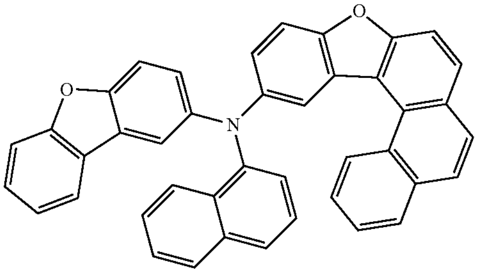
H2-214
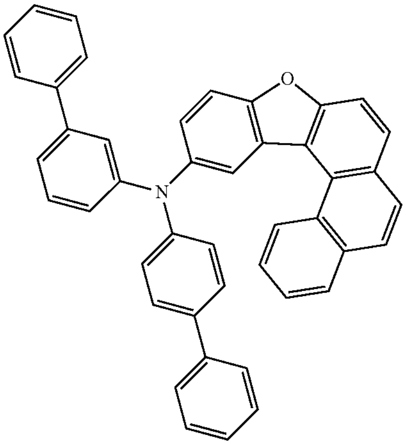
-continued
H2-215
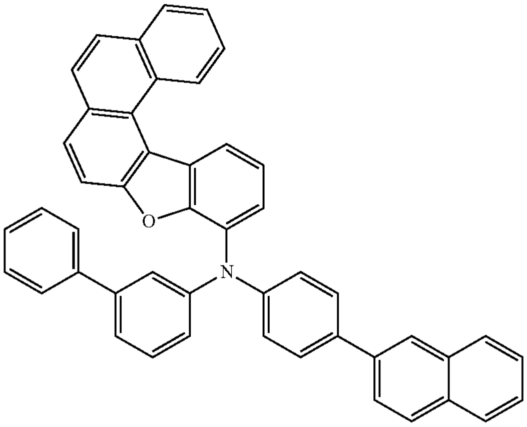
H2-216
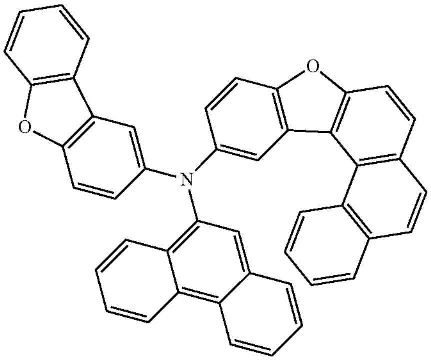
H2-217
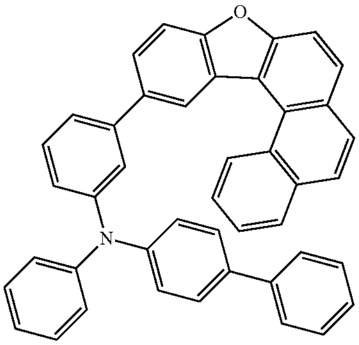
H2-218
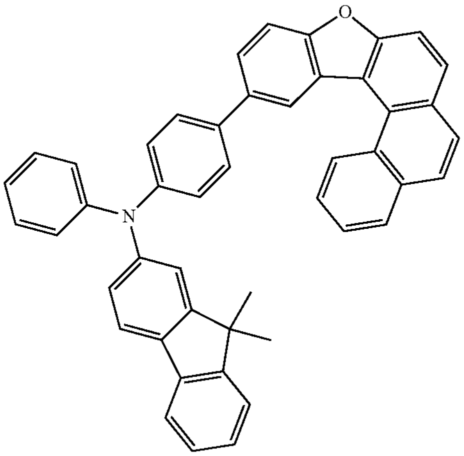

-continued
H2-219
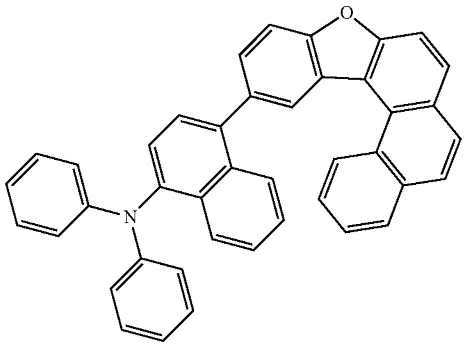
H2-220
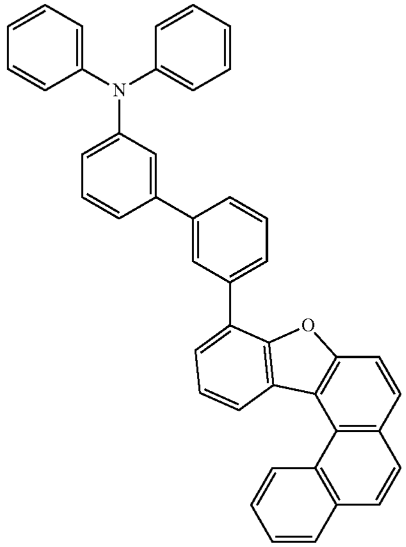
H2-221
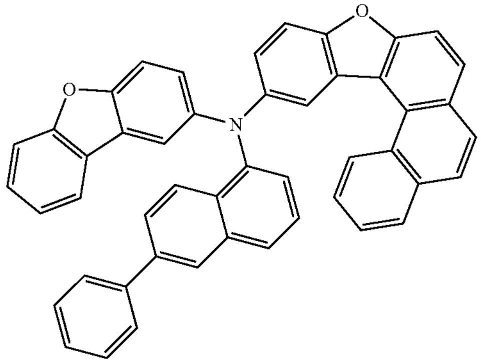
H2-222
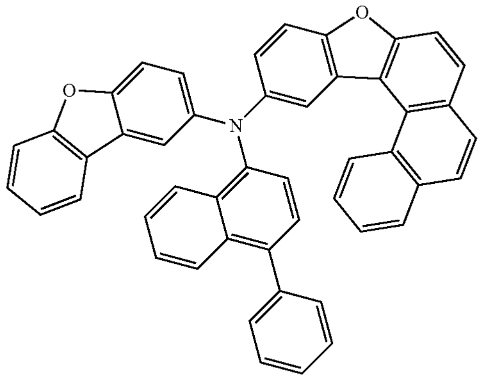
-continued
H2-223
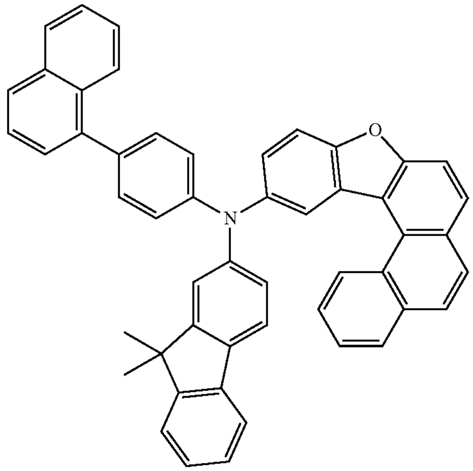
H2-224
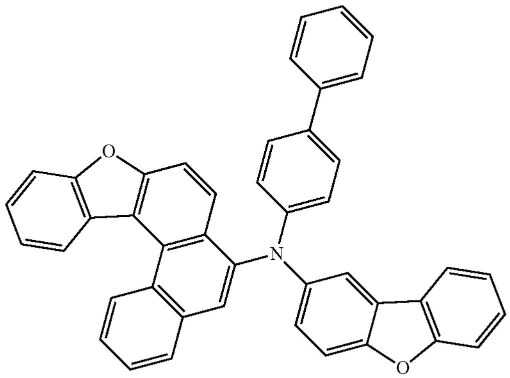
H2-225
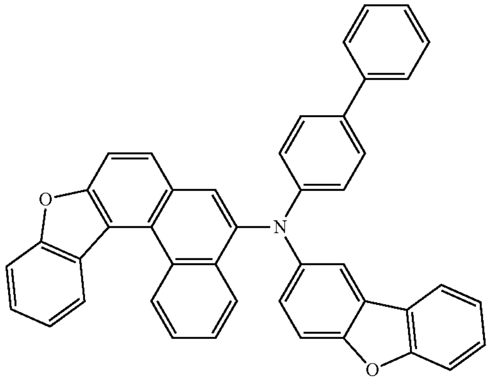

-continued
H2-226
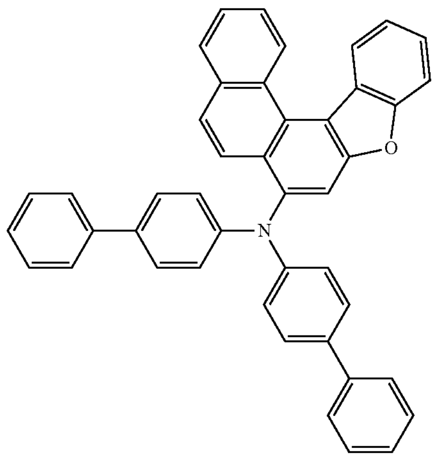
H2-227
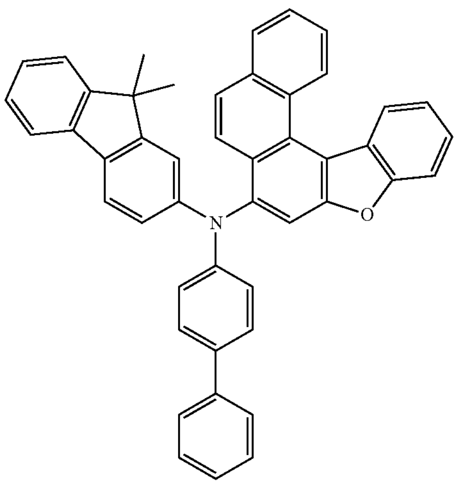
H2-228
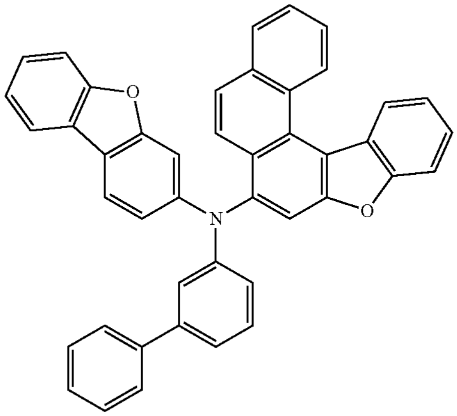
-continued
H2-229
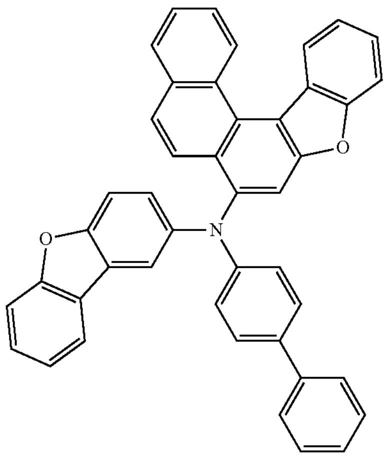
H2-230
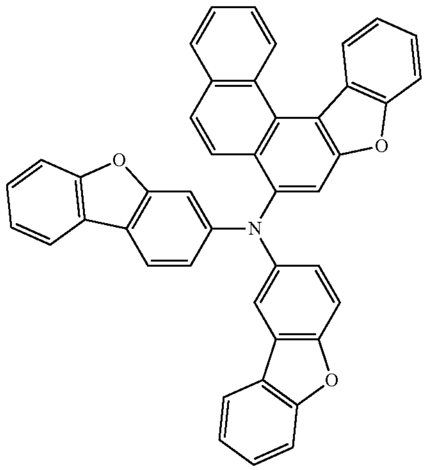
H2-231
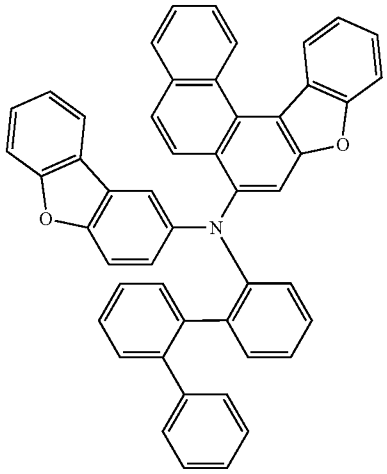

-continued
H2-232
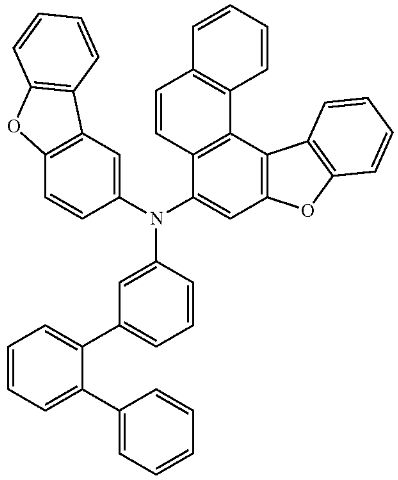
H2-233
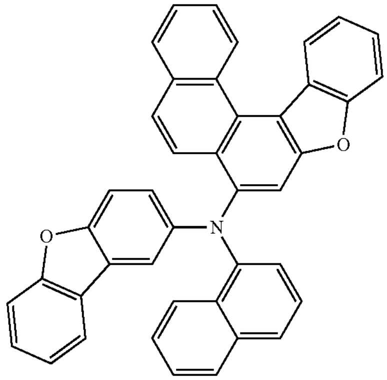
H2-234
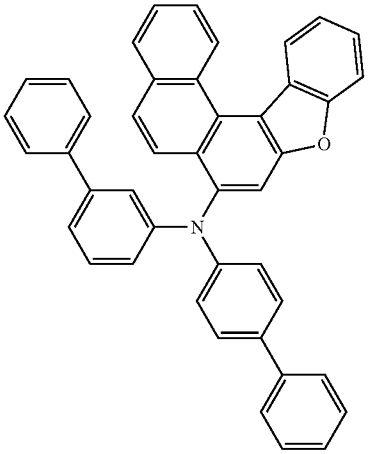
-continued
H2-235
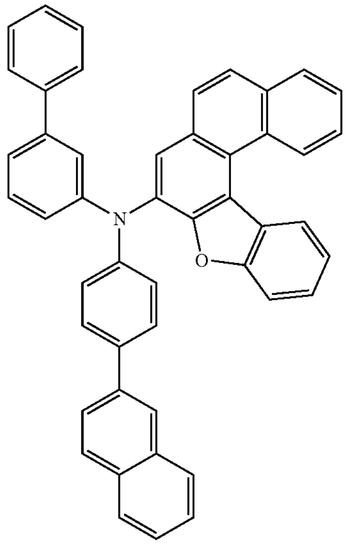
H2-236
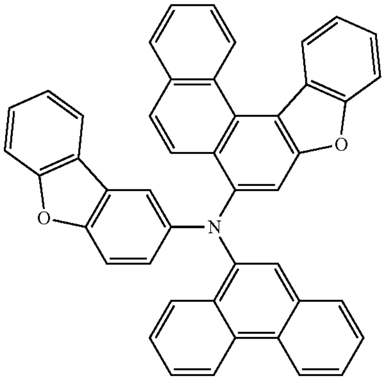
H2-237
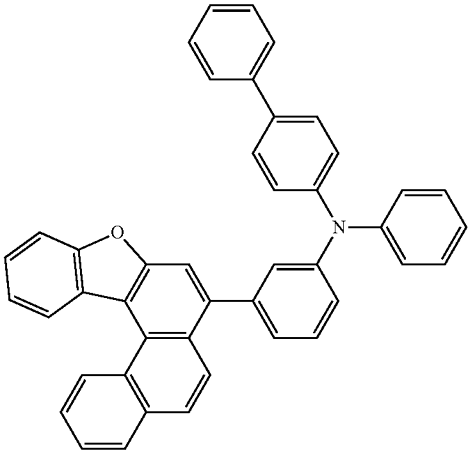

-continued
H2-238
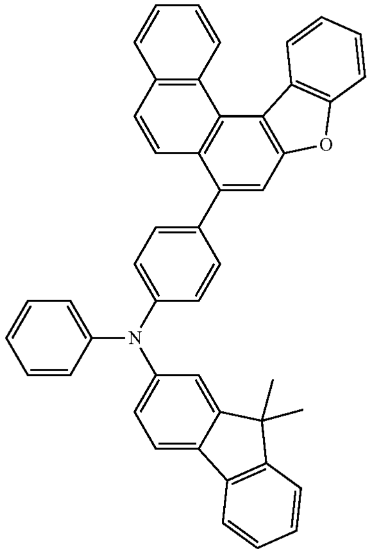
H2-239
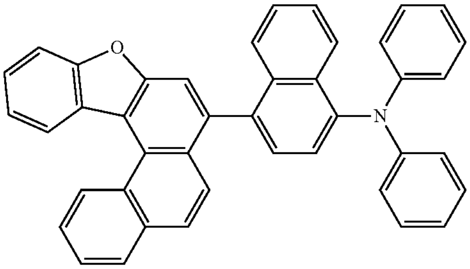
H2-240
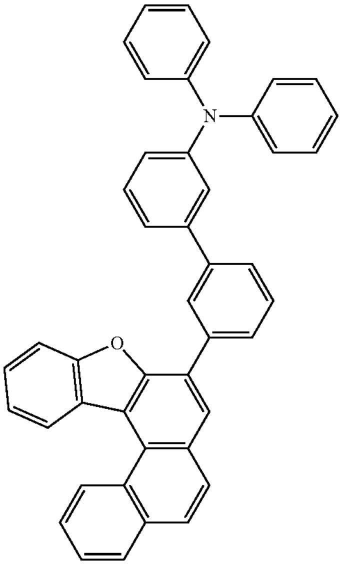
-continued
H2-241
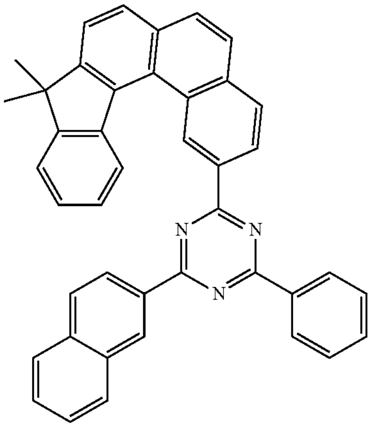
H2-242
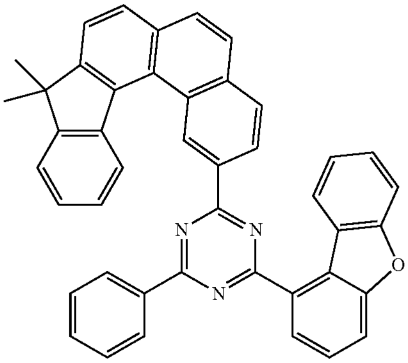
H2-243
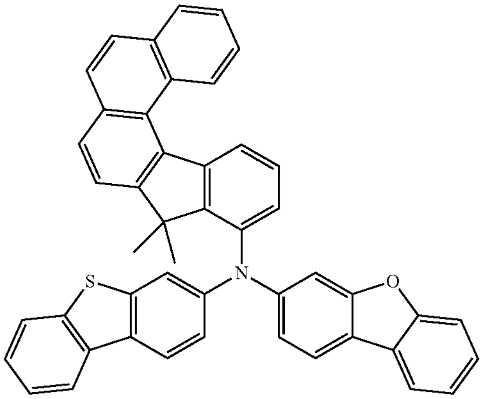
H2-244
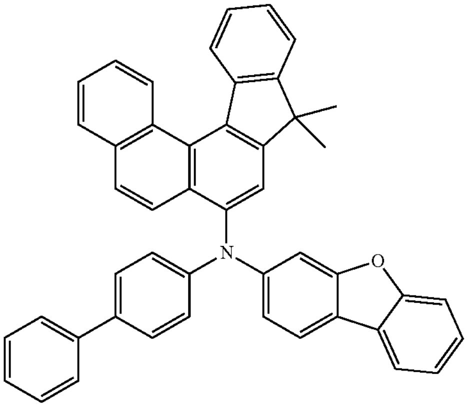

-continued
H2-245
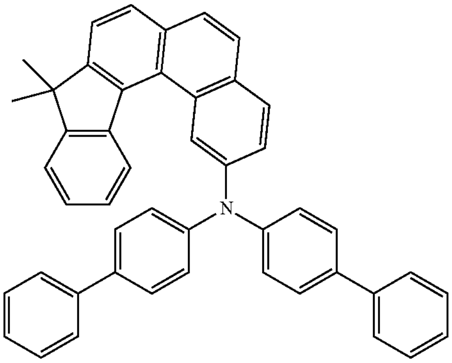
H2-246
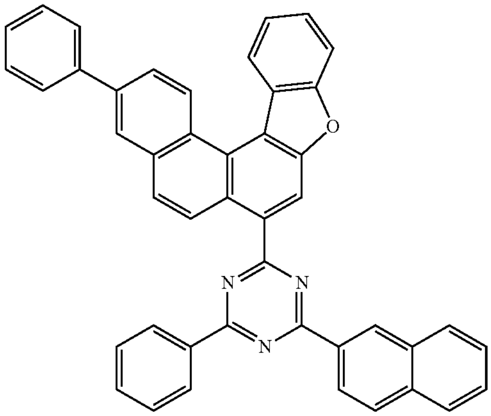
H2-247
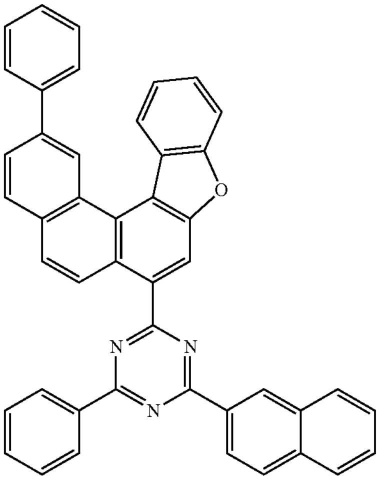
-continued
H2-248
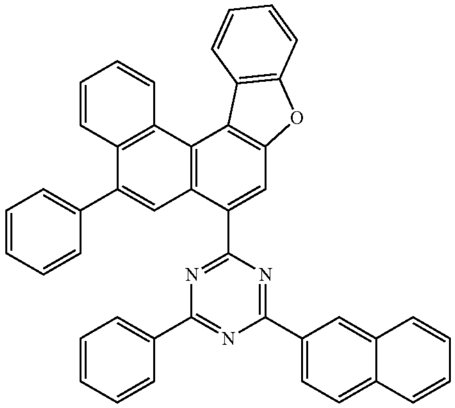
H2-249
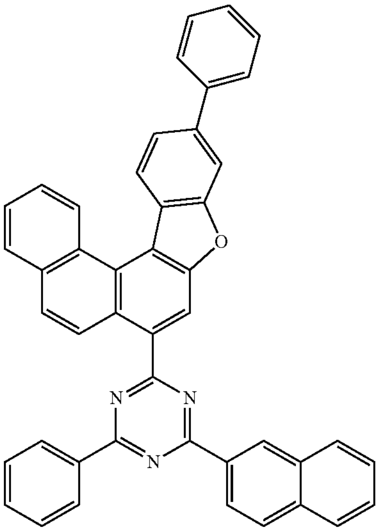
H2-250
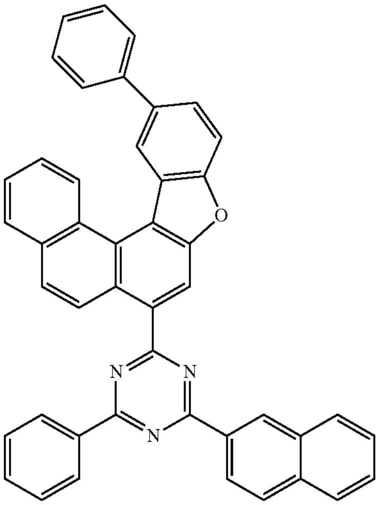

-continued
H2-251
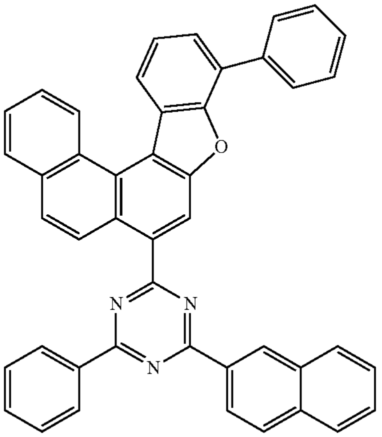
H2-252
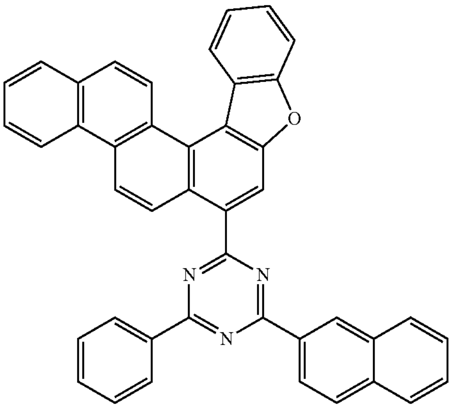
H2-253
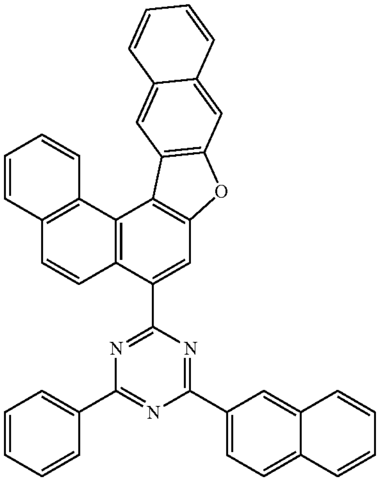
-continued
H2-254
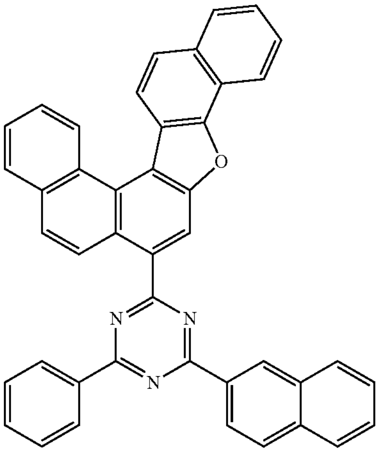
H2-255
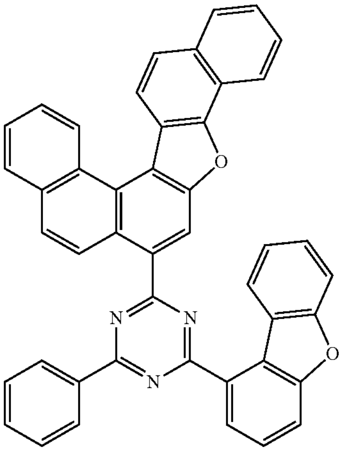
H2-256
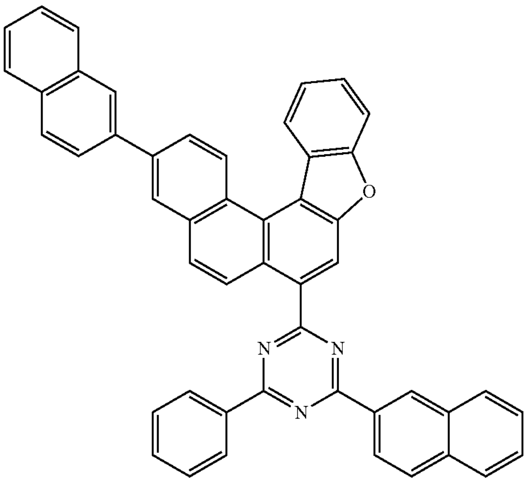

-continued
H2-257
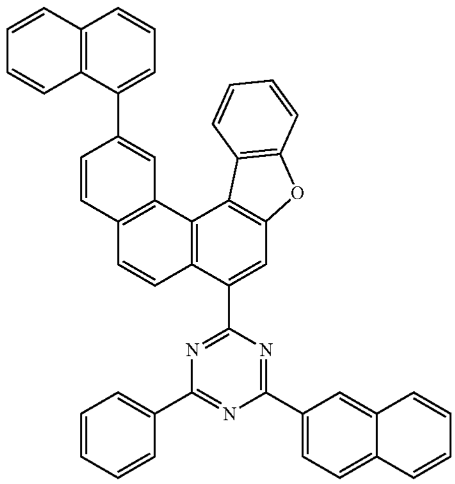
H2-258
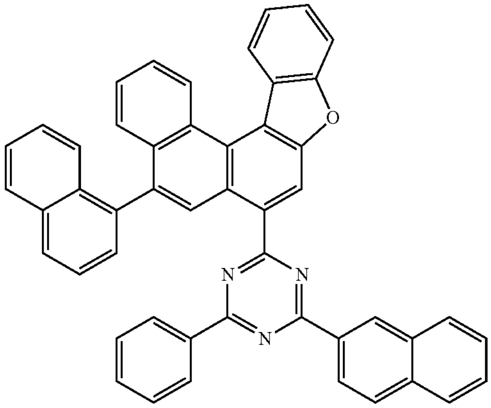
H2-259
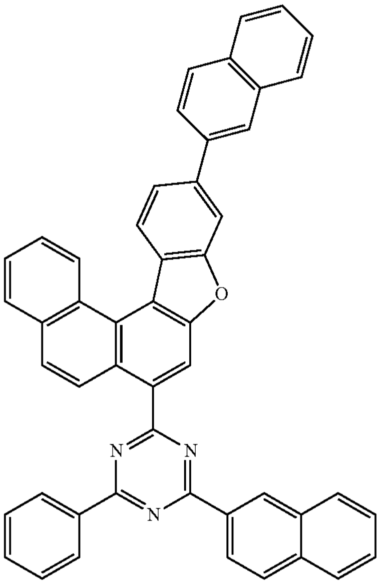
-continued
H2-260
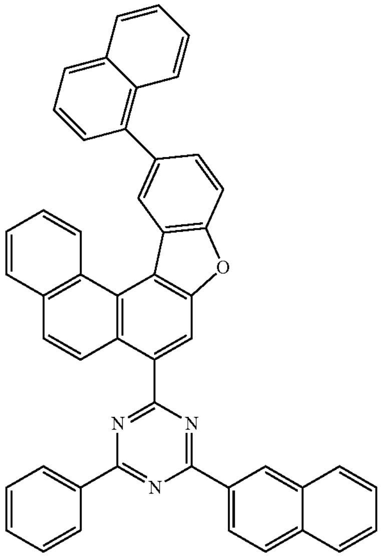
H2-261
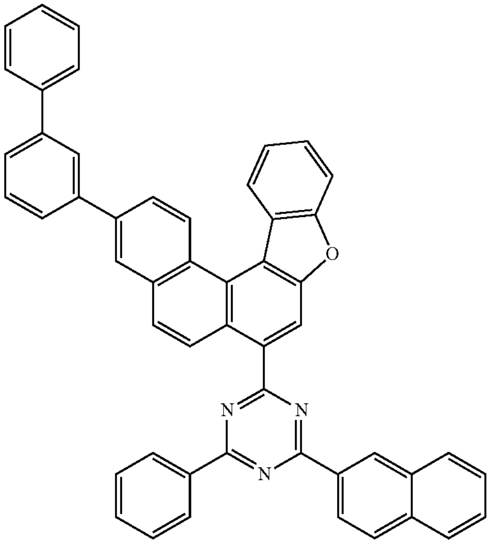

-continued
H2-262
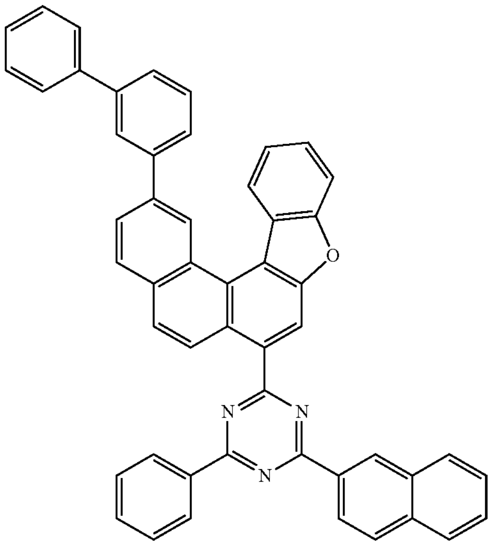
H2-263
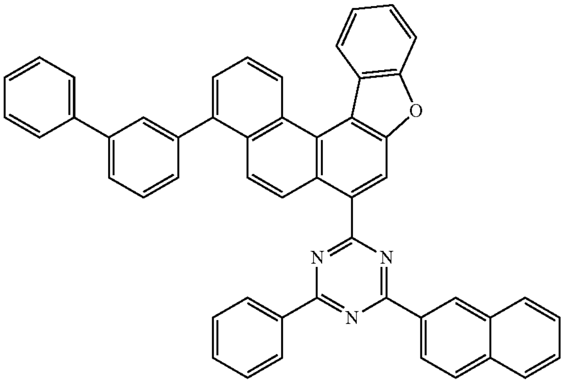
H2-264
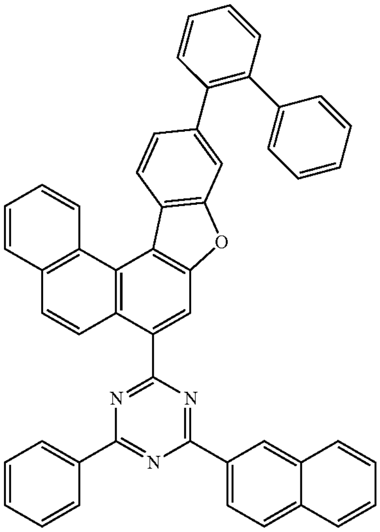
-continued
H2-265
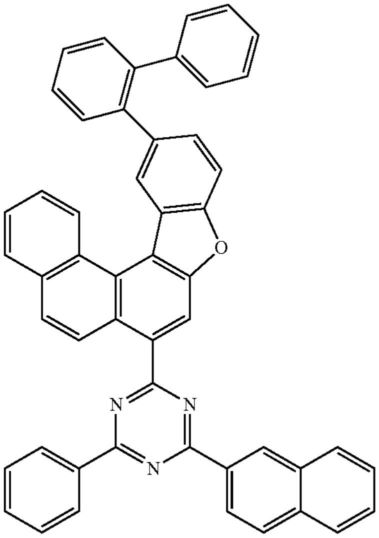
H2-266
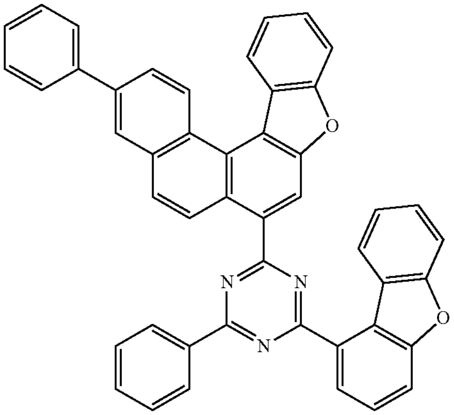
H2-267
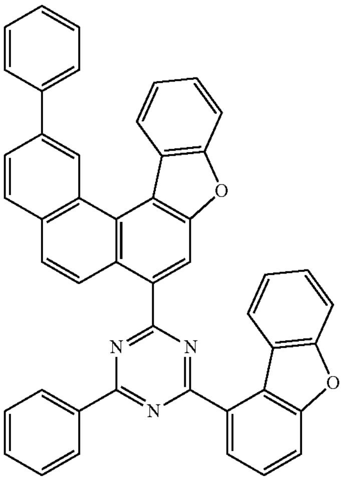

-continued
H2-268
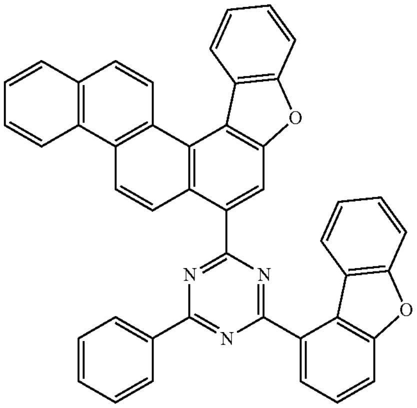
H2-269
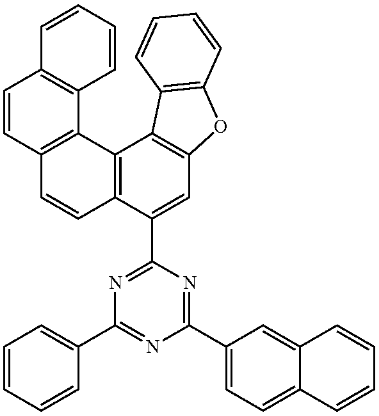
H2-270
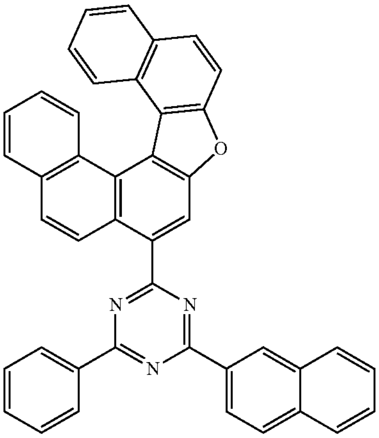
-continued
H2-271
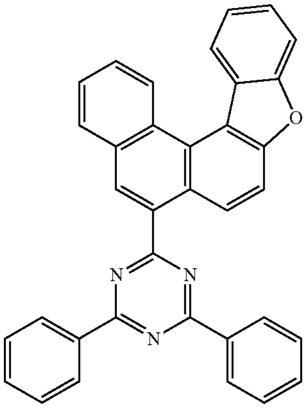
H2-272
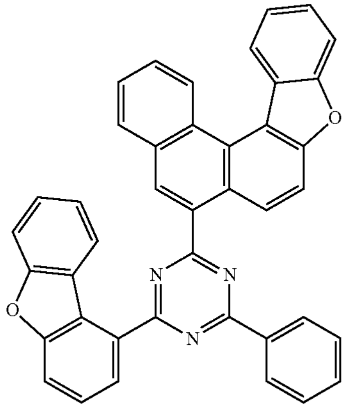
H2-273
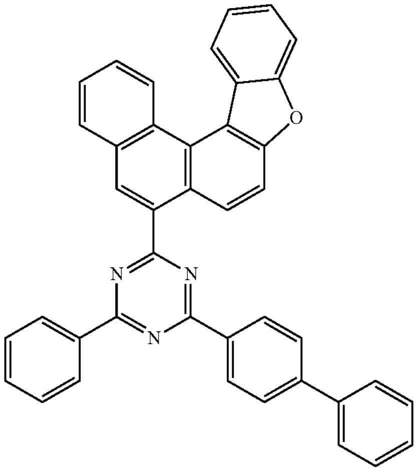

-continued
H2-274
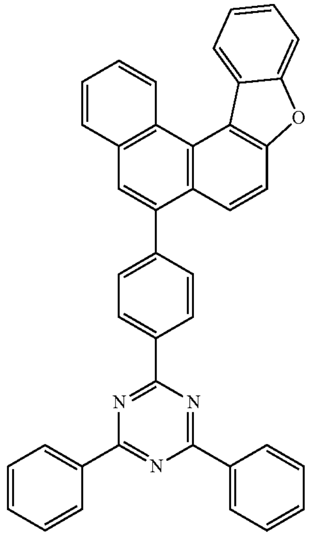
H2-275
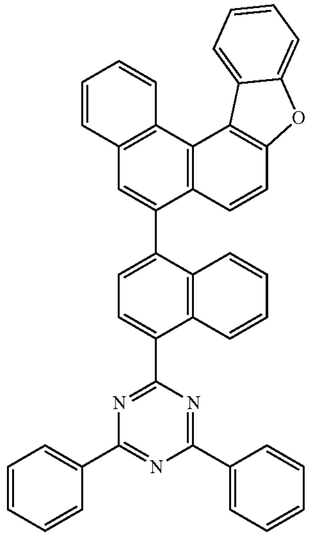
H2-276
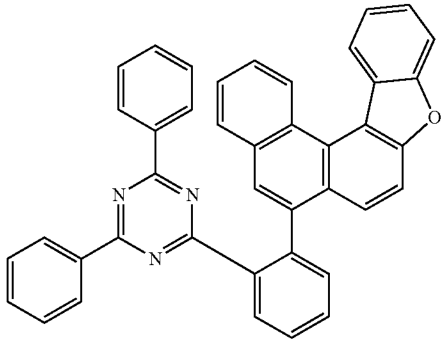
-continued
H2-277
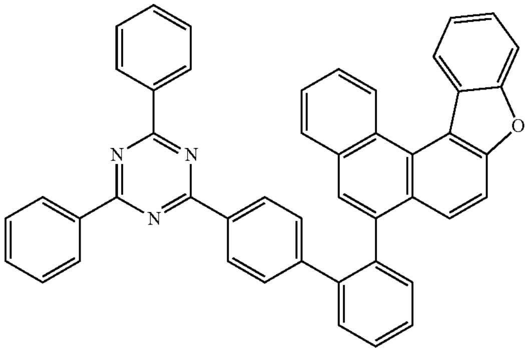
H2-278
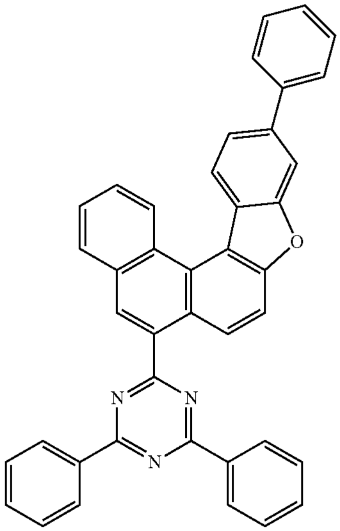
H2-279
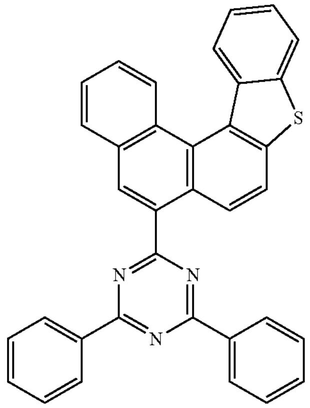

-continued
H2-280
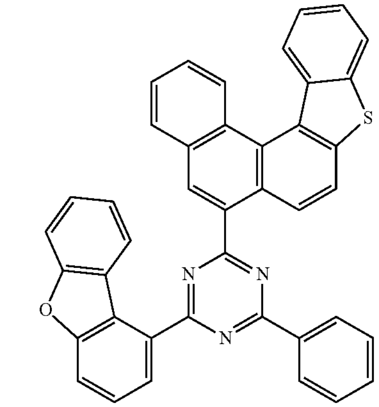
H2-281
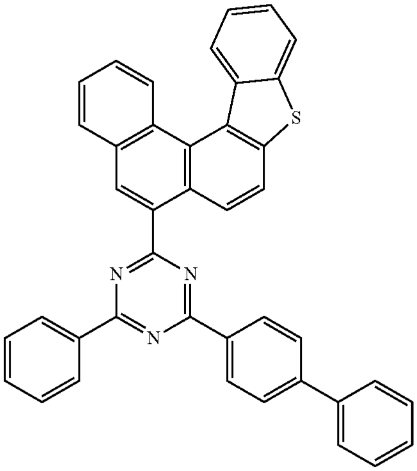
H2-282
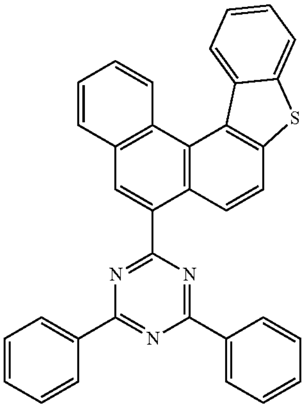
-continued
H2-283
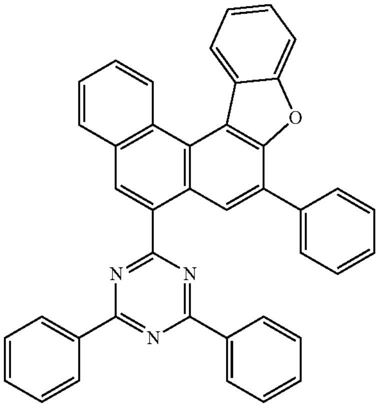
H2-284
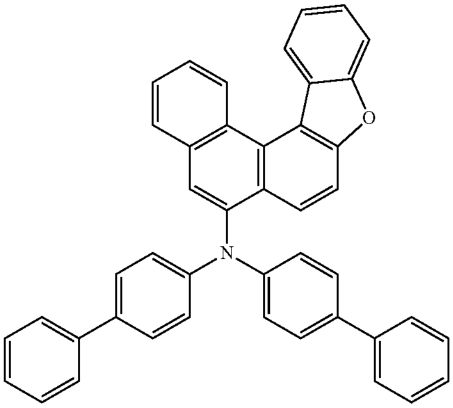
H2-285
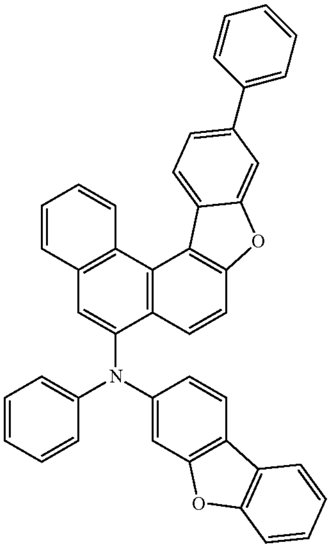

-continued
H2-286
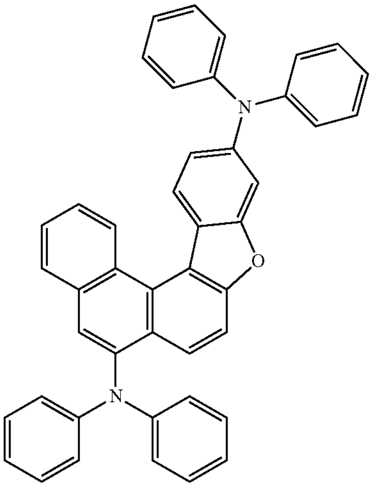
H2-287
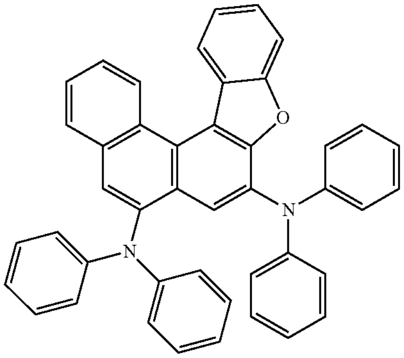
H2-288
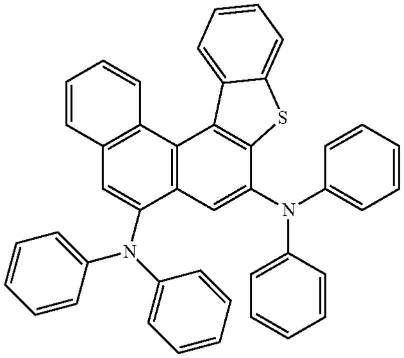
H2-289
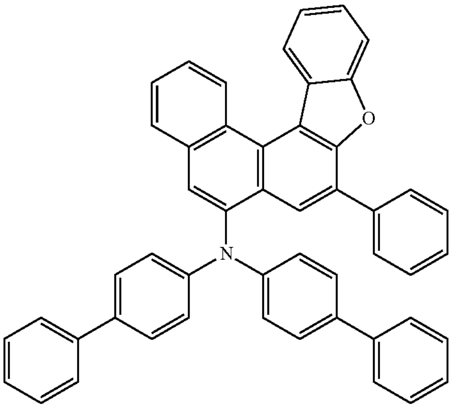
-continued
H2-290
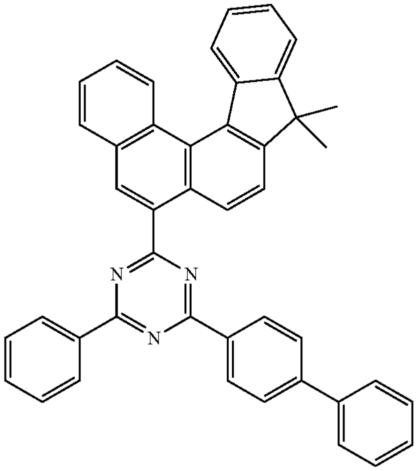
H2-291
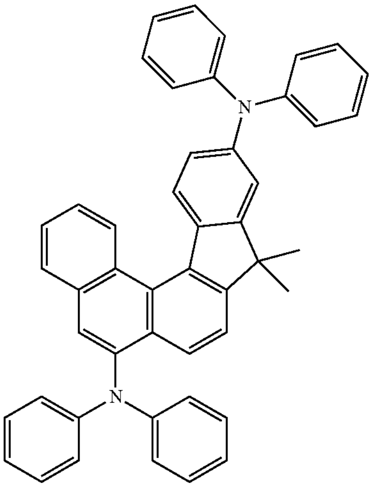
H2-292
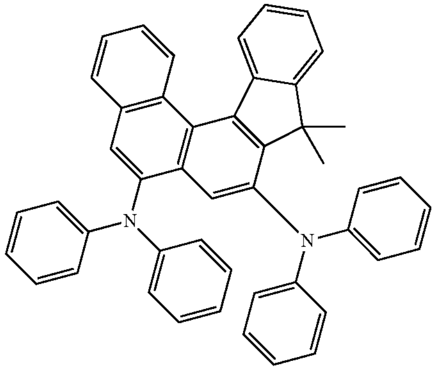

-continued
H2-293
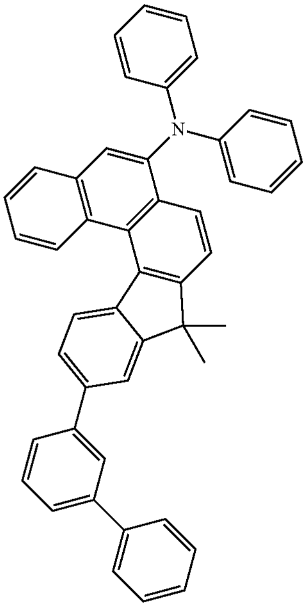
and
-continued
H2-294
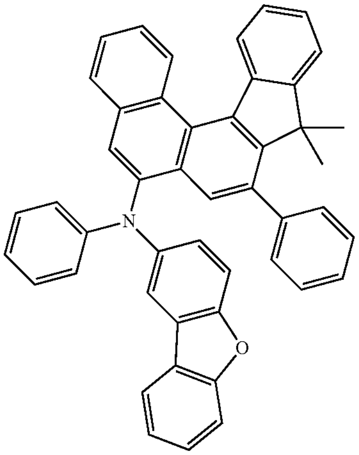
.
9. An organic electroluminescent device comprising anode; cathode; and at least one light-emitting layer between the anode and the cathode in which at least one of the light-emitting layers comprises the plurality of host materials according to claim 1.
* * * * *